(12) United States Patent
Johnson et al.

(10) Patent No.: US 10,730,945 B2
(45) Date of Patent: *Aug. 4, 2020

(54) ANTIBODIES REACTIVE WITH B7-H3 AND USERS THEREOF

(71) Applicant: MacroGenics, Inc., Rockville, MD (US)

(72) Inventors: Leslie S. Johnson, Darnestown, MD (US); Ling Huang, Bethesda, MD (US); Paul A. Moore, North Potomac, MD (US); Deryk T. Loo, Belmont, CA (US); Francine Z. Chen, San Francisco, CA (US)

(73) Assignee: MacroGenics, Inc., Rockville, MD (US)

( * ) Notice: Subject to any disclaimer, the term of this patent is extended or adjusted under 35 U.S.C. 154(b) by 312 days.

This patent is subject to a terminal disclaimer.

(21) Appl. No.: 15/861,966

(22) Filed: Jan. 4, 2018

(65) Prior Publication Data
US 2018/0134790 A1   May 17, 2018

Related U.S. Application Data

(60) Continuation of application No. 15/169,211, filed on May 31, 2016, now Pat. No. 9,896,508, which is a continuation of application No. 14/331,876, filed on Jul. 15, 2014, now Pat. No. 9,441,049, which is a division of application No. 13/463,924, filed on May 4, 2012, now Pat. No. 8,802,091, which is a continuation-in-part of application No. PCT/US2011/026689, filed on Mar. 1, 2011.

(60) Provisional application No. 61/482,771, filed on May 5, 2011, provisional application No. 61/311,057, filed on Mar. 5, 2010, provisional application No. 61/310,695, filed on Mar. 4, 2010, provisional application No. 61/310,692, filed on Mar. 4, 2010.

(51) Int. Cl.
| | |
|---|---|
| *A61K 39/00* | (2006.01) |
| *C07K 16/30* | (2006.01) |
| *A61K 39/395* | (2006.01) |
| *A61K 45/06* | (2006.01) |
| *C07K 16/28* | (2006.01) |
| *G01N 33/574* | (2006.01) |
| *A61K 47/68* | (2017.01) |

(52) U.S. Cl.
CPC .... *C07K 16/2827* (2013.01); *A61K 39/39558* (2013.01); *A61K 45/06* (2013.01); *A61K 47/6849* (2017.08); *A61K 47/6851* (2017.08); *A61K 47/6855* (2017.08); *C07K 16/2809* (2013.01); *C07K 16/30* (2013.01); *C07K 16/3023* (2013.01); *C07K 16/3046* (2013.01); *C07K 16/3069* (2013.01); *G01N 33/57484* (2013.01); *A61K 2039/505* (2013.01); *C07K 2317/24* (2013.01); *C07K 2317/31* (2013.01); *C07K 2317/33* (2013.01); *C07K 2317/622* (2013.01); *C07K 2317/626* (2013.01); *C07K 2317/73* (2013.01); *C07K 2317/76* (2013.01); *C07K 2317/77* (2013.01); *C07K 2317/94* (2013.01)

(58) Field of Classification Search
None
See application file for complete search history.

(56) References Cited

U.S. PATENT DOCUMENTS

| | | |
|---|---|---|
| 3,842,067 A | 10/1974 | Sarantakis |
| 3,862,925 A | 1/1975 | Sarantakis et al. |
| 3,972,859 A | 8/1976 | Fujino et al. |
| 4,105,603 A | 8/1978 | Vale, Jr. et al. |
| 4,179,337 A | 12/1979 | Davis et al. |
| 4,752,601 A | 6/1988 | Hahn |
| 4,816,567 A | 3/1989 | Cabilly et al. |
| 5,024,835 A | 6/1991 | Rao et al. |
| 5,116,964 A | 5/1992 | Capon et al. |
| 5,169,933 A | 12/1992 | Anderson et al. |
| 5,185,432 A | 2/1993 | Hellstrom et al. |
| 5,225,539 A | 12/1993 | Winter |
| 5,348,876 A | 9/1994 | Michaelson et al. |
| 5,565,332 A | 10/1996 | Hoogenboom et al. |
| 5,576,184 A | 11/1996 | Better et al. |
| 5,580,717 A | 12/1996 | Dower et al. |
| 5,585,089 A | 12/1996 | Queen et al. |
| 5,624,821 A | 4/1997 | Winter et al. |

(Continued)

FOREIGN PATENT DOCUMENTS

| | | |
|---|---|---|
| EP | 0327378 | 8/1989 |
| EP | 0332865 | 9/1989 |

(Continued)

OTHER PUBLICATIONS

US 6,331,391 B1, 12/2001, Wittrup et al. (withdrawn)

(Continued)

*Primary Examiner* — Julie Wu
(74) *Attorney, Agent, or Firm* — AuerbachSchrot LLC; William C. Schrot; Jeffrey I. Auerbach

(57) ABSTRACT

The present invention relates to antibodies that are immunoreactive to the mammalian, and more particularly, the human B7-H3 receptor and to uses thereof, particularly in the treatment of cancer and inflammation. The invention thus particularly concerns humanized B7-H3-reactive antibodies that are capable of mediating, and more preferably enhancing the activation of the immune system against cancer cells that are associated with a variety of human cancers.

20 Claims, 36 Drawing Sheets
Specification includes a Sequence Listing.

(56) References Cited

U.S. PATENT DOCUMENTS

| | | |
|---|---|---|
| 5,648,260 A | 7/1997 | Winter et al. |
| 5,656,444 A | 8/1997 | Webb et al. |
| 5,693,761 A | 12/1997 | Queen et al. |
| 5,693,762 A | 12/1997 | Queen et al. |
| 5,698,449 A | 12/1997 | Baumann et al. |
| 5,711,944 A | 1/1998 | Gilbert et al. |
| 5,723,584 A | 3/1998 | Schatz |
| 5,731,168 A | 3/1998 | Carter et al. |
| 5,733,743 A | 3/1998 | Johnson et al. |
| 5,736,135 A | 4/1998 | Goeddel et al. |
| 5,736,137 A | 4/1998 | Anderson et al. |
| 5,807,706 A | 9/1998 | Carter et al. |
| 5,807,715 A | 9/1998 | Morrison et al. |
| 5,821,333 A | 10/1998 | Carter et al. |
| 5,837,243 A | 11/1998 | Deo et al. |
| 5,866,692 A | 2/1999 | Shitara et al. |
| 5,874,239 A | 2/1999 | Schatz |
| 5,877,396 A | 3/1999 | Ravetch et al. |
| 5,885,573 A | 3/1999 | Bluestone et al. |
| 5,888,533 A | 3/1999 | Dunn |
| 5,945,115 A | 3/1999 | Dunn et al. |
| 5,932,433 A | 8/1999 | Schatz |
| 5,985,599 A | 11/1999 | Mckenzie et al. |
| 5,997,867 A | 12/1999 | Waldmann et al. |
| 6,019,968 A | 2/2000 | Platz et al. |
| 6,025,485 A | 2/2000 | Kamb et al. |
| 6,054,297 A | 4/2000 | Carter et al. |
| 6,054,561 A | 4/2000 | Ring |
| 6,114,147 A | 9/2000 | Frenken et al. |
| 6,132,764 A | 10/2000 | Li et al. |
| 6,132,992 A | 10/2000 | Ledbetter et al. |
| 6,165,745 A | 12/2000 | Ward et al. |
| 6,180,370 B1 | 1/2001 | Queen et al. |
| 6,180,377 B1 | 1/2001 | Morgan et al. |
| 6,194,551 B1 | 2/2001 | Idusogie et al. |
| 6,218,149 B1 | 4/2001 | Morrison et al. |
| 6,242,195 B1 | 6/2001 | Idusogie et al. |
| 6,265,150 B1 | 7/2001 | Terstappen et al. |
| 6,277,375 B1 | 8/2001 | Ward |
| 6,300,065 B1 | 10/2001 | Kieke et al. |
| 6,331,415 B1 | 12/2001 | Cabilly et al. |
| 6,339,069 B1 | 1/2002 | Meers et al. |
| 6,420,149 B1 | 7/2002 | Fukuda et al. |
| 6,423,538 B1 | 7/2002 | Wittrup et al. |
| 6,455,263 B2 | 9/2002 | Payan |
| 6,472,511 B1 | 10/2002 | Leung et al. |
| 6,492,123 B1 | 12/2002 | Hollinger et al. |
| 6,528,624 B1 | 3/2003 | Idusogie et al. |
| 6,538,124 B1 | 3/2003 | Idusogie et al. |
| 6,548,640 B1 | 4/2003 | Winter |
| 6,623,940 B1 | 9/2003 | Ledbetter et al. |
| 6,696,550 B2 | 2/2004 | Larosa et al. |
| 6,737,056 B1 | 5/2004 | Presta |
| 6,821,505 B2 | 11/2004 | Ward |
| 6,891,030 B2 | 5/2005 | Chen |
| 6,965,018 B2 | 11/2005 | Mikesell et al. |
| 6,982,321 B2 | 1/2006 | Winter |
| 7,122,637 B2 | 10/2006 | Presta |
| 7,183,387 B1 | 2/2007 | Presta |
| 7,261,890 B2 | 8/2007 | Krah, III et al. |
| 7,276,586 B2 | 10/2007 | Goddard et al. |
| 7,279,567 B2 | 10/2007 | Mikesell et al. |
| 7,315,786 B2 | 1/2008 | Dahiyat et al. |
| 7,317,091 B2 | 1/2008 | Lazar et al. |
| 7,332,581 B2 | 2/2008 | Presta |
| 7,335,742 B2 | 2/2008 | Presta |
| 7,351,803 B2 | 4/2008 | Johnson et al. |
| 7,355,008 B2 | 4/2008 | Stavenhagen et al. |
| 7,358,354 B2 | 4/2008 | Mikesell et al. |
| 7,368,554 B2 | 5/2008 | Mikesell et al. |
| 7,371,826 B2 | 5/2008 | Presta |
| 7,416,727 B2 | 8/2008 | Presta |
| 7,425,619 B2 | 9/2008 | Koenig et al. |
| 7,425,620 B2 | 9/2008 | Koenig et al. |
| 7,429,652 B2 | 9/2008 | Wang et al. |
| 7,521,542 B2 | 4/2009 | Johnson et al. |
| 7,527,969 B2 | 5/2009 | Mather et al. |
| 7,618,628 B2 | 11/2009 | Johnson et al. |
| 7,632,497 B2 | 12/2009 | Stavenhagen |
| 7,642,228 B2 | 1/2010 | Carter et al. |
| 7,655,229 B2 | 2/2010 | Chan et al. |
| 7,662,926 B2 | 2/2010 | Chan et al. |
| 7,695,936 B2 | 4/2010 | Carter et al. |
| 7,700,100 B2 | 4/2010 | Johnson et al. |
| 7,718,774 B2 | 5/2010 | Mather et al. |
| 7,786,270 B2 | 8/2010 | Johnson et al. |
| 7,838,635 B2 | 11/2010 | Johnson et al. |
| 7,960,512 B2 | 6/2011 | Stavenhagen et al. |
| 8,003,774 B2 | 8/2011 | Stavenhagen et al. |
| 8,039,592 B2 | 10/2011 | Lazar et al. |
| 8,044,180 B2 | 10/2011 | Koenig et al. |
| 8,124,731 B2 | 2/2012 | Lazar et al. |
| 8,133,982 B2 | 3/2012 | Johnson et al. |
| 8,137,668 B2 | 3/2012 | Li |
| 8,183,357 B2 | 5/2012 | Mather et al. |
| 8,187,593 B2 | 5/2012 | Koenig et al. |
| 8,187,594 B2 | 5/2012 | Mather et al. |
| 8,188,231 B2 | 5/2012 | Lazar et al. |
| 8,192,737 B2 | 6/2012 | Stavenhagen et al. |
| 8,193,318 B2 | 6/2012 | Koenig et al. |
| 8,216,570 B2 | 7/2012 | Mather et al. |
| 8,216,574 B2 | 7/2012 | Stavenhagen et al. |
| 8,216,578 B2 | 7/2012 | Mather et al. |
| 8,216,579 B2 | 7/2012 | Johnson et al. |
| 8,216,800 B2 | 7/2012 | Fabrega et al. |
| 8,217,147 B2 | 7/2012 | Stavenhagen et al. |
| 8,802,091 B2* | 8/2014 | Johnson ............ C07K 16/2809 424/130.1 |
| 9,441,049 B2* | 9/2016 | Johnson ............ C07K 16/2809 |
| 9,896,508 B2* | 2/2018 | Johnson ............ A61K 39/39558 |
| 2001/0036459 A1 | 11/2001 | Ravetch |
| 2002/0028486 A1 | 3/2002 | Morrison et al. |
| 2002/0127227 A1 | 9/2002 | Holmes et al. |
| 2002/0168762 A1 | 11/2002 | Chen |
| 2003/0077282 A1 | 4/2003 | Bigler et al. |
| 2003/0103963 A1 | 6/2003 | Cheung |
| 2003/0103976 A1 | 6/2003 | Serizawa et al. |
| 2003/0115614 A1 | 6/2003 | Kanda et al. |
| 2003/0158389 A1 | 8/2003 | Idusogie et al. |
| 2003/0185827 A1 | 10/2003 | Rodriguez et al. |
| 2003/0190319 A1 | 10/2003 | Adolf et al. |
| 2003/0207346 A1 | 11/2003 | Arathoon et al. |
| 2004/0002587 A1 | 1/2004 | Watkins et al. |
| 2004/0038339 A1 | 2/2004 | Kufer et al. |
| 2004/0058400 A1 | 3/2004 | Hollinger et al. |
| 2004/0110226 A1 | 6/2004 | Lazar et al. |
| 2004/0132101 A1 | 7/2004 | Lazar et al. |
| 2004/0185045 A1 | 9/2004 | Koenig et al. |
| 2004/0191244 A1 | 9/2004 | Presta |
| 2004/0220388 A1 | 11/2004 | Mertens et al. |
| 2004/0235065 A1 | 11/2004 | Hansen et al. |
| 2004/0236078 A1 | 11/2004 | Carter et al. |
| 2005/0025764 A1 | 2/2005 | Watkins et al. |
| 2005/0037000 A1 | 2/2005 | Stavenhagen et al. |
| 2005/0054832 A1 | 3/2005 | Lazar et al. |
| 2005/0064514 A1 | 3/2005 | Stavenhagen et al. |
| 2005/0090648 A1 | 4/2005 | Tsurushita et al. |
| 2005/0215767 A1 | 9/2005 | Koenig et al. |
| 2005/0202536 A1 | 11/2005 | Chen |
| 2005/0260213 A1 | 11/2005 | Koenig et al. |
| 2006/0013810 A1 | 1/2006 | Johnson et al. |
| 2006/0018899 A1 | 1/2006 | Kao et al. |
| 2006/0024298 A1 | 2/2006 | Lazar et al. |
| 2006/0073142 A1 | 4/2006 | Chan et al. |
| 2006/0134709 A1 | 6/2006 | Stavenhagen et al. |
| 2006/0154313 A1 | 7/2006 | Anderson et al. |
| 2006/0177439 A1 | 8/2006 | Koenig et al. |
| 2006/0193849 A1 | 8/2006 | Krauss et al. |
| 2007/0004909 A1 | 1/2007 | Johnson et al. |
| 2007/0036799 A1 | 2/2007 | Stavenhagen et al. |
| 2007/0077246 A1 | 4/2007 | Koenig et al. |
| 2007/0135338 A1 | 6/2007 | O'Neil et al. |
| 2007/0140966 A1 | 6/2007 | Chang et al. |
| 2007/0244303 A1 | 10/2007 | Johnson et al. |

(56) References Cited

U.S. PATENT DOCUMENTS

| | | |
|---|---|---|
| 2007/0253948 A1 | 11/2007 | Chan et al. |
| 2008/0044417 A1 | 2/2008 | Johnson et al. |
| 2008/0044429 A1 | 2/2008 | Johnson et al. |
| 2008/0050371 A1 | 2/2008 | Johnson et al. |
| 2008/0051563 A1 | 2/2008 | Lazar et al. |
| 2008/0081346 A1 | 4/2008 | Moretta et al. |
| 2008/0085277 A1 | 4/2008 | Cho et al. |
| 2008/0095766 A1 | 4/2008 | Koenig et al. |
| 2008/0112961 A1 | 5/2008 | Stavenhagen et al. |
| 2008/0131435 A1 | 6/2008 | Stavenhagen et al. |
| 2008/0138344 A1 | 6/2008 | Stavenhagen et al. |
| 2008/0138349 A1 | 6/2008 | Stavenhagen et al. |
| 2008/0177045 A1 | 7/2008 | Lee et al. |
| 2008/0286819 A1 | 11/2008 | Ravetch et al. |
| 2009/0017023 A1 | 1/2009 | Koenig et al. |
| 2009/0017026 A1 | 1/2009 | Koenig et al. |
| 2009/0017027 A1 | 1/2009 | Koenig et al. |
| 2009/0018315 A1 | 1/2009 | Chen |
| 2009/0022747 A1 | 1/2009 | Chen |
| 2009/0053218 A1 | 2/2009 | Koenig et al. |
| 2009/0060910 A1 | 3/2009 | Johnson et al. |
| 2009/0074771 A1 | 3/2009 | Koenig et al. |
| 2009/0076251 A1 | 3/2009 | Koenig et al. |
| 2009/0087416 A1 | 4/2009 | Chen |
| 2009/0092610 A1 | 4/2009 | Koenig et al. |
| 2009/0098124 A1 | 4/2009 | Stavenhagen et al. |
| 2009/0191195 A1 | 7/2009 | Tuaillon et al. |
| 2009/0202537 A1 | 8/2009 | Johnson et al. |
| 2009/0262732 A1 | 10/2009 | Wood |
| 2010/0015142 A1 | 1/2010 | Koenig et al. |
| 2010/0086969 A1 | 4/2010 | Mather et al. |
| 2010/0174053 A1 | 7/2010 | Johnson et al. |
| 2010/0183605 A1 | 7/2010 | Mather et al. |
| 2010/0196362 A1 | 8/2010 | Stavenhagen et al. |
| 2010/0196372 A1 | 8/2010 | Johnson et al. |
| 2010/0322851 A1 | 12/2010 | Liang et al. |
| 2010/0322924 A1 | 12/2010 | Johnson et al. |
| 2011/0045006 A1 | 2/2011 | Mather et al. |
| 2011/0081347 A1 | 4/2011 | Gorlatov |
| 2011/0097323 A1 | 4/2011 | Johnson et al. |
| 2011/0117089 A1 | 5/2011 | Johnson et al. |
| 2011/0152504 A1 | 6/2011 | Johnson et al. |
| 2011/0243941 A1 | 10/2011 | Stavenhagen et al. |
| 2011/0305714 A1 | 12/2011 | Stavenhagen et al. |
| 2012/0009186 A1 | 1/2012 | Koenig et al. |
| 2012/0034221 A1 | 2/2012 | Bonvini et al. |
| 2012/0141476 A1 | 6/2012 | Johnson et al. |
| 2013/0149236 A1 | 6/2013 | Johnson et al. |

FOREIGN PATENT DOCUMENTS

| | | |
|---|---|---|
| EP | 0629703 | 12/1994 |
| EP | 0359096 | 11/1997 |
| EP | 0953639 | 11/1999 |
| EP | 1006183 | 6/2000 |
| EP | 0343950 | 10/2000 |
| EP | 1327638 | 7/2003 |
| EP | 1354600 | 10/2003 |
| EP | 1514933 | 3/2005 |
| EP | 1292619 | 2/2008 |
| EP | 1892251 | 2/2008 |
| FR | 2894982 | 6/2007 |
| WO | WO 1988/007089 | 9/1988 |
| WO | WO 1989/007142 | 8/1989 |
| WO | WO 1992/016562 | 10/1992 |
| WO | WO 1993/022332 | 11/1993 |
| WO | WO 1994/018330 | 8/1994 |
| WO | WO 1994/029351 | 12/1994 |
| WO | WO 1995/005468 | 2/1995 |
| WO | WO 1996/040878 | 12/1996 |
| WO | WO 1997/028267 | 8/1997 |
| WO | WO 1997/034631 | 9/1997 |
| WO | WO 1997/044362 | 11/1997 |
| WO | WO 1998/005787 | 2/1998 |
| WO | WO 1998/023289 | 6/1998 |
| WO | WO 1998/052975 | 11/1998 |
| WO | WO 1999/019362 | 4/1999 |
| WO | WO 1999/041285 | 8/1999 |
| WO | WO 1999/043713 | 9/1999 |
| WO | WO 1999/046281 | 9/1999 |
| WO | WO 1999/051642 | 10/1999 |
| WO | WO 1999/058572 | 11/1999 |
| WO | WO 2000/009560 | 2/2000 |
| WO | WO 2000/042072 | 7/2000 |
| WO | WO 2000/047625 | 8/2000 |
| WO | WO 2000/068266 | 11/2000 |
| WO | WO 2001/018021 | 3/2001 |
| WO | WO 2001/018204 | 3/2001 |
| WO | WO 2001/043869 | 6/2001 |
| WO | WO 2001/079299 | 10/2001 |
| WO | WO 2001/094413 | 12/2001 |
| WO | WO 2002/002781 | 1/2002 |
| WO | WO 2002/010187 | 2/2002 |
| WO | WO 2002/032375 | 4/2002 |
| WO | WO 2002/060919 | 8/2002 |
| WO | WO 2002/086070 | 10/2002 |
| WO | WO 2003/035835 | 5/2003 |
| WO | WO 2003/066095 | 8/2003 |
| WO | WO 2003/074679 | 9/2003 |
| WO | WO 2003/094859 | 11/2003 |
| WO | WO 2003/101485 | 12/2003 |
| WO | WO 2004/001381 | 12/2003 |
| WO | WO 2004/016750 | 2/2004 |
| WO | WO 2004/029207 | 4/2004 |
| WO | WO 2004/093894 | 4/2004 |
| WO | WO 2004/063351 | 7/2004 |
| WO | WO 2004/065423 | 8/2004 |
| WO | WO 2004/074455 | 9/2004 |
| WO | WO 2004/099249 | 11/2004 |
| WO | WO 2008/009545 | 1/2005 |
| WO | WO 2005/018669 | 3/2005 |
| WO | WO 2005/061547 | 7/2005 |
| WO | WO 2005/070963 | 8/2005 |
| WO | WO 2005/110474 | 11/2005 |
| WO | WO 2005/115452 | 12/2005 |
| WO | WO 2005/121179 | 12/2005 |
| WO | WO 2006/016276 | 2/2006 |
| WO | WO 2006/020114 | 2/2006 |
| WO | WO 2006/028956 | 3/2006 |
| WO | WO 2006/053301 | 5/2006 |
| WO | WO 2006/066078 | 6/2006 |
| WO | WO 2006/076584 | 7/2006 |
| WO | WO 2006/083852 | 8/2006 |
| WO | WO 2006/084075 | 8/2006 |
| WO | WO 2006/084092 | 8/2006 |
| WO | WO 2006/084226 | 8/2006 |
| WO | WO 2006/088494 | 8/2006 |
| WO | WO 2006/110593 | 10/2006 |
| WO | WO 2006/113665 | 10/2006 |
| WO | WO 2007/009064 | 1/2007 |
| WO | WO 2007/009065 | 1/2007 |
| WO | WO 2007/021841 | 2/2007 |
| WO | WO 2007/024249 | 3/2007 |
| WO | WO 2007/080277 | 7/2007 |
| WO | WO 2007/106707 | 9/2007 |
| WO | WO 2007/117600 | 10/2007 |
| WO | WO 2007/147090 | 12/2007 |
| WO | WO 2008/002933 | 1/2008 |
| WO | WO 2008/019199 | 2/2008 |
| WO | WO 2008/066691 | 6/2008 |
| WO | WO 2008/091908 | 7/2008 |
| WO | WO 2008/105886 | 9/2008 |
| WO | WO 2008/116219 | 9/2008 |
| WO | WO 2008/140603 | 11/2008 |
| WO | WO 2008/157379 | 12/2008 |
| WO | WO 2009/021754 | 2/2009 |
| WO | WO 2009/073533 | 6/2009 |
| WO | WO 2009/083009 | 7/2009 |
| WO | WO 2009/151717 | 9/2009 |
| WO | WO 2009/123894 | 10/2009 |
| WO | WO 2010/027797 | 3/2010 |
| WO | WO 2010/033279 | 3/2010 |
| WO | WO 2010/080538 | 7/2010 |

(56) References Cited

FOREIGN PATENT DOCUMENTS

| WO | WO 2011/044368 | 4/2011 |
|---|---|---|
| WO | WO 2011/109400 | 9/2011 |
| WO | WO 2012/018687 | 2/2012 |

OTHER PUBLICATIONS

Burton et al. (1992) "*Human Antibody Effector Function*," Advances in Immunology 51:1-64.
Johnson et al. (2010) "*Effector Cell Recruitment with Novel Fv-based Dual-affinity Re-targeting Protein Leads to Potent Tumor Cytolysis and in Vivo B-cell Depletion*," J. Mol. Biol (399):436-449.
Abra et al. (2002)"*The Next Generation of Liposome Delivery Systems: Recent Experience With Tumor-Targeted, Sterically-Stabilized Immunoliposomes and Active-Loading Gradients*," J Liposome Res. 12(1-2):1-3.
Abrams, J.R. et al. (1999) "*CTLA4Ig-Mediated Blockade of T-Cell Costimulation in Patients With Psoriasis Vulgaris*," J. Clin Invest. 103(9):1243-1252.
Agarwal, A. et al. (2008) "*The Role of Positive Costimulatory Molecules in Transplantation and Tolerance*," Curr. Opin. Organ Transplant. 13:366-372.
Alegre, M.L. et al. (1994) "*A Non Activating "Humanized" Anti-CD3 Monoclonal Antibody Retains Immunosuppressive Properties In Vivo*," Transplantation 57:1537-1543.
Alison, M.R. et al. (2009) "*Stem Cells and Lung Cancer: Future Therapeutic Targets?*" Expert Opin. Biol. Ther. 9(9):1127-1141.
Alt et al. (1999) "*Novel Tetravalent and Bispecific IgG-Like Antibody Molecules Combining Single-Chain Diabodies With the Immunoglobin Gamma 1 Fc or CH3 Region*," FEBS Letters 454:90-94.
Altman et al. (1996) "*Phenotypic Analysis of Antigen-Specific T Lymphocytes*," Science 274:94-96.
Amit et al. (1986) "*Three-Dimensional Structure of an Antigen Antibody Complex at 2.8 A Resolution*," Science 233:747-753.
Angal et al. (1993) "*A Single Amino Acid Substitution Abolishes the Heterogeneity of Chimeric Mouse/Human (Igg4) Antibody*," Mol. Immunol. 30:105-108.
Anonymous, (2000) "*New Products for Molecular Biotechnology*," Molec. Biol. 16:293-294.
Armour et al. (1999) "*Recombinant Human IgG Molecules Lacking Fcgamma Receptor I Binding and Monocyte Triggering Activities*," Eur. J. Immunol. 29:2613-2624.
Armour et al. (2002) "*The Contrasting IgG-Binding Interactions of Human and Herpes Simplex Virus Fc Receptors*," Biochemical Society Transactions 30:495-500.
Armour et al. (2003) "*Differential Binding to Human Fcgammariia and FcgammaRIIB Receptors by Human IgG Wildtype and Mutant Antibodies*," Mol. Immunol. 40:585-593.
Armstrong, K.M. et al. (2008) "*Conformational Changes and Flexibility in T-Cell Receptor Recognition of Peptide-MHC Complexes*," Biochem. J. 415(Pt 2):183-196.
Armstrong, S.S. et al. (1987) "*Heterogeneityy of IgG1 Monoclonal Anti-Rh (D): An Investigation Using ADCC and Macrophage Binding Assays* ," Br. J. Haematol. 66:257-262.
Aruffo, A. et al. (1987) "*Molecular Cloning of a CD28 cDNA by a High-Efficiency COS Cell Expression System*," Proc. Natl. Acad. Sci. (U.S.A.) 84:8573-8577.
Asano, R. et al. (2004) "*A Diabody for Cancer Immunotherapy and Its Functional Enhancement by Fusion of Human Fc Region*," Abstract 3P-683, J. Biochem. 76(8):992.
Asano, R. et al. (2012) "*Construction and Humanization of a Functional Bispecific EGFR CD16 Diabody Using a Refolding System*," FEBS Journal 279:223-233.
Atwell et al. (1997) "*Stable Heterodimers From Remodeling the Domain Interface of a Homodimer Using a Phage Display Library*," J. Mol. Biol. 270:26-35.
Bachmann et al. (2005) "*Recall Proliferation of Memory CD8+ T Cells and Antiviral Protection*," J. Immunol. 175:4677-4685.

Baeuerle, P et al. (2008) "*BiTE: A New Class of Antibodies That Recruit T Cells*," Drugs of the Future 33:137-147.
Baeuerle, P.A. et al. (Epub Jun. 9, 2009) "*Bispecific T-Cell Engaging Antibodies for Cancer Therapy*," Cancer Res. 69(12):4941-4944.
Baggiolini, M. et al. (1988) "*Cellular Models for the Detection and Evaluation of Drugs That Modulate Human Phagocyte Activity*," Experientia. Oct. 15;44(10):841-848.
Bargou et al. (2008) "*Tumor Regression in Cancer Patients by Very Low Doses of a T Cell-Engaging Antibody*," Science 321:974-977.
Bedzyk et al. (1989) "*Comparison of Variable Region Primary Structures Within an Anti-Fluorescein Idiotype Family*," J. Biol. Chem, 264(3):1565-1569.
Beier, K.C. et al. (2007) "*Master Switches of T-Cell Activation and Differentiation*," Eur. Respir. J. 29:804-812.
Bendas, G. (2001) "*Immunoliposomes: A Promising Approach to Targeting Cancer Therapy*," BioDrugs. 15(4):215-224.
Bendig, M.M. (1995) "*Humanization of Rodent Monoclonal Antibodies*," Methods: A Companion to Methods in Enzymology 8:83-93.
Bernard et al. (1986) "*A Unique Epitope on the CD2 Molecule Defined by the Monoclonal Antibody 9-1: Epitope-Specific Modulation of the E-Rosette Receptor and Effects on T-Cell Functions*," Hum. Immunol. 17(4):388-405.
Bernard, A. et al. (2005) "*T and B Cell Cooperation: A Dance of Life and Death*," Transplantation 79:S8-S11.
Berntzen, G. et al. (2009) "*Identification of a High Affinity FcRIIA-binding Peptide That Distinguishes FcRIIA from FcRIIB and Exploits FcgammaRIIA-mediated Phagocytosis and Degradation*," J. Biol. Chem. 284(2):1126-1135.
Bertram, E.M. et al. (2004) "*Role of T cell Costimulation in anti-viral immunity*," Semin. Immunol. 16:185-198.
Bewarder et al. , 1996, "*In Vivo and In Vitro Specificity of Protein Tyrosine Kinases for Immunoglobulin G Receptor (FcgammaRII) Phosphorylation*," Mol. Cell. Biol. 16(9):4735-43.
Billadeau et al. (2002) "*ITAMs Versus ITIMs: Striking a Balance During Cell Regulation*," J. Clin. Invest. 109(2):161-168.
Bird et al. (1988) "*Single-Chain Antigen Binding Proteins*," Science 242:423-426.
Blazar, B.R. et al. (1999) "*Opposing Roles of CD28/B7 and CTLA-4:B7 Pathways in Regulating In Vivo Alloresponses in Murine Recipients of MHC Disparate T Cells*," J. Immunol 162(11):6368-6377.
Boder et al. (1997) "*Yeast Surface Display for Screening Combinatorial Polypeptide Libraries*", Nature Biotechnology 15:553-557.
Boder et al. (1998) "*Optimal Screening of Surface-Displayed Polypeptide Libraries*," Biotechnol. Prog. 14:55-62.
Boder et al. (2000), "*Directed Evolution of Antibody Fragments With Monovalent Femtomolar Antigen-Binding Affinity*," Proc. Natl. Acad. Sci. U.S.A. 97:10701-10705.
Boder et al. (2000), "*Yeast Surface Display for Directed Evolution of Protein Expression, Affinity, and Stability*," Methods in Enzymology 328:430-444.
Boland et al. (2013) "*Tumor B7-H1 and B7-H3 Expression in Squamous Cell Carcinoma of the Lung*," Clinical Lung Cancer, Mar. 213, pp. 157-163.
Bolland et al. (1999) "*Inhibitory pathways triggered by ITIM-containing receptors*," Adv. Immunol. 72:149-177.
Bolland et al. (2002) "*Genetic Modifiers of Systemic Lupus Erythematosus in Fc.gamma.RIIB(−/−) Mice*," J. Exp. Med. 195(9):1167-1174.
Boorjian et al. (2009) "*T-Cell Co-regulatory Molecule Expression in Renal Angiomyolipoma and Pulmonary Lymphangioleiomyomatosis*," Urology 74(6):1359-1364.
Boruchov et al. (2003) "*Expression and Modulation of the Inhibitory Fcγ Receptor, FcγRIIB (CD32B), on Human Dendritic Cells (DCs)*," Blood 102(11):Abstract #1908.
Boruchov et al. (2005) "*Activating and Inhibitory IgG Fc Receptors on Human DCs Mediate Opposing Functions*," J. Clin. Invest. 115(10):2914-2923.

(56) References Cited

OTHER PUBLICATIONS

Boyer et al. (1999) "*Relative Cytotoxic Activity of Immunotoxins Reactive With Different Epitopes on the Extracellular Domain of the c-erbB-2 (HER-2/neu) Gene Product p185,*" Int. J. Cancer. 82(4):525-531.

Brauweiler et al. (2001) "*Partially Distinct Molecular Mechanisms Mediate Inhibitory Fc.gamma.RIIB Signaling in Resting and Activated B Cells,*" J. Immunol. 167:204-211.

Bredius et al. (1994) "*Role of Neutrophil Fc gamma RIIa (CD32) and Fc gamma RIIb (CD16) Polymorphic Forms in Phagocytosis of Human IgG1- and IgG3-Opsonized Bacteria and Erythrocytes,*" Immunology 83:624-630.

Brekke et al. (1994) "*Human IgG isotype-specific amino acid residues affecting complement-mediated cell lysis and phagocytosis,*" Eur. J. Immunol. 24:2542-2547.

Brown (2001) "*Factors Modifying the Migration of Lymphocytes Across the Blood-Brain Barrier,*" Int. Immunopharmacol. 1(12):2043-2062.

Brown et al. (1987) "*Tumor-Specific Genetically Engineered Murine/Human Chimeric Monoclonal Antibody,*" Cancer Res. 47:3577-3583.

Brown, E.J. (1994) "*In Vitro Assays of Phagocytic Function of Human Peripheral Blood Leukocytes: Receptor Modulation and Signal Transduction,*" vol. 45 (Microbes as Tools for Cell Biology) in *Methods in Cell Biololgy*, Russell ed., Academic Press Inc., NY, pp. 147-164.

Brown, M. et al. (1996) "*Tolerance of single, but not multiple, amino acid replacements in antibody VH CDR 2: α means of minimizing B cell wastage from somatic hypermutation?*" The Journal of Immunology 156(9): 3285-3291.

Brunet, J.F. et al. (1987) "*A New Member of the Immunoglobulin Superfamily-CTLA-4,*" Nature 328:267-270.

Budde et al. (1995) "*Specificity of CD32 mAB for Fc.gamma.RIIa, Fc.gamma.RIIb1, and Fc.gamma.RIIb2 Expressed in Transfected Mouse B cells and BHK-21 Cells,*" Leukocyte Typing V: White cell differentiation antigens. pp. 828-832 (Schlossman, et al. eds.).

Burgess et al. (1990) "*Possible Dissociation of the Heparin-Binding and Mitogenic Activities of the Heparin-Binding (Acidic Fibroblast) Growth Factor-1 From Its Receptor Binding Activities by Site Directed Mutagenesis of a Single Lysine Residue,*" J. Cell Biol. 111:2129-2138.

Burlmeister et al. (1994) "*Crystal Structure of the Complex of Rat Neonatal Fc Receptor With Fc,*" Nature 372:379-383.

Burton (1985) "*Immunoglobulin G: Functional Sites,*" Mol Immunol 22:161-206.

Burton et al. (1988) "*Molecular Recognition of Antibody (IgG) by Cellular Fc Receptor (FcRI),*" Mol. Immunol. 25:1175-1181.

Burton et al. (1992) "*Human Antibody Effector Function,*" Advances in Immunology 51:1-84.

Callanan et al. (2000) "*The IgG Fc Receptor, Fc.Gamma.RIIB Is a Target for Deregulation by Chromosomal Translocation in Malignant Lymphoma,*" Proc. Natl. Acad. Sci. (U.S.A.) 97(1):309-314.

Cameron et al. (2002) "*Differentiation of the Human Monocyte Cell Line, U937, With Dibutyryl Cyclicamp Induces the Expression of the Inhibitory Fc Receptor, Fc.gamma.RIIb,*" Immunol. Lett. 83(3):171-179.

Camilleri-Broet et al. (2004) "*Fc.gamma.RIIB is Differentially Expressed During B Cell Maturation and in B-Cell Lymphomas,*" Br. J. Haematol. 124(1):55-62.

Campbell et al. (2003) "*Monoclonal Antibody Therapy for Lymphoma,*" Blood Rev. 17(3):143-152.

Canfield et al. (1991) "*The Binding Affinity of Human IgG for Its High Affinity Fc Receptor Is Determined by Multiple Amino Acids in the CH2 Domain and Is Modulated by the Hinge Region,*" J. Exp. Med. 173:1483-1491.

Caron et al. (1992) "*Engineered Humanized Dimeric Forms of IgG Are More Effective Antibodies,*" J. Exp. Med. 176:1191-1195.

Carter et al. (1992) "*Humanization of an Anti-p185HER2 Antibody for Human Cancer Therapy,*" Proc. Natl. Acad. Sci. U.S.A. 89:4285-4289.

Cartron et al. (2002) "*Therapeutic Activity of Humanized Anti-CD20 Monoclonal Antibody and Polymorphism in IgG Fc Receptor FcgammaRIIIa Gene,*" Blood 99:754-758.

Cassard et al. (2002) "*Modulation of Tumor Growth by Inhibitory Fc. Gamma. Receptor Expressed by Human Melanoma Cells,*" J. Clin. Invest. 110(10):1549-1557.

Casset et al. (2003) "*A Peptide Mimetic of an Anti-CD4 Monoclonal Antibody by Rational Design,*" Biochem. Biophs. Res. Commun. 307:198-205.

Castriconi et al. (2004) "*Identification of 4Ig-B7-H3 as a Neuroblastoma Associated Molecule That Exerts a Protective Role From an NK Cell-Mediated Lysis,*" Proc. Natl. Acad. Sci. (U.S.A.) 101(34):12640-12645.

Cavacini et al. (1995) "*Influence of Heavy Chain Constant Regions on Antigen Binding and HIV-1 Neutralization by a Human Monoclonal Antibody,*" J. Immunol. 155(7):3638-3644.

Chapoval, A. et al. (2001) "*B7-H3: A Costimulatory Molecule for T Cell Activation and IFN-γ Production,*" Nature Immunol. 2:269-274.

Chapoval, A. et al. (2003) "*B7-H3,*" In: The B7-CD28 Family Molecules, Kluwer Academic, NY; pp. 91-99.

Chappel et al. (1991) "*Identification of the Fc Gamma Receptor Class I Binding Site in Human IgG Through the Use of Recombinant IgG1/IgG2 Hybrid and Point Mutated Antibodies,*" Proc. Natl. Acad. Sci U.S.A. 88:9036-9040, 1991.

Chappel et al. (1993) "*Identification of a Secondary Fc Gamma RI Binding Site Within a Genetically Engineered Human IgG Antibody,*" J. Biol. Chem 268:25124-25131.

Charafe-Jauffret, E. et al. (2009) "*Breast Cancer Stem Cells: Tools and Models to Rely on,*" BMC Cancer 9:202 (10 pages).

Chattergee et al. (1994) "*Idiotypic Antibody Immunotherapy of Cancer,*" Cancer Immunol. Immunother. 38:75-82.

Chen et al. (2000) "*Surface Antigen Expression and Complement Susceptibility of Differentiated Neuroblastoma Clones,*" Amer. J. Pathol. 156(3):1085-1091.

Chen et al. (2008) "*The Immunoregulatory Protein Human B7H3 is a Tumor Associated Antigen that Regulates Tumor Cell Migration and Invasion,*" Curr. Cancer Drug Targets 8:404-413.

Chen, et al. (1999) "*Selection and Analysis of an Optimized Anti-VEGF Antibody: Crystal Structure of an Affinity-Matured Fab in Complex with Antigen,*" J. Molec. Biol. 293:865-881.

Chen. et at. (2011) "*Cloning and Characterization of Porcine 4Ig-B7-H3: A Potent Inhibitor of Porcine T-CellActivation,*" PLOS ONE 6(6):E21341.

Cheung, N.K. et al. (1990) "*Immunology and Targeted Immunotherapy of Human Neuroblastoma,*" In: Neuroblastoma: Tumor Biology and Therapy, CRC Press, Boca Raton; pp. 52-68.

Cheung, N.K. et al. (2000) "*Immunotherapy of Neuroblastoma,*" In: Neuroblastoma, Elsevier, NY (10 pages).

Cheung, N.K. et al. (2002) "*Oral (1→3),(1→4)-beta-D-Glucan Synergizes with Antiganglioside GD2 Monoclonal Antibody 3F8 in the Therapy of Neuroblastoma,*" Clin. Canc. Res. 8:1217-1223.

Chile Search Report (PCT2012002433, dated Mar. 9, 2012) (25 pages).

Chu, P. G. et al. (2001) "*CD79: A Review,*" Appl. Immunohistochem. Molec. Morphol. 9(2):97-106.

Ciccimarra et al. (1975) "*Localization of the IgG Effector Site for Monocyte Receptors,*" Proc. Natl. Acad. Sci. U.S.A. 72 :2081-2083, 1975.

Clinical Trials (8H9), National Institutes of Health, "*Radiolabled Monoclonal Antibody Therapy in Treating Patients with Refractory, Recurrent, or Advanced CNS or Leptomeningeal Cancer,*".

Clinical Trials (MGA271), National Institutes of Health, "*Safety Study of MGA271 in Refractory Center,*".

Clinical Trials (MGD009), National Institutes of Health, "*Safety Study of MGD009 in B7-H3-expressing Tumors,*".

Clynes et al. (1995) "*Cytotoxic Antibodies Trigger Inflammation Through Fc Receptors,*" Immunity 3:21-26.

Clynes et al. (1998) "Fc receptors are required in passive and active immunity to melanoma," Proc. Natl. Acad. Sci U.S.A. 95:652-656.

Clynes et al. (1998) "*Uncoupling OfImmune Complex Formation and Kidney Damage in Autoimmune Glomerulonephritis,*" Science 279:1052-1054.

(56) References Cited

OTHER PUBLICATIONS

Clynes et al. (1999) "Modulation of Immune Complex-Induced Inflammation In Vivo by the Coordinate Expression of Activation and Inhibitory Fc Receptors," J. Exp. Med. 189:179-185.

Clynes et al. (2000) "Inhibitory Fc Receptors Modulate In Vivo Cytoxicity Against Tumor Targets," Nature Medicine 6:443-446.

Co, M. S. et al. (1991) "Humanized Antibodies for Antiviral Therapy," Proc. Natl. Acad. Sci. (U.S.A.) 88:2869-2873.

Co, M.S. et al. (1992) "Chimeric and Humanized Antibodies With Specificity for The CD33 Antigen," J. Immunol. 148:1149-1154.

Collins, M. et al. (2005) "The B7 Family of Immune-Regulatory Ligands," Genome Biol. 6:223.1-223.7.

Colman, P.M. (1994) "Effects of Amino Acid Sequence Changes on Antibody-Antigen Interactions," Res. Immunol. 145:33-36.

Coyle, A.J. et al. (2001) "The Expanding B7 Superfamily: Increasing Complexity in Costimulatory Signals Regulating T Cell Function," Nature Immunol. 2(3):203-209.

Crispen, P.L. et al. (2008) "Tumor Cell and Tumor Vasculature Expression of B7-H3 Predict Survival in Clear Cell Renal Cell Carcinoma," Clin Cancer Res. 14(16):5150-5157 Epub Aug. 11, 2008.

Daeron et al. (1995) "The Same Tyrosine Based Inhibition Motif, in the Intracytoplasmic Domain of Fc.gamma.RIIB, Regulates Negatively BCR, TCR- and FcR Dependent Cell Activation," Immunity 3:635-646.

Daeron, M. (1997) "Fc Receptor Biology," Annu. Rev. Immunol. 15:203-234.

Damle et al. (2002) "B-Cell Chronic Lymphocytic Leukemia Cells Express a Surface Membrane Phenotype of Activated, Antigen-Experienced B Lymphocytes," Blood 99(11):4087-4093.

Daugherty et al. (1991) "Polymerase Chain Reaction Facilitates the Cloning, CDR-Grafting, and Rapid Expression of a Murine Monoclonal Antibody Directed Against the CD18 Component of Leukocyte Integrins," Nucl. Acids Res. 19:2471-2476.

Davies et al. (1995) "Antibody VH Domains as Small Recognition Units," Bio/Technology 13:475-479.

Davies et al. (2001) "Expression of GnTIII in a Recombinant Anti-CD20 CHO Production Cell Line: Expression of Antibodies With Altered Glycoforms Leads to an Increase in ADCC Through Higher Affinity for FCgamma. RIII," Biotechnol. Bioeng. 74(4):288-294.

Davies, J. et at. (1996) "Affinity improvement of single antibody VH domains: residues in all three hypervariable regions affect antigen binding," Immunotechnology 2(3):169-179.

De Haas et al. (2001) "IgG-Fc Receptors and the Clinical Relevance of Their Polymorphisms," Wien Klin Wochenscha 113:825-831.

De Santes et al. (1992) "Radiolabeled Antibody Targeting of the Her-2/neu Oncoprotein," Cancer Res. 52:1916-1923.

Deisenhofer (1981) "Crystallographic Refinement and Atomic Models of a Human Fc Fragment and Its Complex With Fragment B of Protein A from Staphylococcus aureus at 2.9- and 2.8-A Resolution," Biochem. 20:2361-2370.

Deo et al. (1997) "Clinical Significance of IgG Fc Receptors and Fc gamma R-Directed Immunotherapies," Immunology Today 18:127-135.

DePascalis et al. (2002) "Grafting of Abbreviated Complementarity Determining Regions Containing Specificity Determining Residues Essential for Ligand Contact to Engineer a Less Immunogenic humanized monoclonal antibody," J. Immunol. 169:3076-3084.

Dermer (1994) "Another Anniversary for the War on Cancer," Biotechnology 12:320 (1 page).

Ding et al. (2001) "Inhibition of the Function of the Fc.gamma.RIIB by a Monoclonal Antibody to Thymic Shared Antigen-1, a Ly-6 Family Antigen," Immunology 104(1):28-36.

Dong, C. et al. (2003) "Immune Regulation by Novel Costimulatory Molecules," Immunolog. Res. 28(1):39-48.

Dong, H. et al. (1999) "B7-H1, A Third Member of the B7 Family, Co-Stimulates T-Cell Proliferation and Interleukin-10 Secretion," Nature Med. 5(12):1365-1369.

Dumoulin et al. (2002) "Single-Domain Antibody Fragments With High Conformational Stability," Protein Science 11:500-512.

Duncan et al. (1988) "Localization of the Binding Site for the Human High-Affinity Fc Receptor on IgG," Nature 332:563-564.

Duncan et al. (1988) "The Binding Site for C1q on IgG," Nature 332:738-740.

Edberg et al. (1994) "Modulation of Fcgamma and Complement Receptor Function by the Glycosyl-Phosphatidylinositol-Anchored Form of FcgammaRIII," J. Immunol. 152: 5826-5835.

Efferson et al. (2005) "Stimulation of Human T Cells by an Influenza A Vector Expressing a CTL Epitope from the HER-2/neu Protooncogene Results in Higher Numbers ofAntigen Specific TCRhi Cells than Stimulation with Peptide," Anticancer Research 25:715-724.

Elkabetz et al. (2005) "Cysteines in CHI Underlie Retention of Unassembled Ig Heavy Chains," J. Biol. Chem. 280:14402-14412.

Ellman, J. et al. (1991) "Biosynthetic Method for Introducing Unnatural Amino Acids Site-Specifically into Proteins," Methods Enzymol. 202:301-336.

Emamaullee, J. et al (2009) "Costimulatory Blockade With Belatacept in Clinical and Experimental Transplantation—A Review," Expert Opin. Biol. Ther. 9(6):789-796.

English translation of Chinese Search Report (Chinese Application No. 201180022024.1, dated Mar. 4, 2010) (3 pages).

Eppstein et al. (1985) "Biological Activity of Liposome-Encapsulated Murine Interferon .Gamma. Is Mediated by a Cell Membrane Receptor," Proc. Natl. Acad. Sci. (U.S.A.) 82(11):3688-3689.

European Search Report (PCT2011026689, dated Mar. 1, 2011) (10 pages).

Fanger et al. (1994) "Production and Use of Anti-FcR Bispecific Antibodies," Immunomethods. 4(1):72-81.

Farag, et al. (2003) "Fc.gamma.RIIIa and Fc.gamma.RIIIa Polymorphisms Do Not Predict Response to Rituximab in B-Cell Chronic Lymphocytic Leukemia," Blood. [Published Online] (15 pp).

Fidler, I. J. (1985) "Macrophages and Metastasis—A Biological Approach to Cancer Therapy," Cancer Res. 45(10):4714-4726.

Fieger, C.B. et al. (2008) "The Anti-B7-H3-41g Antibody TES7 Recognized Cancer Stem Cell Lines, Modulates Angiogenic Factor Secretion, and Exhibits Potent Anti-Tumor Activity in vivo," Proc. Amer. Assoc. Cancer Re. Annual Meeting (99$^{th}$ Annual Meeting of the American Association for Cancer Research; San Diego, CA, USA (Apr. 12-16, 2008) 49:606; Abstract 2555 (1 page).

FitzGerald, et al. (1997) "Improved Tumour Targeting by Disulphide Stabilized Diabodies Expressed in Pichia pastoris," Protein Engineering 10(10): 1221-1225.

Fleit et al. (1995) "Cross-Linking of mAb to FC.gamma.RII Results in Tyrosine Phosphorylation of Multiple Polypeptides Including FC.gamma.RII Itself," Leukocyte Typing V: White cell differentiation antigens 826-827 (Schlossman, Boumsell, Gilks, Harlan, Kishomoto, eds.).

Flesch et al. (2000) "Functions of the Fc Receptors for Immunoglobulin G," J. Clin. Lab. Anal. 14:141-156.

Flies, D.B. et al. (2007) "The New B7s: Playing a Pivotal Role in Tumor Immunity," J. Immunother. 30(3):251-260.

Fukushima, A. et al. (2007) "B7-H3 Regulates The Development of Experimental Allergic Conjunctivitis in Mice," Immunol. Lett. 113:52-57.

Gamberale et al. (2003) "To the Editor: Expression of Fc.gamma. receptors type II (Fc.gamma.RII) in chronic lymphocytic leukemia B cells," Blood (Correspondence) 102(7):2698-2699.

Ganesan, A. (2006) "Solid-Phase Synthesis in the Twenty-First Century," Mini Rev. Med. Chem 6(1):3-10.

Gerber et al. (2001) "Stimulatory and Inhibitory Signals Originating From The Macrophage Fc.Gamma. Receptors," Microbes Infect. 3(2):131-139.

Gergely et al. (1984) "Fc Receptors on Lymphocytes and K Cells," Biochem. Soc. Trans. 12:739-743.

Gergely et al. (1990) "The Two Binding-Site Models of Human IgG Binding Fc Gamma Receptors," FASEB J. 4:3275-3283.

Ghotra, V. P. et al. (2009) "The Cancer Stem Cell Microenvironment and Anti-Cancer Therapy," Int. J. Radiat. Biol. 85(11):955-962.

(56) References Cited

OTHER PUBLICATIONS

Giusti, A. M. et al. (1987) "Someatic Diversification of S107 from an Antiphosphocholine to an anti-DNA Autoanitbody Is Due to a Single Base Change in its Heavy Chain Variable Region," Proc. Natl. Acad. Sci. (U.S.A.) 84:2926-2930.
Gorman, S. D. et al. (1991) "Reshaping a Therapeutic CD4 Antibody," Proc. Natl. Acad. Sci. (U.S.A.) 88:4181-4185.
Gouw et al. (2011) "Sarcoma Immunotherapy," Cancers 3:4139-4150.
Greenwald, R.I. et al. (2005) "The B7 Family Revisited," Ann. Rev. Immunol. 23:515-548.
Greenwood et al. (1993) "Effector Functions of Matched Sets of Recombinant Human IgG Subclass Antibodies" (final version edited Feb. 11, 1993) pp. 1-23.
Greenwood et al. (1994) "Engineering Multiple-Domain Forms of the Therapeutic Antibody CAMPATH-1H: Effects on Complement Lysis," Therapeutic Immunology 1:247-255.
Greenwood et al. (1993) "Structural Motifs Involved in Human IgG Antibody Effector Functions," Eur. J. Immunol. 23:1098-1104.
Gregorio et al. (2008) "Small round blue cell tumours: diagnostic and prognostic usefulness of the expression of B7-H3 surface molecule," Histopathology 53:73-80.
Gruber, M. et al. (1994) "Efficient Tumor Cell Lysis Mediated by a Bispecific Single Chain Antibody Expressed in Escherichia coli," J. Immunol. 152(11): 5368-5374.
Guery et al. (2015) "B7-H3 protein expression in acute myeloid leukemia," Cancer Medicine, pp. 1879-1883.
Gupta, P.B. et al. (2009) "Cancer Stem Cells: Mirage or Reality?" Nat. Med. 15(9):1010-1012.
Gura (1997) "Systems for Identifying New Drugs Are Often Faulty," Science 278:1041-1042.
Guy, C.S. et al. (2009) "Organization of Proximal Signal Initiation at the TCR: CD3 Complex," Immunol. Rev. 232(1):7-21.
Hadley et al. (1992) "The Functional Activity of Fc Gamma RII and Fc Gamma RIII on Subsets of Human Lymphocytes," Immunology 76:446-451.
Hashiguchi, M. et al. (2008) "Triggering Receptor Expressed on Myeloid Cell-Like Transcript 2 (TLT-2) Is a Counter-Receptor for B7-H3 and Enhances T Cell Responses," Proc. Natl. Acad. Sci. (U.S.A.) 105(30):10495-10500.
Hatta et al. (1999) "Association of Fc Gamma Receptor IIIB, But Not of Fc Gamma Receptor IIA and IIIA Polymorphisms With Systemic Lupus Erythematosus in Japanese," Genes Immunity 1:53-60.
Hayes, Fc (2003) "Engineering to Enhance Monoclonal Antibody Effector Functions," (Xencor Presentation).
Henry et al. (2004) "A Prostate-Specific Membrane Antigen-Targeted Monoclonal Antibody-Chemotherapeutic Conjugate Designed for the Treatment of Prostate Cancer," Cancer Res. 64(21):7995-8001.
Henry, J. et al. (1999) "Structure and Evolution of the Extended B7 Family," Immunol Today. 20(6):285-288.
Hermann, P.C. et al. (2009) "Pancreatic Cancer Stem Cells—Insights and Perspectives," Expert Opin. Biol. Ther. 9(10):1271-1278.
Herzenberg et al. (2002) "The History and Future of the Fluorescence Activated Cell Sorter and Flow Cytometry: A View From Stanford," Clin. Chem. 48:1819-1827.
Heyman (2000) "Regulation of Antibody Responses via Antibodies, Complement, and Fc Receptors," Annu. Rev. Immunol. 18:709-737.
Hofmeyer, K. et al. (2008) "The Contrasting Role of B7-H3," Proc. Natl. Acad. Sci. (U.S.A.) 105(30):10277-10278.
Hogarth et al. (1994) "Characterization of FCR Ig-Binding Sites and Epitope Mapping," Immunomethods 4:17-24.
Holler et al. (2000) "In Vitro Evolution of a T Cell Receptor With High Affinity for Peptide/MHC," Proc. Natl. Acad. Sci. (U.S.A.) 97:5387-5392.
Holliger et al. (2005) "Engineered Antibody Fragments and the Rise of Single Domains," Nature Biotechnol. 23(9):1126-1135.
Holliger, P. (1993) "Diabodies: Small Bivalent and Bispecific Antibody Fragments," Proc. Natl. Acad. Sci. (U.S.A.) 90(14):6444-6448.
Holm et al. (2007) "Functional Mapping and Single Chain Construction of the Anti-Cytokeratin 8 Monoclonal Antibody TS1," Molecular Immunology 44:1075-1084.
Holmes et al. (1985) "Alleles of the Ly-17 Alloantigen Define Polymorphisms of the Murine IgG Fc Receptor," Proc. Natl. Acad. Sci. (U.S.A.) 82(22):7706-7710.
Holt, L.J. (2003) "Domain Antibodies: Proteins for Therapy," Trends in Biochem. 21(11):484-490.
Houghten, R.A. (1985) "General Method for the Rapid Solid-Phase Synthesis of Large Number of Peptides: Specificity of Antigen-Antibody Interaction at the Level of Individual Amino Acids," Proc. Natl. Acad. Sci. (U.S.A.) 82(15):5131-5135.
Houghton, A.N. et al. (2000) "Monoclonal Antibody Therapies—A 'Constant' Threat to Cancer," Nature Medicine 6(4):373-374.
Hu et al. (2015) "Expression of costimulatory molecule B7-H3 and its prognostic implications in human acute leukemia," Hematology 16(20):187-95 (Abstract only).
Hulett et al. (1991) "Chimeric Fc Receptors Identify Functional Domains of the Murine High Affinity Receptor for IgG," J. Immunol. 147:1863-1868.
Hulett et al. (1994) "Identification of the IgG Binding Site of the Human Low Affinity Receptor for IgG Fc Gamma RII. Enhancement and Ablation of Binding by Site-Directed Mutagenesis," J. Biol. Chem. 269:15287-15293.
Hulett et al. (1995) "Multiple Regions of Human Fc Gamma RII (CD32) Contribute to the Binding of IgG," J. Biol. Chem. 270:21188-21194.
Hutchins et al. (1995) "Improved Biodistribution, Tumor Targeting, and Reduced Immunogenicity in Mice With a Gamma 4 Variant of Campath-1H," Proc. Natl. Acad. Sci. (U.S.A.) 92:11980-11984.
Hwang et al. (1980) "Hepatic Uptake and Degradation of Unilamellar Sphingomyelin/Cholesterol Liposomes: A Kinetic Study," Proc. Natl. Acad. Sci. (U.S.A.) 77(7):4030-4034.
Ibragimova et al. (1999) "Stability of the Beta-Sheet of the WW Domain: A Molecular Dynamics Simulation Study," Biophys. J. 77(4):2191-2198.
Idusogie et al. (2000) "Mapping of the C1q Binding Site on Rituxan, A Chimeric Antibody With a Human IgG1 Fc," J Immunol 164:4178-4184.
Idusogie et al. (2001) "Engineered Antibodies With Increased Activity to Recruit Complement," J. Immunol. 166:2571-2575.
Indik, Z.K. et al. (1995) "The Molecular Dissection of Fcgamma Receptor Mediated Phagocytosis," Blood 86(12):4389-4399.
Isaacs et al. (1992) "Therapy With Monoclonal Antibodies. An In Vivo Model for the Assessment of Therapeutic Potential," J. Immunol. 148:3062-3071.
Isaacs et al. (1996) "A Therapeutic Human IgG4 Monoclonal Antibody That Depletes Target Cells in Humans," Clin. Exp. Immunol. 106:427-433.
Isaacs et al. (1998) "Therapy With Monoclonal Antibodies. II. The Contribution of Fc Gamma Receptor Binding and the Influence of C(H)1 and C(H)3 Domains on In Vivo Effector Function," J. Immunol. 161:3862-3869.
Jain et al. (1994) "Barriers to Drug Delivery in Solid Tumors," Scientific American Jul. 1994:58-65.
Jassal et al. (1998) "Remodeling Glycans on IgG by Genetic Re-Engineering," Biochem. Soc. Trans. 26:S113.
Jefferis et al. (1990) "Molecular Definition of Interaction Sites on Human IgG for Fc Receptors (Hufc Gamma R)," Mol. Immunol. 27:1237-1240.
Jefferis et al. (1995) "Recognition Sites on Human IgG for Fc Gamma Receptors: The Role of Glycosylation," Immunol. Lett. 44:111-117.
Jefferis et al. (1998) "IgG-Fc-Mediated Effector Functions: Molecular Definition of Interaction Sites for Effector Ligands and the Role of Glycosylation," Immunol. Rev. 163:59-76.
Jefferis et al. (2002) "Interaction Sites on Human IgG-Fc for FcgammaR: Current Models," Immunology Letters 82:57-65.

(56) References Cited

OTHER PUBLICATIONS

Jefferis, R. et al. (1996) "Modulation of Fc(Gamma)R and Human Complement Activation by IgG3-Core Oligosaccharide Interactions," Immunol. Lett. 54:101-104.
Jendeberg et al. (1997) "Engineering of Fc(1) and Fc(3) From Human Immunoglobulin G to Analyse Subclass Specificity for Staphylococcal Protein A," J. Immunol. Meth. 201:25-34.
Jiang et al. (2004) "A Novel Peptide Isolated From a Phage Display Peptide Library With Trastuzumab Can Mimic Antigen Epitope of HER-2," J. Biol. Chem. 280(6):4656-4662.
Jones et al. (1986) "Replacing the Complementarity-Determining Regions in a Human Antibody With Those From a Mouse," Nature 321:522-525.
Kadar et al. (1991) "Modulatory Effect of Synthetic Human IgG Fc Peptides on the In Vitro Immune Response of Murine Spleen Cells," Int. J. Immunpharmacol. 13:1147-55.
Kadar et al. (1992) "Synthetic Peptides Comprising Defined Sequences of CH-2 and CH-3 Domains of Human IgG1 Induce Prostaglandin E2 Production From Human Peripheral Blood Mononuclear Cells," Immunol. Lett 32:59-63.
Kagari et al. (2003) "Essential Role of Fc.Gamma. Receptors in Anti-Type II Collagen Antibody Induced Arthritis," J. Immunol. 170:4318-24.
Kalergis, A.M. et al. (2002) "Inducing Tumor Immunity through the Selective Engagement of Activating Fcgamma Receptors on Dendritic Cells," J. Exper. Med. 195(12):1653-1659.
Kang, C.Y. et al. (1988) "Inhibition of Self-Binding Antibodies (Autobodies) by a VH-Derived Peptide," Science 240(4855):1034-1036.
Katayama et al. (2011) "Expression of B7-H3 in hypopharyngeal squamous cell carcinoma as a predictive indicator for tumor metastasis and prognosis," Int. J. Oncol. 38:1219-1226.
Kato et al. (2000) "Structural Basis of the Interaction Between IgG and Fcγ Receptors," J. Molec. Biol. 295:213-224.
Keler et al. (2000) "Differential Effect of Cytokine Treatment on Fc Alpha Receptor I- and Fc Gamma Receptor I-Mediated Tumor Cytotoxicity by Monocyte-Derived Macrophages," J. Immunol. 164:5746-5752.
Kelsey, J.L. et al. (1998) "Epidemiologic Studies of Risk Factors for Cancer in Pet Dogs," Epidemiologic Reviews 20(2):204-217.
Kepley et al. (2004) "Co-aggregation of FcgammaRII with FcepsilonRI on Human Mast Cells Inhibits Antigeninduced Secretion and Involves SHIP-Grb2-Dok Complexes" J. Biol. Chem. 279(34) 35139-35149.
Kettleborough, C. A. et al. (1991) "Humanization of a Mouse Monoclonal Antibody by CDR-Grafting: The Importance of Framework Residues on Loop Conformation," Protein Engineering 4:773-3783.
Khawli, L.A. et al. (2008) "Cytokine, Chemokine, and Co-Stimulatory Fusion Proteins for the Immunotherapy of Solid Tumors," Exper. Pharmacol. 181:291-328.
Kieke et al. (1999) "Selection of Functional T Cell Receptor Mutants From a Yeast Surface-Display Library," Proc. Natl. Acad. Sci. (U.S.A.) 96:5651-5656.
Kiick et al. (2001) "Identification of an Expanded Set of Translationally Active Methionine Analogues in Escherichia," FEBS Lett. 502(1-2):25-30.
Kim et al. (2001) "Analysis of FcγRIII and IgG Fc Polymorphism Reveals Functional and Evolutionary Implications of Protein-Protein Interaction," J. Molec. Evol. 53:1-9.
Kim et al. (2002) "Both the Epitope Specificity and Isotype are Important in the Antitumor Effect of Monoclonal Antibodies Against Her-2/Neu Antigen," Int. J. Cancer. 102(4):428-434.
Kimura et al. (1981) "A New Mouse Cell-Surface Antigen (Ly-M20) Controlled by a Gene Linked to Mls Locus and Defined by Monoclonal Antibodies," Immunogenetics. 14(1-2):3-14.
King, R.G. et al. (2006) "Trem-Like Transcript 2 Is Expressed on Cells of the Myeloid/Granuloid and B Lymphoid Lineage and Is Up-Regulated in Response to Inflammation," J. Immunol. 176:6012-6021.
Kipps et al. (1985) "Importance of Immunoglobin Isotype in Human Antibody-Dependent, Cell-Mediated Cytotoxicity Directed by Murine Monoclonal Antbodies," J. Exper. Med. 161:1-17.
Kirk, A.D. et al. (1997) "CTLA4-Ig and Anti-CD40 Ligand Prevent Renal Allograft Rejection in Primates," Proc. Natl. Acad. Sci. (U.S.A.) 94(16):8789-8794.
Klein et al. (1981) "Expression of Biological Effector Functions by Immunoglobulin G Molecules Lacking the Hinge Region," Proc. Natl. Acad. Sci. (U.S.A.) 78:524-528.
Klesney-Tait, J. et al. (2006) "The TREM Receptor Family and Signal Integration," Nat. Immunol. 7:1266-1273.
Koene et al. (1997) "Fc gammaRIIIa-158V/F Polymorphism Influences the Binding of IgG by Natural Killer Cell Fc gammaRIIIa, Independently of the Fc GammaRIIIa-48L/R/H Phenotype," Blood 90:1109-1114.
Köhler G, et al. (1975) "Continuous Cultures of Fused Cells Secreting Antibody of Predefined Specificity," Nature. 256:495-497.
Korman, A.J. et al. (2007) "Checkpoint Blockade in Cancer Immunotherapy," Adv. Immunol. 90:297-339.
Kranz et al. (1982) "Mechanisms of Ligand Binding by Monoclonal Anti-Fluorescyl Antibodies," J. Biol. Chem. 257:6987-6995.
Kristiansen, O.P. et al. (2000) "CTLA-4 in Autoimmune Diseases—A General Susceptibility Gene to Autoimmunity?" Genes Immun 1(3):170-184.
Kudo, T. et al. (1993) "A Novel Human Monoclonal Antibody Directed to a Tumor-associated Antigen," Jpn. J. Cancer Res. 84:760-769.
Kumpel, B.M. (1989) "Human Monoclonal Anti-D Antibodies," Brit. J. Haematol. 71:415-420.
Kurlander et al. (1986) "Comparison of Intravenous Gamma Globulin and a Monoclonal Anti-Fc Receptor Antibody as Inhibitors of Immune Clearance In Vivo in Mice." J. Clin. Invest. 77(6):2010-2018.
Kussie, P.H. et al. (1994) "A Single Engineered Amino Acid Substitution Changes Antibody Fine Specificty," Journal of Immunology 152:146-152.
Larsen, C.P. et al. (1996) "Long-Term Acceptance of Skin and Cardiac Allografts After Blocking CD40 and CD28 Pathways," Nature 381(6581):434-438.
Law, C.L. et al. (2002) "Expression and Characterization of Recombinant Soluble Human CD3 Molecules" Presentation of Antigenic Epitopes Defined on the Native TCR-CD3 Complex, Intl. Immunol. 14(4):389-400.
Lawson, J.C. et al. (2009) "Cancer Stem Cells in Breast Cancer and Metastasis," Breast Cancer Res. Treat. 118(2):241-254.
Lazar et al. (1988) Transforming Growth Factor A: Mutation of Aspartic Acid 47 and Leucine 48 Results in Different Biological Activities, Molec. Cell. Biol. 8:1247-1252.
Le Gall, F. et al. (2004) "Effect of Linker Sequences Between the Antibody Variable Domains on the Formation, Stability and Biological Activity of a Bispecific Tandem Diabody," Protein Eng. Des. Sel. 17(4):357-366.
Leach, D.R. et al. (1996) "Enhancement of Antitumor Immunity by CTLA-4 Blockade," Science. 271(5256):1734-1736.
Lehmann et al. (2000) "Phagocytosis: Measurement by Flow Cytometry," J. Immunol. Meth. 243(1-2):229-242.
Lehrnbecher et al. (1999) "Variant Genotypes of the Low Affinity Fcgamma Receptors in Two Control Populations and a Review of Low-Affinity Fcgamma Receptor Polymorphisms in Control and Disease Populations," Blood 94:4220-4232.
Lenschow, D.J. et al. (1996) "CD28/B7 System of T Cell Costimulation," Ann. Rev. Immunol. 14:233-258.
Lewis et al. (1993) "Differential Responses of Human Tumor Cell Lines to Anti-p185HER2 Monoclonal Antibodies," Cancer Immunol. Immunother. 37(4):255-263.
Li et al. (1996) "Reconstitution of Human Fc Gamma RIII Cell Type Specificity in Transgenic Mice," J. Exp. Med. 183:1259-1263.
Li et al. (2010) "Monocyte Surface Expression of Fcγ Receptor RI (CD64), A Biomarker Reflecting Type-I Interferon Levels in Systemic Lupus Erythematosus," Arthritis Res. Ther. 12:R90 (12 pages).
Li et al. (2013) "Paraphyaryngeal liposarcoma: a case report," Diagnostic Pathology 8:42-45.

(56) References Cited

OTHER PUBLICATIONS

Liang, T.W-y. et al. (2008) "TES7, A Monoclonal Antibody Targeting B7-H3, Potently Inhibits Hs-700T Growth In Vivo," FASEB J. 22:321.11

Lifely et al. (1995) "Glycosylation and Biological Activity of CAMPATH-1H Expressed in Different Cell Lines and Grown Under Different Culture Conditions," Glycobiology 5(8):813-22.

Lim, S.H. et al. (2011) "Fc Gamma Receptor IIb on Target B Cells Promotes Rituximab Internalization and Reduces Clinical Efficacy," Blood 118(9):2530-2540.

Lin et al. (2001) "Colony-Stimulating Factor 1 Promotes Progression of Mammary Tumors to Malignancy," J. Exper. Med. 193(6):727-739.

Lin et al. (2002) "The Macrophage Growth Factor CSF-1 in Mammary Gland Development and Tumor Progression," J. Mammary Gland Biol. Neoplasia.7(2):147-162.

Linsley, P.S. et al. (1994) "Extending the B7 (CD80) Gene Family," Prot. Sci. 3:1341-1343.

Linsley, P.S. et al. (2009) "The Clinical Utility of Inhibiting CD28-Mediated Costimulation," Immunol. Rev. 229:307-321.

Liu et al. (1987) "Production of a Mouse-Human Chimeric Monoclonal Antibody to CD20 With Potent Fc-Dependent Biologic Activity," J. Immunol. 139:3521-3526.

Liu, Z. et al. (1999) "Fine mapping of the antigen-antibody interaction of scFv215, a recombinant antibody inhibiting RNA polymerase II from Drosophia melangogaster," Journal of Molecular Recognition 12:103-111.

LoBuglio, A.F. et al. (1989) "Mouse/Human Chimeric Monoclonal Antibody in Man: Kinetics and Immune Response," Proc. Natl. Acad. Sci. (U.S.A.) 86:4220-4224.

Loke, P. et al. (2004) "Emerging Mechanisms of Immune Regulation: The Extended B7 Family and Regulatory T Cells," Arthritis Res. Ther. 6:208-214.

Lonberg, N. et al. (1995) "Human Antibodies From Transgenic Mice," Int. Rev. Immunol. 13:65-93.

Loo, D. et al. (2012) "Development of an Fc-Enhanced Anti-B7-H3 Monoclonal Antibody with Potent Antitumor Activity," J. Clin. Transl. Res.18(14):3717-3845.

Looney et al., 1986, "Human Monocytes and U937 Cells Bear Two Distinct Fc Receptors for IgG," J. Immunol. 136(5):1641-1647.

Lu, D. et al. (2003) "Di-Diabody: A Novel Tetravalent Bispecific Antibody Molecule by Design," J. Immunol. Meth. 279: 219-232.

Lu, D. et al. (2004) "The Effect of Variable Domain Orientation and Arrangement on the Antigen-Binding Activity of a Recombinant Human Bispecific Diabody," BBRC 318: 507-513.

Lu, et al., (2005) "A Fully Human Recombinant IgG-like Bispecific Antibody to Both the Epidermal Growth Factor Receptor and the Insulin-like Growth Factor Receptor for Enhanced Antitumor Activity," J. Biol. Chem. 280(20):19665-19672.

Lund et al. (2000) "Expression and Characterization of Truncated Forms of Humanized L243 IgG1. Architectural Features Can Influence Synthesis of Its Oligosaccharide Chains and Affect Superoxide Production Triggered Through Human Fcgamma Receptor I," Eur. J. Biochem. 267:7246-7257.

Lund, J. et al. (1991) "Human Fc Gamma RI and Fc Gamma RII Interact With Distinct But Overlapping Sites on Human IgG," J. Immunol. 147:2657-2662.

Lund, J. et al. (1992) "Multiple Binding Sites on the CH2 Domain of IgG for Mouse Fc Gamma RII," Mol. Immunol. 29:53-59.

Lund, J. et al. (1995) "Oligosaccharide-Protein Interactions in IgG Can Modulate Recognition by Fc Gamma Receptors," FASEB J. 9:115-119.

Lund, J. et al. (1996) "Multiple Interactions of IgG With Its Core Oligosaccharide Can Modulate Recognition by Complement and Human Fc Gamma Receptor I and Influence the Synthesis of Its Oligosaccharide Chains," J. Immunol. 157:4963-4969.

Luo et al. (2004) "B7-H3 Enhances Tumor Immunity In Vivo by Costimulating Rapid Clonal Expansion of Antigen-Specific CD8+ Cytolytic T Cells," J Immunol 173:5445-5450.

Lyden et al. (2001) "The Fc Receptor for IgG Expressed in the Villus Endothelium of Human Placenta Is Fc.Gamma.RIIB2," J. Immunol. 166(6):3882-3889.

MacCallum et al. (1996) "Antibody-Antigen Interactions: Contact Analysis and Binding Site Topography," J. Molec. Biol. 262:732-745.

Maeda, H. et al. (1991) "Construction of Reshaped Human Antibodies With HIV-Neutralizing Activity," Human Antibodies Hybridoma 2:124-134 (Abstract Only).

Maenaka et al. (2001) "The Human Low Affinity Fcgamma Receptors Iia, Iib, and III Bind IgG With Fast Kinetics and Distinct Thermodynamic Properties," J. Biol. Chem. 48:44898-904.

Mahato et al. (1997) "Cationic Lipid-Based Gene Delivery Systems: Pharmaceutical Perspectives," Pharm. Res. 14:853-859.

Mahnke, K. et al. (2007) "Induction of Immunosuppressive Functions of Dendritic Cells In Vivo by CD4+CD25+ Regulatory T Cells: Role of B7-H3 Expressions and Antigen Presentation," Eur J Immunol. Aug. 2007;37(8):2117-26.

Malbec et al. (1998) "Fcs Receptor I-Associated Lyn-Dependent Phosphorylation of Fc.Gamma. Receptor IIB During Negative Regulation of Mast Cell Activation," J. Immunol. 160(4):1647-1658.

Mallone, R. et al. (2005) "Targeting T Lymphocytes for Immune Monitoring and Intervention in Autoimmune Diabetes," Amer. J. Ther. 12(6):534-550.

Mangham, D.C. et al. (1999) "A Novel Immunohistochemical Detection System Using Mirror Image Complementary Antibodies (MICA)," Histopathology 35(2):129-33.

Maresco et al. (1999) "The SH2-Containing 5'-Inositol Phosphatase (SHIP) Is Tyrosine Phosphorylated after Fc.gamma. Receptor Clustering in Monocytes," J. Immunol. 162:6458-6465.

Martin-Orozco, N. et al. (2007) "Inhibitory Costimulation and Anti-Tumor Immunity," Semin. Cancer Biol. 17(4):288-298.

Maruyama, K. (2000) "In Vivo Targeting by Liposomes," Biol. Pharm. Bull. 23(7):791-799.

Marvin et al. (2005) "Recombinant Approaches to IgG-Like Bispecific Antibodies," Acta Pharmacologica Sinica, 26(6): 649-658.

Masui et al. (1986) "Mechanism of Antitumor Activity in Mice for Anti-Epidermal Growth Factor Receptor Monoclonal Antibodies With Different Isotypes," Canc. Res. 46:5592-5598.

Maynard, J. et al. (2000) "Anitbody Engineering," Annu. Rev. Biomed. Eng. 2:339-76.

McDevitt et al. (2000) "An Alpha-Particle Emitting Antibody ([213Bi]J591) for Radioimmunotherapy of Prostate Cancer," Cancer Res. 60(21):6095-6100.

Melero et al. (1998) "The Frequent Expansion of a Subpopulation of B Cells That Express RF-Associated Cross-Reactive Idiotypes: Evidence From Analysis of a Panel Autoreactive Monoclonal Antibodies," Scand. J. Immunol. 48:152-158.

Merino, M.E. et al. (2001) "Immunomagnetic Purging of Ewing's Sarcoma From Blood and Bone Marrow: Quantitation by Real-Time Polymerase Chain Reaction," J. Clin. Oncol. 19(16):3649-3659.

Merrifield, C. (1986) "Solid Phase Synthesis," Science 232(4748):341-347.

Mertens, N. et al. ,"New Recombinant Bi- and Trispecific Antibody Derivatives," In: Novel Frontiers in the Production of Compounds for Biomedical Use, vol. 1; van Broekhoven, A. et al. (Eds.); Kluwer Academic Publishers, Dordrecht, The Netherlands.

Metcalfe (1997) "Mast Cells," Physiol Rev. 77(4):1033-1079.

Michaelsen et al. (1994) "One Disulfide Bond in Front of the Second Heavy Chain Constant Region Is Necessary and Sufficient for Effector Functions of Human IgG3 Without a Genetic Hinge," Immunol. 91:9243-9247.

Micklem et al. (1990) "Different isoforms of human FcRII distinguished by CDw 32 antibodies," J. Immunol. 144:2295-2303.

Mittal, S. et al. (2009) "Cancer Stem Cells: The Other Face of Janus", Amer. J. Med. Sci. 338(2):107-112.

Modak, S. et al. (1998) "Novel Tumor Associated Surface Antigen: Broad Distribution among Neuroectodermal, Mesenchymal and Epithelial Tumors, with Restricted Expression among Normal Tissues," Pediatric Res. 43(4):136.

(56) References Cited

OTHER PUBLICATIONS

Modak, S. et al. (2000) "Radioimmunotargeting to Human Rhabdomyosarcoma Using Monoclonal Antibody 8H9," Proc. Am. Assoc. Cancer Res.41:724.

Modak, S. et al. (2001) "Monoclonal Antibody 8H9 Targets a Novel Cell Surface Antigen Expressed by a Wide Spectrum of Human Solid Tumors," Cancer Res. 61(10):4048-4054.

Modak, S. et al. (2002) "Disialoganglioside GD2 and a Novel Tumor Antigen: Potential Targets for Immunotherapy of Desmoplastic Small Round Cell Tumor," Med Pediatr Oncol 39:547-551.

Modak, S. et al. (2005) "Radioimmunotargeting of Human Rhabdomyosarcom Using Monoclonal Antibody 8H9," Cancer Biotherapy & Radiopharmaceuticals 20:534-546.

Modak, S. et al. (2007) "Disialoganglioside Directed Immunotherapy of Neuroblastoma," Cancer Investig. 25:67-77.

Modak, S. et al. (Mar. 1999) "Disialoganglioside GD2 and Antigen 8H9: Potential Targets for Antibody-Based Immunotherapy Against Desmoplastic Small Round Cell Tumor (DSRCT) and Rhabdomyosarcoma (RMS)," Proceedings of the American Association for Cancer Research Annual Meeting, vol. 40:474 (90th Annual Meeting of the American Association for Cancer Research; Philadelphia, Pennsylvania, US; Apr. 10-14, 1999.

Morgan et al. (1995) "The N-Terminal End of the CH2 Domain of Chimeric Human IgG1 Anti-HLA-DR Is Necessary for C1q, Fc Gamma RI and Fc Gamma RIII Binding," Immunol. 86:319-324.

Morrison et al. (1994) "Structural Determinants of IgG Structure," Immunologist 2:119-124.

Munn et al. (1990) "Phagocytosis of Tumor Cells by Human Monocytes Cultured in Recombinant Macrophage Colony-Stimulating Factor," J. Exper. Med. 172(1):231-237.

Nagarajan et al. (1995) "Ligand Binding and Phagocytosis by CD16 (Fc Gamma Receptor III) Isoforms. Phagocytic Signaling by Associated Zeta and Gamma Subunits in Chinese Hamster Ovary Cells," J. Biol. Chem. 270:25762-25770.

Nakamura et al. (2000) "Fc.Gamma. Receptor IIB-Deficient Mice Develop Goodpasture's Syndrome Upon Immunization With Type IV Collagen: A Novel Murine Model for Autoimmune Glomerular Basement Membrane Disease," J. Exper. Med. 191(5):899-905.

Nakamura, T. et al. (1992) "Heterogeneity of Immunoglobulin-Associated Molecules on Human B Cells Identified by Monoclonal Antibodies," Proc. Natl. Acad. Sci. (U.S.A.) 89:8522-8526).

Nakamurama, A. et al. (2005) "Fc Receptor Targeting in the Treatment of Allergy, Autoimmune Diseases and Cancer," Expert Opin. Ther. Targets 9(1):169-190.

Neuberger et al. (1984) "Recombinant Antibodies Possessing Novel Effector Functions," Nature 312:604-608.

Norderhaug et al. (1991) "Chimeric Mouse Human IgG3 Antibodies With an Igg4-Like Hinge Region Induce Complement-Mediated Lysis More Efficiently Than IgG3 With Normal Hinge," Eur. J. Immunol. 21:2379-2384.

Nordstrom, J.L. et al. (2011) "Anti-Tumor Activity and Toxicokinetics Analysis of MGAH22, An Anti-HER2 Monoclonal Antibody With Enhanced FcG Receptor Binding Properties," Breast Cancer Research 13:R123 (14 pages).

Noren, C.J. et al. (1989) "A General Method for Site-Specific Incorporation of Unnatural Amino Acids into Proteins," Science 244:182-188.

Norris et al. (1998) "A Naturally Occurring Mutation in Fc.Gamma. RIIA: A Q to K.Sup. 127 Change Confers Unique IgG Binding Properties to the R.Sup.131 Allelic Form of the Receptor," Blood. 91(2):656-662.

Nose et al. (1989) "Substitution of Asparagine324 With Aspartic Acid in the Fc Portion of Mouse Antibodies Reduces Their Capacity for C1q Binding," Eur. J. Immunol. 19:2179-2181.

Okazaki et al. (2004) "Fucose Depletion From Human IgG1 Oligosaccharide Enhances Binding Enthalpy and Association Rate Between IgG1 and FcgammaRIIIA," J. Molec. Biol. 336:1239-1249.

Olafsen et al. (2004) "Covalent Disulfide-Linked Anti-CEA Diabody Allows Site-Specific Conjugation and Radiolabeling for Tumor Targeting Applications," Protein Eng. Des. Sel. 17(1):21-27.

Onda, M. et al. (2004) "In Vitro and in Vivo Cytotoxic Activities of Recombinant Immunotoxin 8H9(Fv)-PE38 against Breast Cancer, Osteosarcoma, and Neuroblastoma," Canc. Res. 64:1419-1424.

Orfao et al. (1996) "General Concepts About Cell Sorting Techniques," Clinical Biochem. 29:5-9.

Ott, V.L. et al. (2001) "FcGammaRIIB as a Potential Molecular Target for Intravenous Gamma Globulin Therapy," J. Allergy Clin Immunol. 108(4):S95-S98.

Ott, V.L. et al. (2002) "Downstream of Kinase, P62.Sup.Dok, Is a Mediator of Fc.Gamma.RIIB Inhibition of Fc.Epsilon.RI Signaling," J. Immunol. 168:4430-4439.

Panchal, R.G. (1998) "Novel Strategies to Selectively Kill Cancer Cells," Biochem. Pharmacol. 55:247-252.

Panka et al. (1988) "Variable Region Framework Differences Result in Decreased or Increased Affinity of Variant Anti-Digoxin Antibodies," Proc. Natl. Acad. Sci. (U.S.A.) 85:3080-3084.

Pardridge et al. (2003) "Blood-Brain Barrier Drug Targeting: The Future of Brain Drug Development," Molecular Interventions 3(2):90-105 (particularly pp. 91-96).

Park et al. (1997) "Immunoliposomes for Cancer Treatment," Adv. Pharmacol. 40:399-435.

Park, Y.S. (2002) "Tumor-Directed Targeting of Liposomes," Biosci. Rep. 22(2):267-281.

Partridge et al. (1986) "The Use of Anti-IgG Monoclonal Antibodies in Mapping the Monocyte Receptor Site on IgG," Mol Immunol. 23(12):1365-1372.

Paul, William E, (1993) "Fundamental Microbiology, 3 Ed." pf. 242, 292-296.

Peeters et al. (2001) "Production of Antibodies and Antibody Fragments in Plants," Vaccine 19:2756-2761.

Pereira et al. (1998) "Cardiolipin Binding A Light Chain From Lupus-Prone Mice," Biochem. 37:1460-1437.

Perussia (2000) "Human Natural Killer Cell Protocols" in Methods Molecular Biology. vol. 121 (Campbell et al. eds.) Humana Press Inc., Totowa, NJ. 179-192.

Pettersen et al. (1999) "CD47 Signals T Cell Death," J. Immunol. 162(12):7031-7040.

Pini, A. (1998) "Design and Use of a Phage Display Library Human Antibodies With Subnanomolar Affinity Against a Marker of Angiogensis Eluted From a Two-Dimensional Gel," J. Biol. Chem. 272(34):21769-21779.

Pluckthun, A. et al. (1997) "New Protein Engineering Approaches to Multivalent and Bispecific Antibody Fragments," Immunotechnology 3(2):83-105.

Pollock et al. (1999) "Transgenic Milk as a Method for the Production of Recombinant Anitbodies," J. Immunol. Methods 231:147-157.

Polson, A.G. et al. (2007) "Antibody-Drug Conjugates Targeted to CD79 for the Treatment of Non-Hodgkin Lymphoma," Blood. 110(2):616-623.

Poul, M.A. et al. (2000) "Selection of Tumor-Specific Internalizing Human Antibodies from Phage Libraries," J. Molec. Biol. 301:1149-1161.

Prasad, D.V. et al. (2004) "Murine B7-H3 Is a Negative Regulator of T Cells," J. Immunol. 173:2500-2506.

Presta, L.G. (2002) "Engineering Antibodies for Therapy," Curr. Pharm. Biotechnol. 3(3):237-256.

Presta, L.G. et al. (2002) "Engineering Therapeutic Antibodies for Improved Function," Biochem. Soc. Trans. 30(4):487-490.

Presta, L.G. et al. (2005) "Selection, Design and Engineering of Therapeutic Antibodies," J. Allergy Clin. Immunol. 116(4):731-736.

Pricop et al. (2001) "Differential Modulation of Stimulatory and Inhibitory Fc.Gamma. Receptors on Human Monocytes by Th1 and Th2 Cytokines," J. Immunol. 166(1):531-537.

Pulford et al. (1986) "A New Monoclonal Antibody (KB61) Recognizing a Novel Antigen Which Is Selectively Expressed on a Subpopulation of Human B Lymphocytes," Immunol. 57(1):71-76.

Pulford et al. (1995) "M6.5: The Immunocytochemical Distribution of CD16, CD32, and CD64 Antigens," Leukocyte Typing V: White cell differentiation antigens 817-821 (Schlossman, Boumsell, Gilks, Harlan, Kishomoto, eds.); pp. 817-821.

(56) References Cited

OTHER PUBLICATIONS

Qin et al. (2000) "*Fc.Gamma. Receptor IIB on Follicular Dendritic Cells Regulates the B Cell Recall Response*," J. Immunol. 164:6268-6275.
Radaev et al. (2001) "*Recognition of Immunoglobulins by Fcgamma Receptors*," Molec. Immunol. 38:1073-1083.
Rader, C. et al. (1998) "*A Phage Display Approach for Rapid Antibody Humanization: Designed Combinatorial V Gene Libraries*," Proc. Natl. Acad. Sci. (U.S.A.) 95:8910-8915.
Rankin, et al. (2006) "*CD32B, The Human Inhibitory Fc-Y Receptor IIB, As a Target for Monoclonal Antibody Therapy of B-Cell Lymphoma*," Blood J. 108(7):2384-2391.
Ravetch et al. (1991) "*Fc Receptors*," Annu. Rev. Immunol. 9:457-492.
Ravetch et al. (1994) "*Fc Receptors: Rubor Redux*," Cell 78(4):553-560.
Ravetch et al. (1998) "*Divergent Roles for Fc Receptors and Complement In Vivo*," Annu. Rev. Immunol. 16:421-432.
Ravetch et al. (2001) "*IgG Fc receptors*," Annu. Rev. Immunol. 19:275-290.
Ravetech et al. (2000) "*Immune Inhibitory Receptors*," Science 290:84-89.
Reali et al. (2001) "*Iges Targeted on Tumor Cells: Therapeutic Activity and Potential in the Design of Tumor Vaccines*," Cancer Res. 61(14): 5517-5522.
Reddy, M.P. et al. (2000) "*Elimination of Fc Receptor-Dependent Effector Functions of a Modified IgG4 Monoclonal Antibody to Human CD4*," J. Immunol. 164:1925-1933.
Redpath et al. (1998) "*The Influence of the Hinge Region Length in Binding of Human IgG to Human Fcgamma Receptors*," Hum Immunol 59:720-727.
Reff et al. (1994) "*Depletion of B Cells In Vivo by a Chimeric Mouse Human Monoclonal Antibody to CD20*," Blood 83:435-445.
Reff et al. (2001) "*A Review of Modifications to Recombinant Antibodies: Attempt to Increase Efficacy in Oncology Applications*," Critical Reviews in Oncology/Hematology 40: 25-35.
Renders, L. et al. (2003) "*Engineered CD3 Antibodies for Immunosuppression*," Clin. Exp. Immunol. 133(3):307-309.
Ridgway et al. (1996) "'*Knobs-Into-Holes'Engineering of Antibody CH3 Domains for Heavy Chain Heterodimerization*," Protein Engr. 9:617-621.
Riechmann et al. (1988) "*Reshaping Human Antibodies for Therapy*," Nature 332(6162):323-327.
Riemer et al. (2005) "*Matching of Trastuzumab (Herceptin) Epitope Mimics Onto the Surface of Her-2/Neu—A New Method of Epitope Definition*," Molec. Immunol. 42(9):1121-1124.
Routledge et al. (1995) "*The Effect of Aglycosylation on the Immunogenicity of a Humanized Therapeutic CD3 Monoclonal Antibody*," Transplantation 60(8):847-853.
Rudikoff et al. (1982) "*Single Amino Acid Substitution Altering Antigen-Binding Specificity*" Proc. Natl. Acad. Sci. (U.S.A.) 79:1979-1983.
Saatian, B. et al. (2004) "*Expression of Genes for B7-H3 and Other T Cell Ligands by Nasal Epithelial Cells During Differentiation and Activation*," Amer. J. Physiol. Lung Cell. Mol. Physiol. 287:L217-L225.
Samsom et al. (2005) "*Fc Gamma RIIB Regulates Nasal and Oral Tolerance: A Role for Dendritic Cells*," Immunol. 174:5279-5287.
Samuelsson et al. (2001) "*Anti-Inflammatory Activity of IVIG Mediated Through the Inhibitory Fc Receptor*," Science 291:484-486.
Sarkar et al. (1996) "*Negative Signaling via Fc.Gamma.RIIB1 in B Cells Blocks Phospholipase Cgamma2 Tyrosine Phosphorylation But Not Syk or Lyn Activation*," J. Biol. Chem. 271(33):20182-20186.
Sarmay et al. (1984) "*Ligand Inhibition Studies on the Role of Fc Receptors in Antibody-Dependent Cell-Mediated Cytotoxicity*," Molec. Immunol. 21:43-51.
Sarmay et al. (1988) "*The Effect of Synthetic Peptides Corresponding to Fc Sequences in Human IgG1 on Various Steps in the B Cell Activation Pathway*," Eur. J. Immunol. 18:289-294.

Sarmay et al. (1992) "*Mapping and Comparison of the Interaction Sites on the Fc Region of IgG Responsible for Triggering Antibody Dependent Cellular Cytotoxicity (ADCC) Through Different Types of Human Fc Gamma Receptor*," Mol Immunol 29:633-639.
Sato, K. et al. (1993) "*Reshaping a Human Antibody to Inhibit the Interleukin 6-Dependent Tumor Cell Growth*," Cancer Res 53:851-856.
Sautes-Fridman et al. (2003) "*Fc Gamma Receptors: A Magic Link With the Outside World*," ASHI Quarterley, $4^{th}$ Quarter:148-151.
Schaffner et al. (1995) "*Chimeric Interleukin 2 Receptor Alpha Chain Antibody Derivatives With Fused Mu and Gamma Chains Permit Improved Recruitment of Effector Functions*," Mol Immunol 32 :9-20, 1995 (Erratum in 32 :1299).
Schatton, T. et al. (2009) "*Identification and Targeting of Cancer Stem Cells*," Bioessays 31(10):1038-1049.
Schatz et al. (2000) "*Use of Peptide Libraries to Map the Substrate Specificity of a Peptide-Modifying Enzyme: A 13 Residue Consensus Peptide Specifies Biotinylation in Escherichia coli*," Bio/Technology 11:1138-1143.
Schildbach, J. F. et al. (1993) "*Heavy Chain Position 50 is a Determinism of Affinity and Specificity for the Anti-digoxin Antibody 26-10*," The Journal of Biological Chemistry 268(29):21739-21747.
Schildbach, J. F. et al. (1994) "*Contribution of a single heavy chain residue to specificity of an anti-digoxin monoclonal antibody*," Protein Science 3:737-749.
Schoenfeld et al. (2009) "*Immunohistochemical Analysis of Chordoma Targeting B7H3 and HMW-MAA*," Orthopaedic J Harvard Medical School, 11:136-140.
Scholl et al. (1993) "*Is Colony-Stimulating Factor-1 A Key Mediator of Breast Cancer Invasion and Metastasis?*" Molec. Carcinogen. 7(4):207-211.
Schuna et al. (2000) "*New Drugs for the Treatment of Rheumatoid Arthritis*," Amer. J. Health Syst. Pharm. 57:225-237.
Scopelliti, A. et al. (2009) "*Therapeutic Implications of Cancer Initiating Cells*," Expert Opin. Biol. Ther. 9(8):1005-1016.
Seaver (1994) "*Monoclonal Antibodies in Industry: More Difficult than Originally Thought*," Genetic Engineering News 14(14):10, 21.
Sedmak, D.D. et al. (1991) "*Expression of IgG Fc Receptor Antigens in Placenta and on Endothelial Cells in Humans*," Amer. J. Pathol. 138(1):175-181.
Sensel et al. (1997) "*Amino Acid Differences in the N-Terminus of C (H)2 Influence the Relative Abilities of IgG2 and IgG3 to Activate Complement*," Molecular Immunology 34:1019-1029.
Sharpe, A.H. et al. (2002) "*The B7-CD28 Superfamily*," Nature Rev. Immunol. 2:116-126.
Shaw et al. (1987) "*Characterization of a Mouse/Human Chimeric Monoclonal Antibody (17-1A) to a Colon Cancer Tumor-Associated Antigen*," J. Immunol. 138:4534-4538.
Shields et al. (2001) "*High resolution mapping of the binding site on human IgG1 for Fc gamma RI, Fc gamma RII, Fc gamma RIII, and FcRn and design of IgG1 variants with improved binding to the Fc gamma R*," J Biol Chem 276:6591-6604.
Shields et al. (2002) "*Lack of Fucose on Human IgG1 N-Linked Oligosaccharide Improves Binding to Human Fc.Gamma. RIII and Antibody-Dependent Cellular Toxicity*," J. Biol. Chem. 277(30):26733-26740.
Shopes (1992) "*A genetically engineered human IgG mutant with enhanced cytolytic activity*," J. Immunol. 148:2918-2922
Shopes (1993) "*A Genetically Engineered Human IgG With Limited Flexibility Fully Initiates Cytolysis via Complement*," Molec. Immunol. 30:603-609.
Shopes et al. (1990) "*Recombinant Human IgG1 Murine Ige Chimeric Ig. Construction, Expression, and Binding to Human Fc Gamma Receptors*," J. Immunol. 145:3842-3848.
Shusta et al. (1998) "*Increasing the Secretory Capacity of Saccharomyces cerevisiae for Production of Single-Chain Antibody Fragments*," Nature Biotechnology 16:773-777.
Shusta et al. (1999) "*Yeast Polypeptide Fusion Surface Display Levels Predict Thermal Stability and Soluble Secretion Efficiency*," J. Mol. Biol. 292:949-956.

(56) References Cited

OTHER PUBLICATIONS

Shusta et al. (2000) "Directed Evolution of a Stable Scaffold for T-Cell Receptor Engineering," Nature Biotechnology 18:754-759.
Siberil, S. et al. (2006) "Molecular Aspects of Human FcgammaR Interactions with IgG: Functional and Therapeutic Consequences," Immunol. Lett. 106:111-118 (2006).
Skolnick et al. (2000) "From Genes to Protein Structure and Function: Novel Aspects of Computational Approaches in the Genomic Era," Trends in Biotechnology 18:34-39.
Sleister et al. (2002) "Subtractive Immunization; A Tool for the Generation of Discriminatory Antibodies to Proteins of Similar Sequence," J. Immunol. Meth. 261: 213-220.
Smith et al. (1994) "Recombinant Polymeric IgG: An Approach to Engineering More Potent Antibodies," Bio/Technology 12:683-688.
Smith-Garvin, J.E. et al. (2009) "T Cell Activation," Annu. Rev. Immunol. 27:591-619.
Sondermann et al. (1999) "Crystal Structure of the Soluble Form of the Human Fcgamma-Receptor IIB: A New Member of the Immunoglobulin Superfamily at 1.7 A Resolution," EMBO J. 18:1095-1103.
Sondermann et al. (2000) "The 3.2-A Crystal Structure of the Human Igg1 Fc Fragment-Fc GammaRIII Complex," Nature 406:267-273.
Sondermann et al. (2001) "Molecular Basis for Immune Complex Recognition: A Comparison of Fc-Receptor Structures," J. Mol. Biol. 309:737-749.
Sondermann et al. (2002) "The Structure of Fc Receptor/Ig Complexes: Considerations on Stoichiometry and Potential Inhibitors," Immunol. Lett. 82:51-56.
St. Clair, E.W. (2009) "Novel Targeted Therapies for Autoimmunity," Curr. Opin. Immunol. 21(6):648-657.
Stammers, M. et al. (2000) "BTL II : A Polymorphic Locus With Homology to the Butyrophilin Gene Family, Located at the Border of the Major Histocompatibility Complex Class II and Class III Regions in Human and Mouse," Immunogenetics 51:373-382.
Stancovski et al. (1991) "Mechanistic Aspects of the Opposing Effects of Monoclonal Antibodies to the ERBB2 Receptor on Tumor Growth," Proc. Natl. Acad. Sci. (U.S.A.) 88(19):8691-8695.
Stavenhagen, J.B. et al. (2007) "Fc Optimization of Therapeutic Antibodies Enhances Their Ability to Kill Tumor Cells In vitro and Controls Tumor Expansion In vivo via Low Affinity ActivatingFc ; Receptors," Cancer Res 67(18):8882-8890.
Stavenhagen, J.B. et al. (2008) "Enhancing the Potency of Therapeutic Antibodies via Fc Optimization," Advan. Enzyme Regul. 48:152-164.
Stefanescu, R. et al. (2004) "Inhibitory Fc Gamma Receptors: From Gene to Disease," J. Clin. Immuno. 24(4):315-326.
Steinberger et al. (2004), "Molecular Characterization of Human 4Ig-B7-H3, A Member of the B7 Family With Four Ig-Like Domains," J. Immunol. 2004, 172(4):2352-2359.
Stephan et al. (1999) "Distribution and Function of the Adhesion Molecule BEN During Rat Development," Dev. Biol. 212:264-277.
Stephan, J. et al. (1999) "Selective Cloning of Cell Surface Proteins Involved in Organ Development: Epithelial Glycoprotein Is Involved in Normal Epithelial Differentiation," Endocrinol. 140:5841-5854.
Steplewski et al. (1988) "Biological Activity of Human-Mouse IgG1, IgG2, IgG3, and IgG4 Chimeric Monoclonal Antibodies With Antitumor Specificity," Proc. Natl. Acad. Sci. (U.S.A.) 85:4852-4856.
Strohmeier et al. (1995) "Role of the Fc Gamma R Subclasses Fc Gamma RII and Fc Gamma RIII in the Activation of Human Neutrophils by Low and High Valency Immune Complexes," J Leukocyte Biol 58:415-422.
Su et al. (2007) "Expression Profile of Fc.Gamma.RIIB on Leukocytes and Its Dysregulation in Systemic Lupus Erythematosus," J. Immunol. 178:3272-3280.
Subudhi, S.K. et al. (2005) "The Balance of Immune Responses: Costimulation Versus Coinhibition," J. Mol. Med. 83:193-202.
Suh, W.K. et al. (2003) "The B7 Family Member B7-H3 Preferentially Down-Regulates T Helper Type 1-Mediated Immune Responses," Nat Immunol. 4(9):899-906.
Sun, M. et al. (2002) "Characterization of Mouse and Human B7-H3 Genes," J. Immunol. 168:6294-6297.
Sun, Y. et al. (2006) "B7-H3 and B7-H4 Expression in Non-small-cell Lung Cancer," Lung Cancer 53(2):143-151.
Sylvestre et al. (1994) "Fc Receptors Initiate the Arthus Reaction: Redefining the Inflammatory Cascade," Science 265:1095-1098.
Sylvestre et al. (1996) "A Dominant Role for Mast Cell Fc Receptors in the Arthus Reaction," Immunity 5:387-390.
Takai (2002) "Roles of Fc Receptors in Autoimmunity," Nature Reviews 2:580-592.
Takai et al. (1994) "FcR Gamma Chain Deletion Results in Pleiotrophic Effector Cell Defects," Cell 76 :519-529.
Takai et al. (1996) "Augmented Humoral and Anaphylactic Responses in Fc Gamma RII-Deficient Mice," Nature 379:346-349.
Takai et al. (2003) "Fc Receptors as Potential Targets for the Treatment of Allergy, Autoimmune Disease and Cancer," Current Drug Targets—Immune, Endocrine & Metabolic Disorders, 3:187-197.
Takemura, S.I. et al. (2000) "Construction of a Diabody (Small Recombinant Bispecific Antibody) Using a Refolding System," Prot. Engin. 13(8):583-588.
Tam et al. (2004) "A Bispecific Antibody Against Human IgE and Human Fc.gamma.RII That Inhibits Antigen-Induced Histamine Release by Human Mast Cells and Basophils," Allergy 59:772-780.
Tamm et al. (1996) "The IgG Binding Site of Human FcγRIIIb Receptor Involves CC' and FG Loops of the Membrane-Proximal Domain," J. Biol. Chem. 271:3659-3666.
Tang et al. (2001) "Biosynthesis of a Highly Stable Coiled-Coil Protein Containing Hexafluoroleucine in an Engineered Bacterial Host," J. Am. Chem. Soc. 123(44):11089-11090.
Tao et al. (1989) "Studies of Aglycosylated Chimeric Mouse-Human Igg. Role of Carbohydrate in the Structure and Effector Functions Mediated by the Human Igg Constant Region," J. Immunol. 143(8):2595-2601.
Tao et al. (1991) "The Differential Ability of Human IgG1 and IgG4 to Activate Complement Is Determined by The COOH—Terminal Sequence of The CH2 Domain," J Exp Med 173:1025-1028.
Tao et al. (1993) "Structural Features of Human Immunoglobulin G That Determine Isotype-Specific Differences in Complement Activation," J. Exper. Med. 178:661-667.
Tempest, P.R. et al. (1991) "Reshaping a Human Monoclonal Antibody to Inhibit Human Respiratory Syncytial Virus Infection in vivo," Bio/Technology 9:266-271.
Thomas, S. et al. (2010) "Molecular Immunology Lessons From Therapeutic T-Cell Receptor Gene Transfer," Immunology 129(2):170-177.
Tivol, E.A. et al. (1995) "Loss of CTLA-4 Leads to Massive Lymphoproliferation and Fatal Multiorgan Tissue Destruction, Revealing a Critical Negative Regulatory Role of CTLA-4," Immunity 3(5):541-547.
Todorovska et al. (2001) "Design and Application of Diabodies, Triabodies and Tetrabodies for Cancer Targeting," J. Immunol. Methods. 248(1-2):47-66.
Tran, H. et al. (2008) "Interactions of T Cells With Fibroblast-Like Synoviocytes: Role of the B7 Family Costimulatory Ligand B7-H3," J Immunol. 180(5):2989-2998.
Tridandapandi et al. (2002) "Regulated Expression and Inhibitory Function of FcgammaRIIB in Human Monocytic Cells," J. boil. Chem. 277(7):5082-5089.
Umana et al. (1999) "Engineered Glycoforms of an Antineuroblastoma Igg1 With Optimized Antibody-Dependent Cellular Cytotoxic Activity," Nat. Biotechnol. 17(2):176-80.
Vaccaro, C. et al. (2006) "Divergent Activities of an Engineered Antibody in Murine and Human Systems Have Implications for Therapeutic Antibodies," Proc. Natl. Acad. Sci. (U.S.A.) 103(49):18709-18714.
Vajdos et al. (2002) "Comprehensive Functional Maps of the Antigen-Binding Site of an Anti-ErbB2 Antibody Obtained with Shotgun Scanning Mutagenesis," J. Molec. Biol. 320:415-428.

(56) References Cited

OTHER PUBLICATIONS

Van Antwerp et al. (2000) "Fine Affinity Discrimination by Yeast Surface Display and Flow Cytometry," Biotechnol. Prog. 16:31-37.
Van De Winkel et al. (1995) "CD32 Cluster Workshop Report," Leukocyte Typing V: White Cell differentiation antigens 823-825 (Schlossman, Boumsell, Gilks, Harlan, Kishomoto, eds.).
Van den Beuken et al. (2001) "Building Novel Binding Ligands to B7.1 and B7.2 Based on Human Antibody Single Variable Light Chain Domains," J. Molec. Biol. 310:591-601.
Van Hest et al. (2001) "Protein-Based Materials, Toward a New Level of Structural Control," Chem. Comm. 19:1897-1904.
Van Nguyen et al. (2002) "Colony Stimulating Factor-1 Is Required to Recruit Macrophages Into the Mammary Gland to Facilitate Mammary Ductal Outgrowth," Devel. Biol. 247(1):11-25.
Van Sorge et al. (2003) "FcgammaR Polymorphisms: Implications for Function, Disease Susceptibility and Immunotherapy," Tissue Antigens 61:189-202.
Vandenborre, K. et al. (1999) "Interaction of CTLA-4 (CD152) With CD80 or CD86 Inhibits Human t-Cell Activation," Immunology 98(3):413-421.
Vely et al. (1997) "A New Set of Monoclonal Antibodies Against Human Fc Gamma RII (CD32) and Fc Gamma RIII (CD16): Characterization and Use in Various Assays," Hybridoma 16(6): 519-28.
Verhoeyen, M. et al. (1988) "Reshaping Human Antibodies: Grafting an Antilysozyme Activity," Science 239:1534-1536.
Veri, M.C. et al. (2007) "Monoclonal Antibodies Capable of Discriminating the Human Inhibitory Fcgamma-Receptor IIB (CD32B) From the Activating Fcgamma-Receptor IIA (CD32A): Biochemical, Biological and Functional Characterization," Immunology 121(3):392-404.
Veri, M.C. et al. (2010) "Therapeutic Control of B Cell Activation via Recruitment of Fcgamma Receptor IIb (CD32B) Inhibitory Function With a Novel Bispecific Antibody Scaffold," Arthritis Rheum. 62(7):1933-1943.
Vidarte (2001) "Serine 132 Is the C3 Covalent Attachment Point on the CH1 Domain of Human Igg1," J. Biol. Chem. 276:38217-38233.
Viglietta, V. et al. (2007) "Modulating Co-Stimulation," Neurotherapeutics 4:666-675.
Vingerhoeds et al. (1994) "Immunoliposomes in vivo," Immunomethods 4(3):259-272.
Vitetta, E.S. et al. (2006) "Immunology. Considering Therapeutic Antibodies," Science 313:308-309.
Von Koskull, H. et al. (1984) "Identification of Cells From Fetal Bladder Epithelium in Human Amniotic Fluid," Hum. Genet. 65:262-267.
Vuist et al. (1990) "Two Distinct Mechanisms of Antitumor Activity Mediated by the Combination of Interleukin 2 and Monoclonal Antibodies," Canc. Res. 50:5767-5772.
Wallick et al. (1988) "Glycosylation of a VH Residue of a Monoclonal Antibody Against A(1→46) Dextran Increases Its Affinity for Antigen," J. Exper. Med. 168(3):1099-1109.
Wang et al. (2001) "Expanding The Genetic Code of Escherichia coli," Science. 292:498-500.
Wang et al. (2002) "Expanding The Genetic Code," Chem. Comm. 1:1-11.
Wang et al. (2013) "B7-H3 is Overexpressed in Patients Suffering Osteosarcoma and Associated Tumor Aggressiveness and Metastasis," PLOS ONE 8(8):e70689.
Wang, S. et al. (2004) "Co-Signaling Molecules of the B7-CD28 Family in Positive and Negative Regulation of T Lymphocyte Responses," Microbes Infect. 6:759-766.
Ward et al. (1989) "Building Activities of a repertoire of single immunoglobulin variable domains secreted from Escherichia coli," Nature 341:544-546.
Ward et al. (1995) "The Effector Functions of Immunoglobulins: Implications for Therapy," Therapeutic Immunology 2:77-94.
Warmerdam et al. (1990) "Molecular Basis for a Polymorphism of Human Fc Gamma Receptor II (CD32)," J. Exper. Med. 172(1):19-25.

Warren, H.S. et al. (1999) "NK Cells and Apoptosis," Immunol. Cell. Biol. 77(1):64-75.
Weinrich, V. et al. (1996) "Epitope Mapping of New Monoclonal Antibodies Recognizing Distinct Human FCRII (CD32) Isoforms," Hybridoma 15(2):109-116.
Weng et al. (2003) "Two Immunoglobulin G Fragment C Receptor Polymorphisms Independently Predict Response to Rituximab in Patients With Follicular Lymphoma," J. Clin. Oncol. 21:3940-3947.
Wheeler (1997) "Preventive Vaccines for Cervical Cancer," Salud. Publica d Mexico 39:1-9.
Wiener, E. et al. (1988) "Differences Between the Activities of Human Monoclonal Igg1 and Igg3 Anti-D Antibodies of the Rh Blood Group System in Their Abilities to Mediate Effector Functions of Monocytes," Immunol. 65:159-163.
Willemsen, R. (2008) "Selection of Human Antibody Fragments Directed Against Tumor T-Cell Epitopes for Adoptive T-Cell Therapy," Cytometry A. 73(11):1093-1099.
Wing et al. (1996) "Mechanism of First-Dose Cytokine-Release Syndrome by CAMPATH 1-H: Involvement of CD16 (FcγRIII) and CD11α/CD18 (LFA-1) on NK Cells," J. Clin. Invest. 98:2819-2826.
Wingren et al. (1996) "Comparison of Surface Properties of Human IgA, IgE, IgG and IgM Antibodies With Identical and Different Specificities," Scand. J. Immunol. 44:430-436.
Winter, G. et al. (1991) "Man-made Antibodies," Nature 349:293-299.
Winter, G. et al. (1994) "Making Antibodies by Phage Display Technology," Annu Rev. Immunol. 12.433-455.
Wittrup (2000) "The Single Cell as a Microplate Well," Nature Biotechnol. 18:1039-1040.
Witttrup (2001) "Protein Engineering by Cell-Surface Display," Curr, Opin. Biotechnol. 12:395-399.
Wolff, E.A. et al. (1993) "Monoclonal Antibody Homodimers: Enhanced Antitumor Activity in Nude Mice," Cancer Research 53:2560-2565.
Woof et al. (1986) "Localisation of the Monocyte-Binding Region on Human Immunoglobulin G," Molec. Immunol. 23:319-330.
Wright et al. (1997) "Effect of Glycosylation on Antibody Function: Implications for Genetic Engineering." Trends Biotechnol. 15(1):26-32.
Wu et al. (1997) "A Novel Polymorphism of FcγRIIIA (CD16) Alters Receptor Function and Predisposes to Autoimmune Disease," J. Clin. Invest. 100:1059-1070.
Wu et al. (1999) "Humanization of a Murine Monoclonal Antibody by Simultaneous Optimization of Framework and CDR Residues," J. Molec. Biol. 294:151-162.
Wu et al. (2001) "Multimerization of a Chimeric Anti-DC20 Single-Chain Fv-Fc Fusion Protein Is Mediated Through Variable Domain Exchange," Protein Engineering 14(2):1025-1033.
Xiang, J. et al (2000) "Study of B72.3 combining sites by molecular modeling and site-directed mutagenesis," Protein Eng. 13(5):339-344.
Xie et al. (2005) "A New Format of Bispecific Antibody: Highly Efficient Heterodimerization, Expression and Tumor Cell Lysis," J. Immunol. Methods 296:95-101.
Xu et al. (1993) "Antibody-Induced Growth Inhibition Is Mediated Through Immunochemically and Functionally Distinct Epitopes on the Extracellular Domain of the c-erbB-2 (HER-2/neu) Gene product p185," Int. J. Cancer. 53(3):401-408.
Xu et al. (1994) "Residue at Position 331 in the IgG1 and IgG4 CH2 Domains Contributes to Their Differential Ability to Bind and Activate Complement," J. Biol. Chem. 269:3469-3474.
Xu et al. (2003) "Fc.gamma.Rs Modulate Cytotoxicity of Anti-Fas Antibodies: Implications for Agonistic Antibody Based Therapeutics," J Immunol.171:562-68.
Xu, D. et al. (2000) "In Vitro Characterization of Five Humanized OKT3 Effector Function Variant Antibodies," Cell. Immunol. 200:16-26.
Xu, H. et al. (2009) "MicroRNA miR-29 Modulates Expression of Immunoinhibitory Molecule B7-H3: Potential Implications for Immune Based Therapy of Human Solid Tumors," Cancer Res. 69(15):5275-6281.

(56) References Cited

OTHER PUBLICATIONS

Xu, J. et al. (2006) "*Soluble Mouse B7-H3 Down Regulates Dendritic Cell Stimulatory Capacity to Allogenic T Cell Proliferation and Production of IL-2 and IFN-Gamma*," Cell Mol Immunol. 3(3):235-240.

Yeung et al. (2002) "*Quantitative Screening of Yeast Surface-Displayed Polypeptide Libraries by Magnetic Bead Capture*," Biotechnol. Prog. 18:212-220.

Yi. K.H. et al. (2009) "*Fine Tuning the Immune Response Through B7-H3 and B7-H4*," Immunol. Rev. 229:145-151.

Zang et al. (2010) "*Tumor associated endothelial expression of B7-H3 predicts survival in ovarian carcinomas*," Mod Path. 23(8):1104-1112.

Zang, X. et al. (2003) "*B7x: A Widely Expressed B7 Family Member That Inhibits T Cell Activation*," Proc. Natl. Acad. Sci. (U.S.A.) 100:10388-10392.

Zang, X. et al. (2007) "*B7-H3 and B7x Are Highly Expressed in Human Prostate Cancer and Associated With Disease Spread and Poor Outcome*," Proc. Natl. Acad. Sci. (U.S.A) 104(49):19458-19463.

Zang, X. et al. (2007) "*The B7 Family and Cancer Therapy: Costimulation and Coinhibition*," Clin. Cancer Res. 13:5271-5279.

Zeidler et al. (2000) "*The Fc-Region of a New Class of Intact Bispecific Antibody Mediates Activation of Accessory Cells and NK Cells and Induces Direct Phagocytosis of Tumour Cells*," Brit. J. Cancer 83:261-266.

Zhang, G. et al. (2005) "*B7-H3: Another Molecule Marker for Mo-DCs?*," Cell. Molec. Immunol. 2(4):307-311.

Zhang, G. et al. (2008) "*Soluble CD276 (B7-H3) Is Released From Monocytes, Dendritic Cells and Activated T Cells and Is Detectable in Normal Human Serum*," Immunology 123:538-546.

Zhao et al. "*Relation of B7-H3 Molecule Expression in Multiple Myeloma with Poor Prognosis and Bone Destruction*," Zhongguo Shi Yan Xue Ye Xue Za Zhi. Jun. 2013;21(3):637-42 (Abstract only).

Zhou, P. et al. (2008) "*CD32B Is Highly Expressed on Clonal Plasma Cells From Patients With Systemic Light-Chain Amyloidosis and Provides a Target for Monoclonal Antibody-Based Therapy*," Blood doi:10.1182/blood-2007-11-125526 (5 pages).

Zola et al., 2000, "*CD32 (FcgammaRII)*," J. Biol. Regul. Homeostat. Agents 14(4):311-316.

Zuckier et al. (1998) "Chimeric Human-Mouse IgG Antibodies With Shuffled Constant Region Exons Demonstrate That Multiple Domains Continue to In Vivo Half-Life," Cancer Res 58:3905-3908.

\* cited by examiner

| Normal Tissue Type | BRCA84D 0.625 µg/ml |
|---|---|
| Heart | 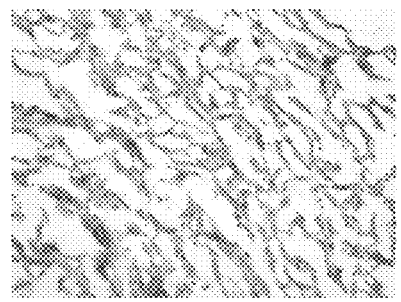 |
| Kidney | 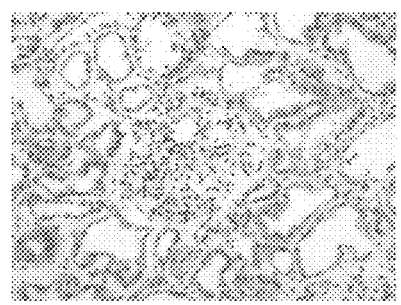 |
| Adrenal | 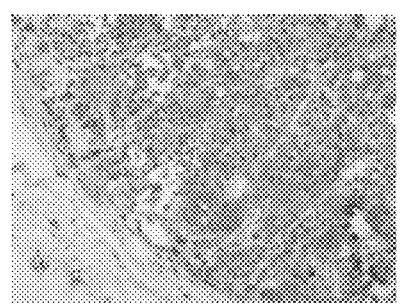 |
Figure 1B

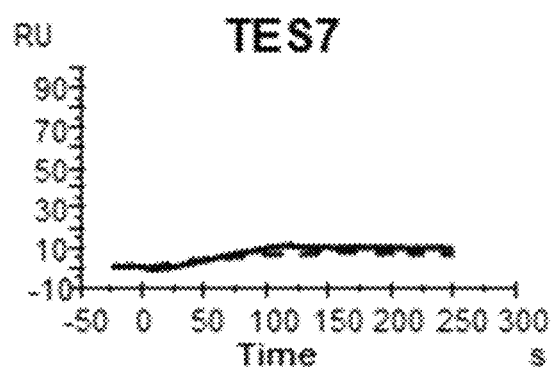
Figure 5S
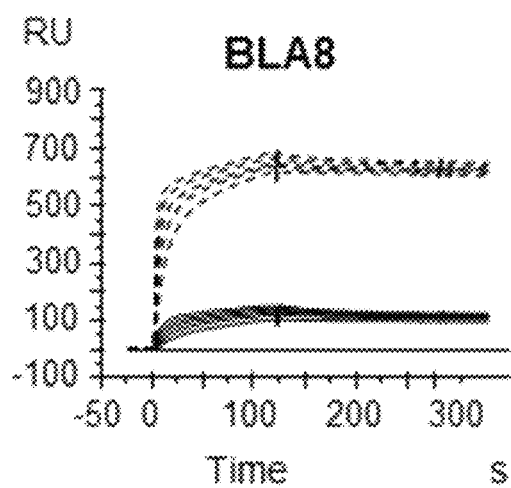 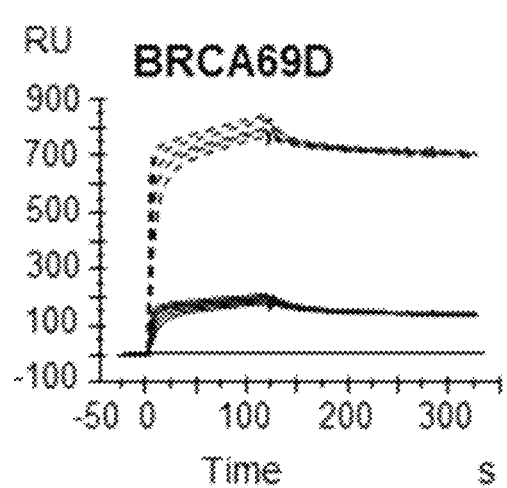
Figure 6A                                    Figure 6B

```
           10         20         30         40         50
            |          |          |          |          |
(1) DIAMTQSQKF MSTSVGDRVS VTCKASQNVD TNVAWYQQKP GQSPKALIYS
(2) DIQLTQSPSF LSASVGDRVT ITCKASQNVD TNVAWYQQKP GKAPKLLIYS 60         70         80         90        100
            |          |          |          |          |
(1) ASYRYSGVPD RFTGSGSGTD FTLTINNVQS EDLAEYFCQQ YNNYPFTFGS
(2) ASYRYSGVPS RFSGSGSGTD FTLTISSLQP EDFATYYCQQ YNNYPFTFGQ (1) GTKLEIK
(2) GTKLEIK
```

(1)    BRCA84D Variable Light Chain (SEQ ID NO:3)
    (2)    Humanized BRCA84D-1 Variable Light Chain (SEQ ID NO:68)

Figure 11A

```
           10         20         30         40         50
            |          |          |          |          |
(1) DVQLVESGGG LVQPGGSRKL SCAASGFTFS SFGMHWVRQA PEKGLEWVAY
(2) EVQLVESGGG LVQPGGSIRL SCAASGFTFS SFGMHWVRQA PGKGLEWVAY 60         70         80         90        100
            |          |          |          |          |
(1) ISSDSSAIYY ADTVKGRFTI SRDNPKNTLF LQMTSLRSED TAMYYCGRGR
(2) ISSDSSAIYY ADTVKGRFTI SRDNAKNSLY LQMNSLRDED TAVYYCARGR
                                              ↑     ↑   ↑
                                              84    89  93

110        120
           |          |
(1) ENIYYGSRLD YWGQGTTLTV SS
(2) ENIYYGSRLD YWGQGTTVTV SS
```

(1)    BRCA84D Variable Heavy Chain (SEQ ID NO:11)
    (2)    Humanized BRCA84D-1 Variable Heavy Chain (SEQ ID NO:80)

Figure 11B

ANTIBODIES REACTIVE WITH B7-H3 AND USERS THEREOF

CROSS-REFERENCE TO RELATED APPLICATIONS

This application is a continuation of U.S. patent application Ser. No. 15/169,211 (filed May 31, 2016), which application is a continuation of U.S. patent application Ser. No. 14/331,876 (filed Jul. 15, 2014; now U.S. Pat. No. 9,441,049), which application is a divisional of U.S. patent application Ser. No. 13/463,924 (filed May 4, 2012; now U.S. Pat. No. 8,802,091), which application claims priority to U.S. Patent Application No. 61/482,771 (filed May 5, 2011), and is a continuation-in-part of PCT/US2011/026689 (filed Mar. 1, 2011; expired), which application claims priority to United States Patent Application Ser. Nos. 61/311,057 (filed Mar. 5, 2010), 61/310,695 (filed Mar. 4, 2010) and 61/310,692 (filed Mar. 4, 2010), each of which applications is herein incorporated by reference in its entirety and to which priority is claimed.

REFERENCE TO SEQUENCE LISTING

This application includes one or more Sequence Listings pursuant to 37 C.F.R. 1.821 et seq., which are disclosed in computer-readable media (filed name: 1301-0073C_ST25, created May 31, 2016, and having a size of 104,070 bytes), which file is herein incorporated by reference in its entirety.

BACKGROUND OF THE INVENTION

Field of the Invention

The present invention relates to antibodies that are immunoreactive to the mammalian, and more particularly, the human B7-H3 receptor and to uses thereof, particularly in the treatment of cancer and inflammation. The invention thus particularly concerns humanized B7-H3-reactive antibodies that are capable of mediating, and more preferably enhancing the activation of the immune system against cancer cells that are associated with a variety of human cancers.

Description of Related Art

The growth and metastasis of tumors depends to a large extent on their capacity to evade host immune surveillance and overcome host defenses. Most tumors express antigens that can be recognized to a variable extent by the host immune system, but in many cases, an inadequate immune response is elicited because of the ineffective activation of effector T cells (Khawli, L. A. et al. (2008) "*Cytokine, Chemokine, and Co-Stimulatory Fusion Proteins for the Immunotherapy of Solid Tumors,*" Exper. Pharmacol. 181: 291-328).

CD4+ T-lymphocytes are the essential organizers of most mammalian immune and autoimmune responses (Dong, C. et al. (2003) "*Immune Regulation by Novel Costimulatory Molecules,*" Immunolog. Res. 28(1):39-48). The activation of CD4+ helper T-cells has been found to be mediated through co-stimulatory interactions between Antigen Presenting Cells and naive CD4+T-lymphocytes. Two interactions are required (Viglietta, V. et al. (2007) "*Modulating Co-Stimulation,*" Neurotherapeutics 4:666-675; Korman, A. J. et al. (2007) "*Checkpoint Blockade in Cancer Immunotherapy,*" Adv. Immunol. 90:297-339). In the first interaction, an Antigen Presenting Cell must display the relevant target antigen bound to the cell's major histocompatibility complex so that it can bind to the T-cell Receptor ("TCR") of a naive CD4+ T-lymphocyte. In the second interaction, a ligand of the Antigen Presenting Cell must bind to a CD28 receptor of the CD4+ T-lymphocyte (Dong, C. et al. (2003) "*Immune Regulation by Novel Costimulatory Molecules,*" Immunolog. Res. 28(1):39-48; Lindley, P. S. et al. (2009) "*The Clinical Utility Of Inhibiting CD28-Mediated Costimulation,*" Immunol. Rev. 229:307-321). CD4+ helper T-cells experiencing both stimulatory signals are then capable of responding to cytokines (such as Interleukin-2 and Interleukin-12 to develop into Th1 cells. Such cells produce interferon-gamma (IFN-γ) and tumor necrosis factor-alpha (TNF-α), which mediate inflammatory responses to target cells expressing the target antigen. B-cell activation and proliferation also occurs, resulting in antibody production specific for the target antigen (Bernard, A. et al. (2005) "*T and B Cell Cooperation: A Dance of Life and Death,*" Transplantation 79:S8-S11). In the absence of both co-stimulatory signals during TCR engagement, T cells enter a functionally unresponsive state, referred to as clonal anergy (Khawli, L. A. et al. (2008) "*Cytokine, Chemokine, and Co-Stimulatory Fusion Proteins for the Immunotherapy of Solid Tumors,*" Exper. Pharmacol. 181:291-328). In pathologic states, Th1 cells are the key players of various organ-specific autoimmune diseases, such as type I diabetes, rheumatoid arthritis, and multiple sclerosis (Dong, C. et al. (2003) "*Immune Regulation by Novel Costimulatory Molecules,*" Immunolog. Res. 28(1):39-48).

I. The B7 Superfamily and B7-H3

Investigations into the ligands of the CD28 receptor have led to the characterization of a set of related molecules known as the B7 Superfamily (Coyle, A. J. et al. (2001) "*The Expanding B7 Superfamily: Increasing Complexity In Costimulatory Signals Regulating T Cell Function,*" Nature Immunol. 2(3):203-209; Sharpe, A. H. et al. (2002) "*The B7-CD28 Superfamily,*" Nature Rev. Immunol. 2:116-126; Greenwald, R. J. et al. (2005) "*The B7 Family Revisited,*" Ann. Rev. Immunol. 23:515-548; Collins, M. et al. (2005) "*The B7 Family Of Immune-Regulatory Ligands,*" Genome Biol. 6:223.1-223.7; Loke, P. et al. (2004) "*Emerging Mechanisms Of Immune Regulation: The Extended B7 Family And Regulatory T Cells.*" Arthritis Res. Ther. 6:208-214; Korman, A. J. et al. (2007) "*Checkpoint Blockade in Cancer Immunotherapy,*" Adv. Immunol. 90:297-339; Flies, D. B. et al. (2007) "*The New B7s: Playing a Pivotal Role in Tumor Immunity,*" J. Immunother. 30(3):251-260; Agarwal, A. et al. (2008) "*The Role Of Positive Costimulatory Molecules In Transplantation And Tolerance,*" Curr. Opin. Organ Transplant. 13:366-372; Lenschow, D. J. et al. (1996) "*CD28/B7 System of T Cell Costimulation,*" Ann. Rev. Immunol. 14:233-258; Wang, S. et al. (2004) "*Co-Signaling Molecules Of The B7-CD28 Family In Positive And Negative Regulation Of T Lymphocyte Responses,*" Microbes Infect. 6:759-766). There are currently seven known members of the family: B7.1 (CD80), B7.2 (CD86), the inducible co-stimulator ligand (ICOS-L), the programmed death-1 ligand (PD-L1), the programmed death-2 ligand (PD-L2), B7-H3 and B7-H4 (Collins, M. et al. (2005) "*The B7 Family Of Immune-Regulatory Ligands,*" Genome Biol. 6:223.1-223.7).

B7 family members are immunoglobulin superfamily members with an immunoglobulin-V-like and an immunoglobulin-C-like domain (e.g., IgV-IgC) (Sharpe, A. H. et al. (2002) "The B7-CD28 Superfamily," Nature Rev. Immunol. 2:116-126). The IgV and IgC domains of B7-family members are each encoded by single exons, with additional exons encoding leader sequences, transmembrane and cytoplasmic domains The cytoplasmic domains are short, ranging in length from 19 to 62 amino-acid residues and can be encoded by multiple exons (Collins, M. et al. (2005) "*The B7 Family Of Immune-Regulatory Ligands*," Genome Biol. 6:223.1-223.7). B7-H3 is unique in that the major human form contains two extracellular tandem IgV-IgC domains (i.e., IgV-IgC-IgV-IgC) (Collins, M. et al. (2005) "*The B7 Family Of Immune-Regulatory Ligands*," Genome Biol. 6:223.1-223.7). Members of the B7 family are predicted to form back-to-back, non-covalent homodimers at the cell surface, and such dimers have been found with respect to B7-1 (CD80) and B7-2 (CD86).

B7-1 (CD80) and B7-2 (CD86) exhibit have dual specificity for the stimulatory CD28 receptor and the inhibitory CTLA-4 (CD152) receptor (Sharpe, A. H. et al. (2002) "*The B7-CD28 Superfamily*," Nature Rev. Immunol. 2:116-126).

Although initially thought to comprise only 2 Ig domains (IgV-IgC) (Chapoval, A. et al. (2001) "*B7-H3: A Costimulatory Molecule For T Cell Activation and IFN-γ Production*," Nature Immunol. 2:269-274; Sun, M. et al. (2002) "*Characterization of Mouse and Human B7-H3 Genes*," J. Immunol. 168:6294-6297) a four immunoglobulin extracellular domain variant ("4Ig-B7-H3") has been identified and found to be more common human form of the protein (Sharpe, A. H. et al. (2002) "*The B7-CD28 Superfamily*," Nature Rev. Immunol. 2:116-126). No functional difference has been observed between these two forms, since the natural murine form (2Ig) and the human 4Ig form exhibit similar function (Hofmeyer, K. et al. (2008) "*The Contrasting Role Of B7-H3*," Proc. Natl. Acad. Sci. (U.S.A.) 105 (30):10277-10278). The 4Ig-B7-H3 molecule inhibits the natural killer cell-mediated lysis of cancer cells (Castriconi, R. et al. "*Identification Of 4Ig-B7-H3 As A Neuroblastoma-Associated Molecule That Exerts A Protective Role From An NK Cell-Mediated Lysis*," Proc. Natl. Acad. Sci. (U.S.A.) 101(34): 12640-12645). The human B7-H3 (2Ig form) has been found to promote T-cell activation and IFN-γ production by binding to a putative receptor on activated T cells (Chapoval, A. et al. (2001) "*B7-H3: A Costimulatory Molecule For T Cell Activation and IFN-γ Production*," Nature Immunol. 2:269-274; Xu, H. et al. (2009) "*MicroRNA miR-29 Modulates Expression of Immunoinhibitory Molecule B7-H3: Potential Implications for Immune Based Therapy of Human Solid Tumors*," Cancer Res. 69(15): 5275-6281). Both B7-H4 and B7-H1 are potent inhibitors of immune function when expressed on tumor cells (Flies, D. B. et al. (2007) "*The New B7s: Playing a Pivotal Role in Tumor Immunity*," J. Immunother. 30(3):251-260).

The mode of action of B7-H3 is complex, as the protein mediates both T cell co-stimulation and co-inhibition (Hofmeyer, K. et al. (2008) "*The Contrasting Role Of B7-H3*," Proc. Natl. Acad. Sci. (U.S.A.) 105(30):10277-10278; Martin-Orozco, N. et al. (2007) "*Inhibitory Costimulation And Anti-Tumor Immunity*," Semin. Cancer Biol. 17(4):288-298; Subudhi, S. K. et al. (2005) "*The Balance Of Immune Responses: Costimulation Verse Coinhibition*," J. Mol. Med. 83:193-202). B7-H3 binds to (TREM)-like transcript 2 (TLT-2) and co-stimulates T cell activation, but also binds to as yet unidentified receptor(s) to mediate co-inhibition of T cells. In addition, B7-H3, through interactions with unknown receptor(s) is an inhibitor for natural killer cells and osteoblastic cells (Hofmeyer, K. et al. (2008) "*The Contrasting Role Of B7-H3*," Proc. Natl. Acad. Sci. (U.S.A.) 105(30):10277-10278). The inhibition may operate through interactions with members of the major signaling pathways through which T cell receptor (TCR) regulates gene transcription (e.g., NFTA, NF-κB, or AP-1 factors).

B7-H3 co-stimulates CD4+ and CD8+ T-cell proliferation. B7-H3 also stimulates IFN-γ production and CD8+ lytic activity (Chapoval, A. et al. (2001) "*B7-H3: A Costimulatory Molecule For T Cell Activation and IFN-γ Production*," Nature Immunol. 2:269-274; Sharpe, A. H. et al. (2002) "*The B7-CD28 Superfamily*," Nature Rev. Immunol. 2:116-126). However, the protein also possibly acts through NFAT (nuclear factor for activated T cells), NF-κB (nuclear factor kappa B), and AP-1 (Activator Protein-1) factors to inhibit T-cell activation (Yi. K. H. et al. (2009) "*Fine Tuning The Immune Response Through B7-H3 And B7-H4*," Immunol. Rev. 229:145-151). B7-H3 is also believed to inhibit Th1, Th2, or Th17 in vivo (Prasad, D. V. et al. (2004) "*Murine B7-H3 Is A Negative Regulator Of T Cells*," J. Immunol. 173:2500-2506; Fukushima, A. et al. (2007) "*B7-H3 Regulates The Development Of Experimental Allergic Conjunctivitis In Mice*," Immunol. Lett. 113:52-57; Yi. K. H. et al. (2009) "*Fine Tuning The Immune Response Through B7-H3 And B7-H4*," Immunol. Rev. 229:145-151). Several independent studies have shown that human malignant tumor cells exhibit a marked increase in expression of B7-H3 protein and that this increased expression was associated with increased disease severity (Zang, X. et al. (2007) "*The B7 Family And Cancer Therapy: Costimulation And Coinhibition*," Clin. Cancer Res. 13:5271-5279), suggesting that B7-H3 is exploited by tumors as an immune evasion pathway (Hofmeyer, K. et al. (2008) "*The Contrasting Role Of B7-H3*," Proc. Natl. Acad. Sci. (U.S.A.) 105(30):10277-10278).

Molecules that block the ability of a B7 molecule to bind to a T-cell receptor (e.g., CD28) inhibit the immune system and have been proposed as treatments for autoimmune disease (Linsley, P. S. et al. (2009) "*The Clinical Utility Of Inhibiting CD28-Mediated Co-Stimulation*," Immunolog. Rev. 229:307-321). Neuroblastoma cells expressing 4Ig-B7-H3 treated with anti-4Ig-B7-H3 antibodies were more susceptible to NK cells. However, it is unclear whether this activity can be attributed to only antibodies against the 4Ig-B7-H3 form because all reported antibodies raised against the 4Ig-B7-H3 also bound the two Ig-like form of B7H3 (Steinberger, P. et al. (2004) "*Molecular Characterization of Human 4Ig-B7-H3, a Member of the B7 Family with Four Ig-Like Domains*," J. Immunol. 172(4): 2352-2359 and Castriconi et al. (2004) "*Identification Of 4Ig-B7-H3 As A Neuroblastoma-Associated Molecule That Exerts A Protective Role From An NK Cell-Mediated Lysis*," Proc. Natl. Acad. Sci. (U.S.A.) 101(34):12640-12645).

B7-H3 is not expressed on resting B or T cells, monocytes, or dendritic cells, but it is induced on dendritic cells by IFN-γ and on monocytes by GM-CSF (Sharpe, A. H. et al. (2002) "*The B7-CD28 Superfamily*," Nature Rev. Immunol. 2:116-126). The receptor(s) that bind B7-H3 have not been fully characterized. Early work suggested one such receptor would need to be rapidly and transiently up-regulated on T cells after activation (Loke, P. et al. (2004) "*Emerging Mechanisms Of Immune Regulation: The Extended B7 Family And Regulatory T Cells.*" Arthritis Res. Ther. 6:208-214). Recently, the (TREM)-like transcript 2 (TLT-2, or TREML2) receptor (King, R. G. et al. (2006) "*Trem-Like Transcript 2 Is Expressed On Cells Of The Myeloid/Granuloid And B Lymphoid Lineage And Is Up-Regulated In Response To Inflammation*," J. Immunol. 176: 6012-6021; Klesney-Tait, J. et al. (2006) "*The TREM Receptor Family And Signal Integration*," Nat. Immunol. 7:1266-1273; Yi. K. H. et al. (2009) "*Fine Tuning The Immune*

Response Through B7-H3 And B7-H4," Immunol. Rev. 229:145-151), which is expressed on myeloid cells has been shown to be capable of binding B7-H3, and of thereby co-stimulating the activation of CD8+ T cells in particular (Zang, X. et al. (2003) "*B7x: A Widely Expressed B7 Family Member That Inhibits T Cell Activation*," Proc. Natl. Acad. Sci. (U.S.A.) 100:10388-10392; Hashiguchi, M. et al. (2008) "*Triggering Receptor Expressed On Myeloid Cell-Like Transcript 2 (TLT-2) Is A Counter-Receptor For B7-H3 And Enhances T Cell Responses*," Proc. Natl. Acad. Sci. (U.S.A.) 105(30):10495-10500; Hofmeyer, K. et al. (2008) "*The Contrasting Role Of B7-H3*," Proc. Natl. Acad. Sci. (U.S.A.) 105 (30): 10277-10278).

In addition to its expression on neuroblastoma cells, human B7-H3 is also known to be expressed on a variety of other cancer cells (e.g., gastric, ovarian and non-small cell lung cancers). B7-H3 protein expression has been immunohistologically detected in tumor cell lines (Chapoval, A. et al. (2001) "*B7-H3: A Costimulatory Molecule For T Cell Activation and IFN-γ Production*," Nature Immunol. 2:269-274; Saatian, B. et al. (2004) "*Expression Of Genes For B7-H3 And Other T Cell Ligands By Nasal Epithelial Cells During Differentiation And Activation*," Amer. J. Physiol. Lung Cell. Mol. Physiol. 287:L217-L225; Castriconi et al. (2004) "*Identification Of 4Ig-B7-H3 As A Neuroblastoma-Associated Molecule That Exerts A Protective Role From An NK Cell-Mediated Lysis*," Proc. Natl. Acad. Sci. (U.S.A.) 101(34):12640-12645); Sun, M. et al. (2002) "*Characterization of Mouse and Human B7-H3 Genes*," J. Immunol. 168:6294-6297). mRNA expression has been found in heart, kidney, testes, lung, liver, pancreas, prostate, colon, and osteoblast cells (Collins, M. et al. (2005) "*The B7 Family Of Immune-Regulatory Ligands*," Genome Biol. 6:223.1-223.7). At the protein level, B7-H3 is found in human liver, lung, bladder, testis, prostate, breast, placenta, and lymphoid organs (Hofmeyer, K. et al. (2008) "*The Contrasting Role Of B7-H3*," Proc. Natl. Acad. Sci. (U.S.A.) 105(30):10277-10278).

II. Therapeutic Antibodies

In addition to their known uses in diagnostics, antibodies have been shown to be useful as therapeutic agents. For example, immunotherapy, or the use of antibodies for therapeutic purposes has been used in recent years to treat cancer. Passive immunotherapy involves the use of monoclonal antibodies in cancer treatments (see for example, DEVITA, HELLMAN, AND ROSENBERG'S CANCER: PRINCIPLES & PRACTICE OF ONCOLOGY, EIGHTH EDITION (2008), DeVita, V. et al. Eds., Lippincott Williams & Wilkins, Philadelphia, Pa., pp. 537-547, 2979-2990). These antibodies can have inherent therapeutic biological activity both by direct inhibition of tumor cell growth or survival and by their ability to recruit the natural cell killing activity of the body's immune system. These agents can be administered alone or in conjunction with radiation or chemotherapeutic agents. Rituximab and Trastuzumab, approved for treatment of non-Hodgkin's lymphoma and breast cancer, respectively, are examples of such therapeutics. Alternatively, antibodies can be used to make antibody conjugates in which the antibody is linked to a toxic agent and directs that agent to the tumor by specifically binding to the tumor. Gemtuzumab ozogamicin is an example of an approved antibody conjugate used for the treatment of leukemia.

Monoclonal antibodies that bind to cancer cells and have potential uses for diagnosis and therapy have been disclosed (see, for example, the following patent applications which disclose, inter alia, some molecular weights of target proteins: U.S. Pat. No. 6,054,561 (200 kD c-erbB-2 (Her2), and other unknown antigens 40-200 KD in size) and U.S. Pat. No. 5,656,444 (50 kD and 55 kD oncofetal protein)). Examples of antibodies in clinical trials and/or approved for treatment of solid tumors include: Trastuzumab (antigen: 180 kD, HER2/neu), Edrecolomab (antigen: 40-50 kD, Ep-CAM), Anti-human milk fat globules (HMFG1) (antigen >200 kD, HMW Mucin), Cetuximab (antigens: 150 kD and 170 kD, EGF receptor), Alemtuzumab (antigen: 21-28 kD, CD52), and Rituximab (antigen: 35 kD, CD20).

The antigen targets of trastuzumab (Her-2 receptor), which is used to treat breast cancer, and cetuximab (EGF receptor), which is in clinical trials for the treatment of several cancers, are present at some detectable level on a large number of normal human adult tissues including skin, colon, lung, ovary, liver, and pancreas. The margin of safety in using these therapeutics is possibly provided by the difference in the levels of antigen expression or in access of or activity of the antibody at these sites.

Another type of immunotherapy is active immunotherapy, or vaccination, with an antigen present on a specific cancer (s) or a DNA construct that directs the expression of the antigen, which then evokes the immune response in the individual, i.e., to induce the individual to actively produce antibodies against their own cancer. Active immunization has not been used as often as passive immunotherapy or immunotoxins.

Several models of disease (including cancer) progression have been suggested. Theories range from causation by a single infective/transforming event to the evolution of an increasingly "disease-like" or "cancer-like" tissue type leading ultimately to one with fully pathogenic or malignant capability. Some argue that with cancer, for example, a single mutational event is sufficient to cause malignancy, while others argue that subsequent alterations are also necessary. Some others have suggested that increasing mutational load and tumor grade are necessary for both initiation as well as progression of neoplasia via a continuum of mutation-selection events at the cellular level. Some cancer targets are found only in tumor tissues, while others are present in normal tissues and are up regulated and/or over-expressed in tumor tissues. In such situations, some researchers have suggested that the over-expression is linked to the acquisition of malignancy, while others suggest that the over-expression is merely a marker of a trend along a path to an increasing disease state.

In some cases, cancer targets, such as oncoproteins expressed or over-expressed in tumors, have been shown to be present during embryonic and fetal development and serve as a regulator of growth and differentiation. Some researchers have found that the expression of these onco-proteins during embryonic and fetal development appear to be restricted to specific tissues and also restricted to specific stages of development. In contrast, the expression of these oncoproteins in the adult has been shown to be associated with over-expression in tumor growth and/or a malfunction of tumor suppressor proteins.

An ideal diagnostic and/or therapeutic antibody would be specific for an antigen present on a large number of cancers, but absent or present only at low levels on any normal tissue. The discovery, characterization, and isolation of a novel antibody capable of binding to an antigen that is specifically associated with cancer(s) would be useful in many ways. First, the antibody would have biological activity against such cancer cells and be able to recruit the immune system's response to thereby treat the disease. The antibody could be administered as a therapeutic alone or in combination with current treatments or used to prepare immunoconjugates linked to toxic agents. An antibody with the same specificity but with low or no biological activity when administered alone could also be useful in that an antibody could be used to prepare an immunoconjugate with a radioisotope, a toxin, or a chemotherapeutic agent or liposome containing a chemotherapeutic agent, with the conjugated form being biologically active by virtue of the antibody directing the toxin to the antigen-containing cells.

As discussed above, antibodies and other molecules that that specifically bind to B7-H3 have been described (see, U.S. Pat. Nos. 7,527,969; 7,368,554; 7,358,354; and 7,279, 567; United States Patent Application Publications Nos. US 20090087416; US 20090022747; US 20090018315; US2008116219; US20080081346; US 20050202536; US20030103963; US20020168762; PCT Publications Nos. WO 2008/116219; WO 2006/016276; WO 2004/093894; WO 04/001381; WO 2002/32375; WO 2002/10187 and WO 2001/094413; EP 1292619B; Modak, S. et al. (March 1999) "*Disialoganglioside GD2 And Antigen 8H9: Potential Targets For Antibody-Based Immunotherapy Against Desmoplastic Small Round Cell Tumor (DSRCT) And Rhabdomyosarcoma (RMS),*" Proceedings Of The American Association For Cancer Research Annual Meeting, Vol. 40:474 (90$^{th}$ Annual Meeting Of The American Association For Cancer Research; Philadelphia, Pa., US; Apr. 10-14, 1999; Modak, S. et al. (March 2000) "*Radioimmunotargeting To Human Rhabdomyosarcoma Using Monoclonal Antibody 8H9,*" Proc. Am. Assoc. Cancer Res. 41:724; Modak, S. et al. (2001) "*Monoclonal Antibody 8H9 Targets A Novel Cell Surface Antigen Expressed By A Wide Spectrum Of Human Solid Tumors,*" Cancer Res. 61(10):4048-4054; Steinberger, P. et al. (2004) "*Molecular Characterization of Human 4Ig-B7-H3, a Member of the B7 Family with Four Ig-Like Domains,*" J. Immunol. 172(4):2352-2359; Xu, H. et al. (2009) "*MicroRNA miR-29 Modulates Expression of Immunoinhibitory Molecule B7-H3: Potential Implications for Immune Based Therapy of Human Solid Tumors,*" Cancer Res. 69(15):5275-6281).

Nevertheless, one aspect desirable for an ideal diagnostic and/or therapeutic antibody would be the discovery and characterization of novel antibodies capable of mediating, and particularly of enhancing the activation of the immune system against cancer cells (especially human cancer cells) that are associated with a variety of cancers. Such compositions would also be useful for drug discovery (e.g., small molecules) and for further characterization of cellular regulation, growth, and differentiation.

Thus, despite all prior advances, a need remains for improved compositions capable of binding to cancer cells and of facilitating or mediating an immune response against cancer cells. Such compositions may be used to diagnose and treat such cancers. There exists a further need, based on the discoveries disclosed herein, for novel compositions that specifically recognize dual targets on the surface of cells, and which can thereby modulate, either by reducing or enhancing, the capabilities of B7-H3 to mediate T-cell activation or by recognizing and killing cancer cells that express B7-H3. It is an object of this invention to identify such compositions. It is another object to provide novel compounds for use in the assay of B7-H3 expression.

As described in detail below, the present invention relates to novel antibodies, including in particular dual affinity retargeting reagents ("DARTS") that comprise modulators of B7-H3 T-cell activation, that are capable of influencing T-cell activation as well as novel antibodies that bind to B7-H3 receptors of cancer cells and facilitate or mediate the death of such cells. The present invention is directed to such compositions and to their uses in diagnostics and in the treatment of diseases such as cancer.

SUMMARY OF THE INVENTION

The present invention relates to antibodies that are immunoreactive to the mammalian, and more particularly, the human B7-H3 receptor and to uses thereof, particularly in the treatment of cancer and inflammation. The invention thus particularly concerns humanized B7-H3-reactive antibodies that are capable of mediating, and more preferably enhancing the activation of the immune system against cancer cells that are associated with a variety of human cancers.

In detail, the invention provides an isolated antibody, wherein the isolated antibody comprises an antibody light chain having the sequence SEQ ID NO: 117 or an antibody heavy chain having the sequence SEQ ID NO: 119. The invention particularly concerns the embodiments of such antibody wherein the isolated antibody comprises the antibody light chain having the sequence SEQ ID NO: 117; wherein the isolated antibody comprises the antibody heavy chain having the sequence SEQ ID NO: 119; and wherein the isolated antibody is an antibody whose light chains each have the sequence SEQ ID NO: 117 and whose heavy chain has the sequence SEQ ID NO: 119.

The invention particularly concerns the embodiments of such antibodies wherein the antibody binds to B7-H3 that is endogenously expressed on the surface of a cancer cell and/or wherein the antibody binds to B7-H3 expressed on the surface of a cancer cell and is internalized into the cell upon binding to the B7-H3.

The invention further provides a nucleic acid molecule that encodes any of the above-described isolated antibodies. The invention particularly concerns the embodiments of such nucleic acid molecule wherein the nucleic acid molecule has the light chain sequence SEQ ID NO: 118; wherein the nucleic acid molecule has the heavy chain sequence SEQ ID NO: 120; or wherein the nucleic acid molecule has both the light chain sequence SEQ ID NO: 118 and the heavy chain sequence SEQ ID NO: 120.

The invention further provides a vector comprising any of the above-described nucleic acid molecules. The invention further provides a host cell comprising any such vector. The invention further provides a cell that expresses any of the above-described antibodies.

The invention further provides a pharmaceutical composition comprising: (i) a therapeutically effective amount of any of the above-described isolated antibodies; and (ii) a pharmaceutically acceptable carrier. The invention particularly concerns the embodiments of such pharmaceutical composition, in which the pharmaceutical composition further comprises one or more additional anti-cancer agents (such as a chemotherapeutic agent, a radiation therapeutic agent, a hormonal therapeutic agent, a toxin or an immunotherapeutic agent). The invention particularly concerns the embodiments of such pharmaceutical composition, wherein such one or more additional anti-cancer agents is a toxin selected from the group consisting of: a taxane, a maytansinoid, an auristatin, a calicheamicin, an anthracycline, a CC-1065 analog, docetaxel, a cathepsin, ricin, gelonin, *Pseudomonas* exotoxin, diphtheria toxin, RNase, and a toxic radioisotope.

The invention further pertains to a use of any of the above-described isolated antibodies in the diagnosis of cancer, wherein the isolated antibody is detectably labeled, and to any of the above-described isolated detectably labeled antibodies for use in the diagnosis of cancer. The invention particularly concerns the embodiments of such use, characterized in that the cancer is characterized by the presence of a cancer cell selected from the group consisting of a cell of an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

The invention further pertains to a use of any of the above-described isolated antibodies or pharmaceutical compositions in the preparation of a medicament for the treatment of cancer in a patient, and to a medicament for use in providing such treatment. The invention further pertains to such use, characterized in that the cancer is characterized by the presence of a cancer cell selected from the group consisting of a cell of an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

The invention further pertains to any such uses, characterized in that the use further comprises administration of one or more additional cancer therapies selected from the group consisting of chemotherapy, immunotherapy, radiation therapy, hormonal therapy, and surgery.

BRIEF DESCRIPTION OF THE DRAWINGS

FIGS. 1A-1B show the results of IHC investigations conducted using normal pancreas, liver, lung and colon tissue specimens with BRCA84D at 0.625 µg/ml and 0.078 µg/ml (FIG. 1A) and normal heart, kidney and adrenal tissue with BRCA84D at 0.625 µg/ml (FIG. 1B).

FIGS. 3A-3B show dose-dependent redirected killing of A498 renal carcinoma cells (with resting PBMC at 18 hours (LDH)) by monoclonal antibodies reactive against B7-H3 (effector:target ratio of 20:1) (FIG. 3A: BRCA68D, BRCA69D, PRCA157, GB8, TCR-4420; FIG. 3B: OVCA22, BRCA84D, TDH6, TES7, TCR-4420). FIGS. 3C-3D show dose-dependent redirected killing of A549 lung cancer cells (with resting PBMC at 18 hours (LDH)) by monoclonal antibodies reactive against B7-H3 (effector:target ratio of 30:1) (FIG. 3C: BRCA84D, OVCA22, PRCA157, TES7; FIG. 3D: TDH6, BRCA68D, BRCA69D).

FIGS. 6A-6I show the results of BIACORE™ analyses of B7-H3 antibodies immobilized to B7-H3-2Ig (dashed gray lines) or B7-H3-4Ig (solid black lines). Antibodies were titrated from 0.063 µM to 1 µM. Time is in seconds.

FIG. 9B, Hs700t pancreatic cells).

FIGS. 11A-11B show the alignment of the amino acid residues of the variable light chains (FIG. 11A) or variable heavy chains (FIG. 11B) of BRCA84D and its humanized derivative, hBRCA84D.

FIG. 18C shows the predicted pharmacokinetic profiles generated using a 2-compartment model with parameters from the 5 mg/kg dose at 0.1, 0.5, 1, 5, and 10 mg/kg.

FIG. 21A shows the ability of anti-B7-H3 antibody Mab1 to prevent or inhibit tumor development in the murine xenograft model. Comparisons vs IgG control: Mab1 (1 and 5 mg/kg) vs IgG control * from day 51; Mab1 (10 mg/kg) vs IgG control  from day 48. FIG. 21B shows the ability of centuximab to prevent or inhibit tumor development in the murine xenograft model. Cetuximab (7 mg/kg) vs IgG control  from day 51; Cetuximab (15 mg/kg) vs IgG control * from day 58. FIG. 21C compares the results obtained at the maximum doses tested.

FIG. 28A shows the ability of anti-B7-H3 antibody Mab1 to prevent or inhibit tumor development in the murine xenograft model. FIG. 28B shows the ability of Docetaxel to prevent or inhibit tumor development in the murine xenograft model. FIG. 28C compares the results obtained at the maximum doses tested.

FIG. 30A shows the ability of anti-B7-H3 antibody Mab1 to prevent or inhibit tumor development in the murine xenograft model. FIG. 30B shows the ability of trastuzumab to prevent or inhibit tumor development in the murine xenograft model. FIG. 30C compares the results obtained at the maximum doses tested.

DETAILED DESCRIPTION OF THE INVENTION

Figure 1A:
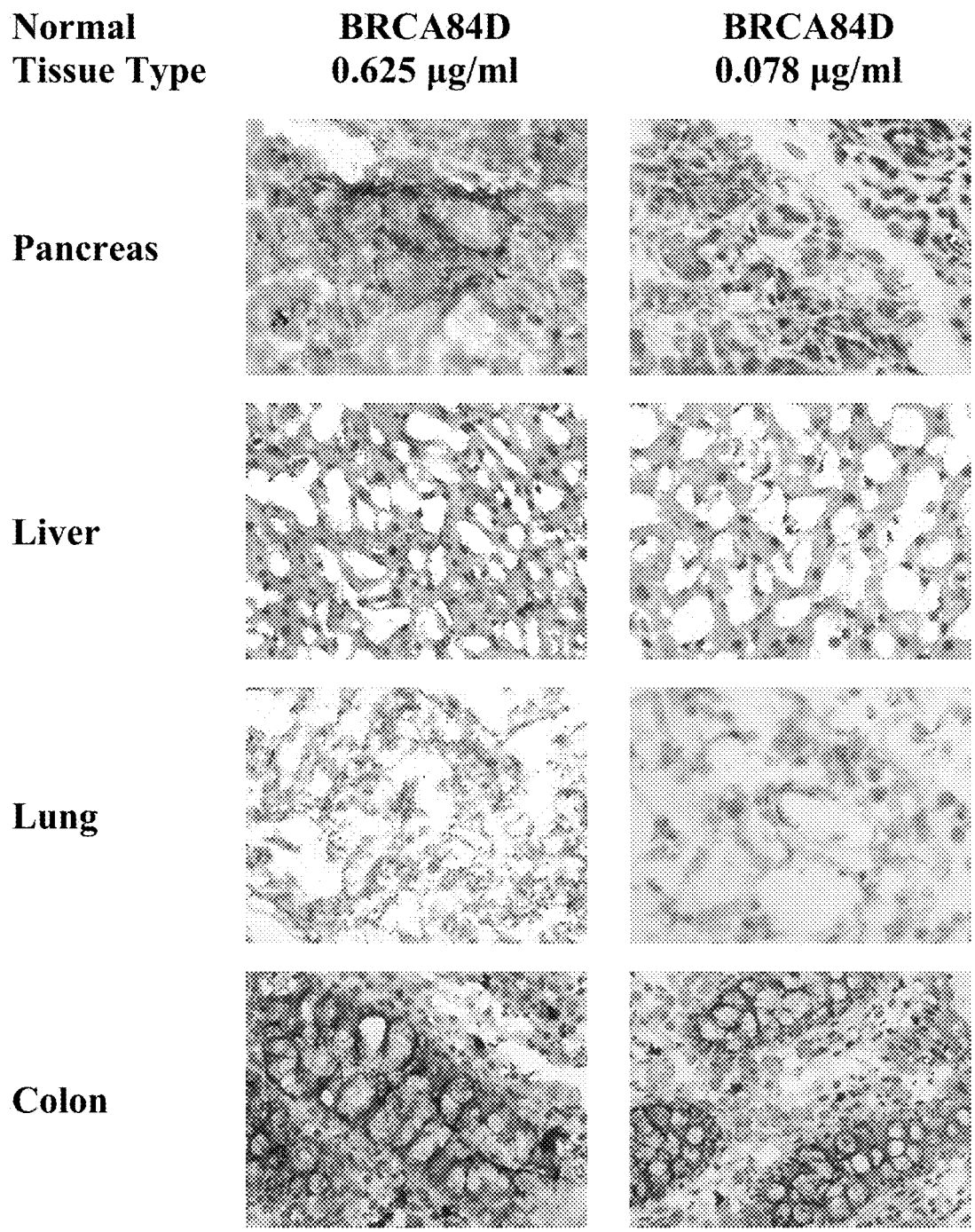

The present invention relates to antibodies that are immunoreactive to the mammalian, and more particularly, the human B7-H3 receptor and to uses thereof, particularly in the treatment of cancer and inflammation. The invention thus particularly concerns humanized B7-H3-reactive antibodies that are capable of mediating, and more preferably enhancing the activation of the immune system against cancer cells that are associated with a variety of human cancers.

I. General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, MOLECULAR CLONING: A LABORATORY MANUAL, Third Edition (Sambrook et al. Eds., 2001) Cold Spring Harbor Press, Cold Spring Harbor, N.Y.; OLIGONUCLEOTIDE SYNTHESIS: METHODS AND APPLICATIONS (Methods in Molecular Biology), Herdewijn, P., Ed., Humana Press, Totowa, N.J.; OLIGONUCLEOTIDE SYNTHESIS (Gait, M. J., Ed., 1984); METHODS IN MOLECULAR BIOLOGY, Humana Press, Totowa, N.J.; CELL BIOLOGY: A LABORATORY NOTEBOOK (Cellis, J. E., Ed., 1998) Academic Press, New York, N.Y.; ANIMAL CELL CULTURE (Freshney, R. I., Ed., 1987); INTRODUCTION TO CELL AND TISSUE CULTURE (Mather, J. P. and Roberts, P. E., Eds., 1998) Plenum Press, New York, N.Y.; CELL AND TISSUE CULTURE: LABORATORY PROCEDURES (Doyle, A. et al., Eds., 1993-8) John Wiley and Sons, Hoboken, N.J.; METHODS IN ENZYMOLOGY (Academic Press, Inc.) New York, N.Y.; WEIR'S HANDBOOK OF EXPERIMENTAL IMMUNOLOGY (Herzenberg, L. A. et al. Eds. 1997) Wiley-Blackwell Publishers, New York, N.Y.; GENE TRANSFER VECTORS FOR MAMMALIAN CELLS (Miller, J. M. et al. Eds., 1987) Cold Spring Harbor Press, Cold Spring Harbor, N.Y.; CURRENT PROTOCOLS IN MOLECULAR BIOLOGY (Ausubel, F. M. et al., Eds., 1987) Greene Pub. Associates, New York, N.Y.; PCR: THE POLYMERASE CHAIN REACTION, (Mullis, K. et al., Eds., 1994) Birkhäuser, Boston Mass.; CURRENT PROTOCOLS IN IMMUNOLOGY (Coligan, I. E. et al., eds., 1991) John Wiley and Sons, Hoboken, N.J.; SHORT PROTOCOLS IN MOLECULAR BIOLOGY (John Wiley and Sons, 1999) Hoboken, N.J.; IMMUNOBIOLOGY 7 (Janeway, C. A. et al. 2007) Garland Science, London, UK; Antibodies (P. Finch, 1997) Stride Publications, Devoran, UK; ANTIBODIES: A PRACTICAL APPROACH (D. Catty., ed., 1989) Oxford University Press, USA, New York N.Y.); MONOCLONAL ANTIBODIES: A PRACTICAL APPROACH (Shepherd, P. et al. Eds., 2000) Oxford University Press, USA, New York N.Y.; USING ANTIBODIES: A LABORATORY MANUAL (Harlow, E. et al. Eds., 1998) Cold Spring Harbor Laboratory Press, Cold Spring Harbor, N.Y.; THE ANTIBODIES (Zanetti, M. et al. Eds. 1995) Harwood Academic Publishers, London, UK); and DEVITA, HELLMAN, AND ROSENBERG'S CANCER: PRINCIPLES & PRACTICE OF ONCOLOGY, EIGHTH EDITION, DeVita, V. et al. Eds. 2008, Lippincott Williams & Wilkins, Philadelphia, Pa.

II. Definitions

As used herein, the term "B7-H3" refers to a member of the human B7 family of proteins, a type I membrane protein with Ig-like domains also known as CD276. The term "2Ig-B7-H3" denotes the B7-H3 form that comprises only two Ig-like domains; the term "4Ig-B7-H3" denotes the B7-H3 form that comprises four Ig-like domains (see, Sun, M. et al. (2002) "Characterization of Mouse and Human B7-H3 Genes," J. Immunol. 168:6294-6297; Steinberger et al. (2004), "Molecular Characterization Of Human 4Ig-B7-H3, A Member Of The B7 Family With Four Ig-Like Domains," J. Immunol. 2004, 172(4):2352-2359 and Castriconi et al. (2004) "Identification Of 4Ig-B7-H3 As A Neuroblastoma-Associated Molecule That Exerts A Protective Role From An NK Cell-Mediated Lysis," Proc. Natl. Acad. Sci. (U.S.A.) 101(34):12640-12645). The antigen "TEST" (WO 2008/066691) is an antigen sharing characteristics of the 4Ig-B7-H3. Accordingly, antibodies that specifically bind to TES7 bind to 41g-B7-H3. The TES7 antigen may have more than one different epitope, and epitopes may be non-linear. Several anti-B7-H3 antibodies are known to bind to non-linear epitopes, including some only present on the 41g-B7-H3 isoform. It is currently believed that TES7 may be over-expressed in certain cancer cells in comparison to their normal tissue counterparts.

Agonists, antagonists, and other modulators of B7-H3 function are expressly included within the scope of this invention. These agonists, antagonists and modulators are polypeptides that comprise one or more of the antigenic determinant sites of B7-H3, or comprise one or more fragments of such sites, variants of such sites, or peptidomimetics of such sites. These agonistic, antagonistic, and B7-H37 modulatory compounds are provided in linear or cyclized form, and optionally comprise at least one amino acid residue that is not commonly found in nature or at least one amide isostere. These compounds may be glycosylated.

More specifically, the terms "B7-H3 modulator" as used herein are defined as any compound that (1) is capable of disrupting or blocking the interaction between human B7-H3 and its native ligands or an anti-B7-H3 antibody; (2) is capable of binding to human B7-H3 and its native ligands or an anti-B7-H3 antibody; (3) contains an antigenic site that can be used in the raising of antibodies capable of binding to human B7-H3 and its native ligands or an anti-B7-H3 antibody; (4) contains an antigenic site that can be used in the screening of antibodies capable of binding to human B7-H3 and its native ligands or an anti-B7-H3 antibody; (5) contains an antigenic site that can be used in the raising of antibodies capable of disrupting or blocking the interaction between human B7-H3 and its native ligands or an anti-B7-H3 antibody; (6) contains an antigenic site that can be used in the screening of antibodies capable of disrupting or blocking the interaction between human B7-H3 and its native ligands or an anti-B7-H3 antibody. B7-H3 modulators may be "B7-H3 agonists" or "B7-H3 antagonists" depending on whether their activity enhances T cell activation or inhibits Tcell activation, respectively.

B7-H3 agonists, antagonists and modulators include B7-H3 variants, B7-H3 peptide antagonists, peptidomimetics, and small molecules, anti-B7-H3 antibodies and immunoglobulin variants, amino acid variants of human B7-H3 including amino acid substitution, deletion, and addition variants, or any combination thereof, and chimeric immunoglobulins. The B7-H3 agonists, antagonists and modulators of this invention are based on the identification of the B7-H3 domains involved in the binding of human B7-H3 to its native ligands or anti-B7-H3 antibodies. Thus, the invention provides B7-H3 agonists, antagonists and modulators with molecular structures that duplicate or mimic one or more of the anti-B7-H3 binding domains of human B7-H3.

As used herein, the term "B7-H3 variant" denotes any amino acid variant of human B7-H3, including amino acid substitution, deletion, and addition variants, or any combination thereof. The definition encompasses chimeric molecules such as human B7-H3/non-human chimeras and other hybrid molecules. Also included in the definition is any fragment of a B7-H3 variant molecule that comprises the variant or hybrid region(s) of the molecule.

As used herein, an "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses polyclonal or monoclonal antibodies, fusion proteins comprising an antibody portion with an antigen recognition site of the required specificity, humanized antibodies, chimeric antibodies, "BiTEs," "DART" molecules and any other modified configuration of the immunoglobulin molecule that comprises an antibody chain of the required specificity.

The term "BiTEs" (bi-specific T-cell engagers) refers to a single polypeptide chain molecule that having two antigen binding domains, one of which binds to a T-cell antigen and the second of which binds to an antigen present on the surface of a target (WO 05/061547; Baeuerle, P et al. (2008) "*BITE®: A New Class Of Antibodies That Recruit T Cells*," Drugs of the Future 33: 137-147; Bargou, et al. 2008) "*Tumor Regression in Cancer Patients by Very Low Doses of a T Cell-Engaging Antibody*," Science 321: 974-977).

The term "DART™" (dual affinity retargeting reagent) refers to an immunoglobulin molecule that comprises at least two polypeptide chains that associate (especially through a covalent interaction) to form at least two epitope binding sites, which may recognize the same or different epitopes. Each of the polypeptide chains of a DART™ comprise an immunoglobulin light chain variable region and an immunoglobulin heavy chain variable region, but these regions do not interact to form an epitope binding site. Rather, the immunoglobulin heavy chain variable region of one (e.g., the first) of the DART™ polypeptide chains interacts with the immunoglobulin light chain variable region of a different (e.g., the second) DART™ polypeptide chain to form an epitope binding site. Similarly, the immunoglobulin light chain variable region of one (e.g., the first) of the DART™ polypeptide chains interacts with the immunoglobulin heavy chain variable region of a different (e.g., the second) DART™ polypeptide chain to form an epitope binding site. DART™s may be monospecific, bispecific, trispecific, etc., thus being able to simultaneously bind one, two, three or more different epitopes (which may be of the same or of different antigens). DART™s may additionally be monovalent, bivalent, trivalent, tetravalent, pentavalent, hexavelent, etc., thus being able to simultaneously bind one, two, three, four, five, six or more molecules. These two attributes of DART™s (i.e., degree of specificity and valency may be combined, for example to produce bispecific antibodies (i.e., capable of binding two epitopes) that are tetravalent (i.e., capable of binding four sets of epitopes), etc. DART™ molecules are disclosed in PCT Publications WO 2006/113665, WO 2008/157379, and WO 2010/080538.

The term "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

The term "humanized antibody" refer to a chimeric molecule, generally prepared using recombinant techniques, having an antigen binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions. This eliminates the constant region as an immunogen in human individuals, but the possibility of an immune response to the foreign variable region remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When nonhuman antibodies are prepared with respect to a particular antigen, the variable regions can be "reshaped" or "humanized" by grafting CDRs derived from nonhuman antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

As used herein, an antibody or a polypeptide is said to "specifically" bind a region of another molecule (i.e., an epitope) if it reacts or associates more frequently, more rapidly, with greater duration and/or with greater affinity with that epitope relative to alternative epitopes. For example, an antibody that specifically binds to a B7-H3 epitope is an antibody that binds this B7-H3 epitope with greater affinity, avidity, more readily, and/or with greater duration than it binds to other B7-H3 epitopes or non-B7-H3 epitopes. It is also understood by reading this definition that, for example, an antibody (or moiety or epitope) that specifically binds to a first target may or may not specifically or preferentially bind to a second target. As such, "specific binding" does not necessarily require (although it can include) exclusive binding. Generally, but not necessarily, reference to binding means "specific" binding.

As used herein, the term "immunologically active" in reference to an epitope being or "remaining immunologically active" refers to the ability of an antibody (e.g., an anti-B7-H3 antibody) to bind to the epitope under different conditions, for example, after the epitope has been subjected to reducing and denaturing conditions.

Different biological functions are associated with anti-B7-H3 antibodies, including, but not limited to one or more of: an ability to specifically bind to B7-H3 (and in particular B7-H3 molecules that are expressed on the surfaces of cancer cells, including but not limited to kidney, prostate, or lung, cancer cells); an ability to competitively inhibits preferential binding of a known anti-B7-H3 antibody to B7-H3, including the ability to preferentially bind to the same B7-H3 epitope to which the original antibody preferentially binds; an ability to bind to a portion of B7-H3 that is exposed on the surface of a living cell in vitro or in vivo; an ability to bind to a portion of B7-H3 that is exposed on the surface of living cancer cells, such as but not limited to prostate, lung or kidney cancer cells; an ability to deliver a chemotherapeutic agent to cancerous cells (such as kidney, prostate, or lung cancer cells) expressing B7-H3 on their surface; and/or an ability to deliver a therapeutic agent or detectable marker into cancer cells expressing B7-H3 on their surface. As discussed herein, polypeptides (including antibodies) of the invention may have any one or more of these characteristics.

An "anti-B7-H3 equivalent antibody" or "anti-B7-H3 equivalent polypeptide" refers to an antibody or a polypeptide having one or more biological functions associated with an anti-B7-H3 antibody, such as, for example binding specificity.

As used herein, the term "agent" refers to a biological, pharmaceutical, or chemical compound. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

Agents that are employed in the methods of this invention can be randomly selected or rationally selected or designed. As used herein, an agent is said to be randomly selected when the agent is chosen without prior consideration or knowledge of the specific amino acid or other chemical moieties involved in the association of the molecule with its native binding partner(s) or known antibodies. An example of a randomly selected agent is an agent that is identified through the use and screening of a chemical library or a peptide combinatorial library.

As used herein, an agent is said to be rationally selected or designed when the agent is chosen on a non-random basis that takes into account the sequence of the target site and/or its conformation in connection with the agent's action. With respect to anti-B7-H3 agents, it is currently believed that there are at least three epitopes on B7-H3 against which antibodies can be raised and therefore at least three sites of action for agents that block B7-H3/anti-B7-H3 interaction. This invention also encompasses agents that act at the sites of interaction between B7-H3 and its native binding partner, although other ligands and their active B7-H3-interactive sites are also encompassed within the scope of this invention, whether currently known or later identified. Agents can be rationally selected or rationally designed by utilizing the peptide sequences that make up the contact sites of the receptor/ligand and/or B7-H3/anti-B7-H3 antibody complex. For example, a rationally selected peptide agent can be a peptide whose amino acid sequence is identical to an epitope appearing on B7-H3 as it is exposed on the surface of a living cell in its native environment. Such an agent will reduce or block the association of the anti-B7-H3 antibody with B7-H3, or the association of B7-H3 with its native ligand, as desired, by binding to the anti-B7-H3 antibody or to the native ligand.

As used herein, the term "labeled," with regard to an antibody, is intended to encompass direct labeling of the antibody by coupling (i.e., physically linking) a detectable substance, such as a radioactive agent or a fluorophore (e.g. phycoerythrin (PE) or fluorescein isothiocyanate (also known as fluoroisothiocyanate or FITC)) to the antibody, as well as indirect labeling of the probe or antibody by reactivity with a detectable substance.

As used herein, the term "association", with regard to an antibody, includes covalent and non-covalent attachment or binding of an agent (e.g., chemotherapeutic agent) to the antibody. The antibody can be associated with an agent (e.g., chemotherapeutic agent) by direct binding or indirect binding via attachment to a common platform, such that the antibody directs the localization of the agent to the cancerous cell to which the antibody binds and wherein the antibody and agent do not substantially dissociate under physiological conditions such that the agent is not targeted to the same cancerous cell to which the antibody binds or such that the agent's potency is not decreased.

The term "biological sample" encompasses a variety of sample types obtained from an individual and can be used in a diagnostic or monitoring assay. The definition encompasses saliva, blood and other liquid samples of biological origin, solid tissue samples such as a biopsy specimen or tissue cultures or cells derived therefrom, and the progeny thereof, for example, cells obtained from a tissue sample collected from an individual suspected of having cancer, in preferred embodiments from ovary, lung, prostate, pancreas, colon, and breast tissue. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

The term "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, the term "delaying development of metastasis" means to defer, hinder, slow, retard, stabilize, and/or postpone development of metastasis. This delay can be of varying lengths of time, depending on the history of the cancer and/or individual being treated. As is evident to one skilled in the art, a sufficient or significant delay can, in effect, encompass prevention, in that the individual does not develop the metastasis.

As used herein, an "effective amount" of a pharmaceutical composition, in one embodiment, is an amount sufficient to effect beneficial or desired results including, without limitation, clinical results such as shrinking the size of the tumor (in the cancer context, for example, breast or prostate cancer), retardation of cancerous cell growth, delaying the development of metastasis, decreasing symptoms resulting from the disease, increasing the quality of life of those suffering from the disease, decreasing the dose of other medications required to treat the disease, enhancing the effect of another medication such as via targeting and/or internalization, delaying the progression of the disease, and/or prolonging survival of individuals. An effective amount can be administered in one or more administrations. For purposes of this invention, an effective amount of drug, compound, or pharmaceutical composition is an amount sufficient to reduce the proliferation of (or destroy) cancerous cells and to reduce and/or delay the development, or growth, of metastases of cancerous cells, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art. Typical dosages comprise 0.1-to 100 mg/kg/body weight. The preferred dosages comprise 1 to 100 mg/kg/body weight. The most preferred dosages comprise 10 to 100 mg/kg/body weight.

As used herein, a nucleic acid molecule or agent, antibody, composition or cell, etc., is said to be "isolated" when that nucleic acid molecule, agent, antibody, composition, or cell, etc. is substantially separated from contaminant nucleic acid molecules, antibodies, agents, compositions, or cells, etc. naturally present in its original source.

The term "individual" refers to a vertebrate animal, preferably a mammal Mammals include, but are not limited to, humans, farm animals, sport animals, pets, primates, mice and rats. In the most preferred embodiment, the term individual denotes a human.

The terms "polypeptide," "oligopeptide," "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

It is understood that, because the polypeptides of this invention are based upon an antibody, the polypeptides can occur as single chains or as associated chains.

Also encompassed within the scope of the invention are peptidomimetics of the B7-H3 peptide agonists, antagonists and modulators (including anti-B7-H3 antibodies) described herein. Such peptidomimetics include peptides wherein at least one amino acid residue is substituted with an amino acid residue that is not commonly found in nature, such as the D isomer of the amino acid or an N-alkylated species of the amino acid. In other embodiments, peptidomimetics are constructed by replacing at least one amide bond (—C(=O)—NH—) in a B7-H3 peptide agonist, antagonist or modulators with an amide isostere. Suitable amide isosteres include —CH$_2$—NH—, —CH$_2$—S—, CH$_2$—S(O)—, —CH$_2$—S(O)$_2$—, —CH$_2$—CH$_2$—, —CH=CH— (E or Z form), —C(=O)—CH$_2$—, —CH(CN)—NH—, —C(OH)—CH$_2$—, and —O—C(=O)—NH—. The amide bonds in a B7-H3 peptide agonist, antagonist or modulator that are suitable candidates for replacement with amide isosteres include bonds that are hydrolyzable by the endogenous esterases or proteases of the intended subject of B7-H3 peptide agonist, antagonist or modulator treatment.

As used herein, the term "substantially pure" refers to material that is at least 50% pure (i.e., free from contaminants), more preferably at least 90% pure, more preferably at least 95% pure, more preferably at least 98% pure, more preferably at least 99% pure, and most preferably greater than 99% pure.

As used herein, the term "toxin" refers to any substance, which effects an adverse response within a cell. For example, a toxin directed to a cancerous cell would have an adverse, sometimes deleterious effect, on the cancerous cell. Examples of toxins include, but are not limited to, a taxane, a maytansinoid, an auristatin (e.g., monomethyl auristatin (MMAE), monomethyl auristatin F (MMAF), auristatin E (AE), etc.) (such as those disclosed in U.S. Pat. Nos. 5,208,020; 5,416,064; 6,333,410; 6,340,701; 6,372,738; 6,436,931; 6,441,163; 6,596,757; 7,276,497; 7,585,857; or 7,851,432), a calicheamicin, an anthracycline (e.g., doxorubicin), a CC-1065 analog, docetaxel; cathepsin B or E; ricin, gelonin, Pseudomonas exotoxin, diphtheria toxin, and RNase; radiolabeled antibodies (e.g., tiuxetan-conjugated or labeled with a toxic radioisotope (for example, $^{90}$Y; $^{131}$I, $^{177}$Lu, $^{186}$Re, $^{188}$Re, $^{211}$At, $^{212}$Bi, $^{213}$Bi, $^{225}$Ac, etc.).

As used herein, the terms "treatment" or "treating" denote an approach for obtaining a beneficial or desired result including and preferably a beneficial or desired clinical result. Such beneficial or desired clinical results include, but are not limited to, one or more of the following: reducing the proliferation of (or destroying) cancerous cells or other diseased, reducing metastasis of cancerous cells found in cancers, shrinking the size of the tumor, decreasing symptoms resulting from the disease, increasing the quality of life of those suffering from the disease, decreasing the dose of other medications required to treat the disease, delaying the progression of the disease, and/or prolonging survival of individuals.

As used herein, the term cancer is intended to encompass cancers characterized by the presence of a cancer cell selected from the group consisting of a cell of an adrenal gland tumor, an AIDS-associated cancer, an alveolar soft part sarcoma, an astrocytic tumor, bladder cancer (squamous cell carcinoma and transitional cell carcinoma), bone cancer (adamantinoma, aneurismal bone cysts, osteochondroma, osteosarcoma), a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular canrcinoma, an islet cell tumor, a Kaposi's Sarcoma, a kidney cancer (nephroblastoma, papillary renal cell carcinoma), a leukemia, a lipoma/benign lipomatous tumor, a liposarcoma/malignant lipomatous tumor, a liver cancer (hepatoblastoma, hepatocellular carcinoma), a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer (carcinoma of the cervix, endometrial carcinoma, and leiomyoma).

III. Methods of Making Antibodies and Polypeptides

Methods of making monoclonal antibodies are known in the art. One method which may be employed is the method of Kohler, G. et al. (1975) "*Continuous Cultures Of Fused Cells Secreting Antibody Of Predefined Specificity*," Nature 256:495-497 or a modification thereof. Typically, monoclonal antibodies are developed in non-human species, such as mice. In general, a mouse or rat is used for immunization but other animals may also be used. The antibodies are produced by immunizing mice with an immunogenic amount of cells, cell extracts, or protein preparations that contain human B7-H3. The immunogen can be, but is not limited to, primary cells, cultured cell lines, cancerous cells, nucleic acids, or tissue. In one embodiment, human lung carcinoma cells are used. Cells used for immunization, for example, human testis or pancreatic adenocarcinoma or stomach cells, may be cultured for a period of time (e.g., at least 24 hours) prior to their use as an immunogen. Cells (e.g., human testis, stomach, or pancreatic adenocarcinoma cells) may be used as immunogens by themselves or in combination with a non-denaturing adjuvant, such as Ribi. In general, cells should be kept intact and preferably viable when used as immunogens. Intact cells may allow antigens to be better detected than ruptured cells by the immunized animal. Use of denaturing or harsh adjuvants, e.g., Freud's adjuvant, may rupture cells and therefore is discouraged. The immunogen may be administered multiple times at periodic intervals such as, b i weekly, or weekly, or may be administered in such a way as to maintain viability in the animal (e g, in a tissue recombinant).

In one embodiment, monoclonal antibodies that bind to B7-H3 are obtained by using host cells that over-express B7-H3 as an immunogen. Such cells include, by way of example and not by limitation, human lung carcinoma cells and human colon cancer cells.

To monitor the antibody response, a small biological sample (e.g., blood) may be obtained from the animal and tested for antibody titer against the immunogen. The spleen and/or several large lymph nodes can be removed and dissociated into single cells. If desired, the spleen cells may be screened (after removal of non-specifically adherent cells) by applying a cell suspension to a plate or to a well coated with the antigen. B-cells, expressing membrane-bound immunoglobulin specific for the antigen, will bind to the plate, and are not rinsed away with the rest of the suspension. Resulting B-cells, or all dissociated spleen cells, can then be fused with myeloma cells (e.g., X63-Ag8.653 and those from the Salk Institute, Cell Distribution Center, San Diego, Calif.). Polyethylene glycol (PEG) may be used to fuse spleen or lymphocytes with myeloma cells to form a hybridoma. The hybridoma is then cultured in a selective medium (e.g., hypoxanthine, aminopterin, thymidine medium, otherwise known as "HAT medium"). The resulting hybridomas are then plated by limiting dilution, and are assayed for the production of antibodies that bind specifically to the immunogen, using, for example, FACS (fluorescence activated cell sorting) or immunohistochemistry (IHC) screening. The selected monoclonal antibody-secreting hybridomas are then cultured either in vitro (e.g., in tissue culture bottles or hollow fiber reactors), or in vivo (e.g., as ascites in mice).

As another alternative to the cell fusion technique, Epstein-Barr Virus (EBV)-immortalized B cells may be used to produce monoclonal antibodies of the subject invention. The hybridomas are expanded and subcloned, if desired, and supernatants are assayed for anti-immunogen activity by conventional assay procedures (e.g., FACS, IHC, radioimmunoassay, enzyme immunoassay, fluorescence immunoassay, etc.).

In another alternative, anti-B7-H3 monoclonal antibody and any other equivalent antibodies can be sequenced and produced recombinantly by any means known in the art (e.g., humanization, use of transgenic mice to produce fully human antibodies, phage display technology, etc.). In one embodiment, anti-B7-H3 monoclonal antibody is sequenced and the polynucleotide sequence is then cloned into a vector for expression or propagation. The sequence encoding the antibody of interest may be maintained in a vector in a host cell and the host cell can then be expanded and frozen for future use.

The polynucleotide sequence of anti-B7-H3 monoclonal antibody and any other equivalent antibodies may be used for genetic manipulation to generate a "humanized" antibody, to improve the affinity, or other characteristics of the antibody. The general principle in humanizing an antibody involves retaining the basic sequence of the antigen-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; and 6,331,415.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains (see, for example, Winter et al. (1991) "Man-made Anditbodies," Nature 349: 293-299; Lobuglio et al. (1989) "Mouse/Human Chimeric Monoclonal Antibody In Man: Kinetics And Immune Response," Proc. Natl. Acad. Sci. (U.S.A.) 86:4220-4224 (1989), Shaw et al. (1987) "Characterization Of A Mouse/Human Chimeric Monoclonal Antibody (17-1A) To A Colon Cancer Tumor-Associated Antigen," J. Immunol. 138:4534-4538, and Brown et al. (1987) "Tumor-Specific Genetically Engineered Murine/Human Chimeric Monoclonal Antibody," Cancer Res. 47:3577-3583). Other references describe rodent CDRs grafted into a human supporting framework region (FR) prior to fusion with an appropriate human antibody constant domain (see, for example, Riechmann, L et al. (1988) "Reshaping Human Antibodies for Therapy," Nature 332:323-327; Verhoeyen, M. et al. (1988) "Reshaping Human Antibodies: Grafting An Antilysozyme Activity," Science 239:1534-1536; and Jones et al. (1986) "Replacing The Complementarity-Determining Regions In A Human Antibody With Those From A Mouse," Nature 321: 522-525). Another reference describes rodent CDRs supported by recombinantly veneered rodent framework regions. See, for example, European Patent Publication No. 519,596. These "humanized" molecules are designed to minimize unwanted immunological response toward rodent anti-human antibody molecules, which limits the duration and effectiveness of therapeutic applications of those moieties in human recipients. Other methods of humanizing antibodies that may also be utilized are disclosed by Daugherty et al. (1991) "Polymerase Chain Reaction Facilitates The Cloning, CDR-Grafting, And Rapid Expression Of A Murine Monoclonal Antibody Directed Against The CD18 Component Of Leukocyte Integrins," Nucl. Acids Res. 19:2471-2476 and in U.S. Pat. Nos. 6,180,377; 6,054,297; 5,997,867; and 5,866,692.

The invention also encompasses single chain variable region fragments ("scFv") of antibodies of this invention, such as mu-anti-B7-H3. Single chain variable region fragments are made by linking light and/or heavy chain variable regions by using a short linking peptide. Bird et al. (1988) ("Single-Chain Antigen-Binding Proteins," Science 242: 423-426) describes example of linking peptides which bridge approximately 3.5 nm between the carboxy terminus of one variable region and the amino terminus of the other variable region. Linkers of other sequences have been designed and used (Bird et al. (1988) "Single-Chain Antigen-Binding Proteins," Science 242:423-426). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

The invention includes modifications to antibodies and polypeptides that bind to B7-H3 and its agonists, antagonists, and modulators, including functionally equivalent antibodies and polypeptides that do not significantly affect their properties and variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tryosine. These polypeptides also include glycosylated and nonglycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention also encompasses fusion proteins comprising one or more of the polypeptides or antibodies of this invention. In one embodiment, a fusion polypeptide is provided that comprises a light chain, a heavy chain or both a light and heavy chain In another embodiment, the fusion polypeptide contains a heterologous immunoglobulin constant region. In another embodiment, the fusion polypeptide contains a light chain variable region and a heavy chain variable region of an antibody produced from a publicly-deposited hybridoma. For purposes of this invention, an antibody fusion protein contains one or more polypeptide domains that specifically bind to B7-H3 and another amino acid sequence to which it is not attached in the native molecule, for example, a heterologous sequence or a homologous sequence from another region.

An anti-B7-H3 polypeptide, and other B7-H3 agonists, antagonists and modulators can be created by methods known in the art, for example, synthetically or recombinantly. One method of producing B7-H3 peptide agonists, antagonists and modulators involves chemical synthesis of the polypeptide, followed by treatment under oxidizing conditions appropriate to obtain the native conformation, that is, the correct disulfide bond linkages. This can be accomplished using methodologies well known to those skilled in the art (see, e.g., Kelley, R. F. et al. (1990) In: GENETIC ENGINEERING PRINCIPLES AND METHODS, Setlow, J. K. Ed., Plenum Press, N.Y., vol. 12, pp 1-19; Stewart, J. M et al. (1984) SOLID PHASE PEPTIDE SYNTHESIS, Pierce Chemical Co., Rockford, Ill.; see also U.S. Pat. Nos. 4,105,603; 3,972,859; 3,842,067; and 3,862,925).

Polypeptides of the invention may be conveniently prepared using solid phase peptide synthesis (Merrifield, B. (1986) "Solid Phase Synthesis," Science 232(4748):341-347; Houghten, R. A. (1985) "*General Method For The Rapid Solid-Phase Synthesis Of Large Numbers Of Peptides: Specificity Of Antigen Antibody Interaction At The Level Of Individual Amino Acids*," Proc. Natl. Acad. Sci. (U.S.A.) 82(15) :5131-5135; Ganesan, A. (2006) "*Solid-Phase Synthesis In The Twenty-First Century*," Mini Rev. Med. Chem. 6(1):3-10).

In yet another alternative, fully human antibodies may be obtained through the use of commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are XENOMOUSE™ (Abgenix, Inc., Fremont, Calif.) and HUMAB-MOUSE® and TC MOUSE™ (both from Medarex, Inc., Princeton, N.J.).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants {e.g., tobacco) or transgenic milk. Suitable methods for expressing antibodies recombinantly in plants or milk have been disclosed (see, for example, Peeters et al. (2001) "*Production Of Antibodies And Antibody Fragments In Plants*," Vaccine 19:2756; Lonberg, N. et al. (1995) "*Human Antibodies From Transgenic Mice*," Int. Rev. Immunol 13:65-93; and Pollock et al. (1999) "*Transgenic Milk As A Method For The Production Of Recombinant Antibodies*," J. Immunol Methods 231:147-157). Suitable methods for making derivatives of antibodies, e.g., humanized, single chain, etc. are known in the art. In another alternative, antibodies may be made recombinantly by phage display technology (see, for example, U.S. Pat. Nos. 5,565,332; 5,580,717; 5,733,743; 6,265,150; and Winter, G. et al. (1994) "*Making Antibodies By Phage Display Technology*," Annu. Rev. Immunol. 12.433-455).

The antibodies or protein of interest may be subjected to sequencing by Edman degradation, which is well known to those of skill in the art. The peptide information generated from mass spectrometry or Edman degradation can be used to design probes or primers that are used to clone the protein of interest.

An alternative method of cloning the protein of interest is by "panning" using purified B7-H3 or portions thereof for cells expressing the antibody or protein of interest. B7-H3 exists in a "2Ig" form and as a "4Ig" form. The amino acid sequence of the "2Ig" form of human B7-H3 is (SEQ ID NO: 1):

```
MLRRRGSPGM GVHVGAALGA LWFCLTGALE VQVPEDPVVA

LVGTDATLCC SFSPEPGFSL AQLNLIWQLT DTKQLVHSFA

EGQDQGSAYA NRTALFPDLL AQGNASLRLQ RVRVADEGSF

TCFVSIRDFG SAAVSLQVAA PYSKPSMTLE PNKDLRPGDT

VTITCSSYRG YPEAEVFWQD GQGVPLTGNV TTSQMANEQG

LFDVHSVLRV VLGANGTYSC LVRNPVLQQD AHGSVTITGQ

PMTFPPEALW VTVGLSVCLI ALLVALAFVC WRKIKQSCEE

ENAGAEDQDG EGEGSKTALQ PLKHSDSKED DGQEIA
```

The cDNA sequence encoding the "2Ig" form of human B7-H3 is (SEQ ID NO: 2):

```
atgctgcgtc ggcggggcag ccctggcatg ggtgtgcatg tgggtgcagc cctgggagca ctgtggttct gcctcacagg agccctggag gtccaggtcc ctgaagaccc agtggtggca ctggtgggca ccgatgccac cctgtgctgc tccttctccc ctgagcctgg cttcagcctg gcacagctca acctcatctg gcagctgaca gataccaaac agctggtgca cagctttgct gagggccagg accagggcag cgcctatgcc aaccgcacgg ccctcttccc ggacctgctg gcacagggca acgcatccct gaggctgcag cgcgtgcgtg tggcggacga gggcagcttc acctgcttcg tgagcatccg ggatttcggc agcgctgccg tcagcctgca ggtggccgct ccctactcga agcccagcat gaccctggag cccaacaagg acctgcggcc aggggacacg gtgaccatca cgtgctccag ctaccggggc taccctgagg ctgaggtgtt ctggcaggat gggcagggtg tgcccctgac tggcaacgtg accacgtcgc agatggccaa cgagcagggc ttgtttgatg tgcacagcgt cctgcgggtg gtgctgggtg cgaatggcac ctacagctgc ctggtgcgca accccgtgct gcagcaggat gcgcacggct ctgtcaccat cacagggcag cctatgacat tccccccaga ggccctgtgg gtgaccgtgg ggctgtctgt ctgtctcatt gcactgctgg tggccctggc tttcgtgtgc tggagaaaga tcaaacagag ctgtgaggag gagaatgcag gagctgagga ccaggatggg gagggagaag gctccaagac agccctgcag cctctgaaac actctgacag caaagaagat gatggacaag aaatagcc
```

The amino acid sequence of the "2Ig" form of human B7-H3 (SEQ ID NO: 1) (shown in bold and underline below) is completely embraced within the "4Ig" form of human B7-H3(SEQ ID NO: 76):

```
MLRRRGSPGM GVHVGAALGA LWFCLTGALE VQVPEDPVVA

LVGTDATLCC SFSPEPGFSL AQLNLIWQLT DTKQLVHSFA

EGQDQGSAYA NRTALFPDLL AQGNASLRLQ RVRVADEGSF

TCFVSIRDFG SAAVSLQVAA PYSKPSMTLE PNKDLRPGDT
```

```
VTITCSSYQG YPEAEVFWQD GQGVPLTGNV TTSQMANEQG

LFDVHSILRV VLGANGTYSC LVRNPVLQQD AHSSVTITPQ

RSPTGAVEVQ VPEDPVVALV GTDATLRCSF SPEPGFSLAQ

LNLIWQLTDT KQLVHSFTEG RDQGSAYANR TALFPDLLAQ

GNASLRLQRV RVADEGSFTC FVSIRDFGSA AVSLQVAAPY

SKPSMTLEPN KDLRPGDTVT ITCSSYRGYP EAEVFWQDGQ

GVPLTGNVTT SQMANEQGLF DVHSVLRVVL GANGTYSCLV

RNPVLQQDAH GSVTITGQPM TFPPEALWVT VGLSVCLIAL

LVALAFVCWR KIKQSCEEEN AGAEDQDGEG EGSKTALQPL

KHSDSKEDDG QEIA
```

The cDNA sequence encoding the "4Ig" form of human B7-H3 is (SEQ ID NO: 77); residues encoding the "2Ig" form of B&-H3 are shown in bold and underlined:

```
atgctgcgtc ggcggggcag ccctggcatg ggtgtgcatgtgggtgcagc cctgggagca ctgtggttct gcctcacagg agccctggag gtccaggtcc ctgaagaccc agtggtggca ctggtgggca ccgatgccac cctgtgctgc tccttctccc ctgagcctgg cttcagcctg gcacagctca acctcatctg gcagctgaca gataccaaac agctggtgca cagctttgct gagggccagg accagggcag cgcctatgcc aaccgcacgg ccctcttccc ggacctgctg gcacagggca acgcatccct gaggctgcag cgcgtgcgtg tggcggacga gggcagcttc acctgcttcg tgagcatccg ggatttcggc agcgctgccg tcagcctgca ggtggccgct ccctactcga agcccagcat gaccctggag cccaacaagg acctgcggcc aggggacacg gtgaccatca cgtgctccag ctaccagggc taccctgagg ctgaggtgtt ctggcaggat gggcagggtg tgccctgac tggcaacgtg accacgtcgc agatgccaa cgagcagggc ttgtttgatg tgcacagcat cctgcgggtg gtgctgggtg caaatggcac ctacagctgc ctggtgcgca accccgtgct gcagcaggat gcgcacagct ctgtcaccat cacaccccag agaagcccca caggagccgt ggaggtccag gtccctgagg accggtggt ggccctagtg ggcaccgatg ccaccctgcg ctgctccttc tccccgagc ctggcttcag cctggcacag ctcaacctca tctggcagct gacagacacc aaacagctgg tgcacagttt caccgaaggc cgggaccagg gcagcgccta tgccaaccgc acggccctct tcccggacct gctggcacaa ggcaatgcat ccctgaggct gcagcgcgtg cgtgtggcgg acgagggcag cttcacctgc ttcgtgagca tccgggattt cggcagcgct gccgtcagcc tgcaggtggc cgctccctac tcgaagccca gcatgaccct ggagcccaac aaggacctgc ggccagggga cacggtgacc atcacgtgct ccagctaccg gggctaccct gaggctgagg tgttctggca ggatgggcag ggtgtgcccc tgactggcaa cgtgaccacg tcgcagatgg ccaacgagca gggcttgttt gatgtgcaca gcgtcctgcg ggtggtgctg ggtgcgaatg gcacctacag ctgcctggtg cgcaaccccg tgctgcagca ggatgcgcac ggctctgtca ccatcacagg gcagcctatg acattccccc cagaggccct gtgggtgacc gtggggctgt ctgtctgtct cattgcactg ctggtggccc tggctttcgt gtgctggaga aagatcaaac agagctgtga ggaggagaat gcaggagctg aggaccagga tgggaggga gaaggctcca agacagccct gcagcctctg aaacactctg acagcaaaga agatgatgga caagaaatag cc
```

The "panning" procedure may be conducted by obtaining a cDNA library from tissues or cells that express B7-H3, over-expressing the cDNAs in a second cell type, and screening the transfected cells of the second cell type for a specific binding to B7-H3. Detailed descriptions of the methods used in cloning mammalian genes coding for cell surface proteins by "panning" can be found in the art (see, for example, Aruffo, A. et al. (1987) "*Molecular Cloning Of A CD28 cDNA By A High-Efficiency COS Cell Expression System*," Proc. Natl. Acad. Sci. (U.S.A.) 84:8573-8577 and Stephan, J. et al. (1999) "*Selective Cloning Of Cell Surface Proteins Involved In Organ Development: Epithelial Glycoprotein Is Involved In Normal Epithelial Differentiation*," Endocrinol. 140:5841-5854).

cDNAs encoding anti-B7-H3 antibodies, and other B7-H3 peptide agonists, antagonists and modulators can be obtained by reverse transcribing the mRNAs from a particular cell type according to standard methods in the art. Specifically, mRNA can be isolated using various lytic enzymes or chemical solutions according to the procedures set forth in Sambrook et al. supra or extracted by commercially available nucleic-acid-binding resins following the accompanying instructions provided by manufacturers (e.g., Qiagen, Invitrogen, Promega). The synthesized cDNAs are then introduced into an expression vector to produce the antibody or protein of interest in cells of a second type. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, and cosmids.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose of isolating the genes encoding the antibody, polypeptide or protein of interest. Non-limiting examples of suitable mammalian host cells include but are not limited to COS, HeLa, and CHO cells. Preferably, the host cells express the cDNAs at a level of about 5-fold higher, more preferably 10-fold higher, even more preferably 20-fold higher than that of the corresponding endogenous antibody or protein of interest, if present, in the host cells. Screening the host cells for a specific binding to B7-H3 is effected by an immunoassay or FACS. A cell over-expressing the antibody or protein of interest can be identified.

Various techniques are also available which may now be employed to produce mutant B7-H3 peptide agonists, antagonists, and modulators which encodes for additions, deletions, or changes in amino acid sequence of the resultant protein relative to the parent B7-H3 peptide agonist, antagonist or modulator molecule.

The invention includes polypeptides comprising an amino acid sequence of the antibodies of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an anti-B7-H3 polypeptide could be produced by an automated polypeptide synthesizer employing the solid phase method.

IV. Methods for Screening Polypeptides and Monoclonal Antibodies

Several methods may be used to screen polypeptides and monoclonal antibodies that bind to B7-H3. It is understood that "binding" refers to biologically or immunologically relevant specific binding, and does not refer to non-specific binding that may occur, for example, when an immunoglobulin is used at a very high concentration against a non-specific target. In one embodiment, monoclonal antibodies are screened for binding to B7-H3 using standard screening techniques. In this manner, anti-B7-H3 monoclonal antibody was obtained. The preferred hybridomas of the present invention are those that produce antibodies BRCA69D, BRCA84D or PRCA157.

Additional monoclonal antibodies that bind to B7-H3 may be identified. For this purpose, monoclonal antibodies are screened for their differential ability to bind to cancerous tissues but not to non-cancerous cells. In one embodiment, monoclonal antibodies which bind to B7-H3 and that are also cross-reactive to human cancerous cells or tissues, but not to normal cells or tissues to the same degree, are selected. One method that may be employed for screening is immunohistochemistry (IHC). Standard immunohistochemical techniques are known to those of average skill in the art. See, for example, ANIMAL CELL CULTURE METHODS (J. P. Mather and D. Barnes, eds., Academic Press, NY, Vol. 57, Ch. 18 and 19, pp. 314-350, 1998). Biological samples (e.g., tissues) may be obtained from biopsies, autopsies, or necropsies. To ascertain if B7-H3 is present only on cancerous cells, anti-B7-H3 antibodies may be used to detect the presence of B7-H3 on tissues from individuals with cancer while other non-cancerous tissues from the individual suffering from cancer or tissues from individuals without cancer are used as a control. The tissue can be embedded in a solid or semi-solid substance that prevents damage during freezing (e.g., agarose gel or OCT) and then sectioned for staining Cancers from different organs and at different grades can be used to screen monoclonal antibodies. Examples of tissues that may be used for screening purposes include but are not limited to ovary, breast, lung, prostate, colon, kidney, skin, thyroid, brain, heart, liver, stomach, nerve, blood vessels, bone, upper digestive tract, and pancreas. Examples of different cancer types that may be used for screening purposes include, but are not limited to, carcinomas, adenocarcinomas, sarcomas, adenosarcomas, lymphomas, and leukemias.

In yet another alternative, cancerous cells lines such as HMEC (BioWhittaker CC-2251), HUVEC (Primary endothelial cells), BT-474 (ATCC # HTB-20), MCF7 (ATCC # HTB22), MDA-MB-175-VII (ATCC # HB-25), MDA-MB-361 (ATCC # HB-27), SKBR3 (ATCC # HTB-30), A549 (ATCC # CCL-185), Calu-3 (ATCC # HTB-55), SKMES-I (ATCC # HTB-58), ES-2 (ATCC # CRL-1978), SKOV3 (ATCC # HTB-77), Panc-1 (ATCC # CRL-1469), AsPC-I (ATCC # CRL-1682), HPAF-II (ATCC # CRL-1997), Hs700T (ATCC # HTB-174), Colo205 (ATCC # CCL-222), HT-29 (ATCC # HTB-38), SW480 (ATCC # CCL-228), SW948 (ATCC # CCL-237), 293 (ATCC # CRL-1573), 786-O (ATCC # CRL-1932), A498 (ATCC # HTB-44), Caki-2 (ATCC # HTB-47), COS-7 (ATCC # CRL-1651), RL-65 (ATCC # CRL-10345), SV-T2 (ATCC # CCL-163.1), 22RV1 (ATCC # CRL-2505), DU145 (ATCC # HTB-81), LNCaP (ATCC # CRL-1740), PC-3 (ATCC # CRL-1435), HT29 (ATCC # HTB-38), Hs746T (ATCC # HTB-135), NCI-N87 (ATCC # CRL-5822) and normal cells from their respective tissues may be used to screen for monoclonal antibodies which are specific for cancerous tissue. Primary, or low passage, cell cultures derived from normal tissues from different organs, including but not limited to, kidney, ovary, breast, lung, prostate, colon, kidney, skin, thyroid, aortic smooth muscle, and endothelial cells can be used as negative controls. The cancerous or non-cancerous cells can be grown on glass slides or coverslips, or on plastic surfaces, or prepared in a CellArray™ device, as described in WO 01/43869, and screened for the binding of antibody using IHC as described above for tissues. Alternatively, cells may be removed from the growth surface using non-proteolytic means and spun into a pellet, which is then embedded and treated as tissues for IHC analysis as described above. Cells may be inoculated into immunodeficient animals, a tumor allowed to grow, and then this tumor may be harvested, embedded, and used as a tissue source for IHC analysis. In another alternative, single cells may be screened by incubating with the primary antibody, a secondary "reporter" antibody linked to a fluorescent molecule and then analyzed using a fluorescent activated cell-sorting (FACS) machine.

Any of several different detection systems may be utilized to detect binding of antibodies to tissue section. Typically, immunohistochemistry involves the binding of a primary antibody to the tissue and then a secondary antibody reactive against the species from the primary antibody was generated and conjugated to a detectable marker (e.g., horseradish peroxidase, HRP, or diaminobenzedine, DAB). One alternative method that may be used is polyclonal mirror image complementary antibodies or polyMICA™ (polyclonal Mirror Image Complementary Antibodies; The Binding Site Limited, Birmingham, UK; Mangham, D. C. et al. (1999) "*A Novel Immunohistochemical Detection System Using Mirror Image Complementary Antibodies (MICA)*," Histopathology 35(2):129-33). The PolyMICA™ technique can be used to test binding of primary antibodies (e.g., anti-B7-H3 antibodies) to normal and cancerous tissue. Several kinds of polyMICA™ Detection kits are commercially available: Product No. HK004.D is a polyMICA™ Detection kit which uses DAB chromagen; Product No. HK004.A is a polyMICA™ Detection kit which uses AEC chromagen. Alternatively, the primary antibody may be directly labeled with the detectable marker.

The first step in IHC screening to select for an appropriate antibody is the binding of primary antibodies raised in mice (e.g., anti-B7-H3 antibodies) to one or more immunogens (e.g., cells or tissue samples). In one embodiment, the tissue sample is sections of frozen tissue from different organs. The cells or tissue samples can be either cancerous or non-cancerous.

Frozen tissues can be prepared, sectioned, with or without fixation, and IHC performed by any of a number of methods known to one familiar with the art (see, for example, Stephan et al. (1999) "*Distribution And Function Of The Adhesion Molecule BEN During Rat Development*," Dev. Biol. 212:264-277 and Stephan et al. (1999) "*Selective Cloning Of Cell Surface Proteins Involved In Organ Development: Epithelial Glycoprotein Is Involved In Normal Epithelial Differentiation*," Endocrinology 140:5841-5854).

V. Methods of Characterizing Anti-B7-H3 Antibodies

Any of several methods can be used to characterize anti-B7-H3 antibodies. One method is to identify the epitope to which it binds. Epitope mapping is commercially available from various sources, for example, Pepscan Systems (Lelystad, The Netherlands). Epitope mapping can be used to determine the sequence to which an anti-B7-H3 antibody binds. The epitope can be a linear epitope, i.e., contained in a single stretch of amino acids, or a conformational epitope formed by a three-dimensional interaction of amino acids that may not necessarily be contained in a single stretch.

Peptides of varying lengths (e.g., preferably at least 4-6 amino acids long) can be isolated or synthesized {e.g., recombinantly) and used for binding assays with anti-B7-H3 antibody. The epitope to which anti-B7-H3 antibody binds can be determined in a systematic screening by using overlapping peptides derived from the extracellular sequence and determining binding by anti-B7-H3 antibody.

Yet another method that can be used to characterize an anti-B7-H3 antibody is to use competition assays with other antibodies known to bind to the same antigen, i.e., B7-H3 to determine if anti-B7-H3 antibodies binds to the same epitope as other antibodies. Examples of commercially available antibodies to B7-H3 may be available and may be identified using the binding assays taught herein. Competition assays are well known to those of skill in the art, and such procedures and illustrative data are detailed further in the Examples. Anti-B7-H3 antibodies can be further characterized by the tissues, type of cancer or type of tumor to which they bind.

Another method of characterizing anti-B7-H3 antibodies is by the antigen to which it binds. Anti-B7-H3 antibodies were used in Western blots with cell lysates from various human cancers. As is known to one of skill in the art, Western blotting can involve running cell lysates and/or cell fractions on a denaturing or non-denaturing gel, transferring the proteins to nitrocellulose paper, and then probing the blot with an antibody (e.g., anti-B7-H3 antibody) to see which proteins are bound by the antibody. B7-H3 is associated with various human cancers of different tissues including, but not limited to colon, breast, ovary, pancreas and lung.

VI. Methods of Diagnosing Cancer Using Anti-B7-H3 Antibodies and B7-H3 Modulators Monoclonal antibodies to B7-H3 made by the methods disclosed herein may be used to identify the presence or absence of cancerous cells in a variety of tissues, including but not limited to, ovary, breast, lung, prostate, colon, kidney, pancreas, skin, thyroid, brain, heart, liver, stomach, nerve, blood vessels, bone, and upper digestive tract, for purposes of diagnosis. Monoclonal antibodies to B7-H3 made by the methods disclosed herein may also be used to identify the presence or absence of cancerous cells, or the level thereof, which are circulating in blood after their release from a solid tumor. Such circulating antigen may be an intact B7-H3 antigen, or a fragment thereof that retains the ability to be detected according to the methods taught herein. Such detection may be effected by FACS analysis using standard methods commonly used in the art.

These uses can involve the formation of a complex between B7-H3 and an antibody that binds specifically to B7-H3. Examples of such antibodies include but are not limited to those anti-B7-H3 monoclonal antibodies produced by the hybridomas BRCA84D, BRCA69D, and PRCA157. The formation of such a complex can be in vitro or in vivo. Without being bound by theory, monoclonal antibody anti-B7-H3 can bind to B7-H3 through the extracellular domain of B7-H3 and may then be internalized.

In a preferred embodiment of the diagnostic methods of this invention, the antibody bears a detectable label. Examples of labels that may be used include a radioactive agent or a fluorophore, such as phycoerythrin or fluorescein isothiocyanate (also known as fluoroisothiocyanate or FITC).

As with other known antibodies used commercially for diagnostic and therapeutic purposes, the target antigen of this invention is broadly expressed in normal tissue. It is also up regulated in some tumors. Therefore, the particular dosages and routes of delivery of the antibodies of this invention as used for diagnostic or therapeutic agents will be tailored to the particular tumor or disease state at hand, as well as to the particular individual being treated.

One method of using the antibodies for diagnosis is in vivo tumor imaging by linking the antibody to a radioactive or radio-opaque agent, administering the antibody to the individual and using an x-ray or other imaging machine to visualize the localization of the labeled antibody at the surface of cancer cells expressing the antigen. The antibody is administered at a concentration that promotes binding at physiological conditions.

In vitro techniques for detection of B7-H3 are routine in the art and include enzyme linked immunosorbent assays (ELISAs), immunoprecipitations, immunofluorescence, enzyme immunoassay (EIA), radioimmunoassay (RIA), and Western blot analysis.

In aspects of this invention, methods of radioimaging of tumors or neoplasms, or of measuring the effectiveness of a method of treatment with a radiolabeled antibody, comprising the step of administering a radiolabeled, tumor-specific antibody to an individual following the practice of this invention. The radiolabeled antibody may be a monoclonal or polyclonal antibody comprising a radiolabel, preferably selected from the group consisting of Technetium-99m, Indium-111, Iodine-131, Rhenium-186, Rhenium-188, Samarium-153, Lutetium-177, Copper-64, Scandium-47, Yttrium-90. Monoclonal antibodies labeled with therapeutic radionuclides such as Iodine-131, Rhenium-188, Holmium-166, Samarium-153 and Scandium-47, which do not compromise the immunoreactivity of antibodies and are not broken down in vivo, are especially preferred. The person skilled in the art will appreciate that other radioactive isotopes are known, and may be suitable for specific applications. The radioimaging may be conducted using Single Photon Emission Computer Tomography (SPECT), Position Emission Tomography (PET), Computer Tomography (CT) or Magnetic Resonance Imaging (MRI). Correlative imaging, which permits greater anatomical definition of location of metastases located by radioimmunoimaging, is also contemplated.

In other methods, the cancerous cells are removed and the tissue prepared for immunohistochemistry by methods well known in the art (e.g., embedding in a freezing compound, freezing and sectioning, with or without fixation; fixation and paraffin embedding with or without various methods of antigen retrieval and counterstaining) The monoclonal antibodies may also be used to identify cancerous cells at different stages of development. The antibodies may also be used to determine which individuals' tumors express the antigen on their surface at a pre-determined level and are thus candidates for immunotherapy using antibodies directed against said antigen. The antibodies may recognize both primary and metastasizing cancers that express B7-H3. As used herein, detection may include qualitative and/or quantitative detection and may include comparing the level measured to a normal cell for an increased level of expression of B7-H3 in cancerous cells.

The invention also provides methods of aiding diagnosis of cancer characterized by cancer cells that express B7-H3 in an individual using any antibody that binds to B7-H3 and any other methods that can be used determine the level of B7-H3 expression. As used herein, methods for "aiding diagnosis" means that these methods assist in making a clinical determination regarding the classification, or nature, of cancer, and may or may not be conclusive with respect to the definitive diagnosis. Accordingly, a method of aiding diagnosis of cancer can comprise the step of detecting the level of B7-H3 in a biological sample from the individual and/or determining the level of B7-H3 expression in the sample. Antibodies recognizing the antigen or a portion thereof may also be used to create diagnostic immunoassays for detecting antigen released or secreted from living or dying cancer cells in bodily fluids, including but not limited to, blood, saliva, urine, pulmonary fluid, or ascites fluid.

Not all cells in a particular tumor of interest will express B7-H3, and cancerous cells in other tissues may express B7-H3, thus an individual should be screened for the presence or absence of B7-H3 on cancerous cells to determine the usefulness of immunotherapy in the individual. The anti-B7-H3 antibodies made by the methods disclosed herein may be used to determine whether an individual diagnosed with cancer may be deemed a candidate for immunotherapy using antibodies directed against B7-H3. In one embodiment, a cancerous tumor or a biopsy sample may be tested for expression of B7-H3, using antibodies directed against B7-H3. Individuals with cancer cells that express B7-H3 are suitable candidates for immunotherapy using antibodies directed against B7-H3. Staining with anti-B7-H3 antibody may also be used to distinguish cancerous tissues from normal tissues.

Methods of using anti-B7-H3 antibodies for diagnostic purposes are useful both before and after any form of anti-cancer treatment, e.g., chemotherapy or radiation therapy, to determine which tumors are most likely to respond to a given treatment, prognosis for individual with cancer, tumor subtype or origin of metastatic disease, and progression of the disease or response to treatment.

The compositions of this invention are also suitable for diagnosis of disease states other than cancer, using the methods generally described above in application with other diseased (non-cancerous) cells. Disease states suitable for use in the methods of this invention include, but are not limited to, diseases or disorders associated with inflammatory or autoimmune responses in individuals. The methods described above may be used for modulating inflammatory or autoimmune responses in individuals. Diseases and conditions resulting from inflammation and autoimmune disorders that may be subject to diagnosis and/or treatment using the compositions and methods of the invention include, by way of illustration and not of limitation, multiple sclerosis, meningitis, encephalitis, stroke, other cerebral traumas, inflammatory bowel disease including ulcerative colitis and Crohn's disease, myasthenia gravis, lupus, rheumatoid arthritis, asthma, acute juvenile onset diabetes, AIDS dementia, atherosclerosis, nephritis, retinitis, atopic dermatitis, psoriasis, myocardial ischemia and acute leukocyte-mediated lung injury.

Still other indications for diagnostic and/or therapeutic use of antibodies and other therapeutic agents of the invention include administration to individuals at risk of organ or graft rejection. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue.

Uses described anywhere in this application for anti-B7-H3 antibodies also encompass the use of other B7-H3 agonists, antagonists and modulators as described herein. In such embodiments, the B7-H3 agonist, antagonist or other non-antibody modulator is substituted for the B7-H3 antibody in the steps described, and alterations within the scope of the ordinarily skilled practitioner are made to tailor the method to the substituted B7-H3 modulatory composition.

Monoclonal antibodies to B7-H3 made by the methods disclosed herein may be used to identify the presence or absence of human cancer stem cells in a variety of tissues. Cancer stem cells (CSCs) have been hypothesized to play a role in tumor growth and metastasis (Ghotra, V. P. et al. (2009) "*The Cancer Stem Cell Microenvironment And Anti-Cancer Therapy*," Int. J. Radiat. Biol. 85(11):955-962; Gupta, P. B. et al. (2009) "*Cancer Stem Cells: Mirage Or Reality?*" Nat. Med. 15(9):1010-1012; Lawson, J. C. et al. (2009) "*Cancer Stem Cells In Breast Cancer And Metastasis*," Breast Cancer Res. Treat. 118(2):241-254; Hermann, P C et al. (2009) "*Pancreatic Cancer Stem Cells Insights And Perspectives*," Expert Opin. Biol. Ther. 9(10):1271-1278; Schatton, T. et al. (2009) "*Identification And Targeting Of Cancer Stem Cells*," Bioessays 31(10):1038-1049; Mittal, S. et al. (2009) "*Cancer Stem Cells: The Other Face Of Janus*," Amer. J. Med. Sci. 338(2):107-112; Alison, M. R. et al. (2009) "*Stem Cells And Lung Cancer: Future Therapeutic Targets?*" Expert Opin. Biol. Ther. 9(9):1127-1141; Charafe-Jauffret, E. et al. (2009) "*Breast Cancer Stem Cells: Tools And Models To Rely On*," BMC Cancer 9:202; Scopelliti, A. et al. (2009) "*Therapeutic Implications Of Cancer Initiating Cells*," Expert Opin. Biol. Ther. 9(8):1005-1016; PCT Publication WO 2008/091908). Under this hypothesis, the CSCs provide a small, distinct subset of cells within each tumor that are capable of indefinite self-renewal and of developing into the more adult tumor cell(s) that are relatively limited in replication capacity. It has been hypothesized that these cancer stem cells might be more resistant to chemotherapeutic agents, radiation or other toxic conditions, and thus, persist after clinical therapies and later grow into secondary tumors, metastases or be responsible for relapse. It has been suggested that CSCs can arise either from 'normal' tissue stem cells or from more differentiated tissue progenitor cells.

Human cancer stem cells have several defining characteristics. Such characteristics are described in PCT Publication WO 2008/091908 and are hereby incorporated by reference. Monoclonal antibodies to cell surface targets on cancer stem cells can be used to identify the presence or absence of cancer stem cells in a variety of tissues. As indicated above, monoclonal antibodies to B7-H3 made by the methods disclosed herein may also be used to identify the presence or absence of cancer stem cells, or the level of cancer stem cells in a sample or tissue or in circulation after their release from a solid tumor. Such circulating antigen may be an intact B7-H3 antigen, or a fragment thereof that retains the ability to be detected according to the methods taught herein. Such detection may be effected by FACS analysis using standard methods commonly used in the art. In another embodiment, such detection may be effected by immunohistochemical analysis of tissue samples using standard methods commonly used in the art.

These uses can involve the formation of a complex between B7-H3 and an antibody that binds specifically to B7-H3 on cancer stem cells. Examples of such antibodies include but are not limited to those anti-B7-H3 monoclonal antibodies produced by the hybridomas BRCA84D, BRCA69D, and PRCA157. The formation of such a complex can be in vitro or in vivo.

Uses described in this application that recite their use for anti-B7-H3 antibodies also encompass the use of other B7-H3 agonists, antagonists and modulators as described herein for the use of identification and treatment of cancer stem cells. In such embodiments, anti-B7-H3 antibodies and other B7-H3 agonists, antagonists and modulators are used for identification, diagnosis or therapeutic treatment of cancer stem cells using similar methods described, and alterations within the scope of the ordinary skilled practitioner are made to tailor the method to the identification/diagnosis or treatment of cancer stem cells.

VII. Preferred Compositions of the Present Invention

The present invention encompasses compositions, including pharmaceutical compositions, comprising anti-B7-H3 antibodies, polypeptides derived from anti-B7-H3 antibodies, polynucleotides comprising sequence encoding anti-B7-H3 antibodies, and other agents as described herein. As used herein, compositions further comprises one or more antibodies, polypeptides and/or proteins that bind to B7-H3, B7-H3 agonists, antagonists, modulators, and/or one or more polynucleotides comprising sequences encoding one or more antibodies, polypeptides and proteins that bind to B7-H3.

The invention further provides for conjugates of any B7-H3 peptide agonist, antagonist or modulator, and additional chemical structures that support the intended function or functions of the particular B7-H3 peptide agonist, antagonist or modulator.

These conjugates include B7-H3 peptide agonist, antagonist or modulator covalently bound to a macromolecule such as any insoluble, solid support matrix used in the diagnostic, screening or purification procedures discussed herein. Suitable matrix materials include any substance that is chemically inert, has high porosity and has large numbers of functional groups capable of forming covalent linkages with peptide ligands. Examples of matrix materials and procedures for preparation of matrix-ligand conjugates are described in Dean et al. (Eds) AFFINITY CHROMATOGRAPHY: A PRACTICAL APPROACH, IRL Press (1985); Lowe, "*An Introduction to Affinity Chromatography*", in Work et al. (eds) LABORATORY TECHNIQUES IN BIOCHEMISTRY AND MOLECULAR BIOLOGY, Vol. 7, Part II, North-Holland (1979); Porath et al., "*Biospecific Affinity Chromatography*", in Neurath, H. et al. (eds), THE PROTEINS, 3rd ed., Vol. 1, pp. 95-178 (1975); and Schott, H. AFFINITY CHROMATOGRAPHY, Macel Dekker, Inc. NY (1984).

Also provided herein are conjugates of B7-H3 peptide agonist, antagonist or modulator and any reporter moiety used in the diagnostic procedures discussed herein. The B7-H3 peptide agonist, antagonist or modulator agents, polypeptides and proteins of this invention, including anti-B7-H3 antibodies, are further identified and characterized by any (one or more) of the following criteria:
- (a) an ability to specifically bind to B7-H3 (and in particular B7-H3 molecules that are expressed on the surfaces of cancer cells, including but not limited to kidney, prostate, or lung, cancer cells);
- (b) an ability to competitively inhibits preferential binding of a known anti-B7-H3 antibody to B7-H3, including the ability to preferentially bind to the same B7-H3 epitope to which the original antibody preferentially binds;
- (c) an ability to bind to a portion of B7-H3 that is exposed on the surface of a living cell in vitro or in vivo;
- (d) an ability to bind to a portion of B7-H3 that is exposed on the surface of living cancer cells that express B7-H3;
- (e) an ability to deliver a chemotherapeutic agent to cancerous cells (such as kidney, prostate, or lung cancer cells) expressing B7-H3 on their surface; and/or (f) an ability to deliver a therapeutic agent or detectable marker into cancer cells (such as but not limited to prostate cancer cells) expressing B7-H3 on their surface.

A preferred antibody of the invention will exhibit differential IHC staining of tumor tissue relative to normal, non-cancerous tissue, and will moreover be capable of testing in primate (and particularly cynomolgus monkey) models of antibody efficacy. Preferred antibodies of the present invention will additionally exhibit desirable levels of affinity and antigen specificity. Preferred antibodies of the present invention will additionally exhibit desirable levels of immunomodulatory activity and cellular internalization.

In some embodiments, the antibody of the invention is an antibody that is produced by hybridoma BRCA84D, BRCA69D, or PRCA157, or progeny thereof. The present invention also encompasses various formulations of antibodies produced by these deposited hybridomas and equivalent antibodies, chimeric antibodies, single chain (scFv), mutants thereof, fusion proteins comprising an antibody portion, humanized antibodies, and any other modified configuration of any of these or equivalent antibodies that comprises an antigen (B7-H3), recognition site of the required specificity. The invention also provides human antibodies displaying one or more of the biological characteristics of an anti-B7-H3 family member. The equivalent antibodies of the anti-B7-H3 family (including humanized antibodies and human antibodies), polypeptide fragments, and polypeptides comprising any of these fragments are identified and characterized by any (one or more) of the five criteria described above. Murine and exemplary humanized variable domain sequences of an anti-B7-H3 antibody are provided in PCT Publication WO 2008/066691. Such sequences are provided by way of illustration not limitation, and different sequences as well as fragments and variants of the provided sequences, are encompassed within the scope of this invention.

BRCA84D, BRCA69D, and PRCA157 are the preferred B7-H3 antibodies of the present invention due to their cleaner normal tissue IHC profiles, stronger tumor/normal IHC differential, moderate to strong binding (BIACORE™/IHC), cross-reactivity to B7-H3 of cynomolgus monkeys and potent activity toward universal DART molecules ("UDARTs") relative to the other antibodies. In particularly preferred embodiments, the invention encompasses chimeric and humanized variants of these preferred antibodies, as well as native and chimeric and humanized variants of these preferred antibodies that possess modified Fc regions as described below. The invention additionally encompasses DART molecules that possess the epitope binding regions of such antibodies, particularly in concert with epitope binding region(s) that bind to the T-cell receptor, NKG2D receptor, or to a tumor-associated antigen or to a hapten such as fluorescein (e.g., fluorescein isothiocyanate (also known as fluoroisothiocyanate or FITC).

In some embodiments, the antibodies, polypeptides and proteins of the invention that bind to B7-H3 are antibodies, polypeptides and proteins that competitively inhibit preferential binding of a herein-specified anti-B7-H3 antibody to B7-H3. In some embodiments, the antibodies, the polypeptides and the proteins preferentially bind to the same epitope on B7-H3 as the antibody mu-anti-B7-H3 preferentially binds.

Accordingly, the invention provides any of the following (or compositions, including pharmaceutical compositions, comprising any of the following): (a) an antibody produced by the host cell with a deposit number identified above or its progeny; (b) a humanized form of such an antibody; (c) an antibody comprising one or more of the light chain and/or heavy chain variable regions of such an antibody; (d) a chimeric antibody comprising variable regions homologous or derived from variable regions of a heavy chain and a light chain of such an antibody, and constant regions homologous or derived from constant regions of a heavy chain and a light chain of a human antibody; (e) an antibody comprising one or more of the light chain and/or heavy chain CDRs (at least one, two, three, four, five, or six) of such an antibody; (f) an antibody comprising a heavy and/or a light chain of such an antibody; (g) a human antibody that is equivalent to such an antibody. A humanized form of the antibody may or may not have CDRs identical to that original antibody, or antibody produced by a host cell with a deposit number identified above. Determination of CDR regions is well within the skill of the art. In some embodiments, the invention provides an antibody which comprises at least one CDR that is substantially homologous to at least one CDR, at least two, at least three, at least four, at least 5 CDRs of an antibody produced by one of the above-identified deposited hybridomas (or, in some embodiments substantially homologous to all 6 CDRs of one of these antibodies, or derived from one of these antibodies), or antibody produced by the host cell with a deposit number identified above. Other embodiments include antibodies that have at least two, three, four, five, or six CDR(s) that are substantially homologous to at least two, three, four, five or six CDRs of an antibody produced from a hybridoma deposited as identified herein, or derived from such an antibody. It is understood that, for purposes of this invention, binding specificity and/or overall activity (which may be in terms of delivering a chemotherapeutic agent to or into cancerous cells to reduce the growth and/or proliferation of cancer cells, to induce apoptotic cell death in the cancer cell, to delay the development of metastasis, and/or treating palliatively) is generally retained, although the extent of activity may vary compared to an antibody produced by a deposited hybridoma (may be greater or lesser). The invention also provides methods of making any of these antibodies. Methods of making antibodies are known in the art and are described herein.

The invention also provides polypeptides comprising an amino acid sequence of the antibodies of the invention. In some embodiments, the polypeptide comprises one or more of the light chain and/or heavy chain variable regions of the antibody. In some embodiments, the polypeptide comprises one or more of the light chain and/or heavy chain CDRs of the antibody. In some embodiments, the polypeptide comprises three CDRs of the light chain and/or heavy chain of the antibody. In some embodiments, the polypeptide comprises an amino acid sequence of the antibody that has any of the following: at least 5 contiguous amino acids of a sequence of the original antibody, at least 8 contiguous amino acids, at least about 10 contiguous amino acids, at least about 15 contiguous amino acids, at least about 20 contiguous amino acids, at least about 25 contiguous amino acids, at least about 30 contiguous amino acids, wherein at least 3 of the amino acids are from a variable region of the antibody. In one embodiment, the variable region is from a light chain of the original antibody. In another embodiment, the variable region is from a heavy chain of the antibody. In another embodiment, the 5 (or more) contiguous amino acids are from a complementarity-determining region (CDR) of the antibody.

In some embodiments of this invention, cells of this invention that express B7-H3, a portion of B7-H3, anti-B7-H3 antibodies or other B7-H3-binding polypeptides of this invention are administered directly to an individual to modulate in vivo B7-H3 biological activity.

The preferred anti-B7-H3 antibodies of the present invention are BRCA84D, BRCA69D and PRCA157, all of which antibodies are murine antibodies reactive toward the human B7-H3 molecule. The amino acid and encoding polynucleotide sequences of the variable light chain and variable heavy chain of BRCA84D, BRCA69D and PRCA157 are shown below along with the respective $CDR_1$, $CDR_2$ and $CDR_3$ domains of each such chain. Those of skill in the art will therefore be able to construct antibodies having such CDRs, as well as derivatives thereof, capable of binding to the epitopes recognized by BRCA84D, BRCA69D and PRCA157.

A. Sequences of BRCA84D (1) BRCA84D Light Chain Sequences

Amino Acid Sequence of BRCA84D Variable Light Chain (SEQ ID NO: 3):

```
DIAMTQSQKF MSTSVGDRVS VTCKASQNVD TNVAWYQQKP

GQSPKALIYS ASYRYSGVPD RFTGSGSGTD FTLTINNVQS

EDLAEYFCQQ YNNYPFTFGS GTKLEIK
```

Polynucleotide Sequence Encoding BRCA84D Variable Light Chain (SEQ ID NO: 4):

```
gacattgcga tgacccagtc tcaaaaattc atgtccacat cagtaggaga cagggtcagc gtcacctgca aggccagtca gaatgtggat actaatgtag cctggtatca acagaaacca gggcaatctc ctaaagcact gatttactcg gcatcctacc ggtacagtgg agtccctgat cgcttcacag gcagtggatc tgggacagat ttcactctca ccatcaacaa tgtgcagtct gaagacttgg cagagtattt ctgtcagcaa tataacaact atccattcac gttcggctcg gggacaaagt tggaaataaa a
```

BRCA84D Variable Light Chain $CDR_1$ (SEQ ID NO: 5): KASQNVDTNVA

Polynucleotide Sequence Encoding BRCA84D Variable Light Chain $CDR_1$ (SEQ ID NO: 6): aaggccagtc agaatgtgga tactaatgta gcc BRCA84D Variable Light Chain $CDR_2$ (SEQ ID NO: 7): SASYRYS Polynucleotide Sequence Encoding BRCA84D Variable Light Chain $CDR_2$ (SEQ ID NO: 8): tcggcatcct accggtacag t BRCA84D Variable Light Chain $CDR_3$ (SEQ ID NO: 9): QQYNNYPFT Polynucleotide Sequence Encoding BRCA84D Variable Light Chain $CDR_3$ (SEQ ID NO: 10): cagcaatata acaactatcc attcacg (2) BRCA84D Heavy Chain Sequences Amino Acid Sequence of BRCA84D Variable Heavy Chain (SEQ ID NO: 11):

```
DVQLVESGGG LVQPGGSRKL SCAASGFTFS SFGMHWVRQA

PEKGLEWVAY ISSDSSAIYY ADTVKGRFTI SRDNPKNTLF

LQMTSLRSED TAMYYCGRGR ENIYYGSRLD YWGQGTTLTV SS
```

Polynucleotide Sequence Encoding BRCA84D Variable Heavy Chain (SEQ ID NO: 12):

```
gatgtgcagc tggtggagtc tgggggaggc ttagtgcagc ctggagggtc ccggaaactc tcctgtgcag cctctggatt cactttcagt agctttggaa tgcactgggt tcgtcaggct ccagagaagg ggctggagtg ggtcgcatac attagtagtg acagtagtgc catctactat gcagacacag tgaagggccg attcaccatc tccagagaca atcccaagaa caccctgttc ctgcaaatga ccagtctaag gtctgaggac acggccatgt attactgtgg aagagggagg gaaaacattt actacggtag taggcttgac tactggggcc aaggcaccac tctcacagtc tcctca
```

BRCA84D Variable Heavy Chain $CDR_1$ (SEQ ID NO: 13): FGMH

Polynucleotide Sequence Encoding BRCA84D Variable Heavy Chain $CDR_1$ (SEQ ID NO: 14): tttggaatgcac BRCA84D Variable Heavy Chain $CDR_2$ (SEQ ID NO: 15): YISSDSSAIYYADTVK Polynucleotide Sequence Encoding BRCA84D Variable Heavy Chain $CDR_2$ (SEQ ID NO: 16): tacattagta gtgacagtag tgccatctac tatgcagaca cagtgaag BRCA84D Variable Heavy Chain $CDR_3$ (SEQ ID NO: 17): GRENIYYGSRLDY Polynucleotide Sequence Encoding BRCA84D Variable Heavy Chain $CDR_3$ (SEQ ID NO: 18): gggagggaaa acatttacta cggtagtagg cttgactac B. Sequences of BRCA69D (1) BRCA69D Light Chain Sequences Amino Acid Sequence of BRCA69D Variable Light Chain (SEQ ID NO: 19):

```
DIQMTQTTSS LSASLGDRVT ISCRASQDIS NYLNWYQQKP

DGTVKLLIYY TSRLHSGVPS RFSGSGSGTD YSLTIDNLEQ

EDIATYFCQQ GNTLPPTFGG GTKLEIK
```

Polynucleotide Sequence Encoding BRCA69D Variable Light Chain (SEQ ID NO: 20):

```
gatatccaga tgacacagac tacatcctcc ctgtctgcct ctctgggaga cagagtcacc atcagttgca gggcaagtca ggacattagt aattatttaa actggtatca gcagaaacca gatggaactg ttaaactcct gatctactac acatcacgat tacactcagg agtcccatca aggttcagtg gcagtgggtc tggaacagat tattctctca ccattgacaa cctggagcaa gaagatattg ccacttactt ttgccaacag ggtaatacgc ttcctccgac gttcggtgga ggcaccaaac tggaaatcaa a
```

BRCA69D Variable Light Chain $CDR_1$ (SEQ ID NO: 21): RASQDISNYLN

Polynucleotide Sequence Encoding BRCA69D Variable Light Chain $CDR_1$ (SEQ ID NO: 22): agggcaagtc aggacattag taattattta aac BRCA69D Variable Light Chain CDR$_2$ (SEQ ID NO: 23): YTSRLHS Polynucleotide Sequence Encoding BRCA69D Variable Light Chain CDR$_2$ (SEQ ID NO: 24): tacacatcac gattacactc a BRCA69D Variable Light Chain CDR$_3$ (SEQ ID NO: 25): QQGNTLPPT Polynucleotide Sequence Encoding BRCA69D Variable Light Chain CDR$_3$ (SEQ ID NO: 25): caacaggta atacgcttcc tccgacg (2) BRCA69D Heavy Chain Sequences Amino Acid Sequence of BRCA69D Variable Heavy Chain (SEQ ID NO: 27):

```
QVQLQQSGAE LARPGASVKL SCKASGYTFT SYWMQWVKQR

PGQGLEWIGT IYPGDGDTRY TQKFKGKATL TADKSSSTAY

MQLSSLASED SAVYYCARRG IPRLWYFDVW GAGTTVTVSS
```

Polynucleotide Sequence Encoding BRCA69D Variable Heavy Chain (SEQ ID NO: 28]:

```
caggttcagc tccagcagtc tggggctgag ctggcaagac ctggggcttc agtgaagttg tcctgcaagg cttctggcta cacctttact agctactgga tgcagtgggt aaaacagagg cctggacagg gtctggaatg gattgggact atttatcctg gagatggtga tactaggtac actcagaagt tcaagggcaa ggccacattg actgcagata atcctccag cacagcctac atgcaactca gcagcttggc atctgaggac tctgcggtct attactgtgc aagaagaggg attccacggc tttggtactt cgatgtctgg ggcgcaggga ccacggtcac cgtctcctca
```

BRCA69D Variable Heavy Chain CDR$_1$ (SEQ ID NO: 29): SYWMQ

Polynucleotide Sequence Encoding BRCA69D Variable Heavy Chain CDR$_1$ (SEQ ID NO: 30): agctactgga tgcag BRCA69D Variable Heavy Chain CDR$_2$ (SEQ ID NO: 31): TIYPGDGDTR YTQKFKG Polynucleotide Sequence Encoding BRCA69D Variable Heavy Chain CDR$_2$ (SEQ ID NO: 32): actatttatc ctggagatgg tgatactagg tacactcag aagttcaagg gc BRCA69D Variable Heavy Chain CDR$_3$ (SEQ ID NO: 33): RGIPRLWYFD V Polynucleotide Sequence Encoding BRCA69D Variable Heavy Chain CDR$_3$ (SEQ ID NO: 34): agagggattc cacg-gctttg gtacttcgat gtc C. Sequences of PRCA157

(1) PRCA157 Light Chain Sequences

Amino Acid Sequence of PRCA157 Variable Light Chain (SEQ ID NO: 35):

```
DIQMTQSPAS LSVSVGETVT ITCRASESIY SYLAWYQQKQ

GKSPQLLVYN TKTLPEGVPS RFSGSGSGTQ FSLKINSLQP

EDFGRYYCQH HYGTPPWTFG GGTNLEIK
```

Polynucleotide Sequence Encoding PRCA157 Variable Light Chain (SEQ ID NO: 36):

```
gacatccaga tgactcagtc tccagcctcc ctatctgtat ctgtgggaga aactgtcacc attacatgtc gagcaagtga gagtatttac agttatttag catggtatca gcagaaacag ggaaaatctc ctcagctcct ggtctataat acaaaaacct taccagaggg tgtgccatca aggttcagtg gcagtggatc aggcacacag ttttctctga agatcaacag cctgcagcct gaagattttg ggagatatta ctgtcaacat cattatggta ctcctccgtg gacgttcggt ggaggcacca acctggaaat caaa
```

PRCA157 Variable Light Chain CDR$_1$ (SEQ ID NO: 37): RASESIYSYLA

Polynucleotide Sequence Encoding PRCA157 Variable Light Chain CDR$_1$ (SEQ ID NO: 38): cgagcaagtg agagtattta cagttattta gca PRCA157 Variable Light Chain CDR$_2$ (SEQ ID NO: 39): NTKTLPE Polynucleotide Sequence Encoding PRCA157 Variable Light Chain CDR$_2$ (SEQ ID NO: 40): aatacaaaaa ccttaccaga g PRCA157 Variable Light Chain CDR$_3$ (SEQ ID NO: 41): QHHYGTPPW Polynucleotide Sequence Encoding PRCA157 Variable Light Chain CDR$_3$ (SEQ ID NO: 42): caacatcatt atggtactcc tccgtgg (2) PRCA157 Heavy Chain Sequences Amino Acid Sequence of PRCA157 Variable Heavy Chain (SEQ ID NO: 43):

```
EVQQVESGGD LVKPGGSLKL SCAASGFTFS SYGMSWVRQT

PDKRLEWVAT INSGGSNTYY PDSLKGRFTI SRDNAKNTLY

LQMRSLKSED TAMYYCARHD GGAMDYWGQG TSVTVSS
```

Polynucleotide Sequence Encoding PRCA157 Variable Heavy Chain (SEQ ID NO: 44):

```
gaggtgcagc aggtggagtc ggggggagac ttagtgaagc ctggagggtc cctgaaactc tcctgtgcag cctctggatt cactttcagt tcctatggca tgtcttgggt tcgccagact ccagacaaga ggctggagtg ggtcgcaacc attaatagtg gtggaagtaa cacctactat ccagacagtt tgaagggcg attcaccatc tccagagaca atgccaagaa cacctttac ctgcaaatgc gcagtctgaa gtctgaggac acagccatgt attactgtgc aagacatgac gggggagcta tggactactg gggtcaagga acctcagtca ccgtctcctc a
```

PRCA157 Variable Heavy Chain CDR$_1$ (SEQ ID NO: 45): SYGMS

Polynucleotide Sequence Encoding PRCA157 Variable Heavy Chain CDR$_1$ (SEQ ID NO: 46): tcctatggca tgtct PRCA157 Variable Heavy Chain CDR$_2$ (SEQ ID NO: 47): VATINSGGSN TYYPDSLKG Polynucleotide Sequence Encoding PRCA157 Variable Heavy Chain CDR$_2$ (SEQ ID NO: 48): gtcgcaacca ttaatagtgg tggaagtaac acctactatc cagacagttt gaagggg PRCA157 Variable Heavy Chain CDR$_3$ (SEQ ID NO: 49): HDGGAMDY Polynucleotide Sequence Encoding PRCA157 Variable Heavy Chain CDR$_3$ (SEQ ID NO: 50): catgacgggg gagctatgga ctac D. Fc-Engineered B7-H3 Antibodies In traditional immune function, the interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All of these interactions are initiated through the binding of the Fc domain of antibodies or immune complexes to specialized cell surface receptors on hematopoietic cells. The diversity of cellular responses triggered by antibodies and immune complexes results from the structural heterogeneity of the three Fc receptors: FcγRI (CD64), FcγRII (CD32), and FcγRIII (CD16). FcγRI (CD64), FcγRIIA (CD32A) and FcγRIII (CD16) are activating (i.e., immune system enhancing) receptors; FcγRIIB (CD32B) is an inhibiting (i.e., immune system dampening) receptor. The amino acid sequence of the IgG1 Fc region is shown below (as SEQ ID NO: 51, numbered according to Kabat et al., SEQUENCE OF PROTEINS OF IMMUNOLOGICAL INTEREST, 5$^{th}$ Ed. Public Health Service, NIH, MD (1991), expressly incorporated herein by reference, and hereafter referred to as "Kabat EU"):

```
                                          SEQ ID NO: 51
PAPELLGGPS  VFLFPPKPKD  TLMISRTPEV  TCVVVDVSHE
230         240         250         260

DPEVKFNWYV  DGVEVHNAKT  KPREEQYNST  YRVVSVLTVL
270         280         290         300

HQDWLNGKEY  KCKVSNKALP  APIEKTISKA  KGQPREPQVY
310         320         330         340

TLPPSREEMT  KNQVSLTCLV  KGFYPSDIAV  EWESNGQPEN
350         360         370         380

NYKTTPPVLD  SDGSFFLYSK  LTVDKSRWQQ  GNVFSCSVMH
390         400         410         420

EALHNHYTQK  SLSLSPGK
430         440
```

Residues 230-341 are the Fc CH2 region. Residues 342-447 are the Fc CH3 region.

The present invention includes antibodies that specifically bind to B7-H3 that comprise a variant Fc region having one or more amino acid modifications (e.g., substitutions, deletions, insertions) in one or more portions, which modifications increase the affinity and avidity of the variant Fc region for an FcγR (including activating and inhibitory FcγRs). In some embodiments, said one or more amino acid modifications increase the affinity of the variant Fc region for FcγRIIIA and/or FcγRIIA. In another embodiment, the variant Fc region further specifically binds FcγRIIB with a lower affinity than does the Fc region of the comparable parent antibody (i.e., an antibody having the same amino acid sequence as the antibody of the invention except for the one or more amino acid modifications in the Fc region). In some embodiments, such modifications increase the affinity of the variant Fc region for FcγRIIIA and/or FcγRIIA and also enhance the affinity of the variant Fc region for FcγRIIB relative to the parent antibody. In other embodiments, said one or more amino acid modifications increase the affinity of the variant Fc region for FcγRIIIA and/or FcγRIIA but do not alter the affinity of the variant Fc regions for FcγRIIB relative to the Fc region of the parent antibody. In another embodiment, said one or more amino acid modifications enhance the affinity of the variant Fc region for FcγRIIIA and FcγRIIA but reduce the affinity for FcγRIIB relative to the parent antibody. Increased affinity and/or avidity results in detectable binding to the FcγR or FcγR-related activity in cells that express low levels of the FcγR when binding activity of the parent molecule (without the modified Fc region) cannot be detected in the cells. In other embodiments, the modified molecule exhibits detectable binding in cells which express non-FcγR receptor target antigens at a density of 30,000 to 20,000 molecules/cell, at a density of 20,000 to 10,000 molecules/cell, at a density of 10,000 to 5,000 molecules/cell, at a density of 5,000 to 1,000 molecules/cell, at a density of 1,000 to 200 molecules/cell or at a density of 200 molecules/cell or less (but at least 10, 50, 100 or 150 molecules/cell).

In another embodiment, said one or more modifications to the amino acids of the Fc region reduce the affinity and avidity of the antibody for one or more FcγR receptors. In a specific embodiment, the invention encompasses antibodies comprising a variant Fc region, wherein said variant Fc region comprises at least one amino acid modification relative to a wild type Fc region, which variant Fc region only binds one FcγR, wherein said FcγR is FcγRIIIA. In another specific embodiment, the invention encompasses antibodies comprising a variant Fc region, wherein said variant Fc region comprises at least one amino acid modification relative to a wild type Fc region, which variant Fc region only binds one FcγR, wherein said FcγR is FcγRIIA.

Preferably, the binding properties of the molecules of the invention are characterized by in vitro functional assays for determining one or more FcγR mediator effector cell functions (See Section 5.2.7). The affinities and binding properties of the molecules, e.g., antibodies, of the invention for an FcγR can be determined using in vitro assays (biochemical or immunological based assays) known in the art for determining antibody-antigen or Fc-FcγR interactions, i.e., specific binding of an antigen to an antibody or specific binding of an Fc region to an FcγR, respectively, including but not limited to ELISA assay, surface plasmon resonance assay, immunoprecipitation assays. In most preferred embodiments, the molecules of the invention have similar binding properties in in vivo models (such as those described and disclosed herein) as those in in vitro based assays. However, the present invention does not exclude molecules of the invention that do not exhibit the desired phenotype in in vitro based assays but do exhibit the desired phenotype in vivo.

In some embodiments, the molecules of the invention comprising a variant Fc region comprise at least one amino acid modification (for example, possessing 1, 2, 3, 4, 5, 6, 7, 8, 9, or more amino acid modifications) in the CH3 domain of the Fc region, which is defined as extending from amino acids 342-447. In other embodiments, the molecules of the invention comprising a variant Fc region comprise at least one amino acid modification (for example, possessing 1, 2, 3, 4, 5, 6, 7, 8, 9, or more amino acid modifications) in the CH2 domain of the Fc region, which is defined as extending from amino acids 231-341. In some embodiments, the molecules of the invention comprise at least two amino acid modifications (for example, possessing 2, 3, 4, 5, 6, 7, 8, 9, or more amino acid modifications), wherein at least one such modification is in the CH3 region and at least one such modification is in the CH2 region. The invention further encompasses amino acid modification in the hinge region. In a particular embodiment, the invention encompasses amino acid modification in the CH1 domain of the Fc region, which is defined as extending from amino acids 216-230.

In particularly preferred embodiments, the invention encompasses molecules comprising a variant Fc region wherein said variant confers or has an increased ADCC activity and/or an increased binding to FcγRIIA (CD32A), as measured using methods known to one skilled in the art and exemplified herein. The ADCC assays used in accordance with the methods of the invention may be NK dependent or macrophage dependent.

In particularly preferred embodiments, the invention encompasses molecules comprising a variant Fc region wherein said variant confers or has an increased ADCC activity and/or an increased binding to FcγRIIIA (CD16A), as measured using methods known to one skilled in the art and exemplified herein. The ADCC assays used in accordance with the methods of the invention may be NK dependent or macrophage dependent.

The Fc variants of the present invention may be combined with other Fc modifications, such as those disclosed in U.S. Pat. Nos. 7,632,497; 7,521,542; 7,425,619; 7,416,727; 7,371,826; 7,355,008; 7,335,742; 7,332,581; 7,183,387; 7,122,637; and 6,737,056; in PCT Publications Nos. WO 2008/105886; WO 2008/002933; WO 2007/021841; WO 2007/106707; WO 06/088494; WO 05/115452; WO 05/110474; WO 04/1032269; and in WO 04/063351; and in Presta, L. G. et al. (2002) "*Engineering therapeutic antibodies for improved function*," Biochem. Soc. Trans. 30(4): 487-490; Shields, R. L. et al. (2002) "*Lack of fucose on human IgG1 N-linked oligosaccharide improves binding to human Fcgamma RIII and antibody-dependent cellular toxicity*," J. Biol. Chem. 26; 277(30):26733-26740 and Shields, R. L. et al. (2001) "*High resolution mapping of the binding site on human IgG1 for Fc gamma RI, Fc gamma RII, Fc gamma RIII, and FcRn and design of IgG1 variants with improved binding to the Fc gamma R*," J. Biol. Chem. 276(9):6591-6604). The invention encompasses combining an Fc variant of the invention with other Fc modifications to provide additive, synergistic, or novel properties to the modified antibody. Preferably, the Fc variants of the invention enhance the phenotype of the modification with which they are combined. For example, if an Fc variant of the invention is combined with a mutant known to bind FcγRIIIA with a higher affinity than a comparable wild type Fc region; the combination with a mutant of the invention results in a greater fold enhancement in FcγRIIIA affinity.

The invention encompasses antibodies that specifically bind to B7-H3 which comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, provided that the variant Fc region does not have or is not solely a substitution at any one or more of positions 243, 255, 256, 258, 267, 268, 269, 270, 272, 276, 278, 280, 283, 285, 286, 289, 290, 292, 293, 294, 295, 296, 298, 300, 301, 303, 305, 307, 309, 312, 320, 322, 326, 329, 330, 332, 331, 333, 334, 335, 337, 338, 339, 340, 359, 360, 373, 376, 416, 419, 430, 434, 435, 437, 438, 439. In a specific embodiment, the invention encompasses such antibodies comprising a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule binds an FcγR with an altered affinity relative to a molecule comprising a wild-type Fc region, provided that the variant Fc region does not have or is not solely a substitution at any one or more of positions 243, 255, 258, 267, 269, 270, 276, 278, 280, 283, 285, 289, 292, 293, 294, 295, 296, 300, 303, 305, 307, 309, 320, 322, 329, 332, 331, 337, 338, 340, 373, 376, 416, 419, 434, 435, 437, 438, 439 and does not have an alanine at any of positions 256, 290, 298, 312, 326, 333, 334, 359, 360, or 430; an asparagine at position 268; a glutamine at position 272; a glutamine, serine, or aspartic acid at position 286; a serine at position 290; a methionine at position 301; a methionine, glutamine, glutamic acid, or arginine at position 320; a glutamic acid at position 322; an asparagine, serine, glutamic acid, or aspartic acid at position 326; a lysine at position 330; a glutamine at position 334; a glutamic acid at position 334; a methionine at position 334; a histidine at position 334; a valine at position 334; a leucine at position 334; a glutamine at position 335; a lysine at position 335; or a threonine at position 339.

The invention also encompasses antibodies that specifically bind to B7-H3 which comprise a variant Fc region, wherein the variant Fc region comprises such antibodies comprising a variant Fc region, wherein the variant Fc region does not have or is not solely a substitution at any one or more of positions 268, 269, 270, 272, 276, 278, 283, 285, 286, 289, 292, 293, 301, 303, 305, 307, 309, 320, 331, 333, 334, 335, 337, 338, 340, 360, 373, 376, 416, 419, 430, 434, 435, 437, 438 or 439 and does not have a histidine, glutamine, or tyrosine at position 280; a serine, glycine, threonine or tyrosine at position 290, an asparagine at position 294, a lysine at position 295; a proline at position 296; a proline, asparagine, aspartic acid, or valine at position 298; or a leucine or isoleucine at position 300. In another embodiment, the invention encompasses such antibodies comprising a variant Fc region, wherein the variant Fc region comprises at least one amino acid modification relative to a wild-type Fc region, such that the molecule binds an FcγR with a reduced affinity relative to molecule comprising a wild-type Fc region provided that the variant Fc region does not have or is not solely a substitution at any one or more of positions 243, 252, 254, 265, 268, 269, 270, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438, or 439. In yet another embodiment, the invention encompasses such antibodies comprising a variant Fc region, wherein the variant Fc region comprises at least one amino acid modification relative to a wild-type Fc region, such that the molecule binds an FcγR with an enhanced affinity relative to a molecule comprising a wild-type Fc region provided that the variant Fc region does not have or is not solely a substitution at any one or more of positions 280, 283, 285, 286, 290, 294, 295, 298, 300, 301, 305, 307, 309, 312, 315, 331, 333, 334, 337, 340, 360, 378, 398, or 430.

The invention also encompasses antibodies that specifically bind to B7-H3 which comprise a variant Fc region, wherein the variant Fc region does not include or are not solely a substitution at any one or more of positions 330, 243, 247, 298, 241, 240, 244, 263, 262, 235, 269, or 328 and does not have a leucine at position 243, an asparagine at position 298, a leucine at position 241, and isoleucine or an alanine at position 240, a histidine at position 244, a valine at position 330, or an isoleucine at position 328.

The invention particularly encompasses antibodies that specifically bind to B7-H3 which comprise a variant Fc region with enhanced effector function and/or altered affinities for activating and/or inhibitory receptors, wherein the variant Fc region comprises: (a) any 1, 2, 3, 4, 5, or 6 of the following substitutions: S239D, S298A, A330L, 1332E, E333A, or K334A; or (b) any of the combinations of substitutions: (1) S298A, E333A, and K334A; (2) S239D and I332E; or (3) S239D, A330L and I332E.

The invention particularly encompasses antibodies that specifically bind to B7-H3 which comprise a variant Fc region with enhanced effector function and/or altered affinities for activating and/or inhibitory receptors, wherein the variant Fc region comprises a substitution:

(1) at position 288 with asparagine, at position 330 with serine and at position 396 with leucine;
(2) at position 334 with glutamic acid, at position 359 with asparagine, and at position 366 with serine;
(3) at position 316 with aspartic acid, at position 378 with valine, and at position 399 with glutamic acid;
(4) at position 247 with leucine, and a substitution at position 421 with lysine;
(5) at position 392 with threonine, and at position 396 with leucine;
(6) at position 221 with glutamic acid, at position 270 with glutamic acid, at position 308 with alanine, at position 311 with histidine, at position 396 with leucine, and at position 402 with aspartic acid;
(7) at position 419 with histidine, and a substitution at position 396 with leucine;
(8) at position 240 with alanine, and at position 396 with leucine;
(9) at position 410 with histidine, and at position 396 with leucine;
(10) at position 243 with leucine, at position 305 with isoleucine, at position 378 with aspartic acid, at position 404 with serine, and at position 396 with leucine;
(11) at position 255 with isoleucine, and at position 396 with leucine;
(12) at position 370 with glutamic acid and at position 396 with leucine;
(13) at position 270 with glutamic acid;
or
(14) any combination of the foregoing (1)-(12) substitutions.

In a specific embodiment, the invention encompasses an antibody that specifically binds B7-H3 that comprises a variant Fc region which comprises the substitution: F243L, R292P, and Y300L. In a further specific embodiment, the invention encompasses an antibody that specifically binds B7-H3 that comprises a variant Fc region which comprises the substitution: L235V, F243L, R292P, Y300L, and P396L. In yet a further specific embodiment, the invention encompasses an antibody that specifically binds B7-H3 that comprises a variant Fc region which comprises the substitution F243L, R292P, Y300L, V305I, and P396L.

In a further specific embodiment, the invention encompasses an antibody that specifically binds B7-H3 that comprises a variant Fc region which comprises a substitution at position 396 with leucine, at position 270 with glutamic acid and at position 243 with leucine. In another specific embodiment the molecule further comprises one or more amino acid modification such as those disclosed herein.

The invention particularly encompasses antibodies that specifically bind to B7-H3 which comprise a variant Fc region with enhanced effector function and/or altered affinities for activating and/or inhibitory receptors, that have an amino acid modification at one or more of the following positions: 119, 125, 132, 133, 141, 142, 147, 149, 162, 166, 185, 192, 202, 205, 210, 214, 215, 216, 217, 218, 219, 221, 222, 223, 224, 225, 227, 229, 231, 232, 233, 235, 240, 241, 242, 243, 244, 246, 247, 248, 250, 251, 252, 253, 254, 255, 256, 258, 261, 262, 263, 268, 269, 270, 272, 274, 275, 276, 279, 280, 281, 282, 284, 287, 288, 289, 290, 291, 292, 293, 295, 298, 301, 303, 304, 305, 306, 307, 308, 309, 310, 311, 312, 313, 315, 316, 317, 318, 319, 320, 323, 326, 327, 328, 330, 333, 334, 335, 337, 339, 340, 343, 344, 345, 347, 348, 352, 353, 354, 355, 358, 359, 360, 361, 362, 365, 366, 367, 369, 370, 371, 372, 375, 377, 378, 379, 380, 381, 382, 383, 384, 385, 386, 387, 388, 389, 390, 392, 393, 394, 395, 396, 397, 398, 399, 400, 401, 402, 404, 406, 407, 408, 409, 410, 411, 412, 414, 415, 416, 417, 419, 420, 421, 422, 423, 424, 427, 428, 431, 433, 435, 436, 438, 440, 441, 442, 443, 446, or 447. Preferably such mutations result in molecules that have been conferred an effector cell mediated function and, optionally, have an altered affinity for an FcγR as determined using methods disclosed and exemplified herein and known to one skilled in the art.

The invention particularly encompasses antibodies that specifically bind to B7-H3 which comprise a variant Fc region with altered effector function and/or altered affinities for activating and/or inhibitory receptors, that have:

(I) an amino acid modification at one or more of the following positions: 235, 240, 241, 243, 244, 247, 262, 263, 269, 298, 328, or 330 and more preferably one or more of the following modifications: V240A, V240I, F241L, F243L, P244H, S298N, L328I, A330V; wherein such antibodies exhibit altered effector function relative to antibodies having a wild-type Fc region that lacks such modification;

(II) an amino acid modification at one or more of the following positions: 268, 269, 270, 272, 276, 278, 283, 285, 286, 289, 292, 293, 301, 303, 305, 307, 309, 331, 333, 334, 335, 337, 338, 340, 360, 373, 376, 416, 419, 430, 434, 435, 437, 438 or 439 and more preferably one or more of the following modifications: D280H, D280Q, D280Y, K290G, K290S, K290T, K290Y, E294N, Q295K, Y296P, S298D, S298N, S298P, S298V, Y300I, Y300L; wherein such antibodies exhibit altered effector function relative to antibodies having a wild-type Fc region that lacks such modification;

(III) an amino acid modification at one or more of the following positions: 255, 256, 258, 267, 268, 269, 270, 272, 276, 278, 280, 283, 285, 286, 289, 290, 292, 293, 294, 295, 296, 298, 300, 301, 303, 305, 307, 309, 312, 320, 322, 326, 329, 330, 332, 331, 333, 334, 335, 337, 338, 339, 340, 359, 360, 373, 376, 416, 419, 430, 434, 435, 437, 438, 439, and more preferably one or more of the following modifications: T256A, H268N, E272Q, N286D, N286Q, N286S, K290A, K290S, S298A, R301M, D312A, K320E, K320M, K320Q, K320R, K322E, K326A, K326D, K326E, K326N, K326S, A330K, A339T, E333A, K334A, K334E, K334H, K334L, K334M, K334Q, K334V, T335K, T335Q, T359A, K360A, E430A; wherein such antibodies exhibit altered effector function relative to antibodies having a wild-type Fc region that lacks such modification; (IV) an amino acid modification at one or more of the following positions: 252, 254, 265, 268, 269, 270, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438, or 439; wherein such antibodies exhibit reduced effector function relative to antibodies having a wild-type Fc region that lacks such modification;

(V) an amino acid modification at one or more of the following positions: 280, 283, 285, 286, 290, 294, 295, 298, 300, 301, 305, 307, 309, 312, 315, 331, 333, 334, 337, 340, 360, 378, 398, or 430; wherein such antibodies exhibit enhanced effector function relative to antibodies having a wild-type Fc region that lacks such modification; or (VI) an amino acid modification at one or more of the following positions: R255A, T256A, E258A, S267A, H268A, H268N, E272A, E272Q, N276A, D280A, E283A, H285A, N286A, N286D, N286Q, N286S, K290A, K290S, R301M, K320E, K320M, K320Q, K320R, K322E, K326A, K326D, K326E, K326S, A330K, P331A, T335Q, S337A, E430A; wherein such antibodies exhibit enhanced effector function relative to antibodies having a wild-type Fc region that lacks such modification.

In other embodiments, the invention encompasses the use of any Fc variant known in the art, such as those disclosed in Jefferis, B. J. et al. (2002) *"Interaction Sites On Human IgG-Fc For FcgammaR: Current Models,"* Immunol. Lett. 82:57-65; Presta, L. G. et al. (2002) *"Engineering Therapeutic Antibodies For Improved Function,"* Biochem. Soc. Trans. 30:487-90; Idusogie, E. E. et al. (2001) *"Engineered Antibodies With Increased Activity To Recruit Complement,"* J. Immunol. 166:2571-75; Shields, R. L. et al. (2001) *"High Resolution Mapping Of The Binding Site On Human IgG1 For Fc Gamma RI, Fc Gamma RII, Fc Gamma RIII, And FcRn And Design Of IgG1 Variants With Improved Binding To The Fc gamma R,"* J. Biol. Chem. 276:6591-6604; Idusogie, E. E. et al. (2000) *"Mapping Of The C1 q Binding Site On Rituxan, A Chimeric Antibody With A Human IgG Fc,"* J. Immunol. 164:4178-84; Reddy, M. P. et al. (2000) *"Elimination Of Fc Receptor-Dependent Effector Functions Of A Modified IgG4 Monoclonal Antibody To Human CD4,"* J. Immunol. 164:1925-1933; Xu, D. et al. (2000) *"In Vitro Characterization of Five Humanized OKT3 Effector Function Variant Antibodies,"* Cell. Immunol. 200:16-26; Armour, K. L. et al. (1999) *"Recombinant human IgG Molecules Lacking Fcgamma Receptor I Binding And Monocyte Triggering Activities,"* Eur. J. Immunol. 29:2613-24; Jefferis, R. et al. (1996) *"Modulation Of Fc(Gamma)R And Human Complement Activation By IgG3-Core Oligosaccharide Interactions,"* Immunol. Lett. 54:101-04; Lund, J. et al. (1996) *"Multiple Interactions Of IgG With Its Core Oligosaccharide Can Modulate Recognition By Complement And Human Fc Gamma Receptor I And Influence The Synthesis Of Its Oligosaccharide Chains,"* J. Immunol. 157:4963-4969; Hutchins et al. (1995) *"Improved Biodistribution, Tumor Targeting, And Reduced Immunogenicity In Mice With A Gamma 4 Variant Of Campath-1H,"* Proc. Natl. Acad. Sci. (U.S.A.) 92:11980-84; Jefferis, R. et al. (1995) *"Recognition Sites On Human IgG For Fc Gamma Receptors: The Role Of Glycosylation,"* Immunol. Lett. 44:111-17; Lund, J. et al. (1995) *"Oligosaccharide-Protein Interactions In IgG Can Modulate Recognition By Fc Gamma Receptors,"* FASEB J. 9:115-19; Alegre, M. L. et al. (1994) *"A Non Activating "Humanized" Anti-CD3 Monoclonal Antibody Retains Immunosuppressive Properties In Vivo,"* Transplantation 57:1537-1543; Lund et al. (1992) *"Multiple Binding Sites On The CH2 Domain Of IgG For Mouse Fc Gamma R11,"* Mol. Immunol. 29:53-59; Lund et al. (1991) *"Human Fc Gamma RI And Fc Gamma RII Interact With Distinct But Overlapping Sites On Human IgG,"* J. Immunol. 147:2657-2662; Duncan, A. R. et al. (1988) *"Localization Of The Binding Site For The Human High-Affinity Fc Receptor On IgG,"* Nature 332:563-564; U.S. Pat. Nos. 5,624,821; 5,885,573; 6,194,551; 7,276,586; and 7,317,091; and PCT Publications WO 00/42072 and PCT WO 99/58572.

The invention encompasses molecules comprising variant Fc regions consisting of or comprising any of the mutations listed in the table below in Table 1.

TABLE 1

Exemplary Fc Modifications

Substitutions of a Single Site

| | | | | | | | |
|---|---|---|---|---|---|---|---|
| S132I | F241W | D265N | D280Q | Y296T | D312A | L328I | K334E |
| A162V | F241Y | D265Q | D280Y | N297D | W313F | L328K | K334H |
| S219Y | F241Y | D265T | G281D | N297E | N315I | L328M | K334I |
| K222N | F243D | D265V | G281K | N297I | E318K | L328N | K334L |
| H224L | F243H | D265Y | G281P | N297S | K320E | L328P | K334M |
| T225S | F243L | V266A | G281Y | S298A | K320M | L328Q | K334N |
| P228E | F243L | V266I | V282M | S298D | K320Q | L328R | K334Q |
| P228G | F243Q | V266M | E283A | S298N | K320R | L328S | K334V |
| P228K | F243R | V266T | V284E | S298N | K322E | L328T | T335K |
| P228Y | F243W | S267A | V284L | S298N | V323I | L328V | T335Q |
| P230A | F243Y | H268A | V284N | S298P | N325A | L328W | I336E |
| P230E | P244H | H268N | V284T | S298V | N325D | L328Y | I336K |
| P230G | P245A | D270E | V284Y | T299A | N325E | A330I | I336Y |
| P230Y | P247G | P271A | H285A | T299D | N325F | A330K | S337A |
| A231E | P247L | P271D | N286A | T299E | N325G | A330L | A339T |
| A231G | P247V | P271E | N286D | T299F | N325H | A330S | M352L |
| A231K | K248M | P271F | N286S | T299G | N325I | A330V | T359A |
| A231P | R255A | P271G | K288N | T299H | N325K | A330Y | T359N |
| A231Y | T256A | P271H | K290A | T299I | N325L | P331A | K360A |
| P232E | E258A | P271I | K290G | T299K | N325M | I332A | T366N |
| P232G | V262A | P271K | K290S | T299L | N325P | I332D | T366S |
| P232K | V262E | P271L | K290T | T299M | N325R | I332E | F372Y |
| P232Y | V262F | P271M | K290Y | T299N | N325S | I332F | F372Y |
| E233D | V262I | P271N | P291D | T299P | N325T | I332G | I377F |
| E233G | V262T | P271Q | P291E | T299Q | N325V | I332H | I377N |
| L234I | V263A | P271R | P291G | T299R | N325W | I332K | V379L |
| L235D | V263I | P271S | P291H | T299S | N325Y | I332L | V379M |
| S239D | V263M | P271T | P291I | T299V | K326A | I332M | K392R |
| S239E | V263T | P271V | P291Q | T299W | K326D | I332N | P396H |

TABLE 1-continued

Exemplary Fc Modifications

| | | | | | | | |
|---|---|---|---|---|---|---|---|
| S239N | V264A | P271W | P291T | T299Y | K326E | I332P | P396L |
| S239Q | V264E | P271Y | R292G | Y300I | K326E | I332Q | L398V |
| V240A | V264F | E272A | R292L | Y300L | K326N | I332R | S400P |
| V240I | V264I | E272Q | E294N | R301M | K326S | I332S | D401V |
| V240M | V264R | V273I | Q295K | R301M | K326T | I332T | S407I |
| V240T | V264T | F275L | Y296D | V302I | L328A | I332V | K414N |
| F241E | V264W | F275W | Y296E | S304D | L328D | I332W | E430A |
| V241I | D265F | F275Y | Y296H | S304H | L328E | I332Y | |
| F241L | D265H | N276A | Y296N | S304L | L328F | E333A | |
| F241R | D265I | D280A | Y296P | S304N | L328G | K334A | |
| F241S | D265L | D280H | Y296Q | S304T | L328H | K334E | |

Substitutions of Two Sites

| | | | |
|---|---|---|---|
| I332E, A330L | S239N/I332Q | V279L, P395S | P396L, P217S |
| I332E, L328D | S239Q/I332D | V284A, F372L | P396L, P227S |
| I332E, L328E | S239Q/I332E | K288N, K326N | P396L, V323I |
| I332E, L328H | S239Q/I332N | K288N, A330S | P396L, V240A |
| I332E, L328I | S239Q/I332Q | K290E, L142P | P396L, L242F |
| I332E, L328M | V240I, V281M | K290E, P227S | P396L, P244H |
| I332E, L328N | F241L, E258G | K290T, G371D | P396L, T250A |
| I332E, L328Q | F241L/V262I | P291S, P353Q | P396L, R255L |
| I332E, L328T | F243L, E318K | R292P, V305I | P396L, E258D |
| I332E, L328V | F243I, V379L | S298A/I332E | P396L, H268D |
| I332E, N297D | P243L/V264I | S298N, W381R | P396L, H268N |
| I332E, N297E | K246T, Y319F | S298N, S407R | P396L, V303I |
| I332E, N297S | K246T, P396H | K317N, F423-DEL | P396L, K326I |
| S166N, K409R | P247H, G285E | K326E, K320E | P396L, V305L |
| P232S, S304G | P247L, I377F | K326E, A330T | P396L, L358P |
| S239D/I332D | P247L, E389G | K326E, G385E | P396L, K370E |
| S239D/I332E | P247S, P396L | A330V, Q419H | P396L, S375C |
| S239D/I332N | P247L, L398Q | K334E, E233D | P396L, V379M |
| S239D/I332Q | P247L, L406F | K334N, K246I | P396L, N384K |
| S239E/D265N | P247L, N421K | K334E, K288M | P396L, K392T |
| S239E/D265Q | L251F, F372L | K334E, R292L | P396L, S400F |
| S239E/I332D | L251F, S415I | K334E, E308D | P396L, L410H |
| S239E/I332E | R255L, E318K | K334E, E380D | P396L, Q419H |
| S239E/I332N | R255Q, K326E | K334E, P396L | P396L, Q419L |
| S239E/I332Q | E258D, N384K | A339V, Q347H | P396L, V427A |
| S239N/I332D | V263Q, E272D | K370N, S440N | D399E, G402D |
| S239N/I332E | V264I/I332E | T394M, V397M | D399E, M428L |
| S239N/I332N | H268D, E318D | P396L, K210M | |

Substitutions of Three Sites

| | | |
|---|---|---|
| V185M, R292L, D399E | P217S, A378V, S408R | K218R, G281D, G385R |
| S192T, M252L, R301C | P247L, I253N, K334N | P247L, A330T, S440G |
| V125L, V215I, S408I | D312E, K327N, I378S | T355N, P387S, H435Q |
| R292L, T359N, P396L | E216D, E345K, S375I | P247L, A431V, S442F |
| F275I, K334N, V348M | K288N, A330S, P396L | A378V, N390I, V422I |
| F243L, R255L, E318K | G316D, A378V, D399E | V282E, V369I, L406F |
| K334E, T359N, T366S | N315I, V379M, T394M | V397M, T411A, S415N |
| K288N, A330S, P396L | P247L, W313R, E388G | T223I, T256S, L406F |
| F243I, V379L, G420V | R301H, K340E, D399E | K246N, P396L, Q419R |
| A231V, Q386H, V412M | K326I, P396L, S408N | P217A, T359A, P396L |
| E216D, K334R, S375I | K210M, K261N, P396L | V215I, K290V, P396L |
| T335N, P387S, H435Q | A330V, G427M, K438R | V263Q, E272D, Q419H |
| K246I, Q362H, K370E | K222E, V263Q, S298N | N276Y, T393N, W417R |
| K334E, E380D, G446V | E233G, P247S, L306P | D270E, G316D, R416G |
| V303I, V369F, M428L | S219T, T225K, D270E | D270E, K392T, P396L |
| K246E, V284M, V308A | R292P, F243L, V305I | R255L, D270E, P396L |
| E293V, Q295E, A327T | V284M, R292L, K370N | V240A, D270E, P396L |
| Y319F, P352L, P396L | D270E, K370E, P396L | 270E, P396L, Q419HD |
| K290T, N390I, P396L | P247L, D270E, N421K | S239D, A330L, I332E |
| N297D, A330Y, I332E | Y296D, N297D, I332E | S239D, A330Y, I332E |
| N297D, T299L, I332E | Y296E, N297D, I332 E | S239D, I332E, A330I |
| N297D, T299I, I332E | Y296H, N297D, I332E | S239D, N297D, I332E |
| N297D, T299L, I332E | Y296N, N297D, I332E | S239D, S298A, I332E |
| N297D, T299V, I332E | Y296Q, N297I, I332E | S239D, V264II, I332E |
| F243L, V262I, V264W | Y296T, N297D, I332E | S239E, N297D, I332E |
| D265F, N297E, I332E | P230A, E233D, I332E | S239E, V264I, I332 E |
| D265Y, N297D, I332E | P244H, P245A, P247V | S239N, A330L, I332E |
| V264E, N297D, I332E | V264I, A330Y, I332E | S239N, A330Y, I332E |
| V264I, A330L, I332E | V264I, S298A, I332E | S239Q, V264I, I332E |

Substitutions of Four Sites

| | |
|---|---|
| A141V, H268L, K288E, P291S | T256S, V305I, K334E, N390S |
| E258D, T289A, H310Y, Y407V | D280E, S354F, A431D, L441I |
| K334E, T359N, T366S, Q386R | P343S, P353L, S375I, S383N |
| K326Q, K334E, T359N, T366S | E269K, K290N, Q311R, H433Y |

TABLE 1-continued

Exemplary Fc Modifications

| | |
|---|---|
| K288R, T307A, K344E, P396L | K290E, V369A, T393A, P396L |
| V273I, K326E, L328I, P396L | K210N, K222I, K320M, P396L |
| F275L, Q362H, N384K, P396L | S219T, T225K, D270E, K360R |
| V282L, A330V, H433Y, T436R | P243L, S254T, A330V, N361D |
| R255L, D270E, Y300L, P396L, | F243L, D270E, K392N, P396L |
| R255L, D270E, R292G, P396L | F243L, R255L, D270E, P396L |
| V284M, S298N, K334E, R355W | S239D, D265F, N297D, I332E |
| D265Y, N297D, T299L, I332E | S239D, D265H, N297D, I332E |
| F241E, F2430, V262T, V264F | S239D, D265I, N297D, I332E |
| F241E, F243R, V262E, V264R | S239D, 0265L, N297D, I332E |
| F241E, F243Y, V262T, V264R | S239D, D265T, N297D, I332E |
| F241L, F243L, V262I, V264I | S239D, D265V, N297D, I332E |
| F241R, F2430, V262T, V264R | S239D, D265Y, N297D, I332E |
| F241W, F243W, V262A, V264A | S239D, N297D, I332E, A330Y |
| F241Y, F243Y, V262T, V264T | S239D, N297D, I332E, K326E |
| N297D, I332E, S239D, A330L | S239D, N297D, I332E, L235D |
| N297D, S298A, A330Y, I 332E | S239D, V264I, A330L, I332E |
| S239D, A330Y, I332E, K326E | S239D, V264I, S298A, I332E |
| S239D, A330Y, I332E, K326T | S239E, V264I, A330Y, I332 E |
| S239D, A330Y, I332E, L234I | S239D, A330Y, I332E, V264T |
| S239D, A330Y, I332E, L235D | S239D, A330Y, I332E, V266I |
| S239D, A330Y, I332E, V240I | |

Substitutions of Five Sites

| | |
|---|---|
| V284M, S298N, K334E, R355W, R416T | K147T, Y202M, F275I, K334N, V348M |
| P217S, V305I, I309L, N390H, P396L | T335N, K370E, A378V, T394M, S424L |
| F243L, V305I, A378D, P396L, F404S | P244H, L358M, V379M, N384K, V397M |
| K222N, T335N, K370E, A378V, T394M | P244A, K326I, C367R, S375I, K447T |
| L235S, S304G, V305I, V323I, V382M | C229Y, A287T, V379M, P396L, L443V |
| F241E, F2430, V262T, V264E, I332E | F241R, F243Q, V262T, V264R, I332E |
| F241E, F243R, V262E, V264R, I332E | S239E, V264I, S298A, A330Y, I332E |
| F241E, F243Y, V262T, V264R, I332E | |

Substitutions of More Than Five Sites

D221E, D270E, V308A, Q311H, P396L, G402D
T215P, K274N, A287G, K334N, L365V, P396L
F241Y, F243Y, V262T, V264T, N297D, I332E
N297D, T299F, I332E, N297D, T299H, I332E
D221Y, M252I, A330G, A339T, T359N, V422I, H433L
S239D, N297D, I332E, A330Y, F241S, F243H, V262T, V264T
K133M, F149Y, K205E, R214I, K218E, S383N, N384K, T256N, V262L

In specific embodiments, the variant Fc region of such antiB7-H3 antibodies has:
(1) a leucine at position 247, a lysine at position 421 and a glutamic acid at position 270;
(2) a threonine at position 392, a leucine at position 396, a glutamic acid at position 270, and a leucine at position 243
(3) a histidine at position 419, a leucine at position 396, and a glutamic acid at position 270;
(4) a histidine at position 419, a leucine at position 396, a glutamic acid at position 270, and a leucine at position 243;
(5) an alanine at position 240, a leucine at position 396, and a glutamic acid at position 270;
(6) a lysine at position 255 and a leucine at position 396;
(7) a lysine at position 255, a leucine at position 396, and a glutamic acid at position 270;
(8) a lysine at position 255, a leucine at position 396, a glutamic acid at position 270, and a lysine at position 300;
(9) a lysine at position 255, a leucine at position 396, a glutamic acid at position 270, and a glycine at position 292;
(10) a lysine at position 255, a leucine at position 396, a glutamic acid at position 270, and a leucine at position 243;
(11) a glutamic acid at position 370, a leucine at position 396, and a glutamic acid at position 270;
(12) a glutamic acid at position 270, an aspartic acid at position 316, and a glycine at position 416;
(13) a leucine at position 243, a proline at position 292, an isoleucine at position 305, and a leucine at position 396;
(14) a leucine at position 243, a glutamic acid at position 270, an asparagine at position 392 and a leucine at position 396;
(15) a leucine at position 243, a leucine at position 255, a glutamic acid at position 270 and a leucine at position 396;
(16) a glutamine at position 297;
or
(17) any combination of the foregoing (1)-(16) substitutions.

In some embodiments, the molecules of the invention further comprise one or more glycosylation sites, so that one or more carbohydrate moieties are covalently attached to the molecule. Preferably, the molecules of the invention with one or more glycosylation sites and/or one or more modifications in the Fc region confer or have an enhanced antibody mediated effector function, e.g., enhanced ADCC activity, compared to a parent antibody. In some embodiments, the invention further comprises molecules comprising one or more modifications of amino acids that are directly or indirectly known to interact with a carbohydrate moiety of the antibody, including but not limited to amino acids at positions 241, 243, 244, 245, 245, 249, 256, 258, 260, 262, 264, 265, 296, 299, and 301. Amino acids that directly or indirectly interact with a carbohydrate moiety of an antibody are known in the art, see, e.g., Jefferis et al., 1995 *Immunology Letters,* 44: 111-7, which is incorporated herein by reference in its entirety.

In another embodiment, the invention encompasses molecules that have been modified by introducing one or more glycosylation sites into one or more sites of the molecules, preferably without altering the functionality of the molecules, e.g., binding activity to target antigen or FcγR. Glycosylation sites may be introduced into the variable and/or constant region of the molecules of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. The molecules of the invention may comprise one or more glycosylation sites, including N-linked and O-linked glycosylation sites. Any glycosylation site for N-linked or O-linked glycosylation known in the art may be used in accordance with the instant invention. An exemplary N-linked glycosylation site that is useful in accordance with the methods of the present invention is the amino acid sequence: Asn-X-Thr/Ser, wherein X may be any amino acid and Thr/Ser indicates a threonine or a serine. Such a site or sites may be introduced into a molecule of the invention using methods well known in the art to which this invention pertains (see for example, IN VITRO MUTAGENESIS, RECOMBINANT DNA: A SHORT COURSE, J. D. Watson, et al. W. H. Freeman and Company, New York, 1983, chapter 8, pp. 106-116, which is incorporated herein by reference in its entirety. An exemplary method for introducing a glycosylation site into a molecule of the invention may comprise: modifying or mutating an amino acid sequence of the molecule so that the desired Asn-X-Thr/Ser sequence is obtained.

In some embodiments, the invention encompasses methods of modifying the carbohydrate content of a molecule of the invention by adding or deleting a glycosylation site. Methods for modifying the carbohydrate content of antibodies are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety. In other embodiments, the invention encompasses methods of modifying the carbohydrate content of a molecule of the invention by deleting one or more endogenous carbohydrate moieties of the molecule. In a specific embodiment, the invention encompasses shifting the glycosylation site of the Fc region of an antibody, by modifying positions adjacent to 297. In a specific embodiment, the invention encompasses modifying position 296 so that position 296 and not position 297 is glycosylated.

Effector function can also be modified by techniques such as by introducing one or more cysteine residues into the Fc region, thereby allowing interchain disulfide bond formation in this region to occur, resulting in the generation of a homodimeric antibody that may have improved internalization capability and/or increased complement-mediated cell killing and ADCC (Caron, P. C. et al. (1992) "*Engineered Humanized Dimeric Forms Of IgG Are More Effective Antibodies*," J. Exp. Med. 176:1191-1195; Shopes, B. (1992) "*A Genetically Engineered Human IgG Mutant With Enhanced Cytolytic Activity*," J. Immunol. 148(9):2918-2922. Homodimeric antibodies with enhanced anti-tumor activity may also be prepared using heterobifunctional cross-linkers as described in Wolff, E. A. et al. (1993) "*Monoclonal Antibody Homodimers: Enhanced Antitumor Activity In Nude Mice*," Cancer Research 53:2560-2565. Alternatively, an antibody can be engineered which has dual Fc regions and may thereby have enhanced complement lysis and ADCC capabilities (Stevenson, G. T. et al. (1989) "*A Chimeric Antibody With Dual Fc Regions (bisFabFc) Prepared By Manipulations At The IgG Hinge*," Anti-Cancer Drug Design 3:219-230).

E. B7-H3 DART (Dual Affinity Retargeting Reagents)

As discussed above, the present invention additionally encompasses "DART" (dual affinity retargeting reagent) molecules that comprise at least two polypeptide chains which form at least two epitope binding sites, at least one of which specifically binds to B7-H3.

In preferred embodiments, the first polypeptide chain of the DART comprises:

(i) a domain (A) comprising a binding region of a light chain variable domain of a first immunoglobulin (VL1) specific for an epitope (1);

(ii) a domain (B) comprising a binding region of a heavy chain variable domain of a second immunoglobulin (VH2) specific for an epitope (2); and (iii) a domain (C).

The second polypeptide chain of such a DART comprises:

(i) a domain (D) comprising a binding region of a light chain variable domain of the second immunoglobulin (VL2) specific for epitope (2);

(ii) a domain (E) comprising a binding region of a heavy chain variable domain of the first immunoglobulin (VH1) specific for epitope (1); and (iii) a domain (F).

The DART domains (A) and (B) do not associate with one another to form an epitope binding site. Similarly, the DART domains (D) and (E) do not associate with one another to form an epitope binding site. Rather, DART domains (A) and (E) associate to form a binding site that binds epitope (1); said DART domains (B) and (D) associate to form a binding site that binds said epitope (2). Domains (C) and (F) are covalently associated together.

Each polypeptide chain of the DART molecule comprises a VL domain and a VH domain, which are covalently linked such that the domains are constrained from self assembly. Interaction of two of the polypeptide chains will produce two VL-VH pairings, forming two epitope binding sites, i.e., a bivalent molecule. Neither the VH or VL domain is constrained to any position within the polypeptide chain, i.e., restricted to the amino (N) or carboxy (C) terminus, nor are the domains restricted in their relative positions to one another, i.e., the VL domain may be N-terminal to the VH domain and vice-versa. The only restriction is that a complimentary polypeptide chain be available in order to form functional DARTs. Where the VL and VH domains are derived from the same antibody, the two complimentary polypeptide chains may be identical. For example, where the binding domains are derived from an antibody specific for epitope A (i.e., the binding domain is formed from a $VL_A$-$VH_A$ interaction), each polypeptide will comprise a $VH_A$ and a $VL_A$. Homodimerization of two polypeptide chains of the antibody will result in the formation two $VL_A$-$VH_A$ binding sites, resulting in a bivalent monospecific antibody. Where the VL and VH domains are derived from antibodies specific for different antigens, formation of a functional bispecific DART requires the interaction of two different polypeptide chains, i.e., formation of a heterodimer. For example, for a bispecific DART, one polypeptide chain will comprise a $VL_A$ and a $VH_B$; homodimerization of said chain will result in the formation of two $VL_A$-$VH_B$ binding sites, either of no binding or of unpredictable binding. In contrast, where two differing polypeptide chains are free to interact, e.g., in a recombinant expression system, one comprising a $VL_A$ and a $VH_B$ and the other comprising a $VL_B$ and a $VH_A$, two differing binding sites will form: $VL_A$-$VH_A$ and $VL_B$-$VH_B$. For all DART polypeptide chain pairs, the possibly of misalignment or mis-binding of the two chains is a possibility, i.e., interaction of VL-VL or VH-VH domains; however, purification of functional diabodies is easily managed based on the immunospecificity of the properly dimerized binding site using any affinity based method known in the art or exemplified herein, e.g., affinity chromatography.

One or more of the polypeptide chains of the DART may optionally comprise an Fc domain domain or portion thereof (e.g. a CH2 domain, or CH3 domain) The Fc domain or portion thereof may be derived from any immunoglobulin isotype or allotype including, but not limited to, IgA, IgD, IgG, IgE and IgM. In preferred embodiments, the Fc domain (or portion thereof) is derived from IgG. In specific embodiments, the IgG isotype is IgG1, IgG2, IgG3 or IgG4 or an allotype thereof. In one embodiment, the diabody molecule comprises an Fc domain, which Fc domain comprises a CH2 domain and CH3 domain independently selected from any immunoglobulin isotype (i.e. an Fc domain comprising the CH2 domain derived from IgG and the CH3 domain derived from IgE, or the CH2 domain derived from IgG1 and the CH3 domain derived from IgG2, etc.). The Fc domain may be engineered into a polypeptide chain comprising the diabody molecule of the invention in any position relative to other domains or portions of said polypeptide chain (e.g., the Fc domain, or portion thereof, may be c-terminal to both the VL and VH domains of the polypeptide of the chain; may be n-terminal to both the VL and VH domains; or may be N-terminal to one domain and c-terminal to another (i.e., between two domains of the polypeptide chain)).

The Fc domains in the polypeptide chains of the DART molecules preferentially dimerize, resulting in the formation of a DART molecule that exhibits immunoglobulin-like properties, e.g., Fc-FcγR, interactions. Fc comprising diabodies may be dimers, e.g., comprised of two polypeptide chains, each comprising a VH domain, a VL domain and an Fc domain. Dimerization of said polypeptide chains results in a bivalent DART comprising an Fc domain, albeit with a structure distinct from that of an unmodified bivalent antibody. Such DART molecules will exhibit altered phenotypes relative to a wild-type immunoglobulin, e.g., altered serum half-life, binding properties, etc. In other embodiments, DART molecules comprising Fc domains may be tetramers. Such tetramers comprise two 'heavier' polypeptide chains, i.e., a polypeptide chain comprising a VL, a VH and an Fc domain, and two 'lighter' polypeptide chains, i.e., polypeptide chain comprising a VL and a VH. The lighter and heavier chains interact to form a monomer, and said monomers interact via their unpaired Fc domains to form an Ig-like molecule. Such an Ig-like DART is tetravalent and may be monospecific, bispecific or tetraspecific.

Formation of a tetraspecific diabody molecule as described supra requires the interaction of four differing polypeptide chains. Such interactions are difficult to achieve with efficiency within a single cell recombinant production system, due to the many variants of potential chain mispairings. One solution to decrease the probability of mispairings, is to engineer "knobs-into-holes" type mutations into the desired polypeptide chain pairs. Such mutations favor heterodimerization over homodimerization. For example, with respect to Fc-Fc-interactions, an amino acid substitution (preferably a substitution with an amino acid comprising a bulky side group forming a 'knob', e.g., tryptophan) can be introduced into the CH2 or CH3 domain such that steric interference will prevent interaction with a similarly mutated domain and will obligate the mutated domain to pair with a domain into which a complementary, or accommodating mutation has been engineered, i.e., 'the hole' (e.g., a substitution with glycine). Such sets of mutations can be engineered into any pair of polypeptides comprising the diabody molecule, and further, engineered into any portion of the polypeptides chains of said pair. Methods of protein engineering to favor heterodimerization over homodimerization are well known in the art, in particular with respect to the engineering of immunoglobulin-like molecules, and are encompassed herein (see e.g., Ridgway et al. (1996) "'*Knobs-Into-Holes*' *Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety.

The invention also encompasses diabody molecules comprising variant Fc or variant hinge-Fc domains (or portion thereof), which variant Fc domain comprises at least one amino acid modification (e.g. substitution, insertion deletion) relative to a comparable wild-type Fc domain or hinge-Fc domain (or portion thereof). Molecules comprising variant Fc domains or hinge-Fc domains (or portion thereof) (e.g., antibodies) normally have altered phenotypes relative to molecules comprising wild-type Fc domains or hinge-Fc domains or portions thereof. The variant phenotype may be expressed as altered serum half-life, altered stability, altered susceptibility to cellular enzymes or altered effector function as assayed in an NK dependent or macrophage dependent assay. Fc domain modifications identified as altering effector function are disclosed above.

The present invention also encompasses molecules comprising a hinge domain. The hinge domain be derived from any immunoglobulin isotype or allotype including IgA, IgD, IgG, IgE and IgM. In preferred embodiments, the hinge domain is derived from IgG, wherein the IgG isotype is IgG1, IgG2, IgG3 or IgG4, or an allotpye thereof. Said hinge domain may be engineered into a polypeptide chain comprising the diabody molecule together with an Fc domain such that the diabody molecule comprises a hinge-Fc domain. In certain embodiments, the hinge and Fc domain are independently selected from any immunoglobulin isotype known in the art or exemplified herein. In other embodiments the hinge and Fc domain are separated by at least one other domain of the polypeptide chain, e.g., the VL domain. The hinge domain, or optionally the hinge-Fc domain, may be engineered in to a polypeptide of the invention in any position relative to other domains or portions of said polypeptide chain In certain embodiments, a polypeptide chain of the invention comprises a hinge domain, which hinge domain is at the C-terminus of the polypeptide chain, wherein said polypeptide chain does not comprise an Fc domain. In yet other embodiments, a polypeptide chain of the invention comprises a hinge-Fc domain, which hinge-Fc domain is at the C-terminus of the polypeptide chain In further embodiments, a polypeptide chain of the invention comprises a hinge-Fc domain, which hinge-Fc domain is at the N-terminus of the polypeptide chain Each domain of the polypeptide chain of the DART, i.e., the VL, VH and Fc domain may be separated by a peptide linker. The peptide linker may be 0, 1, 2, 3, 4, 5, 6, 7, 8, or 9 amino acids in length. In certain embodiments the amino acid linker sequence is GGGSGGGG (SEQ ID NO: 52) encoded by the nucleic acid sequence ggaggcggat ccggaggcgg aggc (SEQ ID NO: 53). The polypeptide chains of the DART molecule may be engineered to comprise at least one cysteine residue that will interact with a counterpart cysteine residue on a second polypeptide chain of the DART to form an inter-chain disulfide bond. Such interchain disulfide bonds serve to stabilize the DART molecule, thereby improving expression and recovery in recombinant systems, resulting in a stable and consistent formulation and improving the stability of the isolated and/or purified product in vivo. The cysteine residue may be introduced as a single amino acid or as part of larger amino-acid sequence, e.g. a hinge domain, in any portion of the polypeptide chain. In a specific embodiment, the cysteine residue may be engineered to occur at the C-terminus of the polypeptide chain In some embodiments, the cysteine residue is introduced into the polypeptide chain within the amino acid sequence LGGC. In a specific embodiment, the C-terminus of the polypeptide chains comprising the DART molecule of the invention comprises the amino acid sequence LGGC (SEQ ID NO: 54). In another embodiment, the cysteine residue is introduced into the polypeptide within an amino acid sequence comprising a hinge domain, e.g. EPKSCDKTHTCPP (SEQ ID NO: 55) or ESKYGPPCPS (SEQ ID NO: 56). In a specific embodiment, the C-terminus of a polypeptide chain of the DART molecule of the invention comprises the amino acid sequence of an IgG hinge domain, e.g. SEQ ID NO: 55 or SEQ ID NO: 56. In another embodiment, the C-terminus of a polypeptide chain of a DART molecule of the invention comprises the amino acid sequence VEPKSC (SEQ ID NO: 57), which can be encoded by nucleotide sequence gttgagccca aatcttgt (SEQ ID NO: 58). In other embodiments, the cysteine residue in introduced into the polypeptide chain within the amino acid sequence LGGCFNRGEC (SEQ ID NO: 59), which can be encoded by the nucleotide sequence ctgggaggct gcttcaacag gggagagtgt (SEQ ID NO: 60). In a specific embodiment, the C-terminus of a polypeptide chain comprising the DART of the invention comprises the amino acid sequence LGGCFNRGEC (SEQ ID NO: 59). In yet other embodiments, the cysteine residue in introduced into the polypeptide chain within the amino acid sequence FNRGEC (SEQ ID NO: 61), which can be encoded by the nucleotide sequence ttcaacaggg gagagtgt (SEQ ID NO: 62). In a specific embodiment, the C-terminus of a polypeptide chain comprising the DART of the invention comprises the amino acid sequence FNRGEC (SEQ ID NO: 61).

In certain embodiments, the diabody molecule comprises at least two polypeptide chains, each of which comprise the amino acid sequence LGGC (SEQ ID NO: 54) and are covalently linked by a disulfide bond between the cysteine residues in the LGGC (SEQ ID NO: 54) sequences. In another specific embodiment, the diabody molecule comprises at least two polypeptide chains, one of which comprises the sequence FNRGEC (SEQ ID NO: 61) while the other comprises a hinge domain (containing at least one cysteine residue), wherein said at least two polypeptide chains are covalently linked by a disulfide bond between the cysteine residue in FNRGEC (SEQ ID NO: 61) and a cysteine residue in the hinge domain. In particular aspects, the cysteine residue responsible for the disulfide bond located in the hinge domain is Cys-128 (as numbered according to Kabat EU; located in the hinge domain of an unmodified, intact IgG heavy chain) and the counterpart cysteine residue in SEQ ID NO: 23 is Cys-214 (as numbered according to Kabat EU; located at the C-terminus of an unmodified, intact IgG light chain) (Elkabetz et al. (2005) "*Cysteines In CH1 Underlie Retention Of Unassembled Ig Heavy Chains,*" J. Biol. Chem. 280:14402-14412). In yet other embodiments, the at least one cysteine residue is engineered to occur at the N-terminus of the amino acid chain In still other embodiments, the at least one cysteine residue is engineered to occur in the linker portion of the polypeptide chain of the diabody molecule. In further embodiments, the VH or VL domain is engineered to comprise at least one amino acid modification relative to the parental VH or VL domain such that said amino acid modification comprises a substitution of a parental amino acid with cysteine.

In still another aspect of this embodiment, the Domain (C) of the first polypeptide chain comprises the amino acid sequence VEPKSC (SEQ ID NO: 57), derived from the hinge domain of a human IgG, and which can be encoded by the nucleotide sequence gttgagccca aatcttgt (SEQ ID NO: 58). In another aspect of this embodiment, the Domain (F) of the second polypeptide chain comprises the amino acid sequence VEPKSC (SEQ ID NO: 57). In certain aspects of this embodiment, Domain (C) of the first polypeptide chain comprises the C-terminal 6 amino acids of the human kappa light chain, FNRGEC (SEQ ID NO: 61); and Domain (F) of the second polypeptide chain comprises the amino acid sequence VEPKSC (SEQ ID NO: 57) or a hinge domain. In other aspects of this embodiment, Domain (F) of the second polypeptide chain comprises the C-terminal 6 amino acids of the human kappa light chain, FNRGEC (SEQ ID NO: 61); and Domain (C) of the first polypeptide chain comprises the amino acid sequence VEPKSC (SEQ ID NO: 57) or a hinge domain.

As will be appreciated in view of the foregoing, the individual polypeptides of a bispecific DART can form two species of homodimers and one species of heterodimer. In one embodiment of the present invention, a charged polypeptide can be added to the C-terminus of one, or more preferably, both DART polypeptides. By selecting charged polypeptides of opposite charge for the individual polypeptides of the bispecific DART, the inclusion of such charged polypeptides favors formation of heterodimers and lessens formation of homodimers. Preferably, a positively charged polypeptide will contain a substantial content of arginine, glutamine, histidine and/or lysine (or mixtures of such amino acids) and a negatively charged polypeptide will contain a substantial content of aspartate or glutamate (or a mixture of such amino acids). Positively charged polypeptides containing a substantial content of lysine and negatively charged polypeptides containing a substantial content of glutamate are particularly preferred. In order to maximize the electrostatic attraction between such opposingly charged polypeptides, it is preferred to employ polypeptides capable of spontaneously assuming a helical conformation.

Thus, in a preferred embodiment, a positively charged, "E-coil" will be appended to one of the polypeptides being used to form a bispecific DART and a negatively charged "K-coil" will be appended to the second of the DART's polypeptides. A particularly preferred E-coil will have the sequence: $(EVAALEK)_4$ [i.e. (SEQ ID NO: 63) EVAALEKEVAALEKEVAALEKEVAALEK]. A particularly preferred K-coil will have the sequence: (KVAALKE)$_4$ [i.e. (SEQ ID NO: 64) KVAALKEKVAALKEKVAALKEK-VAALKE].

A preferred DART polypeptide possessing such an E-coil will have the general sequence: [VL Domain]-[GGGSGGGG]-[VH Domain]-[(EVAALEK)$_4$]-GGGNS, where VL is the DART's variable light Ig domain, GGGSGGGG is SEQ ID NO: 52, VH is the DART's variable heavy Ig domain, (EVAALEK)$_4$ is SEQ ID NO: 63, and GGGNS is SEQ ID NO: 65. A preferred DART polypeptide possessing such a K-coil will have the general sequence: [VL Domain]-[GGGSGGGG]-[VH Domain]-[(KVAALKE)$_4$]-GGGNS, where VL is the DART's variable light Ig domain, GGGSGGGG is SEQ ID NO: 52, VH is the DART's variable heavy Ig domain, (KVAALKE)$_4$ is SEQ ID NO: 64, and GGGNS is SEQ ID NO: 65.

In a further embodiment, Fc-regions can be linked to the E and/or K coils of E-coil or K-*coli* DARTs. Furthering the separation between the Fc regions and the DART VH domain of an Fc-containing DART is desirable in cases in which a less separated arrangement of such domains results in diminished interaction between such domains and their binding ligands or otherwise interferes with DART assembly. Although separators of any amino acid sequence may be employed, it is preferable to employ separators that form an a helix coils, so as to maximally extend and project the Fc domain away from the variable domains. Because the above-described coiled polypeptides of opposing charge additionally function to promote heterodimer formation, such molecules are particularly preferred separators. Such coil-containing Fc-DART molecules provide benefits similar to those of Fc-DARTS, including improved serum half-life and effector function recruitment. The above-described E-coil and K-coil polypeptides are particularly preferred for this purpose. Thus, in a preferred embodiment, the E-coil Fc-containing DART will have the general sequence: [VL Domain]-[GGGSGGGG]-[VH Domain]-[(KEVAALEK)$_4$]-GGG-Fc domain starting with D234 (Kabat numbering), where VL is the DART's variable light Ig domain, GGGSGGGG is SEQ ID NO: 52, VH is the DART's variable heavy Ig domain and (EVAALEK)$_4$ is SEQ ID NO: 63. Similarly, in a preferred embodiment, the K-coil Fc-containing DART will have the general sequence: [VL Domain]-[GGGSGGGG]-[VH Domain]-[(KKVAALEK)$_4$]-GGG-Fc domain starting with D234 (Kabat numbering), where VL is the DART's variable light Ig domain, GGGSGGGG is SEQ ID NO: 51, VH is the DART's variable heavy Ig domain and (KVAALKE)$_4$ is SEQ ID NO: 64.

As indicated above, a coil-containing DART molecule or a coil-containing Fc-containing DART molecule may contain only a single such coil separator, or it may contain more than one such separators (e.g., two separators, preferably of opposite charge, of which one is linked to each of the VH domain of the DART's polypeptides). By linking the Fc region to such separator molecule(s), the ability to make bivalent, tetravalent, etc. versions of the Fc-DART molecules by chain swapping is enhanced. Fc-DART molecules can thus be produced that form monomers or dimers depending upon whether the Fc domain is linked to one or both of the DART VH domains 1. Versatility of B7-H3 DART Molecules The bispecific DARTs of the invention can simultaneously bind two separate and distinct epitopes. In certain embodiments the epitopes are from the same antigen. In other embodiments, the epitopes are from different antigens. In preferred embodiments, at least one epitope binding site is specific for a determinant expressed on an immune effector cell (e.g. CD3, CD16, CD32, CD64, T-cell receptor, etc.) which are expressed on T lymphocytes, natural killer (NK) cells or other mononuclear cells. In one embodiment, the DART molecule binds to the effector cell determinant and also activates said effector cell. In this regard, DART molecules of the invention may exhibit Ig-like functionality independent of whether they further comprise an Fc domain (e.g., as assayed in any effector function assay known in the art or exemplified herein (e.g., ADCC assay). In certain embodiments the bispecific DART of the invention binds both a cancer antigen on a tumor cell and an effector cell determinant while activating said cell. In alternative embodiments, the bispecific DART or DART molecule of the invention may inhibit activation of a target, e.g., effector, cell by simultaneously binding, and thus linking, an activating and inhibitory receptor on the same cell (e.g., bind both CD32A and CD32B, BCR and CD32B, or IgERI and CD32B) as described supra (see, Background Section). In a further aspect of this embodiment, the bispecific DART may exhibit antiviral properties by simultaneously binding two neutralizing epitopes on a virus (e.g., RSV epitopes; WNV epitopes such as E16 and E53).

2. Universal B7-H3 DART Molecules

In one embodiment, the bispecific DART molecules of the invention may be constructed to comprise one epitope binding domain that specifically binds to B7-H3 and a second epitope binding domain that specifically binds a hapten, e.g. fluorescein isothiocyanate (also known as fluoroisothiocyanate or FITC). Such a DART serves as a universal adaptor ("UDART"), able to co-ligate B7-H3 with molecules that interact with fluorescein-conjugated binding partners. For example, the FITC-reactive arm of the DART may be used to bind to an FITC labeled antibody that is bound to a non-B7-H3 target involved in intercellular clustering, intercellular recruitment, cell-free recruitment, multiple targets, etc. The chimeric mouse Fv/human Fc version of the anti-fluorescein MAb, 4420 may be employed as a source of FITC-specific CDR domains (Gruber, M. et al. (1994) "*Efficient Tumor Cell Lysis Mediated By A Bispecific Single Chain Antibody Expressed In Escherichia coli*," J. Immunol. 152(11): 5368-5374).

3. Cell-Target Specific B7-H3 DART Molecules

The bispecific DART molecules of the invention offer unique opportunities to target specific cell types. For example, the bispecific DART or DART molecule can be engineered to comprise a combination of epitope binding sites that recognize a set of antigens unique to a target cell or tissue type. Additionally, where either or both of the individual antigens is/are fairly common separately in other tissue and/or cell types, low affinity biding domains can be used to construct the DART or DART molecule. Such low affinity binding domains will be unable to bind to the individual epitope or antigen with sufficient avidity for therapeutic purposes. However, where both epitopes or antigens are present on a single target cell or tissue, the avidity of the DART or DART molecule for the cell or tissue, relative to a cell or tissue expressing only one of the antigens, will be increased such that said cell or tissue can be effectively targeted by the invention. Such a bispecific molecule can exhibit enhanced binding to one or both of its target antigens on cells expressing both of said antigens relative to a monospecific DART or an antibody with a specificity to only one of the antigens.

For Example, the B7-H3 specific DARTS of the present invention may be constructed to comprise a domain that is a binding ligand for the Natural Killer Group 2D (NKG2D)

receptor. The NKG2D receptor is expressed on all human (and other mammalian) Natural Killer cells (Bauer, S. et al. (1999) "*Activation Of NK Cells And T Cells By NKG2D, A Receptor For Stress Inducible MICA*," Science 285(5428): 727-729; Jamieson, A. M. et al. (2002) "*The Role Of The NKG2D Immunoreceptor In Immune Cell Activation And Natural Killing*," Immunity 17(1):19-29) as well as on all CD8+ T cells (Groh, V. et al. (2001) "*Costimulation Of CD8αβ T Cells By NKG2D Via Engagement By MIC Induced On Virus-Infected Cells*," Nat. Immunol. 2(3):255-260; Jamieson, A. M. et al. (2002) "*The Role Of The NKG2D Immunoreceptor In Immune Cell Activation And Natural Killing*," Immunity 17(1):19-29). Such binding ligands, and particularly those which are not expressed on normal cells, include the histocompatibility 60 (H60) molecule, the product of the retinoic acid early inducible gene-1 (RAE-1), and the murine UL16-binding proteinlike transcript 1 (MULTI) (Raulet D. H. (2003) "*Roles Of The NKG2D Immunoreceptor And Its Ligands*," Nature Rev. Immunol. 3:781-790; Coudert, J. D. et al. (2005) "*Altered NKG2D Function In NK Cells Induced By Chronic Exposure To Altered NKG2D Ligand-Expressing Tumor Cells*," Blood 106:1711-1717). Additional ligands reactive with human NKG2D include the polymorphic MHC class I chain-related molecules MICA and MICB (Diefenbach, A. et al. (1999) "*Natural Killer Cells: Stress Out, Turn On, Tune In*," Curr. Biol. 9(22): R851-R8533; Bauer, S. et al. (1999) "*Activation Of NK Cells And T Cells By NKG2D, A Receptor For Stress-Inducible MICA*," Science 285(5428):727-729; Stephens, H. A. (2001) "*MICA And MICB Genes: Can The Enigma Of Their Polymorphism Be Resolved?*" Trends Immunol. 22:378-385. The sequence of MICA is SEQ ID NO: 66:

```
MGLGPVFLLL  AGIFPFAPPG  AAAEPHSLRY  NLTVLSWDGS

VQSGFLTEVH  LDGQPFLRCD  RQKCRAKPQG  QWAEDVLGNK

TWDRETRDLT  GNGKDLRMTL  AHIKDQKEGL  HSLQEIRVCE

IHEDNSTRSS  QHFYYDGELF  LSQNLETKEW  TMPQSSRAQT

LAMNVRNFLK  EDAMKTKTHY  HAMHADCLQE  LRRYLKSGVV

LRRTVPPMVN  VTRSEASEGN  ITVTCRASGF  YPWNITLSWR

QDGVSLSHDT  QQWGDVLPDG  NGTYQTWVAT  RICQGEEQRF

TCYMEHSGNH  STHPVPSGKV  LVLQSHWQTF  HVSAVAAAAI

FVIIIFYVRC  CKKKTSAAEG  PELVSLQVLD  QHPVGTSDHR

DATQLGFQPL  MSDLGSTGST  EGA
```

The sequence of MICB is SEQ ID NO: 67:

```
PHSLRYNLMV  LSQDGSVQSG  FLAEGHLDGQ  PFLRYDRQKR

RAKPQGQWAE  DVLGAKTWDT  ETEDLTENGQ  DLRRTLTHIK

DQKGGLHSLQ  EIRVCEIHED  SSTRGSRHFY  YDGELFLSQN

LETQESTVPQ  SSRAQTLAMN  VTNFWKEDAM  KTKTHYRAMQ

ADCLQKLQLP  PMVNVICSEV  SEGNITVTCR  ASSFYPRNIT

LTWRQDGVSL  SHNTQQWGDV  LPDGNGTYQT  WVATRIRQGE

EQRFTCYMEH  SGNHGTHPVP  SGKALVLQSQ  RTDFPYVSAA

MPCFVIIIIL  CVPCCKKKTS  AAEGP
```

Alternatively, the DART molecules of the present invention may be constructed to comprise a domain that is a binding ligand for the T-cell receptor ("TCR") or for CD3 (the T-cell co-receptor). The TCR is natively expressed by CD4+ or CD8+ T-cells, and permits such cells to recognize antigenic peptides that are bound and presented by class I or class II MHC proteins of antigen-presenting cells. Recognition of a pMHC (peptide-MHC) complex by a TCR initiates the propagation of a cellular immune response that leads to the production of cytokines and the lysis of the antigen-presenting cell (see, e.g., Armstrong, K. M. et al. (2008) "*Conformational Changes And Flexibility In T-Cell Receptor Recognition Of Peptide MHC Complexes*," Biochem. J. 415(Pt 2):183-196; Willemsen, R. (2008) "*Selection Of Human Antibody Fragments Directed Against Tumor T-Cell Epitopes For Adoptive T-Cell Therapy*," Cytometry A. 73(11):1093-1099; Beier, K. C. et al. (2007) "*Master Switches Of T-Cell Activation And Differentiation*," Eur. Respir. J. 29:804-812; Mallone, R. et al. (2005) "*Targeting T Lymphocytes For Immune Monitoring And Intervention In Autoimmune Diabetes*," Am. J. Ther. 12(6):534-550). CD3 is the receptor that binds to the TCR (Thomas, S. et al. (2010) "*Molecular Immunology Lessons From Therapeutic T-Cell Receptor Gene Transfer*," Immunology 129(2):170-177; Guy, C. S. et al. (2009) "*Organization Of Proximal Signal Initiation At The TCR:CD3 Complex*," Immunol. Rev. 232(1):7-21; St. Clair, E. W. (Epub 2009 Oct. 12) "*Novel Targeted Therapies For Autoimmunity*," Curr. Opin. Immunol. 21(6):648-657; Baeuerle, P. A. et al. (Epub 2009 Jun. 9) "*Bispecific T-Cell Engaging Antibodies For Cancer Therapy*," Cancer Res. 69(12):4941-4944; Smith-Garvin, J. E. et al. (2009) "*T Cell Activation*," Annu. Rev. Immunol. 27:591-619; Renders, L. et al. (2003) "*Engineered CD3 Antibodies For Immunosuppression*," Clin. Exp. Immunol. 133(3):307-309).

By constructing such DART molecules to additionally comprise at least one epitope-binding domain capable of binding to, for example, a receptor present on the surface of a target cell, such DART molecules will thus be capable of binding to the target cells and thereby cause the target cells to display the binding ligand for the Natural Killer Group 2D (NKG2D) receptor or to the TCR (whichever is present on the target cell-bound DART) (see, e.g., Germain, C. et al. (2008) "*Redirecting NK Cells Mediated Tumor Cell Lysis By A New Recombinant Bifunctional Protein*," Prot. Engineer. Design Selection 21(11):665-672). Such DARTs can be used to redirect any desired target cell into a cell that is a target of NK cell-mediated cell lysis or T-cell mediated cytotoxicity. In one embodiment, the epitope-binding domain of the DART capable of binding to a receptor present on the surface of a target cell is an epitope that binds to a tumor-associated antigen so as to redirect such cancer cells into substrates for NK cell-mediated cell lysis or T-cell mediated cytotoxicity. Of particular interest is a tumor-associated antigens that is a breast cancer antigen, an ovarian cancer antigen, a prostate cancer antigen, a cervical cancer antigen, a pancreatic carcinoma antigen, a lung cancer antigen, a bladder cancer antigen, a colon cancer antigen, a testicular cancer antigen, a glioblastoma cancer antigen, an antigen associated with a B cell malignancy, an antigen associated with multiple myeloma, an antigen associated with non-Hodgkins lymphoma, or an antigen associated with chronic lymphocytic leukemia.

Suitable tumor-associated antigens for such use include A33 (a colorectal carcinoma antigen; Almqvist, Y. 2006, *Nucl Med Biol*. November; 33(8):991-998); B1 (Egloff, A. M. et al. 2006, *Cancer Res.* 66(1):6-9); BAGE (Bodey, B.

2002 *Expert Opin Biol Ther.* 2(6):577-84); beta-catenin (Prange W. et al. 2003 *J Pathol.* 201(2):250-9); CA125 (Bast, R. C. Jr. et al. 2005 *Int J Gynecol Cancer* 15 Suppl 3:274-81); CD5 (Calin, G. A. et al. 2006 *Semin Oncol.* 33(2):167-73; CD19 (Troussard, X. et al. 1998 *Hematol Cell Ther.* 40(4):139-48); CD20 (Thomas, D. A. et al. 2006 Hematol Oncol Clin North Am. 20(5):1125-36); CD22 (Kreitman, R. J. 2006 AAPS J. 18; 8(3):E532-51); CD23 (Rosati, S. et al. 2005 *Curr Top Microbiol Immunol.* 5; 294:91-107); CD25 (Troussard, X. et al. 1998 *Hematol Cell Ther.* 40(4): 139-48); CD27 (Bataille, R. 2006 *Haematologica* 91(9): 1234-40); CD28 (Bataille, R. 2006 *Haematologica* 91(9): 1234-40); CD36 (Ge, Y. 2005 *Lab Hematol.* 11(1):31-7); CD40/CD154 (Messmer, D. et al. 2005 *Ann N Y Acad Sci.* 1062:51-60); CD45 (Jurcic, J. G. 2005 *Curr Oncol Rep.* 7(5):339-46); CD56 (Bataille, R. 2006 *Haematologica* 91(9):1234-40); CD79a/CD79b (Troussard, X. et al. 1998 *Hematol Cell Ther.* 40(4):139-48; Chu, P. G. et al. 2001 Appl Immunohistochem Mol Morphol. 9(2):97-106); CD103 (Troussard, X. et al. 1998 *Hematol Cell Ther.* 40(4):139-48); CDK4 (Lee, Y. M. et al. 2006 *Cell Cycle* 5(18):2110-4); CEA (carcinoembryonic antigen; Mathelin, C. 2006 *Gynecol Obstet Fertil.* 34(7-8):638-46; Tellez-Avila, F. I. et al. 2005 *Rev Invest Clin.* 57(6):814-9); CTLA4 (Peggs, K. S. et al. 2006 *Curr Opin Immunol.* 18(2):206-13); EGF-R (epidermal growth factor receptor; Adenis, A. et al. 2003 *Bull Cancer.* 90 Spec No:S228-32); Erb (ErbB1; ErbB3; ErbB4; Zhou, H. et al. 2002 *Oncogene* 21(57):8732-40; Rimon, E. et al. 2004 Int J Oncol. 24(5):1325-38); GAGE (GAGE-1; GAGE-2; Akcakanat, A. et al. 2006 *Int J Cancer.* 118(1): 123-8); GD2/GD3/GM2 (Livingston, P. O. et al. 2005 Cancer Immunol Immunother. 54(10):1018-25); gp100 (Lotem, M. et al. 2006 *J Immunother.* 29(6):616-27); HER-2/neu (Kumar, Pal S et al. 2006 Semin Oncol. 33(4):386-91); human papillomavirus-E6/human papillomavirus-E7 (Di-Maio, D. et al. 2006 *Adv Virus Res.* 66:125-59; KSA (17-1A) (Ragupathi, G. 2005 *Cancer Treat Res.* 123:157-80); MAGE (MAGE-1; MAGE-3; (Bodey, B. 2002 *Expert Opin Biol Ther.* 2(6):577-84); MART (Kounalakis, N. et al. 2005 *Curr Oncol Rep.* 7(5):377-82); MUC-1 (Mathelin, C. 2006 *Gynecol Obstet Fertil.* 34(7-8):638-46); MUM-1 (Castelli, C. et al. 2000 *J Cell Physiol.* 182(3):323-31); N-acetylglucosaminyltransferase (Dennis, J. W. 1999 *Biochim Biophys Acta.* 6; 1473(1):21-34); p15 (Gil, J. et al. 2006 *Nat Rev Mol Cell Biol.* 7(9):667-77); PSA (prostate specific antigen; Cracco, C. M. et al. 2005 *Minerva Urol Nefrol.* 57(4):301-11); PSMA (Ragupathi, G. 2005 *Cancer Treat Res.* 123:157-80); sTn (Holmberg, L. A. 2001 *Expert Opin Biol Ther.* 1(5): 881-91); TNF-receptor (TNF-α receptor, TNF-β receptor; or TNF-γ receptor; van Horssen, R. et al. 2006 *Oncologist.* 11(4):397-408; Gardnerova, M. et al. 2000 *Curr Drug Targets.* 1(4):327-64); or VEGF receptor (O'Dwyer. P. J. 2006 *Oncologist.* 11(9):992-8).

Additional tumor-associated antigens for such use (and publications disclosing specifically reactive antibodies for such antigens) include ADAM-9 (United States Patent Publication No. 2006/0172350; PCT Publication No. WO 06/084075); ALCAM (PCT Publication No. WO 03/093443); Carboxypeptidase M (United States Patent Publication No. 2006/0166291); CD46 (U.S. Pat. No. 7,148, 038; PCT Publication No. WO 03/032814); Cytokeratin 8 (PCT Publication No. WO 03/024191); Ephrin receptors (and in particular EphA2 (U.S. Pat. No. 7,569,672; PCT Publication No. WO 06/084226); Integrin Alpha-V-Beta-6 (PCT Publication No. WO 03/087340); JAM-3 (PCT Publication No. WO 06/084078); KID3 (PCT Publication No. WO 05/028498); KID31 (PCT Publication No. WO 06/076584); LUCA-2 (United States Patent Publication No. 2006/0172349; PCT Publication No. WO 06/083852); Oncostatin M (Oncostatin Receptor Beta) (U.S. Pat. No. 7,572,896; PCT Publication No. WO 06/084092); PIPA (U.S. Pat. No. 7,405,061; PCT Publication No. WO 04/043239); ROR1 (U.S. Pat. No. 5,843,749); and the Transferrin Receptor (U.S. Pat. No. 7,572,895; PCT Publication No. WO 05/121179).

Also of interest are antigens specific to particular infectious agents, e.g., viral agents including, but not limited to human immunodeficiency virus (HIV), hepatitis B virus (HBV), influenza, human papilloma virus (HPV), foot and mouth (coxsackieviruses), the rabies virus, herpes simplex virus (HSV), and the causative agents of gastroenteritis, including rotaviruses, adenoviruses, caliciviruses, astroviruses and Norwalk virus; bacterial agents including, but not limited to *E. coli, Salmonella thyphimurium, Pseudomonas aeruginosa, Vibrio cholerae, Neisseria gonorrhoeae, Helicobacter pylori, Hemophilus influenzae, Shigella dysenteriae, Staphylococcus aureus, Mycobacterium tuberculosis* and *Streptococcus pneumoniae*, fungal agents and parasites such as Giardi.

In some embodiments, molecules of the invention are engineered to comprise an altered glycosylation pattern or an altered glycoform relative to the comparable portion of the template molecule. Engineered glycoforms may be useful for a variety of purposes, including, but not limited to, enhancing effector function. Engineered glycoforms may be generated by any method known to one skilled in the art, for example by using engineered or variant expression strains, by co-expression with one or more enzymes, for example, DI N-acetylglucosaminyltransferase III (GnTI11), by expressing a DART of the invention in various organisms or cell lines from various organisms, or by modifying carbohydrate(s) after the DART has been expressed and purified. Methods for generating engineered glycoforms are known in the art, and include but are not limited to those described in Umana et al. (1999) "*Engineered Glycoforms Of An Anti-neuroblastoma IgG1 With Optimized Antibody-Dependent Cellular Cytotoxic Activity*," Nat. Biotechnol 17:176-180; Davies et al. (2001) "*Expression Of GnTIII In A Recombinant Anti-CD20 CHO Production Cell Line: Expression Of Antibodies With Altered Glycoforms Leads To An Increase In Adcc Through Higher Affinity For Fc Gamma RIII*," Biotechnol Bioeng 74:288-294; Shields et al. (2002) "*Lack Of Fucose On Human IgG1 N-Linked Oligosaccharide Improves Binding To Human Fcgamma RIII And Antibody-Dependent Cellular Toxicity*," J Biol Chem 277:26733-26740; Shinkawa et al. (2003) "*The Absence Of Fucose But Not The Presence Of Galactose Or Bisecting N-Acetylglucosamine Of Human IgG1 Complex-Type Oligosaccharides Shows The Critical Role Of Enhancing Antibody-Dependent Cellular Cytotoxicity*," J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland); each of which is incorporated herein by reference in its entirety. See, e.g., WO 00061739; EA01229125; US 20030115614; Okazaki et al. (2004) "*Fucose Depletion From Human IgG1 Oligosaccharide Enhances Binding Enthalpy And Association Rate Between IgG1 And FcGammaRIIIA*," JMB, 336: 1239-49 each of which is incorporated herein by reference in its entirety.

The invention further encompasses incorporation of unnatural amino acids to generate the DARTs of the invention. Such methods are known to those skilled in the art such as those using the natural biosynthetic machinery to allow incorporation of unnatural amino acids into proteins, see, e.g., Wang et al. (2002) "*Expanding The Genetic Code,*" Chem. Comm. 1: 1-11; Wang et al. (2001) "*Expanding The Genetic Code Of Escherichia coli,*" Science, 292: 498-500; van Hest et al. (2001) "*Protein-Based Materials, Toward A New Level Of Structural Control,*" Chem. Comm. 19: 1897-1904, each of which is incorporated herein by reference in its entirety. Alternative strategies focus on the enzymes responsible for the biosynthesis of amino acyl-tRNA, see, e.g., Tang et al. (2001) "*Biosynthesis Of A Highly Stable Coiled-Coil Protein Containing Hexafluoroleucine In An Engineered Bacterial Host,*" J. Am. Chem. Soc. 123(44): 11089-11090; Kiick et al. (2001) "*Identification Of An Expanded Set Of Translationally Active Methionine Analogues In Escherichia coli,*" FEBS Lett. 502(1-2):25-30; each of which is incorporated herein by reference in its entirety. In some embodiments, the invention encompasses methods of modifying a VL, VH or Fc domain of a molecule of the invention by adding or deleting a glycosylation site. Methods for modifying the carbohydrate of proteins are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety.

VIII. Methods of Using B7-H3 Modulators and Anti-B7-H3 Antibodies for Therapeutic Purposes Monoclonal antibodies to B7-H3 may be used for therapeutic purposes in individuals with cancer or other diseases. Therapy with anti-B7-H3 antibodies can involve formation of complexes both in vitro and in vivo as described above. In one embodiment, monoclonal antibody anti-B7-H3 can bind to and reduce the proliferation of cancerous cells. It is understood that the antibody is administered at a concentration that promotes binding at physiological (e.g., in vivo) conditions. In another embodiment, monoclonal antibodies to B7-H3 can be used for immunotherapy directed at cancerous cells of different tissues such as colon, lung, breast, prostate, ovary, pancreas, kidney and other types of cancer such as sarcoma. In another embodiment, monoclonal antibody anti-B7-H3 alone can bind to and reduce cell division in the cancer cell. In another embodiment, monoclonal antibody anti-B7-H3 can bind to cancerous cells and delay the development of metastasis. In yet another embodiment, an individual with cancer is given palliative treatment with anti-B7-H3 antibody. Palliative treatment of a cancer individual involves treating or lessening the adverse symptoms of the disease, or iatrogenic symptoms resulting from other treatments given for the disease without directly affecting the cancer progression. This includes treatments for easing of pain, nutritional support, sexual problems, psychological distress, depression, fatigue, psychiatric disorders, nausea, vomiting, etc.

In such situations, the anti-B7-H3 antibody may be administered with agents that enhance or direct an individual's own immune response, such as an agent that strengthens ADCC.

In yet another embodiment, anti-B7-H3 antibody be conjugated to or associated with a radioactive molecule, toxin (e.g., calicheamicin), chemotherapeutic molecule, liposomes or other vesicles containing chemotherapeutic compounds and administered to an individual in need of such treatment to target these compounds to the cancer cell containing the antigen recognized by the antibody and thus eliminate cancerous or diseased cells. Without being limited to any particular theory, the anti-B7-H3 antibody is internalized by the cell bearing B7-H3 at its surface, thus delivering the conjugated moiety to the cell to induce the therapeutic effect. In yet another embodiment, the antibody can be employed as adjuvant therapy at the time of the surgical removal of a cancer expressing the antigen in order to delay the development of metastasis. The antibody can also be administered before surgery (neoadjuvant therapy) in an individual with a tumor expressing the antigen in order to decrease the size of the tumor and thus enable or simplify surgery, spare tissue during surgery, and/or decrease the resulting disfigurement.

Cell cycle dosing is contemplated in the practice of this invention. In such embodiments, a chemotherapeutic agent is used to synchronize the cell cycle of the tumor or other target diseased cells at a pre-determined stage. Subsequently, administration of the anti-B7-H3 antibody of this invention (alone or with an additional therapeutic moiety) is made. In alternative embodiments, an anti-B7-H3 antibody is used to synchronize the cell cycle and reduce cell division prior to administration of a second round of treatment; the second round may be administration of an anti-B7-H3 antibody and/or an additional therapeutic moiety.

Chemotherapeutic agents include radioactive molecules, toxins, also referred to as cytotoxins or cytotoxic agents, which includes any agent that is detrimental to the viability of cancerous cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), antimitotic agents, cis-dichlorodiamine platinum (II) (DDP) cisplatin), diaminodichloroplatinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxyanthracindione, Docetaxel, dolasetronmesylate, doxorubicin HCL, dronabinol, *E. coli* L-asparaginase, emetine, epoetin alpha, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon alpha-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptupurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 (with carmustine implant), porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

In a preferred embodiment, the cytotoxin is especially effective in dividing or rapidly dividing cells, such that non-dividing cells are relatively spared from the toxic effects.

The antibodies of the invention can be internalized within the diseased or carcinoma cells to which they bind and are therefore particularly useful for therapeutic applications, for example, delivering into the cells toxins that need to be internalized for their adverse activity. Examples of such toxins include, but are not limited to, saporin, calicheamicin, auristatin, and maytansinoid.

The antibodies or polypeptides of the invention can be associated (including conjugated or linked) to a radioactive molecule, a toxin, or other therapeutic agents, or to liposomes or other vesicles containing therapeutic agents covalently or non-covalently, directly or indirectly. The antibody may be linked to the radioactive molecule, the toxin, or the chemotherapeutic molecule at any location along the antibody so long as the antibody is able to bind its target B7-H3.

A toxin or a chemotherapeutic agent may be administered concurrently with (before, after, or during administration), or coupled (e.g., covalently bonded) to a suitable monoclonal antibody either directly or indirectly (e.g., via a linker group, or, alternatively, via a linking molecule with appropriate attachment sites, such as a platform molecule as described in U.S. Pat. No. 5,552,391). The toxin and chemotherapeutic agent of the present invention can be coupled directly to the particular targeting proteins using methods known in the art. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies or polypeptides can also be linked to a chemotherapeutic agent via a microcarrier. The term "microcarrier" refers to a biodegradable or a non-biodegradable particle which is insoluble in water and which has a size of less than about 150 µm, 120 µm or 100 µm in size, more commonly less than about 50-60 µm, preferably less than about 10, 5, 2.5, 2 or 1.5 µm. Microcarriers include "nanocarriers", which are microcarriers have a size of less than about 1 µm, preferably less than about 500 nm. Such particles are known in the art. Solid phase microcarriers may be particles formed from biocompatible naturally occurring polymers, synthetic polymers or synthetic copolymers, which may include or exclude microcarriers formed from agarose or cross-linked agarose, as well as other biodegradable materials known in the art. Biodegradable solid phase microcarriers may be formed from polymers which are degradable (e.g., poly(lactic acid), poly(glycolic acid) and copolymers thereof) or erodible (e.g., poly(orthoesters), such as 3,9-diethylidene-2,4,8,10-tetraoxaspiro [5.5]undecane (DETOSU) or poly(anhydrides), such as poly(anhydrides) of sebacic acid) under mammalian physiological conditions. Microcarriers may also be liquid phase (e.g., oil or lipid based), such as liposomes, iscoms (immune-stimulating complexes, which are stable complexes of cholesterol, and phospholipid, adjuvant-active saponin) without antigen, or droplets or micelles found in oil-in-water or water-in-oil emulsions, provided the liquid phase microcarriers are biodegradable. Biodegradable liquid phase microcarriers typically incorporate a biodegradable oil, a number of which are known in the art, including squalene and vegetable oils. Microcarriers are typically spherical in shape, but microcarriers that deviate from spherical shape are also acceptable (e.g., ellipsoid, rod-shaped, etc.). Due to their insoluble nature (with respect to water), microcarriers are filterable from water and water-based (aqueous) solutions.

The antibody or polypeptide conjugates of the present invention may include a bifunctional linker that contains both a group capable of coupling to a toxic agent or chemotherapeutic agent and a group capable of coupling to the antibody. A linker can function as a spacer to distance an antibody from an agent in order to avoid interference with binding capabilities. A linker can be cleavable or non-cleavable. A linker can also serve to increase the chemical reactivity of a substituent on an agent or an antibody, and thus increase the coupling efficiency. An increase in chemical reactivity may also facilitate the use of agents, or functional groups on agents, which otherwise would not be possible. The bifunctional linker can be coupled to the antibody by means that are known in the art. For example, a linker containing an active ester moiety, such as an N-hydroxysuccinimide ester, can be used for coupling to lysine residues in the antibody via an amide linkage. In another example, a linker containing a nucleophilic amine or hydrazine residue can be coupled to aldehyde groups produced by glycolytic oxidation of antibody carbohydrate residues. In addition to these direct methods of coupling, the linker can be indirectly coupled to the antibody by means of an intermediate carrier such as an aminodextran. In these embodiments the modified linkage is via either lysine, carbohydrate, or an intermediate carrier. In one embodiment, the linker is coupled site-selectively to free thiol residues in the protein. Moieties that are suitable for selective coupling to thiol groups on proteins are well known in the art. Examples include disulfide compounds, α-halocarbonyl and α-halocarboxyl compounds, and maleimides. When a nucleophilic amine function is present in the same molecule as an α-halo carbonyl or carboxyl group the potential exists for cyclization to occur via intramolecular alkylation of the amine Methods to prevent this problem are well known to one of ordinary skill in the art, for example by preparation of molecules in which the amine and α-halo functions are separated by inflexible groups, such as aryl groups or trans-alkenes, that make the undesired cyclization stereochemically disfavored. See, for example, U.S. Pat. No. 6,441,163 for preparation of conjugates of maytansinoids and antibody via a disulfide moiety.

One of the cleavable linkers that can be used for the preparation of antibody-drug conjugates is an acid-labile linker based on cis-aconitic acid that takes advantage of the acidic environment of different intracellular compartments such as the endosomes encountered during receptor mediated endocytosis and the lysosomes. See, for example, Shen, W. C. et al. (1981) ("*cis-Aconityl Spacer Between Daunomycin And Macromolecular Carriers: A Model Of pH-Sensitive Linkage Releasing Drug From A Lysosomotropic Conjugate*," Biochem. Biophys. Res. Comtnun. 102:1048-1054 (1981)) for the preparation of conjugates of daunorubicin with macromolecular carriers; Yang et al. (1988) ("*Pharmacokinetics And Mechanism Of Action Of A Doxorubicin Monoclonal Antibody 9.2.27 Conjugate Directed To*

A Human Melanoma Proteoglycan," J. Natl. Canc. Inst. 80:1154-1159) for the preparation of conjugates of daunorubicin to an anti-melanoma antibody; Dillman et al. (1988) ("*Superiority Of An Acid-Labile Daunorubicin Monoclonal Antibody Immunoconjugate Compared To Free Drug*," Cancer Res. 48:6097-6102) for using an acid-labile linker in a similar fashion to prepare conjugates of daunorubicin with an anti-T cell antibody; and Trouet et al. (1982) "*A Covalent Linkage Between Daunorubicin And Proteins That Is Stable In Serum And Reversible By Lysosomal Hydrolases, As Required For A Lysosomotropic Drug-Carrier Conjugate: In Vitro And In Vivo Studies*," Proc. Natl. Acad. Sci. (U.S.A.) 79:626-629) for linking daunorubicin to an antibody via a peptide spacer arm.

An antibody (or polypeptide) of this invention may be conjugated (linked) to a radioactive molecule or toxin by any method known to the art. For a discussion of methods for radiolabeling antibody (see, CANCER THERAPY WITH MONOCLONAL ANTIBODIES, D. M. Goldenberg (Ed.) CRC Press, Boca Raton, 1995). Suitable toxins include taxanes, maytansinoids, auristatins (e.g., monomethyl auristatin (MMAE), monomethyl auristatin F (MMAF), auristatin E (AE), etc.) (such as those disclosed in U.S. Pat. Nos. 5,208,020; 5,416,064; 6,333,410; 6,340,701; 6,372,738; 6,436,931; 6,441,163; 6,596,757; 7,276,497; 7,585,857; or 7,851,432), calicheamicin, anthracyclines (e.g., doxorubicin), CC-1065 analog, docetaxel; cathepsin B or E; ricin, gelonin, *Pseudomonas* exotoxin, diphtheria toxin, and RNase; tiuxetan or toxic radioisotope (such as $^{90}$Y; $^{131}$I, $^{177}$Lu, $^{186}$Re, $^{188}$Re, $^{211}$At, $^{212}$Bi, $^{213}$Bi, $^{225}$Ac, etc.).

Alternatively, an antibody can be conjugated to a second antibody to form an antibody heteroconjugate as described in U.S. Pat. No. 4,676,980. The formation of cross-linked antibodies can target the immune system to specific types of cells, for example, cancer or diseased cells expressing B7-H3.

This invention also provides methods of delaying development of metastasis in an individual with cancer (including, but not limited to, prostate, lung, or kidney cancer) using an anti-B7-H3 antibody or other embodiments that bind to B7-H3 in combination with a chemotherapeutic agent, or linked to a chemotherapeutic agent. In some embodiments, the antibody is a humanized or chimeric form of a non-human anti-B7-H3 antibody.

In yet another embodiment, the antibody can be employed as adjuvant therapy at the time of the surgical removal of a cancer expressing the antigen in order to delay the development of metastasis. The antibody or antibody associated with a chemotherapeutic agent can also be administered before surgery (neoadjuvant therapy) in an individual with a tumor expressing the antigen in order to decrease the size of the tumor and thus enable or simplify surgery, spare tissue during surgery, and/or decrease the resulting disfigurement.

In yet another embodiment, any of the B7-H3 binding compositions described herein can bind to B7-H3-expressing cancerous cells and induce an active immune response against the cancerous cells expressing B7-H3. In some cases, the active immune response can cause the death of the cancerous cells (e.g., antibody binding to cancer cells inducing apoptotic cell death), or inhibit the growth (e.g., block cells cycle progression) of the cancerous cells. In other cases, any of the novel antibodies described herein can bind to cancerous cells and antibody dependent cellular cytotoxicity (ADCC) can eliminate cancerous cells to which anti-B7-H3 binds. Accordingly, the invention provides methods of stimulating an immune response comprising administering any of the compositions described herein.

In some cases, antibody binding can also activate both cellular and humoral immune responses and recruit more natural killer cells or increased production of cytokines (e.g., IL-2, IFN-gamma, IL-12, TNF-alpha, TNF-beta, etc.) that further activate an individual's immune system to destroy cancerous cells. In yet another embodiment, anti-B7-H3 antibodies can bind to cancerous cells, and macrophages or other phagocytic cell can opsonize the cancerous cells.

Various formulations of anti-B7-H3 antibodies may be used for administration. In some embodiments, anti-B7-H3 antibodies may be administered neat. In addition to the pharmacologically active agent, the compositions of the present invention may contain suitable pharmaceutically acceptable carriers comprising excipients and auxiliaries that are well known in the art and are relatively inert substances that facilitate administration of a pharmacologically effective substance or which facilitate processing of the active compounds into preparations that can be used pharmaceutically for delivery to the site of action. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers.

Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulation may be used simultaneously to achieve systemic administration of the active ingredient. Excipients as well as formulations for parenteral and nonparenteral drug delivery are set forth in REMINGTON: THE SCIENCE AND PRACTICE OF PHARMACY, 21st Edition, Lippincott Williams & Wilkins Publishing (2005). Suitable formulations for oral administration include hard or soft gelatin capsules, pills, tablets, including coated tablets, elixirs, suspensions, syrups or inhalations and controlled release forms thereof. Generally, these agents are formulated for administration by injection {e.g., intraperitoneally, intravenously, subcutaneously, intramuscularly, etc.), although other forms of administration (e.g., oral, mucosal, etc) can be also used. Accordingly, anti-B7-H3 antibodies are preferably combined with pharmaceutically acceptable vehicles such as saline, Ringer's solution, dextrose solution, and the like.

The particular dosage regimen, i.e., dose, timing and repetition, will depend on the particular individual and that individual's medical history. Generally, a dose of at least about 100 µg/kg body weight, more preferably at least about 250 µg/kg body weight, even more preferably at least about 750 µg/kg body weight, even more preferably at least about 3 mg/kg body weight, even more preferably at least about 5 mg/kg body weight, even more preferably at least about 10 mg/kg body weight is administered.

Empirical considerations, such as the half-life, generally will contribute to the determination of the dosage. Antibodies, which are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is based on reducing the number of cancerous cells, maintaining the reduction of cancerous cells, reducing the proliferation of cancerous cells, or delaying the development of metastasis. Alternatively, sustained continuous release formulations of anti-B7-H3 antibodies may be appropriate. Various formulations and devices for achieving sustained release are known in the art.

In one embodiment, dosages for anti-B7-H3 antibodies may be determined empirically in individuals who have been given one or more administration(s). Individuals are given incremental dosages of an anti-B7-H3 antibody. To assess efficacy of anti-B7-H3 antibodies, a marker of the specific cancer disease state can be followed. These include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer), a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of cancer, the stage of cancer, whether the cancer has begun to metastasize to other location in the individual, and the past and concurrent treatments being used.

Other formulations include suitable delivery forms known in the art including, but not limited to, carriers such as liposomes. See, for example, Mahato et al. (1997) "*Cationic Lipid-Based Gene Delivery Systems: Pharmaceutical Perspectives*," Pharm. Res. 14:853-859. Liposomal preparations include, but are not limited to, cytofectins, multilamellar vesicles and unilamellar vesicles.

In some embodiments, more than one antibody may be present. The antibodies can be monoclonal or polyclonal. Such compositions may contain at least one, at least two, at least three, at least four, at least five different antibodies that are reactive against carcinomas, adenocarcinomas, sarcomas, or adenosarcomas. Anti-B7-H3 antibody can be admixed with one or more antibodies reactive against carcinomas, adenocarcinomas, sarcomas, or adenosarcomas in organs including but not limited to ovary, breast, lung, prostate, colon, kidney, skin, thyroid, bone, upper digestive tract, and pancreas. In one embodiment, a mixture of different anti-B7-H3 antibodies is used. A mixture of antibodies, as they are often denoted in the art, may be particularly useful in treating a broader range of population of individuals.

Having now generally described the invention, the same will be more readily understood through reference to the following examples, which are provided by way of illustration and are not intended to be limiting of the present invention unless specified.

Example 1

Immunohistocompatability Investigations

A panel of 49 mAbs was generated from tumor cell/fetal progenitor cell immunizations. The antibodies were evaluated for their ability to exhibit differential IHC staining of tumor tissue relative to normal, non-cancerous tissue, capability of use in primate (and particularly cynomolgus monkey) models of antibody efficacy, levels of affinity and antigen specificity and levels of immunomodulatory activity and cellular internalization. 21 of the mAbs were initially identified by MS analysis and/or binding to B7-H3-CHO cells. The remaining 28 mAbs were identified by rescreening the library by ELISA with B7-H3 protein. Characteristics of 46 of the 49 members of the panel are provided in Table 2.

TABLE 2

| Name | Isotype | IHC | ATCC Array | Internalization | U-DART | BIACORE ™ Analysis | Cyno B7-H3 Binding |
|---|---|---|---|---|---|---|---|
| BRCA84D | IgG1/k | 2a | 2 | + | + | + | ++ |
| TDH6 | IgG1/k | 2a | 1 | + | + | +/− | + |
| TES7 | IgG1/k | 2a | 1 | + | + | + | − |
| BRCA68D | IgG1/k | 2b | 3 | + | + | ++ | ++ |
| BRCA69D | IgG1/k | 2b | 3 | + | + | ++ | ++ |
| GB8 | IgG1/k | 2b | 3 | + | + | + | ++ |
| SG27 | IgG2b/k | 2b | 1 | | + | + | + |
| OVCA22 | IgG1/k | 2c | 3 | + | + | +/− | + |
| PRCA157 | IgG1/k | 2c | 2 | + | + | | ++ |
| BLA8 | IgG1/k | 2c | | +/− | + | ++ | ++ |
| KID35 | IgG1/k | 2c | 2 | | | | ++ |
| LUCA50 | IgG2a/k | 2c | 1 | | | + | ++ |
| OVCA21 | IgG1/k | 2c | 1 | + | | + | + |
| PRCA135 | IgG1/k | 2c | 3 | | + | | ++ |
| SG24 | IgG2a/k | 2c | 3 | | | ++ | ++ |
| TDH5 | IgG1/k | 2c | 3 | + | | ++ | ++ |
| BCCA66 | IgG1/k | 2c | 2 | + | | | − |
| RECA13 | IgG1/k | 2c | 3 | + | | | − |
| RECA9 | IgG1/k | 2c | 3 | | | | − |
| PRCA123 | IgG1/k | 2c/3 | 3 | | + | | ++ |
| BRCA126 | IgG1/k | 3/F | | | | | |
| BRCA192 | IgG1/k | 3/F | | | | | |
| BRCA34 | IgG1/k | 3/F | | | | | |
| KID1 | IgG1/k | 3/F | ND | + | + | | + |
| KID13 | IgG2a/k | 3/F | 3 | | | | ++ |
| LU14 | IgG2b/k | 3/F | | | | | − |
| LUCA1 | IgG1/k | 3/F | 1 | + | + | ++ | ++ |
| MCLY42 | IgG2a/k | 3/F | | | | | ++ |
| MCLY46 | IgG1/k | 3/F | | | | | ++ |

TABLE 2-continued

| Name | Isotype | IHC | ATCC Array | Internalization | U-DART | BIACORE™ Analysis | Cyno B7-H3 Binding |
|---|---|---|---|---|---|---|---|
| OVCA40 | IgG1/k | 3/F | | | | | ++ |
| PA20 | IgG1/k | 3/F | | + | | ++ | − |
| PA40 | IgG2b/k | 3/F | 3 | | | | − |
| PA41 | IgG1/k | 3/F | 3 | | | | |
| PRO6 | IgG1/k | 3/F | 2 | | | | − |
| RECA22 | IgG1/k | 3/F | 3 | | − | | + |
| SAL3 | IgG2a/k | 3/F | | | +++ | | ++ |
| SG20 | IgG1/k | 3/F | | | | | + |
| SG29 | IgG1/k | 3/F | | | | | ++ |
| SKIN2 | IgG1/k | 3/F | 3 | | +++ | | ++ |
| STO5 | IgG2b/k | 3/F | 3 | | ++ | | + |
| TDH36 | IgG1/k | 3/F | 2 | | | | ++ |
| TDH37 | IgG1/k | 3/F | 3 | | | | + |
| TDH4 | IgG1/k | 3/F | | | +++ | ++ | ++ |
| TDH40 | IgG2b/k | 3/F | 3 | | | | ++ |
| TDH44 | IgG2b/k | 3/F | | | | | ++ |
| OVCA25 | IgG1/k | 3/F | 3 | | | | + |

IHC staining confirmed that the panel comprised antibodies that elicited a strong tumor to normal tissue binding differential in many of the identified antibodies, exhibited a range of binding properties by BIACORE™ analysis, exhibited reactivity to range of overlapping and non-overlapping epitopes and exhibited a range of specificity to 4Ig vs. 2Ig B7-H3. The characteristics of the nine best candidates are shown in Table 3 and Table 4.

TABLE 3

| Name | Normal Tissue | | Colon Cancer | Lung Cancer | Prostate Cancer | Breast Cancer |
|---|---|---|---|---|---|---|
| BRCA84D | Colon | 1+ | 1231 * | 1130 | 112 | 1111 |
| | Lung | 1+ | | | | |
| | Liver | 1+ | | | | |
| TDH6 | Colon | 1+ | 1110 * | 1010 | 111 | 1011 |
| | Panc | 1+ | | | | |
| | Kidney | 1+ | | | | |
| | Lung | 1+ | | | | |
| | Liver | 1+ | | | | |
| TES7 | | | 1.5 | 1.75 | 3 | 3 |
| BRCA68D | Panc | 1+ | 2321 * | 3332 | 333 | 3333 |
| | Kidney | 1+ | | | | |
| | Lung | 1+ | | | | |
| | Liver | 2+ | | | | |
| BRCA69D | Colon | 1+ | 2231 * | 3231 | 333 | 3333 |
| | Panc | 1+ | | | | |
| | Kidney | 1+ | | | | |
| | Liver | 1+ | | | | |
| GB8 | | | | | | |
| SG27 | Colon | 1+ | 1221 * | 1120 | 222 | 1122 |
| | Panc | 1+ | | | | |

TABLE 3-continued

| Name | Normal Tissue | | Colon Cancer | Lung Cancer | Prostate Cancer | Breast Cancer |
|---|---|---|---|---|---|---|
| | Kidney | 1+ | | | | |
| | Liver | 1+ | | | | |
| OVCA22 | Colon | 2+ | 1122 | 3131 ** | 222 | 3233 |
| | Panc | 2+ | | | | |
| | Liver | 2+ | | | | |
| PRCA157 | Colon | 2+ | 2231 * | 3231 | 333 | 2333 |
| | Liver | 2+ | | | | |
| | Skin | 2+ | | | | |

\* +str also;
\*\* str 3+

TABLE 4

| Name | 2Ig/4Ig Specificity | Epitope Group |
|---|---|---|
| BRCA84D | 4Ig/2Ig | 1 |
| TDH6 | 4Ig/2Ig | 2 |
| TES7 | 4Ig | 3 |
| BRCA68D | 4Ig/2Ig | 4 |
| BRCA69D | 4Ig/2Ig | 4 |
| GB8 | 4Ig/2Ig | 5 |
| SG27 | 4Ig/2Ig | 6 |
| OVCA22 | 4Ig | 7 |
| PRCA157 | 4Ig/2Ig | 8 |

Table 5 provides a summary of the activity profiles of these antibodies.

TABLE 5

| Name | Normal Tissue Staining | Tumor/Normal Differential | Tumor Tissue Positive | Cyno Cross-Reactivity | IHC * | Binding BIACORE™ | UDART Activity |
|---|---|---|---|---|---|---|---|
| BRCA84D | 1 | 1 | Tumor Stroma bv | Positive (not 1:1) | 78 | ++ | ++ |
| TES7 | 1 | 1 | Tumor Stroma bv | negative | 1250 | + | ++ |
| BRCA68D | 3 | 3 | Tumor | Positive (1:1) | 20 | +++ | ++ |
| BRCA69D | 3 | 3 | Tumor Stroma | Positive (1:1) | 20 | +++ | ++ |

TABLE 5-continued

| Name | Normal Tissue Staining | Tumor/Normal Differential | Tumor Tissue Positive | Cyno Cross-Reactivity | IHC * | Binding BIACORE ™ | UDART Activity |
|---|---|---|---|---|---|---|---|
| GB8 | 2/3 (Adrenal ND) | 3/4 | Tumor Stroma | ND, + recomb. | 625 | + | + |
| SG27 | 2/3 | ND | ND | ND, + recomb. | 20000 | + | + |
| OVCA22 | 1 | 1 | Tumor Stroma | Negative + recomb. | 2500 | + | ++ |
| PRCA157 | 2 | 3 | Tumor Stroma bv | Positive (1:1) | 20 | ND | ++ |

* Optimal Concentration in ng/ml;
ND, Not Determined

An analysis of the activities of the antibodies shown in Table 6 revealed that their respective profiles differed and that each antibody was associated with both advantages and disadvantages relative to each other (Table 6).

TABLE 6

| Antibody | Advantages | Disadvantages |
|---|---|---|
| BRCA84D | #1 normal tissue staining<br>#1 tumor/normal differential<br>stain tumor, stroma, BV<br>mid affinity, unique binding site (titratable binding) | Cyno cross-reactivity not 1:1 |
| BRCA68D | #3 normal tissue staining<br>#3 tumor/normal differential<br>Cyno cross-reactivity 1:1<br>high affinity<br>Potent UDART activity | Stain tumor only |
| BRCA69D | #3 normal tissue staining<br>#3 tumor/normal differential<br>Cyno cross-reactivity 1:1<br>stain tumor, stroma<br>high affinity<br>Potent UDART activity | |
| PRCA157 | #2 normal tissue staining<br>#3 tumor/normal differential<br>Cyno cross-reactivity 1:1<br>stain tumor, stroma, BV<br>Potent UDART activity | BIACORE ™ |
| TES7 | #½ normal tissue staining<br>#½ tumor/normal differential<br>stain tumor, stroma, BV<br>4Ig specific<br>Potent UDART activity | No Cyno cross-reactivity<br>low affinity |
| OVCA22 | #½ normal tissue staining<br>#½ tumor/normal differential low affinity<br>stain tumor, stroma<br>4Ig specific<br>Potent UDART activity | No Cyno cross-reactivity<br>low affinity |
| GB8 | #⅔ normal tissue staining (adrenal not determined)<br>#¾ tumor/normal differential<br>stain tumor, stroma<br>Modest UDART activity | Cyno cross-reactivity not determined<br>low affinity |
| SG27 | #⅔ normal tissue staining<br>tumor/normal differential not determined<br>Modest UDART activity | Cyno cross-reactivity not determined<br>low affinity |

Because BRCA84D, BRCA68D, BRCA69D and PRCA157 exhibited cleaner normal tissue IHC profiles, stronger tumor/normal IHC differential, moderate to strong binding (BIACORE™/IHC), cross-reactivity to B7-H3 of cynomolgus monkeys, and potent UDART activity, these antibody species were selected for further development. These antibodies differed from TEST and OVCA2, which exhibited low affinity (in the BIACORE™ assay), and no cross-reactivity to B7-H3 of cynomolgus monkeys. These antibodies differed from SG27, which exhibited low affinity (in the BIACORE™ assay), poor IHC performance (weak binding) and lower UDART activity. These antibodies differed from GB8, which exhibited low affinity (in the BIACORE™ assay), poor tumor/normal IHC differential, and lower UDART activity.

Using Caki-2 and Hs700T positive control cells, IHC investigations revealed that each of the antibodies exhibited a different optimal concentration and a different differential concentration relative to one another (Table 7).

TABLE 7

| Antibody | Optimal IHC Concentration | Differential IHC Concentration |
|---|---|---|
| BRCA84D | 0.625 µg/ml | 0.078 µg/ml |
| BRCA68D | 0.156 µg/ml | 0.0195 µg/ml |
| BRCA69D | 0.156 µg/ml | 0.0195 µg/ml |
| PRCA157 | 0.078 µg/ml | 0.0195 µg/ml |
| TES7 | 5 µg/ml | 1.25 µg/ml |
| OVCA22 | 10 µg/ml | 2.5 µg/ml* |
| GB8 | 1.25 µg/ml | 0.625 µg/ml |
| SG27 | 20 µg/ml | Not Determined** |
| TDH6 | 20 µg/ml | Not Determined*** |

*OVCA22 only showed binding to caki2 cells, did not show binding to Hs700T cells. Optimization decision based on the binding of caki2 cells.
**Because SG27 did not show consistent titration analysis results between two operators, low affinity and differential concentration were not determined.
***TDH6 study not done due to too low affinity to positive control cells Using the optimal and differential concentrations indicated in Table 7, the IHC responses of the B7-H3 antibodies in human tissues were determined. The results of these analyses for Adrenal, Liver, Pancreatic, Kidney Lung and Colon are shown in Tables 8A-8B and Tables 9A-9B (all antibodies exhibited negative IHC responses for heart tissue).

TABLE 8A

B7H3 mAb IHC at Optimal Concentration in Human Tissues

| mAb | Adrenal | Liver | Pancreas |
|---|---|---|---|
| BRCA84D 0.625 µg/ml | Negative | Sinousoid lining cells++ Hepatocytes+, 5-10% | Epithelium+ 5% Fibre++ |
| BRCA68D 0.156 µg/ml | Cortex+++ | Sinousoid lining cells++ Hepatocytes++ (m) | Epithelium+ Fibre++ |
| BRCA69D 0.156 µg/ml | Cortex+++ | Hepatocytes++ (m) | Epithelium+ Fibre++ |
| TES7 5 µg/ml | Cortex+ | Sinousoid lining cells+ | Epithelium+ 5% Fibre++ |
| OVCA22 10 µg/ml | Cortex+ | Sinousoid lining cells++ Hepatocytes+ (m) | Epithelium+ 5% Fibre++ |
| PRCA157 0.078 µg/ml | Cortex++ | Sinousoid lining cells++ Hepatocytes+ (m) | Epithelium+ 5% Fibre++ |
| GB8 1.25 µg/ml | Not Determined | Sinousoid lining cells++ Hepatocytes+ (m) | Epithelium+ Fibre++ |

TABLE 8B

B7H3 mAb IHC at Optimal Concentration in Human Tissues

| mAb | Kidney | Lung | Colon |
|---|---|---|---|
| BRCA84D 0.625 µg/ml | Negative | Epithelium+ (5-10%) | Epithelium+ |
| BRCA68D 0.156 µg/ml | Fibroblast+, rare | Epithelium+ | Mucosa++ |
| BRCA69D 0.156 µg/ml | Fibroblast+, rare | Epithelium+ | Mucosa+ |
| TES7 5 µg/ml | Negative | Negative | Epithelium+ |
| OVCA22 10 µg/ml | Fibroblast+ | Negative | Epithelium+ |
| PRCA157 0.078 µg/ml | Negative | Negative | Mucosa+ |
| GB8 1.25 µg/ml | Negative | Epithelium+ | Mucosa+ |

TABLE 9A

B7H3 mAb IHC at Differential Concentration in Human Tissues

| mAb | Adrenal | Liver | Pancreas |
|---|---|---|---|
| BRCA84D 0.078 µg/ml | Negative | Sinousoid lining cells+ | Fibre+ (rare) |
| BRCA68D 0.0195 µg/ml | Cortex++ | Hepatocytes+ (m) | Fibre+ |
| BRCA69D 0.0195 µg/ml | Cortex++ | Hepatocytes+ (m) | Fibre+ |
| TES7 1.25 µg/ml | Fibroblast+ | Sinousoid lining cells+ | Epithelium+, 5% Fibre++ |
| OVCA22 2.5 µg/ml | Fibroblast+ | Sinousoid lining cells+ | Fibre+ |
| PRCA157 0.0195 µg/ml | Not Determined | Sinousoid lining cells+ Hepatocytes+ (m) | Fibre+ |
| GB8 0.625 µg/ml | Not Determined | Sinousoid lining cells++ Hepatocytes+ (m) | Fibre+ |

TABLE 9B

B7H3 mAb IHC at Differential Concentration in Human Tissues

| mAb | Kidney | Lung | Colon |
|---|---|---|---|
| BRCA84D 0.078 µg/ml | Negative | Negative | Epithelium+ |
| BRCA68D 0.0195 µg/ml | Negative | Fibrin+ (rare) | Mucosa + |
| BRCA69D 0.0195 µg/ml | Negative | Negative | Mucosa+ |
| TES7 1.25 µg/ml | Negative | Negative | Epithelium+ |
| OVCA22 2.5 µg/ml | Negative | Negative | Epithelium+ |
| PRCA157 0.0195 µg/ml | Negative | Negative | Mucosa+ |
| GB8 0.625 µg/ml | Negative | Negative | Mucosa+ |

IHC investigations conducted using cancer specimens showed that the B7-H3 antibodies of the present invention could be used to identify and diagnose cancer in multiple tissue sources (Table 10). In Table 10, the numbers indicate the number of plus signs (1=+, 2=++, 3=+++); each number referring to a different tested sample.

TABLE 10

| mAbs | µg/ml | Prostate Cancer | Breast Cancer | Lung Cancer | Colon Cancer |
|---|---|---|---|---|---|
| BRCA84D | 0.625 µg/ml | 2, 2, 1 | 3, 3, 3, 3 | 2, 3, 2 (stroma), 1 (b.v.) | 2 (stroma), 3, 3, 3 (stroma) |
|  | 0.078 µg/ml | 0, 2, 3, 2 | 1 (stroma), 1 (stroma), 1 (stroma), 2, 3 | 1, 1, 0, 1 | 2, 2 (stroma), 2 (stroma), 1 (stroma), 2 (stroma) |
| BRCA68D | 0.156 µg/ml | 2, 3, 3, 3 | 2, 3, 3, 3, 3 | 3, 3, 2, 2 | 3, 3, 3, 3 |
|  | 0.0195 µg/ml | 0, 1, 1, 1 | 0, 0, 2, 2, 1 | 0, 1, 1, 0 | 1, 1, 1, 1 |
| BRCA69D | 0.156 µg/ml | 3, 3, 3 | 3, 3, 3, 3 | 3, 3, 2, 2 (stroma) | 3, 3, 3, 3 |
|  |  | 0, 1, 2, 1 | 1, 2, 1, 1 | 1, 1, 0, 1 | 1 (b.v.), 2 (stroma), 1, 1 |
| GB8 | 1.25 µg/ml | 2, 3, 1 | 2, 2, 1, 2 | 3, 3, 0, 0 | 2 (stroma), 2, 2, 2 |
|  | 0.625 µg/ml | 0, 1, 1 | 0, 0, 0, 0, 1 | 1, 0, 0, 0 | 1 (stroma), 1 (stroma), 0, 0 |
| TES7 | 5 µg/ml | 2, 3, 2, 3 | 1 (stroma), 3, 3, 3, 2 | 3, 2, 1 (stroma), 1 (b.v.) | 3, 3, 2, 2 |
|  | 1.25 µg/ml | 1, 2, 2, 3 | 1 (stroma), 2, 3, 3, 2 | 3, 1, 1 (stroma), 1 (b.v.) | 3, 2 (stroma), 2 (stroma), 2 |
| OVCA22 | 10 µg/ml | 3, 2, 2, 1 | 1 (stroma), 2, 2, 3, 3 | 3, 2, 1 (stroma), 0 | 1 (stroma), 1, 1, 2 (stroma) |
|  | 2.5 µg/ml | 1, 1, 3, 1 | 1 (stroma), 1 (stroma), 1 (stroma), 3, 2, 2 | 2, 1, 0, 0 | 1, 0, 2 (stroma), 0 |
| PRCA157 | 0.078 µg/ml | 2, 2, 2, 3 | 1, 2, 2, 3, 3 | 2, 2, 1 (stroma), 1 (b.v.) | 3, 3, 2 (stroma), 2 (stroma) |
|  | 0.0195 µg/ml | 0, 1, 2, 1 | 1 (stroma), 0, 2, 1 (stroma) | 0, 1, 0, 0 | 1, 1, 1 (stroma), 1 (stroma) |

For prostate, breast, colon and lung cancer cells treated with B7-H3 antibody BRCA84D, tumor sample staining was present in tumor cells and stromal cells, including the tumor vasculature. In some tumor samples, stromal staining was much stronger than tumor cells. When BRCA84D mAb was titrated to lower concentration, some cases showed reduced staining in tumor cells, but still maintained strong stromal staining Upon staining with BRCA84D at 0.625 µg/ml, prostate cancer cells exhibited an IHC of 3/3+; breast cancer cells exhibited an IHC of 4/4+; colon cancer cells exhibited an IHC of 4/4+ and lung cancer cells exhibited an IHC of 4/4+. Upon staining with BRCA84D at 0.078 µg/ml, prostate cancer cells exhibited an IHC of 3/4+; breast cancer cells exhibited an IHC of 5/5+; colon cancer cells exhibited an IHC of 4/4+ and lung cancer cells exhibited an IHC of of 3/4+.

Normal liver was treated with B7-H3 antibody BRCA68D, and staining was seen in hepatocytes and sinousoid lining cells. Normal pancreas stained with B7-H3 antibody BRCA68D exhibited multi-focal staining in collagen fibre and epithelium. Normal adrenal cells treated with B7-H3 antibody BRCA68D, exhibited staining in the cortex. Upon staining with BRCA68D at 0.156 µg/ml, gastric, renal and ovarian cancer cells all exhibited an IHC of 5/5+.

Additional IHC staining analyses were conducted on samples of gastric, kidney and ovarian cancer tissues. The results of such analyses are shown in Table 12. In Table 11, the numbers indicate the number of plus signs (1=+, 2=++, 3=+++); each number referring to a different tested sample.

TABLE 11

| mAbs | µg/ml | Gastric Cancer | Kidney Cancer | Ovarian Cancer |
|---|---|---|---|---|
| BRCA84D | 0.625 µg/ml | 2, 1, 2, 2, 2 | 1, 2, 1, 1, 1 | 0, 3, 1, 2, 2 |
|  | 0.078 µg/ml | 1, 0, 0, 1, 0 | 0, 1, 0, 1, 0, 1 | 0, 2, 0, 1, 1 |
| BRCA68D | 0.156 µg/ml | 3, 2, 3, 3, 3 | 3, 3, 2, 3, 3, 3 | 2, 3, 3, 2, 2 |
|  | 0.0195 µg/ml | 2, 1, 2, 1, 1 | 2, 2, 2, 2, 2, 2 | 1, 2, 2, 1, 1 |
| OVCA22 | 10 µg/ml | 3, 1, 3, 1, 1 | 3, 1, 2, 3, 0, 2 | 2, 3, 2, 1, 1 |
|  | 2.5 µg/ml | 2, 0, 2, 1, 0 | 2, 1, 1, 2, 0, 1 | 1, 2, 1, 0, 1 |
| TES7 | 5 µg/ml | 2, 1, 3, 2, 1 | 2, 3, 1, 2, 2, 1 | 1, 3, 1, 2, 2 |
|  | 1.25 µg/ml | 2, 0, 2, 1, 1 | 2, 2, 1, 1, 1, 1 | 1, 3, 1, 2, 2 |

In summary, all of the tested mAbs showed various degrees of staining intensity in normal liver, pancreas, colon and lung. FIG. 1A shows the results of IHC investigations conducted using normal pancreas, liver, lung and colon tissue specimens with BRCA84D at 0.625 µg/ml and 0.078 µg/ml. Liver staining was relatively restricted in sinusoid lining cells (fibroblast and kupffer cells) with BRCA84D and TES7. OVCA22 showed membrane hepatocyte staining besides that of the sinusoid ling cells at the optimal concentration. However, the staining in hepatocytes disappeared at the differential concentration. All of the other mAbs showed staining in hepatocytes including either membrane or cytoplasm staining at both the optimal and differential concentration. Pancreas staining was observed in collagen fiber mainly and a small percentage of the epithelium (acinar cells or/and intercalated duct cells). The staining in epithelium diminished or disappeared at differential concentration. Colon staining was relatively restricted in apical membrane of crypt epithelium and fibroblast in mucosa. No binding was observed in lymphoid nodules of colon. Lung showed very weak and patchy staining in epithelium with BRCA84D, BRCA68D, BRCA69D and GB8. However, the staining disappeared at the differential concentration. No staining was observed in lung with TES7, OVCA22 and PRCA157 at both concentrations. Adrenal cortex staining was observed with almost all of the mAbs at optimal concentration, except BRCA84D. The staining in adrenal obviously diminished with TES7 and OVCA22 at differential concentration. Heart and kidney did not show obvious staining with all mAbs (FIG. 1B). In light of these properties, BRCA84D was considered the best of the mAbs, followed in order by (2) TES7, (3) OVCA22, (4) the group BRCA68D, BRCA69D and PRCA157, and lastly (5) GB8.

Figure 2:
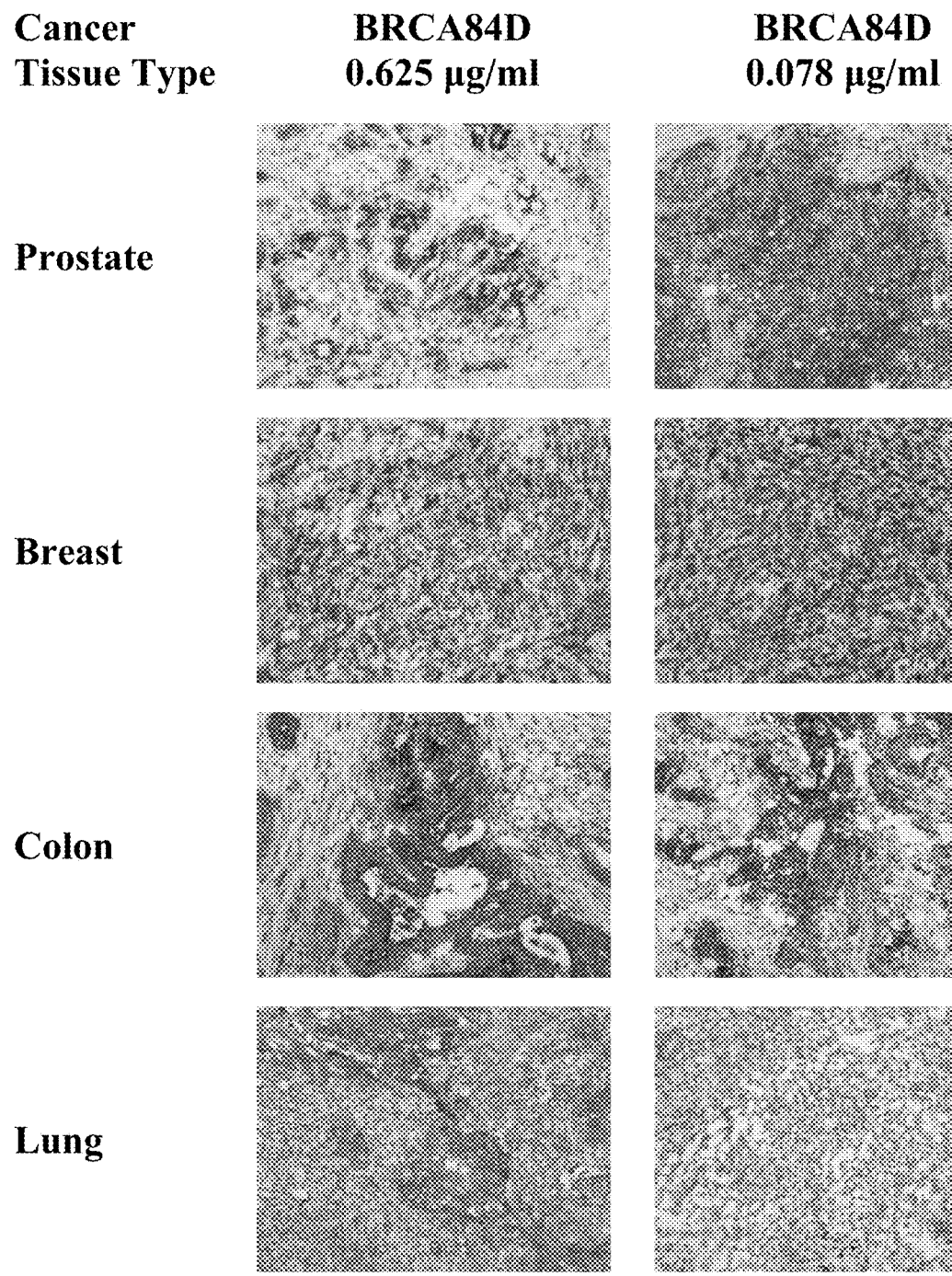
FIG. 2 shows the results of IHC investigations conducted using cancerous pancreas, breast, colon and lung tissue specimens with BRCA84D at 0.625 µg/ml and 0.078 µg/ml.

All of the mAbs included in the study showed positive staining in 4 cancer types at the optimal concentration. At the differential concentration, BRCA84D still maintained good staining in prostate cancer, breast cancer, and colon cancer. TES7 maintained good staining in 4 study cancer types. The remaining mAbs showed various staining intensities in different tumor types. Tumor sample staining was observed in tumor cells and stromal cells, including vasculature. Some tumor samples showed positive staining only in vasculature, i.e. BRCA84D, BRCA69D, TES7, and PRCA157. Some tumors showed stronger stromal staining than tumor cell staining. When mAbs were titrated to lower concentration on these samples, some cases showed diminished or no staining in tumor cells, but still maintained strong stromal staining In general, in terms of expression in human normal tissues and differential expression in normal vs. tumor tissues, the mAb order from the best IHC performance to the poorest performance is as follows: (1) BRCA84D, (2) TES7, (3) OVCA22, (4) the group BRCA68D, BRCA69D and PRCA157, and lastly (5) GB8. Table 12 and FIG. 2 show results for antibody BRCA84D.

TABLE 12

| Cancer Tissue Type | BRCA84D 0.625 µg/ml | BRCA84D 0.078 µg/ml |
|---|---|---|
| Prostate | 3/3+ | 3/4+ |
| Breast | 4/4+ | 5/5+ |
| Colon | 4/4+ | 4/4+ |
| Lung | 4/4+ | 3/4+ |

Example 2

Cynomolgus Monkey B7-H3 Cross-Reactivity

The sequence of cynomolgus monkey B7-H3 shares approximately 90% homology to its human counterpart, suggesting that the cynomolgus monkey is an excellent model for human B7-H3 interactions. Investigations were conducted to evaluate the cross-reactivity of B7H3 candidates BRCA84D, BRCA68D, BRCA69D, TES7, OVCA22 and PRCA157 with adrenal, liver, kidney, pancreas and lung as well as one case full term placenta of cynomolgus monkey, in order to compare any cross-reactivity with the staining intensity and staining patterns observed for human tissues.

Staining concentration for each tested Mab is the optimal concentration which was determined in Caki-2 and Hs700T positive control cells (see, Table 8). Commercial goat anti human B7-H3 (cross-reacted with cyno) was selected as a positive control antibody to stain cynomolgus placental tissue. Corresponding isotype controls were applied in each run of the experiments. The results of thes investigations are shown in Table 13.

TABLE 13

| mAb | Adrenal(2) | Liver(2) | Pancreas(2) | Kidney(2) | Lung(2) | Placenta(1) |
|---|---|---|---|---|---|---|
| BRCA84D 0.625 µg/ml | Negative | Negative | Negative | Negative | 1/2 Epithelium 1+ | Decidual cells 2+ Mesenchymal cells negative |
| BRCA68D 0.156 µg/ml | Cortex 3+ | 2/2 Hepatocytes 1+ (m) Sinousoid lining cells 1+ | 1/2 Fiber 2+ Epithelium 1+ | Fibroblast 1+ | Negative | Decidual cells, villi, Mesenchymal cells 3+ |
| BRCA69D 0.156 µg/ml | Cortex 2+ | 1/2 Hepatocytes 1+ (m) | 1/2 Epithelium 1+ | Fibroblast 1+ rare | Negative | Decidual cells 2+, villi, Mesenchymal cells 2+ |
| TES7 5 µg/ml | Negative | Negative | Negative | Negative | Negative | Negative |
| OVCA22 10 µg/ml | Negative | Negative | Negative | Negative | negative | Negative |
| PRCA157 0.078 µg/ml | Cortex 1+ | 1/2 Hepatocytes 1+ (m) | Negative | Negative | Negative | Decidual cells 2+, villi, Mesenchymal cells 1+ |

Note:
BRCA84D showed negative staining in liver and pancreas at up to 5 µg/ml. Although OVCA22 did not bind to cyno tissue in IHC, modest binding was observed to recombinant cyno B7H3 on CHO cells. IHC score in normal tissues is negative, 1+, 2+ and 3+ 4 grade system; m = membrane; 2/2 = 2 of 2 cases, 1/2 = 1 of 2 cases The investigation of BRCA84D (0.625 µg/ml) IHC staining in cynomolgus placenta exhibited staining in decidual cells, but not in villi. No staining was observed in cyno liver and pancreas, however, staining of sinousoid lining cells was observed in human liver and localized fibre and epithellium staining was observed in human pancreas tissue.

The investigation of BRCA68D (0.156 µg/ml) IHC staining in cynomolgus placenta exhibited staining in decidual cells, mesenchymal cells (endothelium and fibroblasts) and villi. Staining was present in membrane of hepatocytes and cytoplasm of liver fibroblasts, as well as in pancreatic fibre and in the cytoplasm of pancreatic epithelium. Thus, human and cyno liver and pancreatic tissue exhibit similar staining patterns with BRCA68D.

In summary, BRCA84D, BRCA68D, BRCA69D and PRCA157 all showed cross-reactivity in cyno tissues. BRCA84D did not show staining in monkey liver and pancreas; such staining was observed in human liver and pancreatic tissues. BRCA68D and BRCA69D showed similar staining intensity and staining patterns in monkey tissues. Although BRCA68D, BRCA69D and PRCA157 showed comparable staining pattern with human tissues, the staining intensity is not identical with human tissues at optimal conditions. TEST and OVCA22 did not show any staining in monkey tissues at optimal conditions.

A summary of the comparative results of IHC staining in cynomolgus tissue and human tissue is provided in Table 14.

TABLE 14

| mAb | Adrenal | Liver | Pancreas | Kidney | Lung | Placenta |
| --- | --- | --- | --- | --- | --- | --- |
| BRCA84D 0.625 µg/ml Cynomolgus | Negative | Negative | Negative | Negative | 1/2 Epithelium 1+ | Decidual cells 2+ Mesenchymal cells negative |
| BRCA84D 0.625 µg/ml Human | Negative | 2/2 Sinousoid lining cells 2+, Hepatocytes 1+ 5-10% | Epithelium 1+, fibre2+ | Negative | Epithelium 1+, 5-10% | Decidual cells 1+, villi, Mesenchymal cells 1+ |
| BRCA68D 0.156 µg/ml Cynomolgus | Cortex 3+ | 2/2 Hepatocytes 1+ (m) Sinousoid lining cells 1+ | 1/2 Fiber 2+ Epithelium 1+ | Fibroblast 1+ | Negative | Decidual cells, villi, Mesenchymal cells 3+ |
| BRCA68D 0.156 µg/ml Human | Cortex 3+ | Sinousoid lining cells 2+, Hepatocytes 2+ (m) | Epithelium 1+ Fibre2+ | Fibroblast 1+ rare | Epithelium 1+ | Decidual cells 3+, villi, Mesenchymal cells 3+ |
| BRCA69D 0.156 µg/ml Cynomolgus | Cortex 2+ | 1/2 Hepatocytes 1+ (m) | 1/2 Epithelium 1+ | Fibroblast 1+ rare | Negative | Decidual cells 2+, villi, Mesenchymal cells 2+ |
| BRCA69D 0.156 µg/ml Human | Cortex 3+ | Hepatocytes 2+ (m) | Epithelium 1+ Fibre2+ | Fibroblast 1+ rare | Epithelium 1+ | Decidual cells 3+, villi, Mesenchymal cells 3+ |
| PRCA157 0.078 µg/ml Cynomolgus | Cortex 1+ | 1/2 Hepatocytes 1+ (m) | Negative | Negative | Negative | Decidual cells 2+, villi, Mesenchymal cells 1+ |
| PRCA157 0.078 µg/ml Human | Cortex 2+ | Sinousoid lining cells 2+, Hepatocytes 1+ (m) | Epithelium 1+ 5% Fibre2+ | Negative | Negative | Not Determined |

Example 3

B7-H3 mAbs Bind to Multiple ATCC Cancer Cell Lines

The antibodies of the present invention were found to be capable of binding to multiple cancer cell lines contained in the collections of the American Type Culture Collection. Table 15 and Table 16 summarize the binding results.

TABLE 15

| Cell Lines | Antibody | | | | |
|---|---|---|---|---|---|
| | BLA08 | BRCA68D | BRCA69D | BRCA84D | PRCA157 |
| Normal Human Lines | | | | | |
| HMEC | ++/+++ | +++ | +++ | ++ | |
| HUVEC | ND | ++ | +/++ | +/− | +/++ |
| Human Breast Cancer Lines | | | | | |
| BT474 | +++ | ++ | ++/+++ | +/++ | ++/+++ |
| MCF7 | +++ | ++ | ++/+++ | + | ++ |
| MDA175 | ND | | | | |
| MDA361 | ND | ++ | | +/+/− | ++ |
| SKBR3 | +++ | | ++ | | |
| Human Lung Cancer Lines | | | | | |
| A549 | +++ | +/+/− | +/− | | +/− |
| Calu3 | +++ | +/++ | + | | +/++ |
| SKMES1 | +++ | ++ | ++/+++ | +/++ | ++ |
| Human Ovarian Cancer Lines | | | | | |
| ES-2 | +++ | +/− | | | |
| SKOV3 | +++ | ++ | +/++ | +/+/− | ++ |
| Human Pancreatic Cancer Lines | | | | | |
| Panc-1 | ++/+++ | +/++ | +/++ | +/+/− | +/++ |
| AsPC-1 | +++ | | | | |
| HPAFII | +++ | | | | |
| Hs700T | +++ | ++/+++ | | +++ | +++ |
| Human Colon Cancer Lines | | | | | |
| Colo205 | ND | | | | |
| HT-29 | +++ | + | + | | + |
| SW480 | +++ | +/− | | +/− | |
| SW948 | ND | + | + | | |
| Human Kidney Cancer Lines | | | | | |
| 293 | +++ | ++ | ++ | + | ++/+++ |
| 786-0 | +++ | ++ | ++ | + | ++/+++ |
| A498 | +++ | ++ | ++ | ++ | ++/+++ |
| Caki2 | +++ | +++ | +++ | ++ | ++/+++ |
| Non-Human Cell Lines | | | | | |
| Cos7 | +++ | + | +/++ | +/− | +/++ |
| RL65 | − | | | | |
| SVT2 | ND | | | | |
| Human Prostate Cancer Lines | | | | | |
| 22Rv1 | +++ | | | | |
| DU145 | +++ | + | + | + | +/+/− |
| LNCaP | +++ | ++ | ++ | +/++ | ++/+++ |
| PC3 | +++ | +/+/− | +/− | +/− | +/− |
| TDH | ND | +/+/− | +/+/− | | + |
| Human Stomach Cancer Lines | | | | | |
| HS746T | ND | +/++ | +/++ | + | ++ |
| N87 | ND | +/++ | +/++ | +/− | +/++ |

TABLE 16

| Cell Lines | TDH06 | OVCA22 | GB8 | SG27 | TES7 |
|---|---|---|---|---|---|
| Normal Human Lines | | | | | |
| HMEC | | | | | |
| HUVEC | +/+/− | | +/− | +/− | |
| Human Breast Cancer Lines | | | | | |
| BT474 | +/++ | + | ++ | +/++ | +/++ |
| MCF7 | + | + | ++ | +/+/− | + |
| MDA175 | | ++ | | | |
| MDA361 | +/+/− | | | | + |
| SKBR3 | | ++ | | | |
| Human Lung Cancer Lines | | | | | |
| A549 | | | | | |
| Calu3 | | | + | | |
| SKMES1 | +/++ | +/− | +/++ | + | + |
| Human Ovarian Cancer Lines | | | | | |
| ES-2 | | | | | |
| SKOV3 | + | | | +/+/− | |
| Human Pancreatic Cancer Lines | | | | | |
| Panc-1 | +/+/− | | + | +/− | +/+/− |
| AsPC-1 | | | | | |
| HPAFII | | + | | | |
| Hs700T | + | +++ | +++ | + | +++ |
| Human Colon Cancer Lines | | | | | |
| Colo205 | | + | | | |
| HT-29 | + | +/+/− | | | +/+/− |
| SW480 | +/− | +++ | | | |
| SW948 | +/− | + | | | |
| Human Kidney Cancer Lines | | | | | |
| 293 | +/+/− | | + | +/+/− | + |
| 786-0 | + | | +* | +/− | + |
| A498 | + | | +/++ | | +/++ |
| Caki2 | ++ | + | +++ | +/++ | ++ |
| Non-Human Cell Lines | | | | | |
| Cos7 | + | +/+/−* | +/− | | |
| RL65 | | | | | |
| SVT2 | | | | | |
| Human Prostate Cancer | | | | | |
| 22Rv1 | | + | | | |
| DU145 | +/− | + | | | |
| LNCaP | +/+/− | + | +* | +/+/− | + |
| PC3 | | | | | |
| TDH | | +++ | +/− | | +/− |
| Human Stomach Cancer Lines | | | | | |
| HS746T | + | | +/+/− | +/− | +/− |
| N87 | | +/+/− | +/− | | |

Example 4

B7-H3 mAbs Redirect Killing

The antibodies of the present invention bind to B7-H3 present on the surface of cancer cells. Using conventional methods, such antibodies may be labeled with fluorescein, as described above. When such labeled molecules are incubated in the presence of UDART molecules having an epitope binding domain that binds to the T-cell receptor and an epitope binding domain that binds to fluorescein ("TCR-UDART"), they can bind to the DART molecules and thereby localize them to the surface of cells that express B7-H3 and cause redirected killing A. Redirected Killing of A498 Renal Carcinoma Cells To demonstrate such redirected killing, fluorescein-labeled B7-H3 antibodies were incubated with such TCR-UDART molecules and the ability of the molecules to mediate cytotoxicity of A498 renal carcinoma cells was evaluated (Table 17). On the basis of the attained results, the top candidates were concluded to be: RECA13, BRCA68D, BRCA69D and TDH6.

TABLE 17

Redirected Killing of A498 Renal Carcinoma Cells

| mAb | No UDART Mean | With TCR-UDART Mean | FACS MFI |
|---|---|---|---|
| BCCA66 | −1.04 | 46.39 | 43.30 |
| BLA8 | 1.35 | 49.19 | 50 |
| BRCA165 | 0 | 5.11 | 5.46 |
| BRCA52 | 0 | 55.53 | 41.7 |
| BRCA68D | 0 | 36.89 | 83.7 |
| BRCA69D | 0 | 54.71 | 84.1 |
| BRCA84D | 0 | 72.40 | 30.6 |
| GB8 | 4.00 | 42.00 | 17.9 |
| KID1 | 0.38 | 52.08 | 18.5 |
| KID13 | 26.39 | 58.20 | |
| KID35 | −1.68 | 7.62 | |
| LUCA1 | 9.85 | 52.73 | 52.9 |
| OVCA21 | −0.85 | 47.59 | 6.04 |
| OVCA22 | 0.36 | 38.66 | 53.9 |
| OVCA25 | −2.86 | 16.70 | |
| PA40 | −0.46 | 40.54 | |
| PRCA123 | 0 | 56 | 130 |
| PRCA135 | 0 | 55 | 127 |
| PRCA157 | 0 | 39.14 | 58.8 |
| RECA13 | 0 | 38.62 | 39.8 |
| RECA22 | −0.24 | 51.74 | 99.90 |
| RECA9 | 0 | 62 | 50.1 |
| SAL3 | 4.94 | 52.23 | 60.5 |
| SG24 | −2.25 | 42.00 | |
| SG27 | −3.98 | 0.21 | |
| SKIN2 | 3.11 | 56.44 | 45.8 |
| STO5 | 2.91 | 37.84 | 36.7 |
| TDH36 | −1.03 | 53.52 | 155.00 |
| TDH37 | 0.05 | 65.21 | 47.50 |
| TDH4 | 5.09 | 50.63 | 45.9 |
| TDH40 | −0.65 | 44.55 | |
| TDH5 | 2.92 | 49.60 | 28.8 |
| TDH6 | 0 | 70.10 | 19.5 |
| TES7 | 6.23 | 52.89 | 17.5 |

Figure 3A:
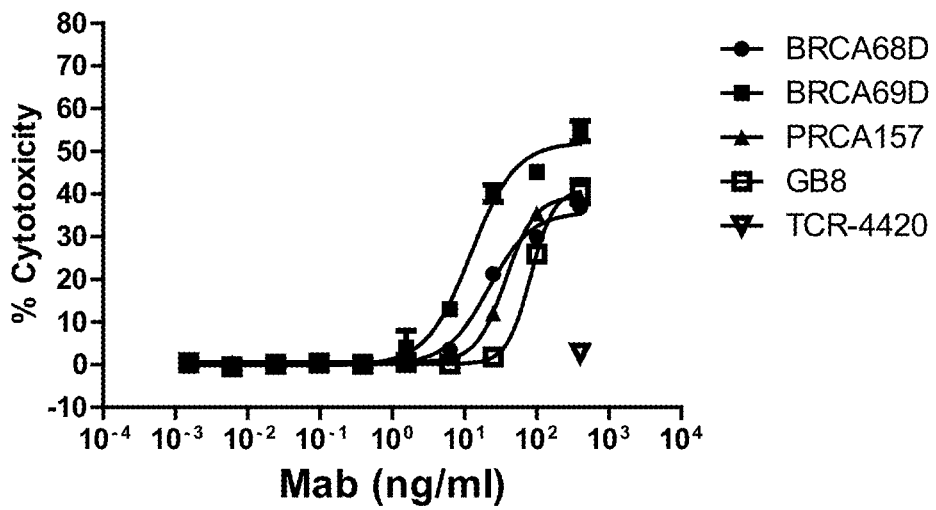
FIGS. 3A-3D show dose-dependent redirected killing mediated by the antibodies of the present invention.
Figure 3B:
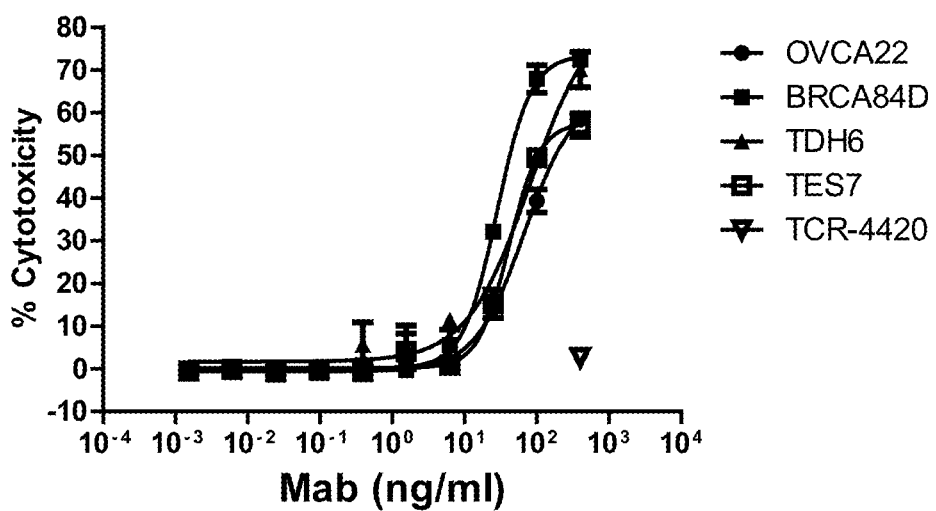

A498 renal carcinoma cells were incubated with different concentrations of monoclonal antibodies reactive against B7-H3 in order to determine the dose-dependent redirected killing mediated by the antibodies. The results of the experiments (FIGS. 3A-3B) show that the redirected killing was dose-dependent.

B. Redirected Killing of A549 Lung Cancer Cells

Figure 3C:
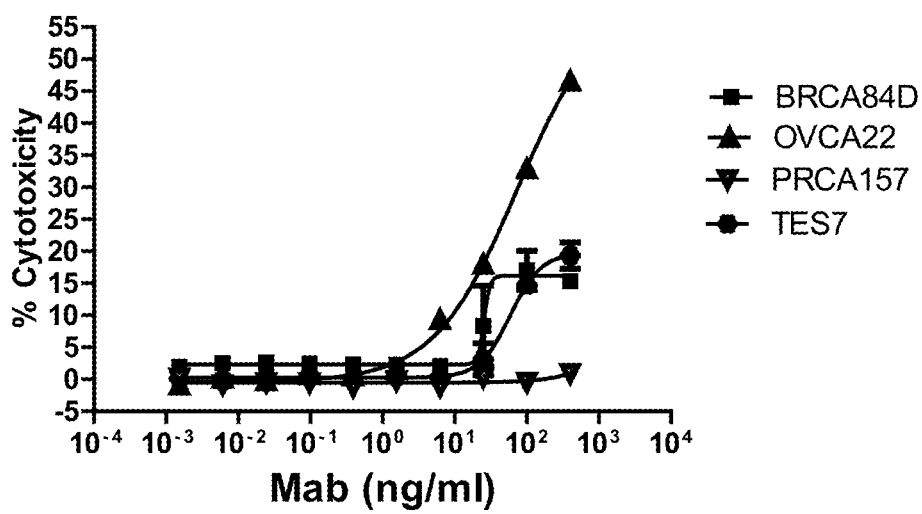
Figure 3D:
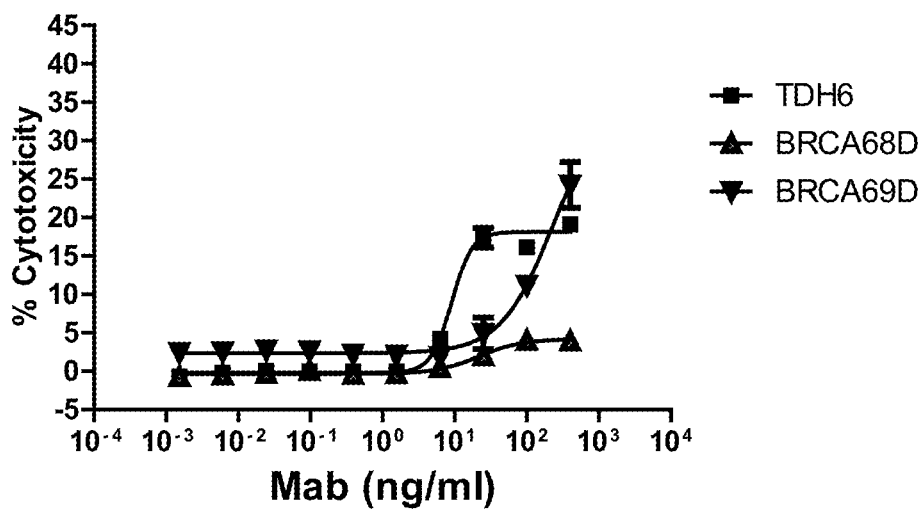

To further demonstrate such redirected killing, fluorescein-labeled B7-H3 antibodies were incubated with the above-described TCR-UDART molecules or with UDART molecules having an epitope binding domain that binds to CD16 and an epitope binding domain that binds to fluorescein ("CD16-UDART"), and the ability of the molecules to mediate cytotoxicity of A549 lung cancer cells was evaluated (Table 18). The results of the experiments (FIGS. 3C-3D) show that the redirected killing was dose-dependent. On the basis of the attained results, the top candidates were concluded to be: BLAB, BRCA68D, BRCA69D and BRCA84D.

TABLE 18

Redirected Killing of A549 Lung Cancer Cells

| mAb | No DART Mean | With TCR-UDART Mean | With CD16-UDART Mean | FACS MFI |
|---|---|---|---|---|
| BCCA66 | 1.89 | 25.17 | 8.22 | 36.1 |
| BLA8 | −7.70 | 10.97 | 3.68 | 34.7 |
| BRCA52 | 0 | 27.63 | | 37 |
| BRCA68D | −4.42 | 13.45 | 15.95 | 58.3 |
| BRCA69D | 0 | 24.25 | | 60.5 |
| BRCA84D | 0 | 15.33 | | 25 |
| GB8 | −8.68 | 2.44 | −4.65 | 17 |
| KID1 | 0 | 22.93 | | 41 |
| LUCA1 | 0 | 14.65 | | 53 |
| OVCA21 | −2.43 | 18.90 | 7.22 | 31.5 |
| OVCA22 | 0 | 32.90 | | 61 |
| PRCA123 | 7.68 | 29.88 | 17.31 | 79.4 |
| PRCA135 | −6.58 | 22.72 | 8.14 | 75.6 |
| PRCA157 | 0.02 | 18.63 | 18.24 | 44.3 |
| PSMA | −0.70 | 5.58 | 9.94 | |
| RECA13 | 0.86 | 17.39 | 11.90 | 34.4 |
| RECA22 | 3.71 | 20.49 | 19.35 | 74.3 |
| RECA9 | 7.01 | 26.89 | 31.80 | 44.3 |
| SAL3 | 0 | 31.80 | | 67.4 |
| SKIN2 | −0.08 | 8.65 | 9.33 | 41.9 |
| STO5 | −10.36 | 9.28 | 1.71 | 54.7 |
| TDH36 | 6.79 | 24.12 | 24.08 | 107 |
| TDH37 | 6.93 | 22.57 | 23.37 | 42.3 |
| TDH4 | −6.26 | 10.07 | 2.21 | 32.4 |
| TDH40 | 4.87 | 22.01 | 24.90 | 53.3 |
| TDH5 | −5.08 | 9.35 | −2.85 | 27.1 |
| TDH6 | 0 | 19.09 | | 21.3 |
| TES7 | 0 | 19.35 | | 15.7 |

C. Redirected Killing of LNcap Prostate Cancer Cells

To further demonstrate such redirected killing, fluorescein-labeled B7-H3 antibodies were incubated with the above-described TCR-UDART molecules or with UDART molecules having an epitope binding domain that binds to CD16 and an epitope binding domain that binds to fluorescein ("CD16-UDART"), and the ability of the molecules to mediate cytotoxicity of LNcap prostate cancer cells was evaluated (Table 19). On the basis of the attained results, the top candidates were concluded to be: BRCA68D, BRCA69D, BRCA84D and PRCA157.

TABLE 19

Redirected Killing of LNcap Prostate Cancer Cells

| mAb | No DART Mean | With TCR-UDART Mean | With CD16-UDART Mean | FACS MFI |
|---|---|---|---|---|
| BCCA4 | −2.96 | 13.29 | 2.47 | 5.1 |
| BCCA66 | −2.13 | 13.42 | 16.40 | 41 |
| BLA8 | 4.32 | 14.97 | 24.00 | 48.4 |
| BRCA165 | 3.59 | 57.26 | 12.02 | 7.6 |
| BRCA183D | −4.65 | 43.09 | 35.30 | 7.6 |
| BRCA52 | 32.34 | 71.23 | 48.28 | 42.5 |
| BRCA68D | −1.40 | 23.00 | 21.91 | 86.9 |
| BRCA69D | 40.08 | 78.02 | 60.55 | 92.4 |
| BRCA84D | 20.11 | 78.70 | 41.27 | 16.4 |
| GB8 | −6.25 | 14.04 | 10.76 | 22 |
| KID1 | 54.65 | 91.87 | 67.86 | 44.8 |
| KID13 | 15.86 | 69.21 | 47.85 | |
| KID133 | 27.51 | 45.65 | 47.12 | 120 |
| KID24 | −4.26 | 34.13 | 41.17 | 14.5 |
| KID35 | 14.17 | 64.01 | 33.05 | |
| KID47 | 11.34 | 39.49 | 15.02 | 10.8 |
| KID8 | 16.98 | 58.80 | 34.77 | 5.5 |
| LUCA1 | 47.40 | 89.31 | 67.15 | 73 |
| LUCA17 | 23.18 | 26.90 | 35.87 | 11.1 |
| LUCAT1 | 8.25 | 22.36 | 21.49 | 6.9 |
| LUCAT7 | 26.50 | 38.29 | 44.77 | 8.7 |
| MCL12 | 26.62 | 35.59 | 46.38 | 17.6 |
| MEL2 | 6.57 | 29.90 | 31.40 | 19 |
| OVCA21 | 12.07 | 26.81 | 31.30 | 41 |
| OVCA22 | 45.09 | 96.50 | 77.30 | 113 |
| OVCA25 | 16.14 | 63.26 | 32.39 | |
| PA22 | 1.73 | 57.70 | 9.89 | 8.9 |
| PA33 | 8.99 | 34.49 | 48.14 | 9.4 |
| PA40 | 38.42 | 73.07 | 63.65 | |
| PRCA123 | 9.96 | 14.39 | 18.38 | 125 |
| PRCA135 | −3.75 | 8.89 | 13.64 | 123 |
| PRCA157 | 1.05 | 17.07 | 15.43 | 16.4 |
| PSMA | 11.52 | 31.38 | 34.79 | |
| PSMA | 52.82 | 71.19 | 66.04 | |
| RECA13 | 5.86 | 22.55 | 15.40 | 37 |
| RECA22 | 7.33 | 24.65 | 23.54 | 22.5 |
| RECA9 | 27.67 | 52.54 | 45.14 | 5.3 |
| SAL1 | 2.76 | 17.87 | 44.52 | 6.5 |
| SAL2 | 8.71 | 30.68 | 29.17 | 14.5 |
| SAL3 | 43.79 | 92.60 | 76.46 | 105 |
| SG24 | 12.64 | 66.82 | 44.99 | |
| SG27 | 1.37 | 55.30 | 16.96 | |
| SKIN2 | −2.04 | 14.81 | 24.23 | 73.8 |
| SPL16 | 9.97 | 29.90 | 23.74 | 5.2 |
| STO5 | −1.48 | 21.11 | 24.97 | 61.3 |
| TDH28 | −4.23 | 18.55 | 15.04 | 13.3 |
| TDH36 | 3.58 | 19.61 | 19.79 | 199 |
| TDH37 | 7.90 | 18.78 | 25.22 | 57.3 |
| TDH4 | 14.48 | 37.96 | 54.64 | 45.2 |
| TDH40 | 8.51 | 44.55 | 43.87 | 79.3 |
| TDH5 | 7.35 | 48.71 | 38.15 | 29.1 |
| TDH6 | 4.50 | 54.59 | 19.73 | 41.7 |
| TES7 | 50.15 | 94.47 | 73.40 | 22.4 |

Example 5

Ability of B7-H3 mAbs to Bind to Soluble B7113-21g and Soluble B7113-41g

Figure 4A:
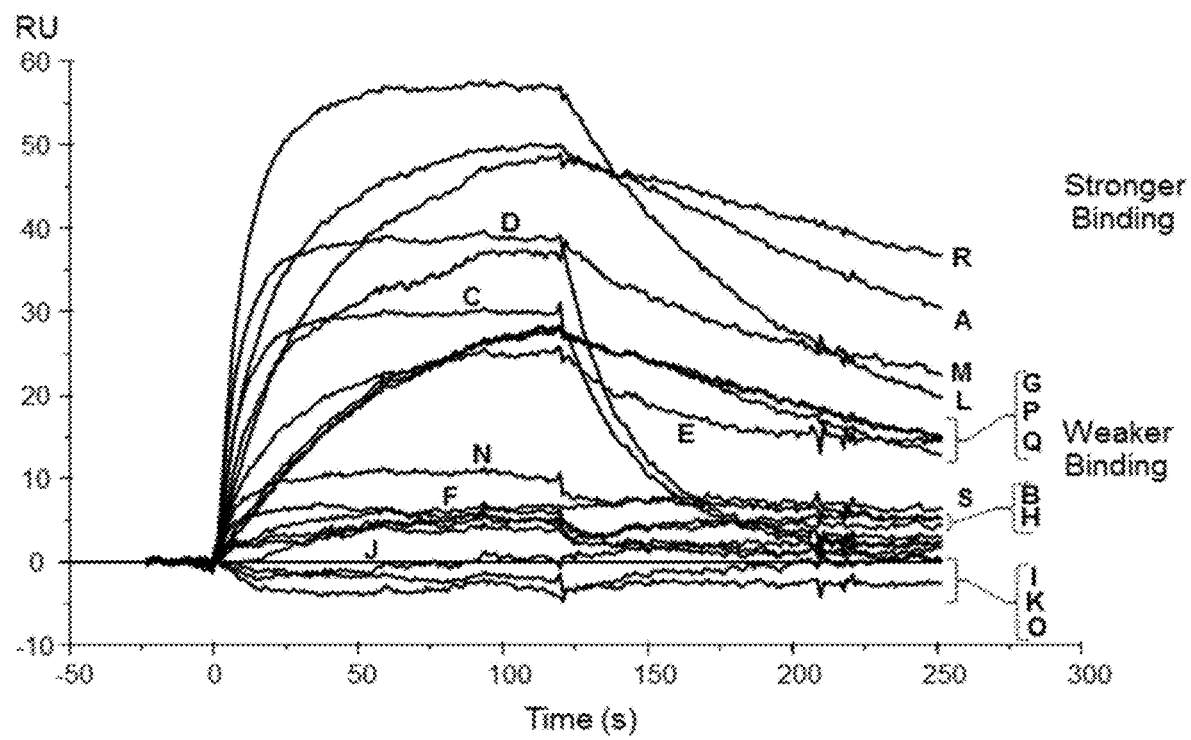
FIGS. 4A-4B show the abilities of anti-B7-H3 antibodies to bind to soluble B7H3-2Ig (FIG. 4A) and soluble B7H3-4Ig B7-H3 (FIG. 4B) (antibody concentration is 100 nM). Legend: (A) BLA8; (B) BRCA165; (C) BRCA68D; (D) BRCA69D; (E) BRCA84D; (F) GB8; (G) LUCA1; (H) LUCA50; (I) OVCA21; (J) OVCA22; (K) PA20; (L) PRCA123; (M) SG24; (N) SG27; (O) STO9; (P) TDH4 (184-192); (Q) TDH4; (R) TDH5; (S) TES7. The vertical position of legend correlates with the position of the corresponding curve.
Figure 4B:
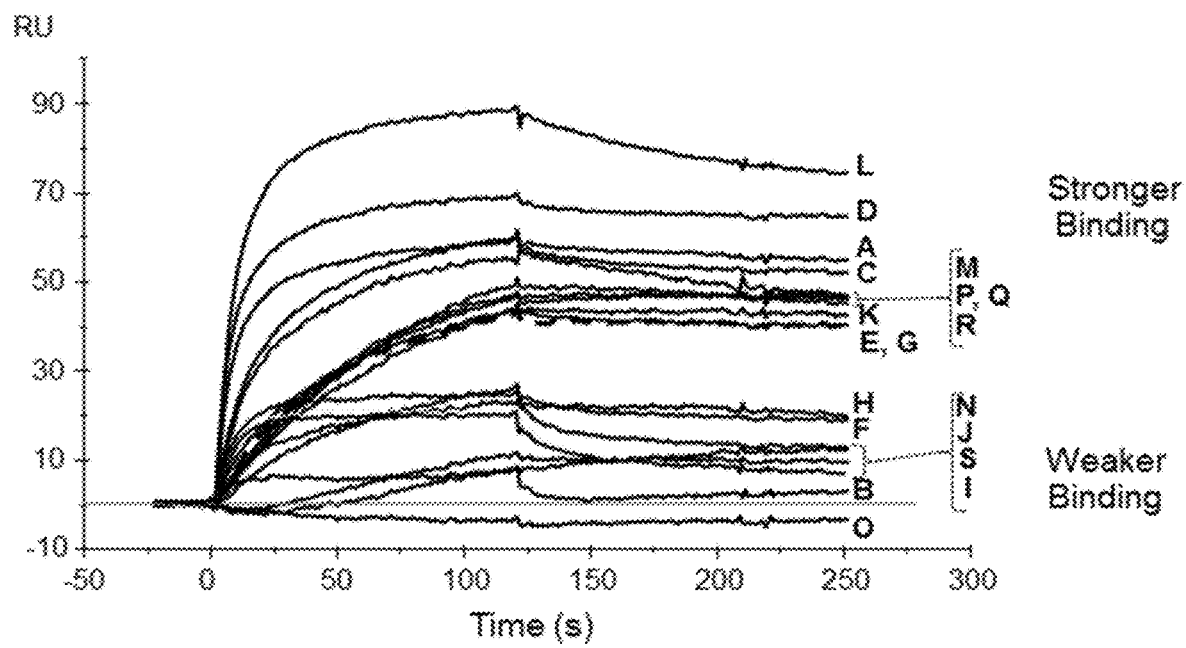

As discussed above, B7-H3 exists in both a 4 Ig domain-containing form (B7H3-4Ig) and a 2 Ig domain-containing form (B7H3-2Ig). The anti-B7-H3 antibodies of the present invention were tested for their abilities to bind to soluble B7H3-2Ig (FIG. 4A) and soluble B7H3-4Ig B7-H3 (FIG. 4B). The antibodies were found to exhibit a broad range of binding characteristics. Antibodies PRCA123, TDH5, BLA8, BRCA68D and SG24 were found to exhibit the strongest binding to soluble B7H3-2Ig and antibodies TES7, LUCA50, BRCA165, OVCA22, STO9 and PA20 were found to exhibit the weakest binding to soluble B7H3-2Ig. Antibodies PRCA123, BRCA69A, BLA8 and BRCA68D were found to exhibit the strongest binding to soluble B7H3-4Ig and antibodies TES7, OVCA21, BRCA165 and STO9 were found to exhibit the weakest binding to soluble B7H3-4Ig.

Example 6

Affinity Binding of Antigens in Solution to Captured Monoclonal Antibodies

Figure 5A:
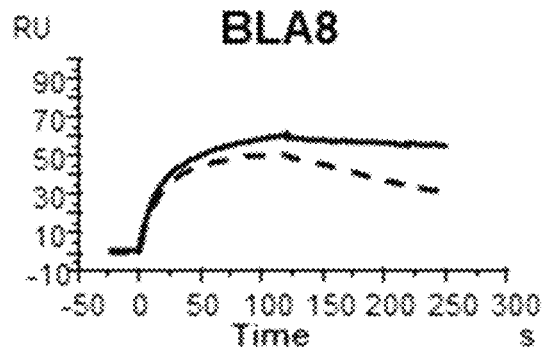
FIGS. 5A-5S demonstrate the binding affinity between antigens in solution and captured monoclonal antibodies (solid lines; B7-H3(4Ig) 100 nM; dashed lines; B7-H3, 100 nM).
Figure 5B:
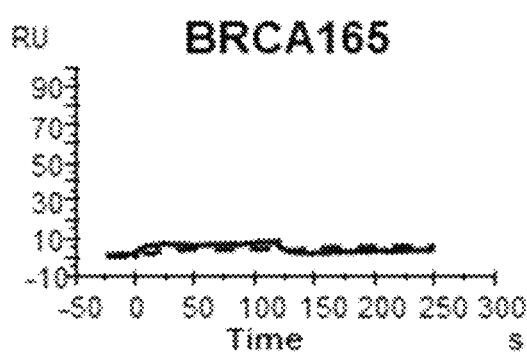
Figure 5C:
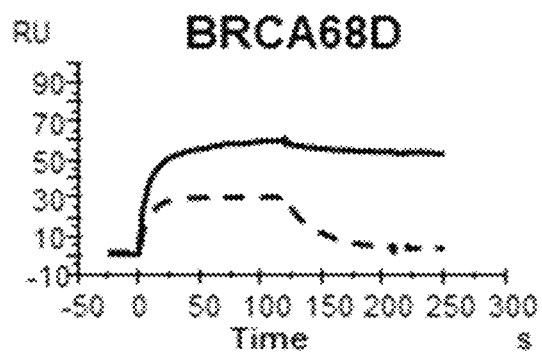
Figure 5D:
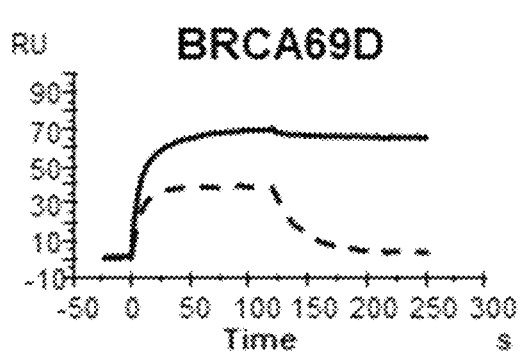
Figure 5E:
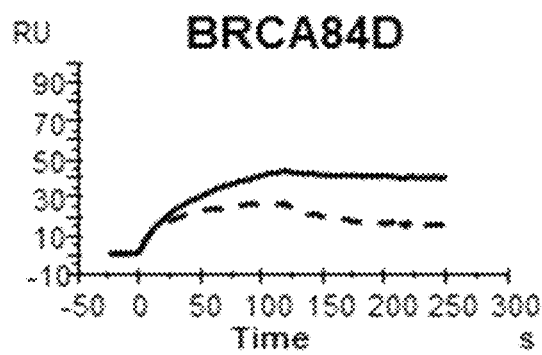
Figure 5F:
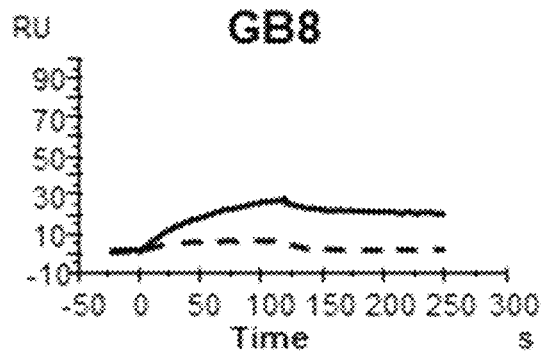
Figure 5G:
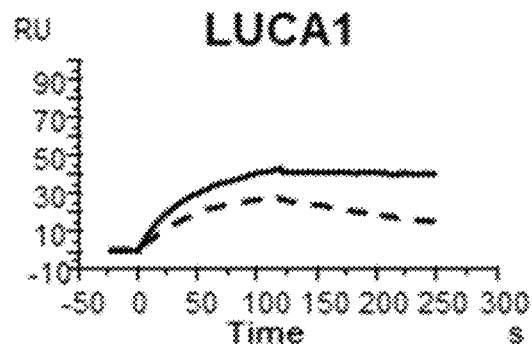
Figure 5H:
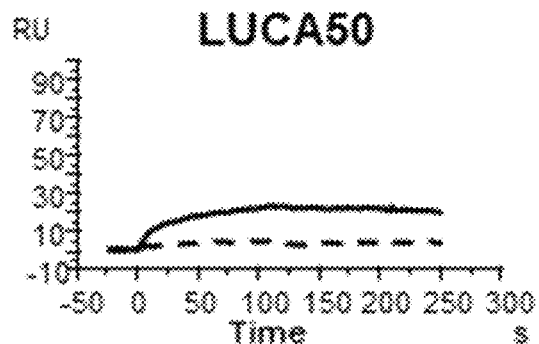
Figure 5I:
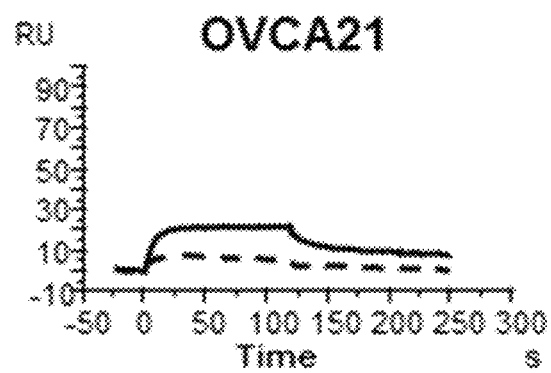
Figure 5J:
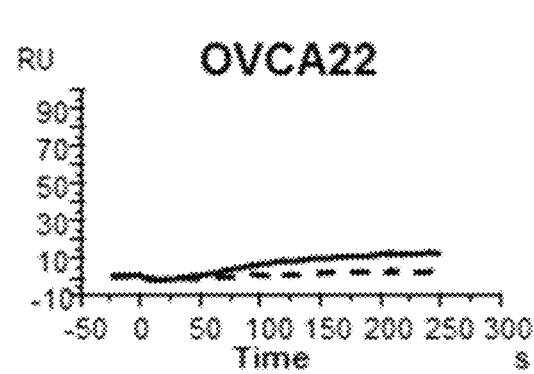
Figure 5K:
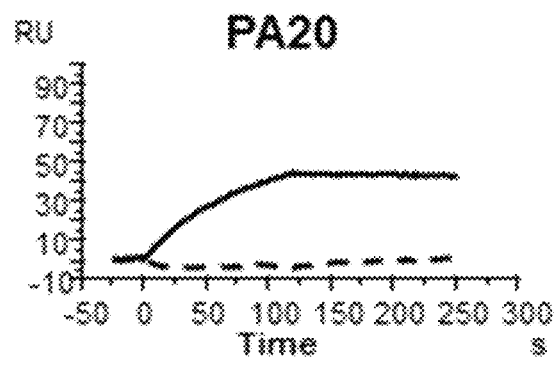
Figure 5L:
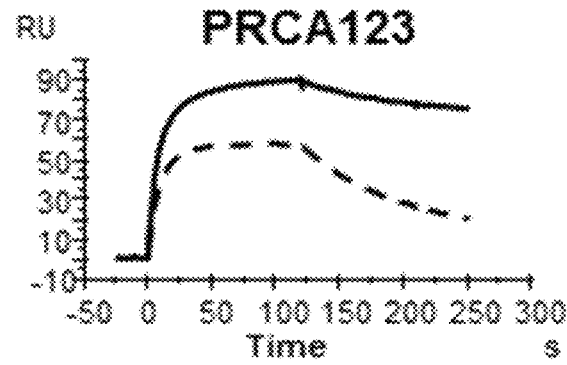
Figure 5M:
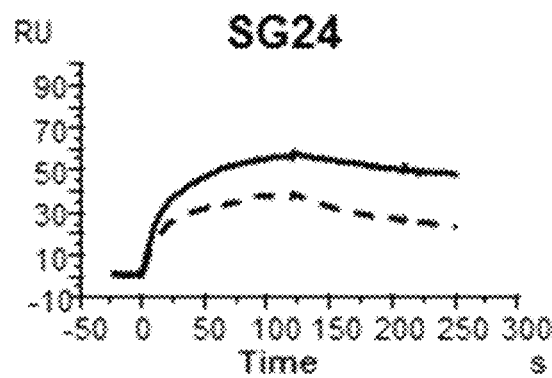
Figure 5N:
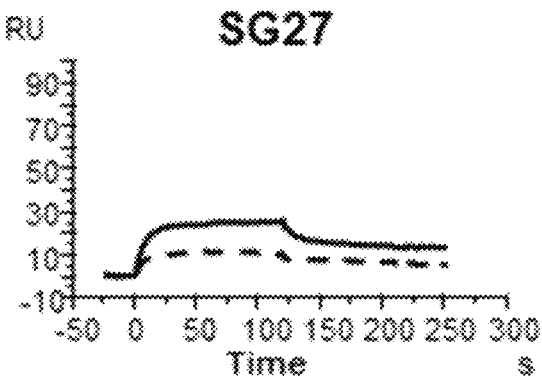
Figure 5O:
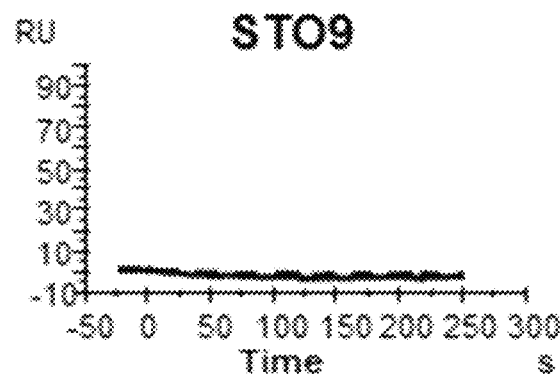
Figure 5P:
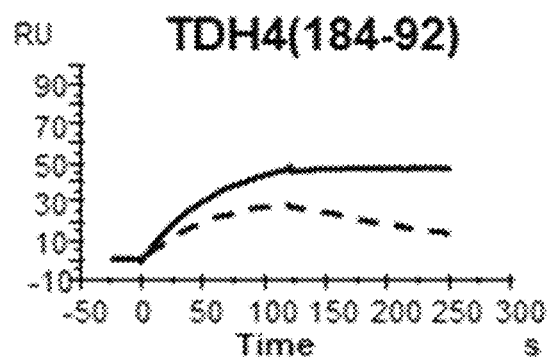
Figure 5Q:
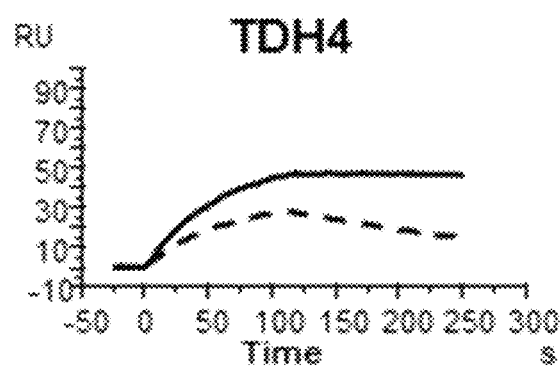
Figure 5R:
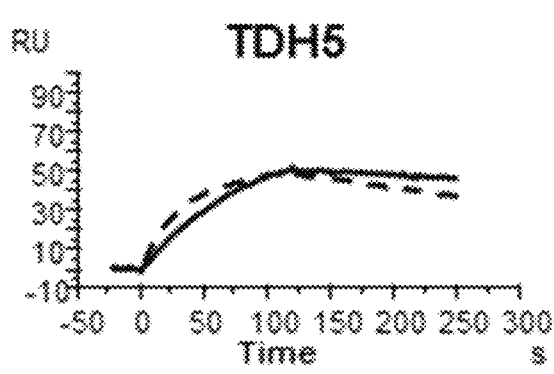
Figure 6C:
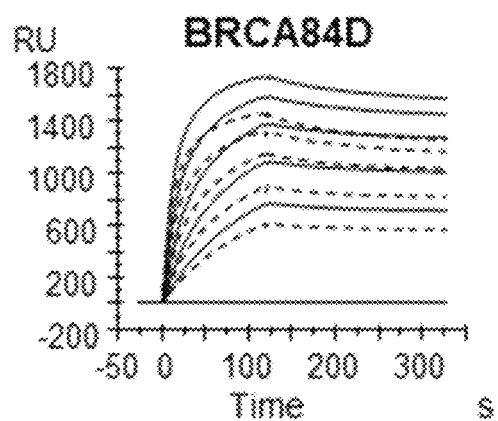
Figure 6D:
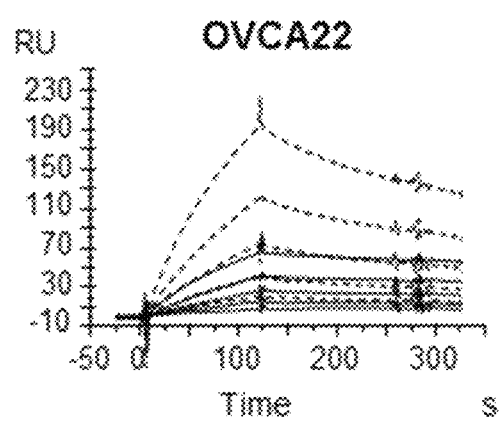
Figure 6E:
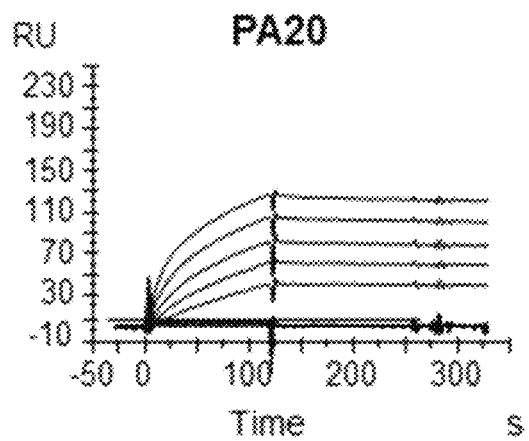
Figure 6F:
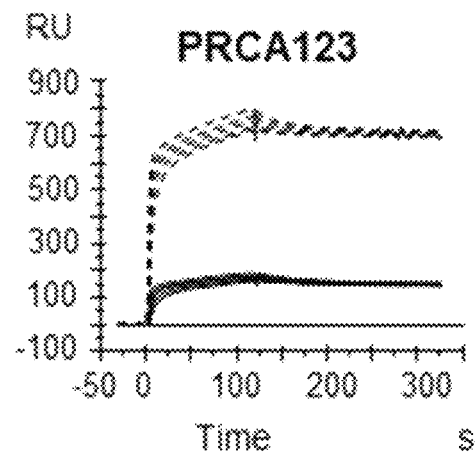
Figure 6G:
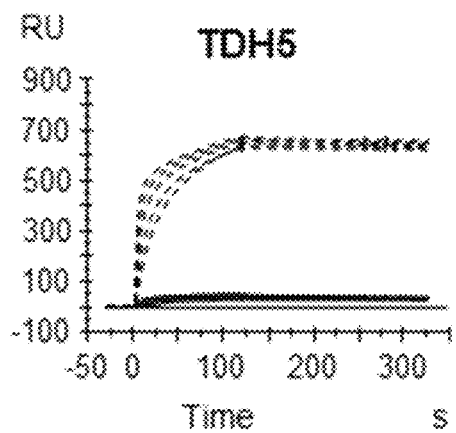
Figure 6H:
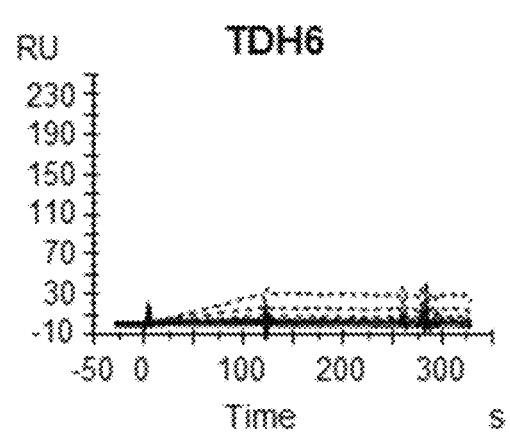
Figure 6I:
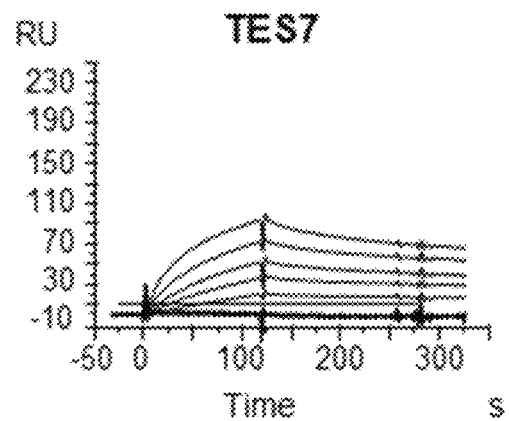

In order to demonstrate the binding affinity between antigens in solution and captured monoclonal antibodies, antibodies were captured on immobilized IgG Fc-specific Fab2 fragments at a level of 100-200 RU. Antigens B7-H3 and B7-H3(4Ig) were injected over the captured antibodies at a concentration of 100 nM (flow rate 20 µl/min for 120 sec, and binding was measured. Binding responses were normalized to the same level of captured mAb and the binding response to m2B6 antibody (mIgG1) control was subtracted as blank The results of this analysis (FIGS. 5A-5S; solid lines; B7-H3(4Ig) 100 nM; dashed lines; B7-H3, 100 nM)) demonstrate that the antibodies of the present invention exhibit strong binding to B7-H3(4Ig).

Example 7

BIACORE™ Analysis: Titration of B7-H3 mAbs to Immobilized B7-H3

In order to demonstrate the relative binding affinities of B7-H3-2Ig and B7-H3-4Ig for the antibodies of the present invention, a BIACORE™ analysis was performed. B7-H3 antibodies of the present invention were permitted to bind to immobilized B7-H3-2Ig or to B7-H3-4Ig and the titration of binding over time was assessed (FIGS. 6A-6I). TDH5, PRCA123, BLA8, BRCA69 were found to have high affinity to both B7-H3-2Ig and B7-H3-4Ig. However their epitope(s) were found to be mostly barred in the B7-H3-4Ig molecule, with just a few being available. OVCA22 was found to have a very low affinity to both B7-H3-2Ig and B7-H3-4Ig with its epitope being equally available on both molecules. However, it is likely that only the B7-H3-4Ig form provides enough proximity for antibody bivalent binding (low off-rate), whereas the B7-H3-2Ig can be bound only monovalently. TDH6 was found to have barely any affinity in this format, with binding to 2Ig likely to be non-specific. TES7 and PA20 were found to be B7-H4-4Ig specific antibodies with low affinity. TES7 probably has a low on-rate and a higher off-rate than PA20. BRCA84D was found to be an intermediate affinity antibody with a possibility of multiple binding sites on both B7-H3-2Ig and B7-H3-4Ig. Based on the BIACORE™ analysis, BRCA84D due to its unusual binding site was considered a preferred antibody. TES7 and PA20 were considered candidates for specific binding to high density antigen surfaces, and one of high affinity-low specificity antibody (e.g., BRCA69D or another).

Figure 7:
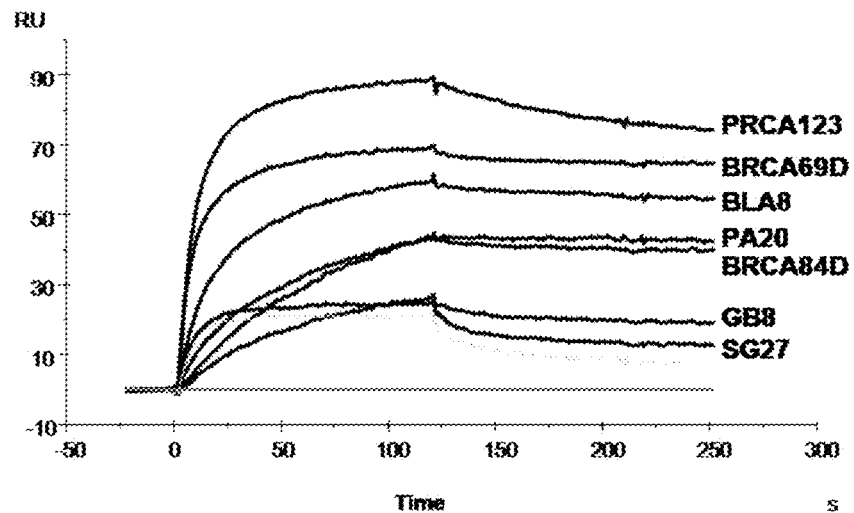
FIG. 7 provides a comparison BIACORE™ analysis of antibodies PRCA157, BRCA69D, BLA8, PA20, BRCA84D, GB8 and SG27.

FIG. 7 provides a comparison BIACORE™ analysis of antibodies PRCA157, BRCA69D, BLA8, PA20, BRCA84D, GB8 and SG27, illustrating that the anti-B7-H3 antibodies of the present invention can exhibit a range of binding properties.

Figure 8:
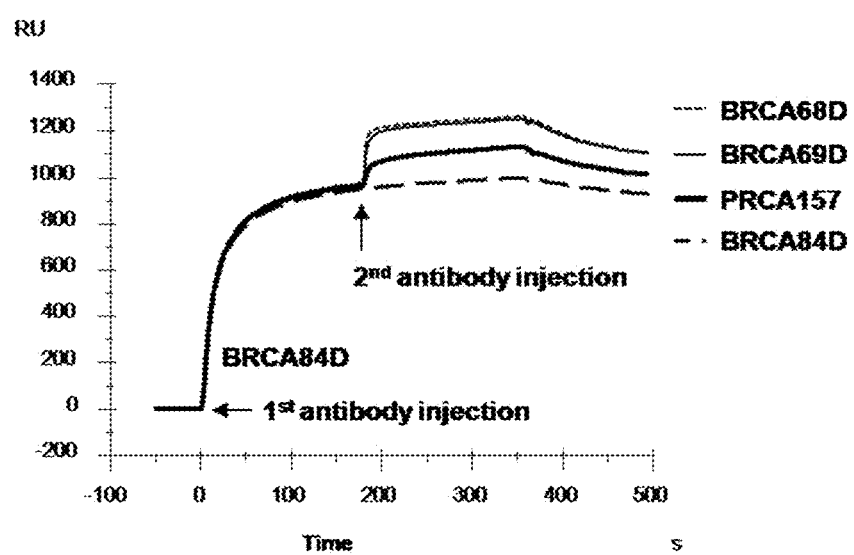
FIG. 8 provides a BIACORE™ analysis demonstrating that antibodies BRCA68D, BRCA69D, and PRCA157 do not compete with BRCA84D for binding to human B7-H3.

FIG. 8 demonstrates the non-competing specificity of several of the anti-B7-H3 antibodies of the present invention. In the experiment, human B7-H3 molecules were incubated in the presence of antibody BRCA84D and subjected to BIACORE™ analysis. After approximately 3 minutes a second anti-B7-H3 antibody was added to the reaction. If the second antibody competed with BRCA84D, it would find the B7-H3 sites occluded and be unable to bind. The results indicate that antibodies BRCA68D, BRCA69D, and PRCA157 do not compete with BRCA84D for binding to human B7-H3.

Example 8

Anti-B7-H3 mAbs Internalize on CSC and ATCC Cell Lines

Figure 9A:
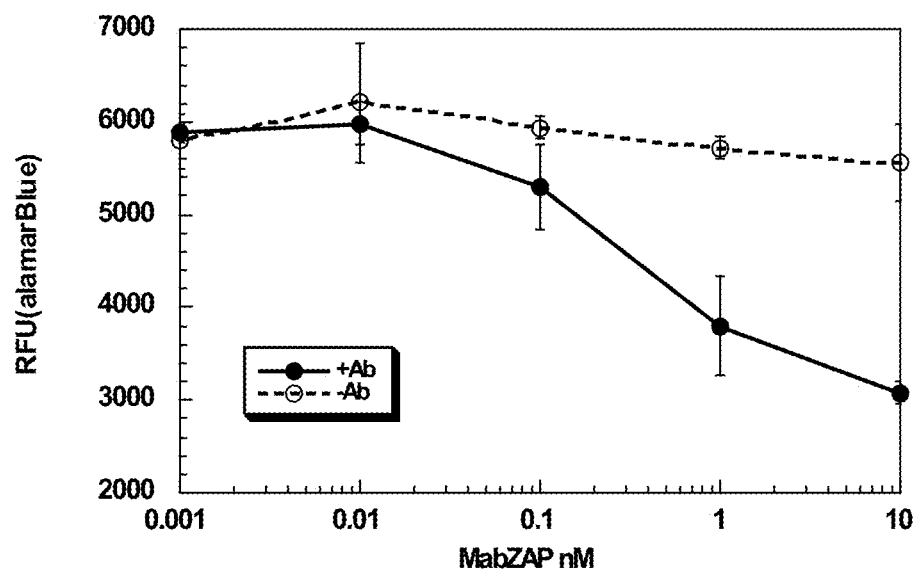
FIGS. 9A-9B show the results of studies on the ability of the anti-B7-H3 antibodies of the present invention to become internalized upon binding to cancer cells (FIG. 9A, prostate CSC cells.
Figure 9B:
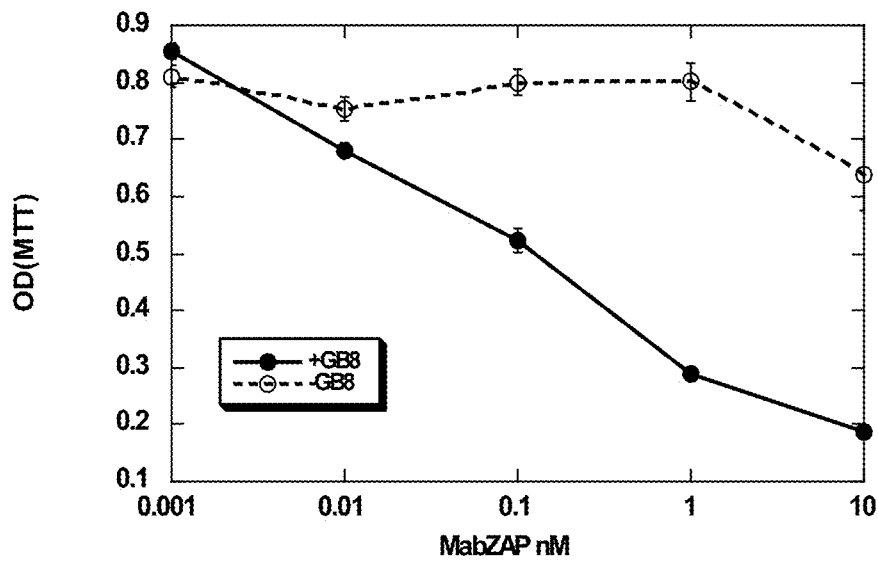
Figure 10A:
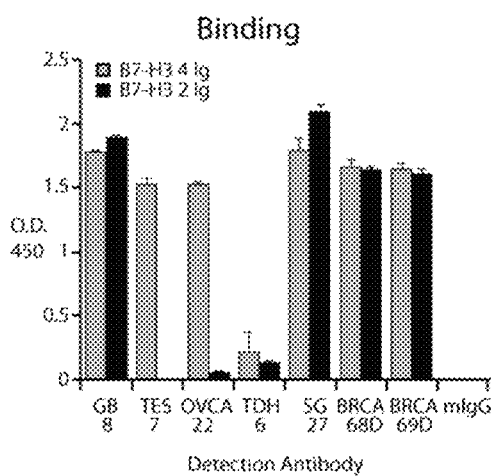
FIGS. 10A-10F show the ability of the anti-B7-H3 antibodies of the present invention to cross-block one another thereby revealing overlapping or distinct epitopes. A tenfold excess of competitor antibody was employed.
Figure 10B:
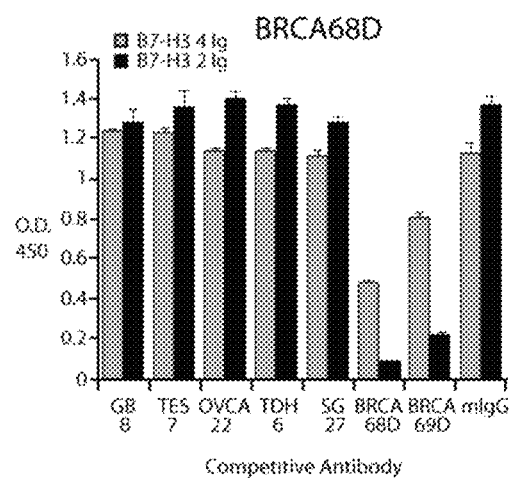
Figure 10C:
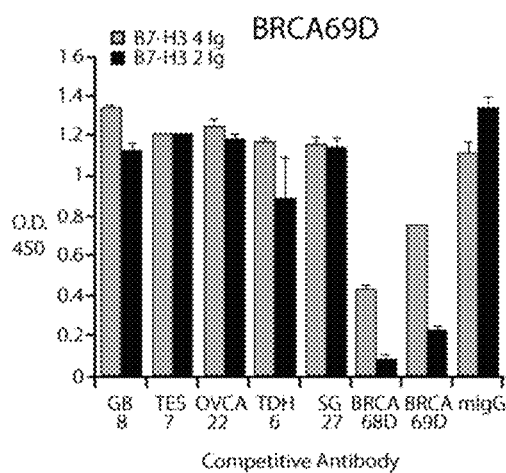
Figure 10D:
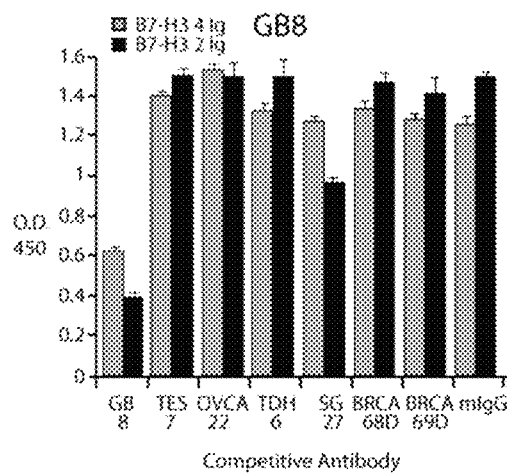
Figure 10E:
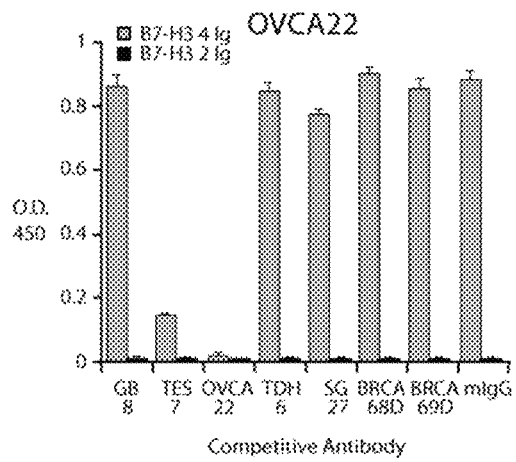
Figure 10F:
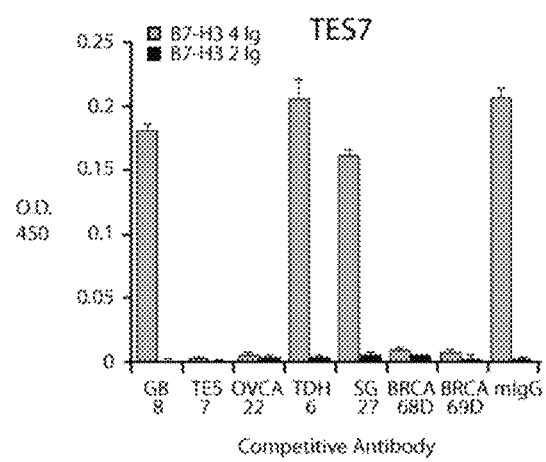

The ability of the anti-B7-H3 antibodies of the present invention to become internalized upon binding to cancer cells was investigated. Prostate CSC cells and Hs700t pancreatic cells were incubated with an anti-B7-H3 antibody. The viability of the cells was determined after incubation in the presence of a saporin-conjugate anti-mouse secondary antibody which will be toxic to the cells if bound to the primary antibody and internalized. The results of this investigation for prostate CSC cells (FIG. 9A) and for Hs700t pancreatic cells (FIG. 9B) demonstrate the capacity of the antibodies of the present invention to become internalized into cells.

Example 9

B7-H3 mAb Binding and Cross-Blocking Analysis by ELISA

In order to explore the cross-reactivity of the antibodies of the present invention and the epitopes recognized by such antibodies, the extent of binding occurring in the presence of a competitor B7-H3 antibody was measured. The results of this analysis are shown in FIGS. 10A-10F, and show that BRCA68D competes with BRCA69D. TES7 and OVCA22 were also found to compete with one another, but TES7 and not OVCA22 was found to also compete with both BRCA68D and BRCA69D. GB8 was found to compete with SG27 for binding to B7-H3-2Ig but not to B7-H3-4Ig. The data are summarized in Table 20 and show at least four distinct epitopes for B7-H3-4Ig (i.e., the epitope recognized by SG27, the epitope recognized by GB8, the epitope recognized by OVCA22 and TES7, and the epitope recognized by BRCA68D, BRCA69D and TES7) and at least two epitopes for B7-H3-2Ig (i.e., the epitope recognized by SG27 and GB8, and the epitope recognized by BRCA68D and BRCA69D).

TABLE 20

Summary of B7-H3 mAb Cross-Blocking Analysis by ELISA

| Competitor Antibody | Antibody (Percent Binding vs. MIgG) | | | | | | | |
|---|---|---|---|---|---|---|---|---|
| | B7-H3 4Ig | | | | | B7-H3-2Ig | | |
| | GB8 | BRCA69D | BRCA68D | TES7 | OVCA22 | GB8 | BRCA69D | BRCA68D |
| GB8 | 50.211 | 119.105 | 108.948 | 87.480 | 98.142 | 26.618 | 84.408 | 94.710 |
| TES7 | 111.234 | 109.390 | 108.425 | 1.605 | 16.268 | 100.645 | 90.734 | 99.515 |
| OVCA22 | 121.783 | 112.322 | 100.813 | 3.371 | 2.048 | 100.423 | 87.991 | 102.766 |
| TDH6 | 105.591 | 105.065 | 100.494 | 99.839 | 96.701 | 100.089 | 66.086 | 100.728 |
| SG27 | 101.266 | 103.021 | 97.763 | 78.331 | 87.789 | 64.421 | 89.927 | 94.225 |
| BRCA68D | 105.934 | 40.284 | 43.144 | 4.815 | 102.655 | 98.888 | 7.635 | 7.425 |

TABLE 20-continued

Summary of B7-H3 mAb Cross-Blocking Analysis by ELISA

| Competitor Antibody | Antibody (Percent Binding vs. MIgG) | | | | | | | |
|---|---|---|---|---|---|---|---|---|
| | B7-H3 4Ig | | | | | B7-H3-2Ig | | |
| | GB8 | BRCA69D | BRCA68D | TES7 | OVCA22 | GB8 | BRCA69D | BRCA68D |
| BRCA69D | 102.558 | 66.291 | 71.441 | 4.334 | 96.928 | 94.952 | 17.346 | 17.059 |
| MIgG | 100.000 | 100.000 | 100.00 | 100.000 | 100.000 | 100.000 | 100.000 | 100.000 |

The attributes of the key anti-B7-H3 antibodies of the present invention are shown in Table 21. Based on their exhibited differential staining of normal and cancer tissues, their ability to bind B7-H3-4Ig as well as B7-H3-2Ig, their binding affinities as measured by the above-described BIACORE™ analysis and their ability to bind to cynomolgus B7H3, antibodies, BRCA68D, BRCA69D, BRCA84D, and PRCA157 were judged to be the most preferred antibodies

TABLE 21

| MAb | BRCA84D | TDH6 | TES7 | BRCA68D | BRCA69D | GB8 | SG27 | OVCA22 | PRCA157 |
|---|---|---|---|---|---|---|---|---|---|
| Isotype | G1/k | G1/k | G1/k | G1/k | G1/k | G1/k | 2b/k | G1/k | G1/k |
| IHC | 2a | 2a | 2a | 2b | 2b | 2b | 2b | 2c | 2c |
| ATCC Array | 2 | 1 | 1 | 3 | 3 | 3 | 1 | 3 | 2 |
| Normal Tissue | | | | | | | | | |
| Colon | 1+ | 1+ | | | 1+ | | 1+ | 2+ | 2+ |
| Lung | 1+ | 1+ | | 1+ | | | | | |
| Liver | 1+ | 1+ | | 2+ | 2+ | | 1+ | 2+ | 2+ |
| Kidney | | 1+ | | 1+ | 1+ | | 1+ | | |
| Pancreas | | 1+ | | 1+ | | | 1+ | 2+ | |
| Skin | | | | | | | | | 2+ |
| Cancerous Tissue | | | | | | | | | |
| Colon | 1231* | 1110* | 1.5 | 2321* | 2231* | | 1221* | 1122 | 2231* |
| Lung | 1130 | 1010 | 1.75 | 3332 | 3231 | | 1120 | 3131** | 3231 |
| Prostate | 112 | 111 | 3 | 333 | 333 | | 222 | 222 | 333 |
| Breast | 1111 | 1011 | 3 | 3333 | 3333 | | 1122 | 3233 | 2333 |
| Internalization | + | + | + | + | + | + | + | + | + |
| U-DART | + | + | + | + | + | + | + | + | + |
| Specificity | 4Ig | 4Ig | 4Ig | 4Ig | 4Ig | 4Ig | 4Ig | 4Ig | 4Ig |
| | 2Ig | 2Ig | | 2Ig | 2Ig | 2Ig | 2Ig | | 2Ig |
| Epitope Group | A | B | C | D | D | E | F | G | H |
| BIACORE ™ | + | +/− | + | ++ | ++ | + | + | + | +/− |
| Cynomolgus B7-H3 Binding | ++ | + | − | ++ | ++ | ++ | + | + | ++ |

Notes:
*Indicates staining of stroma
**stroma staing 3+

Example 10

Humanized Anti-B7-H3 Antibodies

Monoclonal antibody BRCA84D was humanized in order to produce antibodies (generically designated herein as "hBRCA84D") offering improved human therapeutic potential. The sequences of the variable light chain, and the variable heavy chain, and their respective amino acid and polynucleotide sequences of a resulting humanized antibody (designated herein as "hBRCA84D-1") are provided below:

Humanized BRCA84D-1 Variable Light Chain (SEQ ID NO: 68):

```
DIQLTQSPSF LSASVGDRVT ITCKASQNVD TNVAWYQQKP

GKAPKLLIYS ASYRYSGVPS RFSGSGSGTD FTLTISSLQP

EDFATYYCQQ YNNYPFTFGQ GTKLEIK
```

Polynucleotide Sequence Encoding Humanized BRCA84D-1 Variable Light Chain (SEQ ID NO: 69):

```
gacatccagc tgacccagtc ccctccttc ctgtctgcct ccgtgggcga cagagtgacc atcacatgca aggcctccca gaacgtggac accaacgtgg cctggtatca gcagaagcct ggcaaggccc ctaagctgct gatctactcc gcctcctacc ggtactccgg cgtgccttcc aggttctccg gctccggctc tggcaccgac ttcaccctga ccatctccag cctgcagcct gaggacttcg ccacctacta ctgccagcag tacaacaact accctttcac cttcggccag ggcaccaagc tggaaatcaa g
```

Humanized BRCA84D-1 Variable Light Chain CDR₁ (SEQ ID NO: 70): KASQNVDTNVA

Polynucleotide Sequence Encoding Humanized BRCA84D-1 Variable Light Chain CDR₁ (SEQ ID NO: 71): aaggccagtc agaatgtgga tactaatgta gcc Humanized BRCA84D-1 Variable Light Chain CDR₂ (SEQ ID NO: 72): SASYRYS Polynucleotide Sequence Encoding Humanized BRCA84D-1 Variable Light Chain CDR₂ (SEQ ID NO: 73): tcggcatcct accggtacag t Humanized BRCA84D-1 Variable Light Chain CDR₃ (SEQ ID NO: 74): QQYNNYPFT Polynucleotide Sequence Encoding Humanized BRCA84D-1 Variable Light Chain CDR₃ (SEQ ID NO: 75): cagcaatata acaactatcc attcacg Amino Acid Sequence of Humanized BRCA84D-1 Variable Heavy Chain (SEQ ID NO: 80):

```
EVQLVESGGG LVQPGGSLRL SCAASGFTFS SFGMHWVRQA

PGKGLEWVAY ISSDSSAIYY ADTVKGRFTI SRDNAKNSLY

LQMNSLRDED TAVYYCARGR ENIYYGSRLD YWGQGTTVTV

SS
```

Polynucleotide Sequence Encoding Humanized BRCA84D-1 Variable Heavy Chain (SEQ ID NO: 81):

```
gaggtgcagc tggtcgagtc tggcggagga ctggtgcagc ctggcggctc cctgagactg tcttgcgccg cctccggctt caccttctcc agcttcggca tgcactgggt ccgccaggct ccaggcaagg gactggaatg ggtggcctac atctcctccg actcctccgc catctactac gccgacaccg tgaagggcag gttcaccatc tcccgggaca cgccaagaa ctccctgtac ctgcagatga ctccctgcg ggacgaggac accgccgtgt actactgcgc cagaggccgg gagaatatct actacggctc ccggctggat tattgggcc agggcaccac cgtgaccgtg tcctct
```

Humanized BRCA84D-1 Variable Heavy Chain CDR₁ (SEQ ID NO: 82): FGMH

Polynucleotide Sequence Encoding Humanized BRCA84D-1 Variable Heavy Chain CDR₁ (SEQ ID NO: 83): tttggaatgcac Humanized BRCA84D Variable Heavy Chain CDR₂ (SEQ ID NO: 84): YISSDSSAIYYADTVK Polynucleotide Sequence Encoding Humanized BRCA84D-1 Variable Heavy Chain CDR₂ (SEQ ID NO: 85): tacattagta gtgacagtag tgccatctac tatgcagaca cagtgaag Humanized BRCA84D-1 Variable Heavy Chain CDR₃ (SEQ ID NO: 86): GRENIYYGSRLDY Polynucleotide Sequence Encoding Humanized BRCA84D-1 Variable Heavy Chain CDR₃ (SEQ ID NO: 87): gggagggaaa acatttacta cggtagtagg cttgactac FIGS. 11A-11B show the alignment of the amino acid residues of the variable light chains (FIG. 11A) or variable heavy chains (FIG. 11B) of BRCA84D and its humanized derivative, hBRCA84D.

In order to obtain hBRCA84D species that exhibit improved affinity for human B7-H3, polynucleotides encoding the light or heavy chains of hBRCA84D-1 (i.e., hBRCA84D-1VL or hBRCA84D-1VH, respectively) were subjected to mutagenesis, and mutated hBRCA84D-1 light chain derivatives hBRCA84D-2VL, hBRCA84D-3VL, hBRCA84D-4VL, hBRCA84D-5VL, and hBRCA84D-6VL and mutated hBRCA84D-1 heavy chain derivatives hBRCA84D-2VH, hBRCA84D-3VH, and hBRCA84D-4VH were isolated and characterized. The amino acid and polynucleotide sequences of the variable light and heavy chains of these antibodies are presented below:

hBRCA84D-2VL (SEQ ID NO: 89):

```
DIQLTQSPSF LSASVGDRVT ITCKASQNVD TNVAWYQQKP

GKAPKALIYS ASYRYSGVPS RFSGSGSGTD FTLTISSLQP

EDFATYYCQQ YNNYPFTFGQ GTKLEIK
```

Polynucleotide Encoding hBRCA84D-2VL (SEQ ID NO: 90):

```
gacatccagc tgacccagtc ccctccttc ctgtctgcct ccgtgggcga cagagtgacc atcacatgca aggcctccca gaacgtggac accaacgtgg cctggtatca gcagaagcct ggcaaggccc ctaaggcgct gatctactcc gcctcctacc
```

```
                    -continued
ggtactccgg cgtgccttcc aggttctccg gctccggctc tggcaccgac ttcaccctga ccatctccag cctgcagcct gaggacttcg ccacctacta ctgccagcag tacaacaact acccttcac cttcggccag ggcaccaagc tggaaatcaa g
``` hBRCA84D-3VL (SEQ ID NO: 91):

```
DIQLTQSPSF LSASVGDRVS VTCKASQNVD TNVAWYQQKP
GKAPKLLIYS ASYRYSGVPS RFSGSGSGTD FTLTISSLQP
EDFATYYCQQ YNNYPFTFGQ GTKLEIK
```

Polynucleotide Encoding hBRCA84D-3VL (SEQ ID NO: 92):

```
gacatccagc tgacccagtc ccctccttc ctgtctgcct ccgtgggcga cagagtgtcc gtcacatgca aggcctccca gaacgtggac accaacgtgg cctggtatca gcagaagcct ggcaaggccc ctaagctgct gatctactcc gcctcctacc ggtactccgg cgtgccttcc aggttctccg gctccggctc tggcaccgac ttcaccctga ccatctccag cctgcagcct gaggacttcg ccacctacta ctgccagcag tacaacaact acccttcac cttcggccag ggcaccaagc tggaaatcaa g
``` hBRCA84D-4VL (SEQ ID NO: 93):

```
DIQLTQSPSF LSASVGDRVT ITCKASQNVD TNVAWYQQKP
GQAPKLLIYS ASYRYSGVPS RFSGSGSGTD FTLTISSLQP
EDFATYYCQQ YNNYPFTFGQ GTKLEIK
```

Polynucleotide Encoding hBRCA84D-4VL (SEQ ID NO: 94):

```
gacatccagc tgacccagtc ccctccttc ctgtctgcct ccgtgggcga cagagtgacc atcacatgca aggcctccca gaacgtggac accaacgtgg cctggtatca gcagaagcct ggccaggccc ctaagctgct gatctactcc gcctcctacc ggtactccgg cgtgccttcc aggttctccg gctccggctc tggcaccgac ttcaccctga ccatctccag cctgcagcct gaggacttcg ccacctacta ctgccagcag tacaacaact acccttcac cttcggccag ggcaccaagc tggaaatcaa g
``` hBRCA84D-5VL (SEQ ID NO: 95):

```
DIQLTQSPSF LSASVGDRVT ITCKASQNVD TNVAWYQQKP
GQAPKALIYS ASYRYSGVPS RFSGSGSGTD FTLTISSLQP
EDFATYYCQQ YNNYPFTFGQ GTKLEIK
```

Polynucleotide Encoding hBRCA84D-5VL (SEQ ID NO: 96):

```
gacatccagc tgacccagtc ccctccttc ctgtctgcct ccgtgggcga cagagtgacc atcacatgca aggcctccca gaacgtggac accaacgtgg cctggtatca gcagaagcct ggccaggccc ctaaggcgct gatctactcc gcctcctacc ggtactccgg cgtgccttcc aggttctccg gctccggctc tggcaccgac ttcaccctga ccatctccag cctgcagcct gaggacttcg ccacctacta ctgccagcag tacaacaact acccttcac cttcggccag ggcaccaagc tggaaatcaa g
``` hBRCA84D-6VL (SEQ ID NO: 97):

```
DIQLTQSPSF LSASVGDRVT ITCKASQNVD TNVAWYQQKP
GKAPKLLIYS ASYRYSGVPS RFSGSGSGTD FTLTISSLQP
EDFAEYYCQQ YNNYPFTFGQ GTKLEIK
```

Polynucleotide Encoding hBRCA84D-6VL (SEQ ID NO: 98):

```
gacatccagc tgacccagtc ccctccttc ctgtctgcct ccgtgggcga cagagtgacc atcacatgca aggcctccca gaacgtggac accaacgtgg cctggtatca gcagaagcct ggcaaggccc ctaagctgct gatctactcc gcctcctacc ggtactccgg cgtgccttcc aggttctccg gctccggctc tggcaccgac ttcaccctga ccatctccag cctgcagcct gaggacttcg ccgagtacta ctgccagcag tacaacaact acccttcac cttcggccag ggcaccaagc tggaaatcaa g
``` hBRCA84D-2VH (SEQ ID NO: 99):

```
EVQLVESGGG LVQPGGSLRL SCAASGFTFS SFGMHWVRQA
PGKGLEWVAY ISSDSSAIYY ADTVKGRFTI SRDNAKNSLY
LQMNSLRDED TAVYYCGRGR ENIYYGSRLD YWGQGTTVTV SS
```

Polynucleotide Encoding hBRCA84D-2VH (SEQ ID NO: 100):

```
gaggtgcagc tggtcgagtc tggcggagga ctggtgcagc ctggcggctc cctgagactg tcttgcgccg cctccggctt
```

-continued

```
caccttctcc agcttcggca tgcactgggt ccgccaggct
ccaggcaagg gactggaatg ggtggcctac atctcctccg
actcctccgc catctactac gccgacaccg tgaagggcag
gttcaccatc tcccgggaca acgccaagaa ctccctgtac
ctgcagatga actccctgcg ggacgaggac accgccgtgt
actactgcgg cagaggccgg gagaatatct actacggctc
ccggctggat tattggggcc agggcaccac cgtgaccgtg tcctct
``` hBRCA84D-3VH (SEQ ID NO: 101):

```
EVQLVESGGG LVQPGGSLRL SCAASGFTFS SFGMHWVRQA
PGKGLEWVAY ISSDSSAIYY ADTVKGRFTI SRDNAKNSLY
LQMNSLRDED TAMYYCGRGR ENIYYGSRLD YWGQGTTVTV SS
```

Polynucleotide Encoding hBRCA84D-3VH (SEQ ID NO: 102):

```
gaggtgcagc tggtcgagtc tggcggagga ctggtgcagc
ctggcggctc cctgagactg tcttgcgccg cctccggctt
caccttctcc agcttcggca tgcactgggt ccgccaggct
ccaggcaagg gactggaatg ggtggcctac atctcctccg
actcctccgc catctactac gccgacaccg tgaagggcag
gttcaccatc tcccgggaca acgccaagaa ctccctgtac
ctgcagatga actccctgcg ggacgaggac accgccatgt
```

-continued

```
actactgcgg cagaggccgg gagaatatct actacggctc
ccggctggat tattggggcc agggcaccac cgtgaccgtg tcctct
``` hBRCA84D-4VH (SEQ ID NO: 103):

```
EVQLVESGGG LVQPGGSLRL SCAASGFTFS SFGMHWVRQA
PGKGLEWVAY ISSDSSAIYY ADTVKGRFTI SRDNAKNSLY
LQMNSLRSED TAVYYCARGR ENIYYGSRLD YWGQGTTVTV SS
```

Polynucleotide Encoding hBRCA84D-4VH (SEQ ID NO: 104):

```
gaggtgcagc tggtcgagtc tggcggagga ctggtgcagc
ctggcggctc cctgagactg tcttgcgccg cctccggctt
caccttctcc agcttcggca tgcactgggt ccgccaggct
ccaggcaagg gactggaatg ggtggcctac atctcctccg
actcctccgc catctactac gccgacaccg tgaagggcag
gttcaccatc tcccgggaca acgccaagaa ctccctgtac
ctgcagatga actccctgcg gagcgaggac accgccgtgt
actactgcgc cagaggccgg gagaatatct actacggctc
ccggctggat tattggggcc agggcaccac cgtgaccgtg tcctct
```

Table 22 lists the hBRCA84D variable light chain and variable heavy chain mutations studied; numbers refer to the Kabat numbering system used in FIGS. 11A and 11B.

TABLE 22

| | Variable Light Chain | | | | | Variable Heavy Chain | | | |
|---|---|---|---|---|---|---|---|---|---|
| Kabat Position | 20 | 21 | 42 | 46 | 85 | Kabat Position | 84 | 89 | 93 |
| BRCA84D | S | V | Q | A | E | BRCA84D | S | M | G |
| hBRCA84D-1VL | T | I | K | L | T | hBRCA84D-1VH | D | V | A |
| hBRCA84D-2VL | T | I | K | A | T | hBRCA84D-2VH | D | V | G |
| hBRCA84D-3VL | S | V | K | L | T | hBRCA84D-3VH | D | M | G |
| hBRCA84D-4VL | T | I | Q | L | T | hBRCA84D-4VH | S | V | A |
| hBRCA84D-5VL | T | I | Q | A | T | | | | |
| hBRCA84D-6VL | T | I | K | L | E | | | | |

Figure 12:
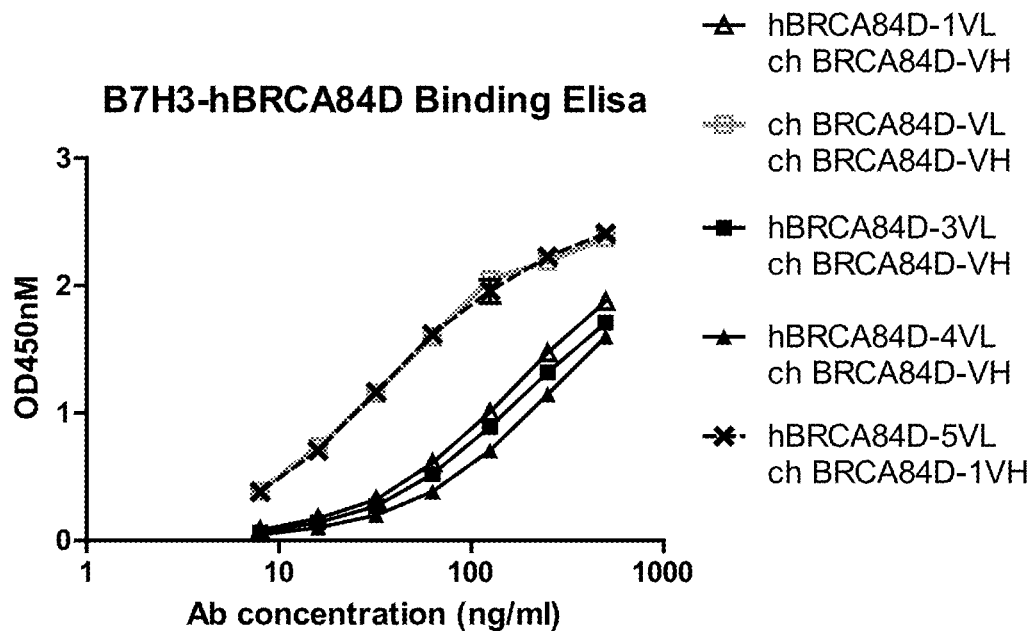
FIG. 12 shows the relative binding affinities of the hBRCA84D light chain derivatives BRCA84D-3VL, BRCA84D-4VL and BRCA84D-5VL for human B7-H3.
Figure 13:
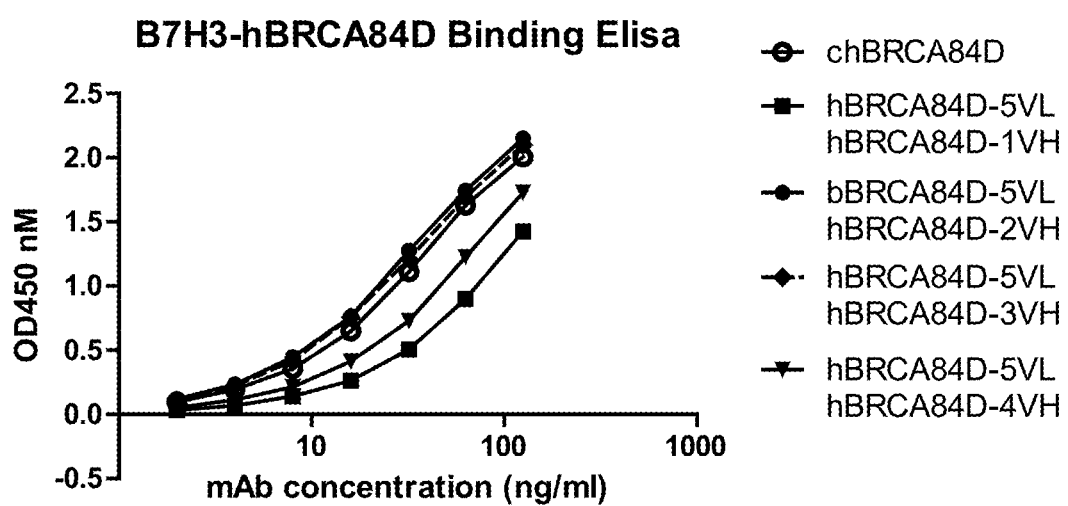
FIG. 13 shows the relative binding affinities of the hBRCA84D heavy chain derivatives BRCA84D-2VH, BRCA84D-3VH and BRCA84D-4VH for human B7-H3.

The relative binding affinities of the hBRCA84D light chain derivatives hBRCA84D-3VL, hBRCA84D-4VL and hBRCA84D-5VL for human B7-H3 were determined by forming antibodies containing these light chain variable regions and a chimeric BRCA84D-1VH heavy chain (FIG. 12). BRCA84D-5VL (K42Q, L46A) was found to have the highest binding affinity of the hBRCA84D-VL tested. BRCA84D-5VL was therefore used as the light chain to investigate the relative binding affinities of the hBRCA84D heavy chains of hBRCA84D-1VH, hBRCA84D-2VH, hBRCA84D-3VH and hBRCA84D-4VH for human B7-H3 (FIG. 13). hBRCA84D-2VH (A93G) was found to have the highest binding affinity of the hBRCA84D-VH tested.

The amino acid and encoding polynucleotide sequences of the chimeric BRCA84D-1 are as follows:

chBRCA84D Light Chain (SEQ ID NO: 105):

```
DIAMTQSQKF MSTSVGDRVS VTCKASQNVD TNVAWYQQKP
GQSPKALIYS ASYRYSGVPD RFTGSGSGTD FTLTINNVQS
EDLAEYFCQQ YNNYPFTFGS GTKLEIKRTV AAPSVFIFPP
SDEQLKSGTA SVVCLLNNFY PREAKVQWKV DNALQSGNSQ
ESVTEQDSKD STYSLSSTLT LSKADYEKHK VYACEVTHQG
LSSPVTKSFN RGEC
```

Polynucleotide Encoding chBRCA84D Light Chain (SEQ ID NO: 106):

```
gacattgcga tgacccagtc tcaaaaattc atgtccacat
cagtaggaga cagggtcagc gtcacctgca aggccagtca
gaatgtggat actaatgtag cctggtatca acagaaacca
gggcaatctc ctaaagcact gatttactcg gcatcctacc
ggtacagtgg agtccctgat cgcttcacag gcagtggatc
tgggacagat ttcactctca ccatcaacaa tgtgcagtct
gaagacttgg cagagtattt ctgtcagcaa tataacaact
atccattcac gttcggctcg gggacaaagt tggaaataaa
acgtacggtg gctgcaccat ctgtcttcat cttcccgcca
tctgatgagc agttgaaatc tggaactgcc tctgttgtgt
gcctgctgaa taacttctat cccagagagg ccaaagtaca
gtggaaggtg gataacgccc tccaatcggg taactcccag
gagagtgtca cagagcagga cagcaaggac agcacctaca
gcctcagcag caccctgacg ctgagcaaag cagactacga
gaaacacaaa gtctacgcct gcgaagtcac ccatcagggc
ctgagctcgc ccgtcacaaa gagcttcaac agggagagt gttag
``` chBRCA84D Heavy Chain (SEQ ID NO: 107):

```
DVQLVESGGG LVQPGGSRKL SCAASGFTFS SFGMHWVRQA
PEKGLEWVAY ISSDSSAIYY ADTVKGRFTI SRDNPKNTLF
LQMTSLRSED TAMYYCGRGR ENIYYGSRLD YWGQGTTLTV
SSASTKGPSV FPLAPSSKST SGGTAALGCL VKDYFPEPVT
VSWNSGALTS GVHTFPAVLQ SSGLYSLSSV VTVPSSSLGT
QTYICNVNHK PSNTKVDKRV EPKSCDKTHT CPPCPAPELL
GGPSVFLFPP KPKDTLMISR TPEVTCVVVD VSHEDPEVKF
NWYVDGVEVH NAKTKPREEQ YNSTYRVVSV LTVLHQDWLN
GKEYKCKVSN KALPAPIEKT ISKAKGQPRE PQVYTLPPSR
DELTKNQVSL TCLVKGFYPS DIAVEWESNG QPENNYKTTP
PVLDSDGSFF LYSKLTVDKS RWQQGNVFSC SVMHEALHNH
YTQKSLSLSP GK
```

Polynucleotide Encoding chBRCA84D Heavy Chain (SEQ ID NO: 108):

```
gatgtgcagc tggtggagtc tgggggaggc ttagtgcagc
ctggagggtc ccggaaactc tcctgtgcag cctctggatt
cactttcagt agctttggaa tgcactgggt tcgtcaggct
ccagaaaagg ggctggagtg ggtcgcatac attagtagtg
acagtagtgc catctactat gcagacacag tgaagggccg
attcaccatc tccagagaca atcccaagaa caccctgttc
ctgcaaatga ccagtctaag gtctgaggac acggccatgt
attactgtgg aagagggagg gaaaacattt actacggtag
taggcttgac tactggggcc aaggcaccac tctcacagtc
tcctcagcct ccaccaaggg cccatcggtc ttccccctgg
caccctcctc caagagcacc tctgggggca gcgcccct
gggctgcctg gtcaaggact acttccccga accggtgacg
gtgtcgtgga actcaggcgc cctgaccagc ggcgtgcaca
ccttcccggc tgtcctacag tcctcaggac tctactccct
cagcagcgtg gtgaccgtgc cctccagcag cttgggcacc
cagacctaca tctgcaacgt gaatcacaag cccagcaaca
ccaaggtgga caagagagtt gagcccaaat cttgtgacaa
aactcacaca tgcccaccgt gcccagcacc tgaactcctg
gggggaccgt cagtcttcct cttccccca aaacccaagg
acaccctcat gatctcccgg acccctgagg tcacatgcgt
ggtggtggac gtgagccacg aagaccctga ggtcaagttc
aactggtacg tggacggcgt ggaggtgcat aatgccaaga
caaagccgcg ggaggagcag tacaacagca cgtaccgtgt
ggtcagcgtc ctcaccgtcc tgcaccagga ctggctgaat
ggcaaggagt acaagtgcaa ggtctccaac aaagccctcc
cagcccccat cgagaaaacc atctccaaag ccaaagggca
gccccgagaa ccacaggtgt acaccctgcc cccatcccgg
gatgagctga ccaagaacca ggtcagcctg acctgcctgg
tcaaaggctt ctatcccagc gacatcgccg tggagtggga
gagcaatggg cagccggaga acaactacaa gaccacgcct
```

```
cccgtgctgg actccgacgg ctccttcttc ctctacagca agctcaccgt ggacaagagc aggtggcagc aggggaacgt cttctcatgc tccgtgatgc atgaggctct gcacaaccac tacacgcaga agagcctctc cctgtctccg ggtaaatga
```

Amino Acid Sequence Of The hBRCA84D-2 Light Chain (SEQ ID NO: 117):

```
DIQLTQSPSF LSASVGDRVT ITCKASQNVD TNVAWYQQKP
GKAPKALIYS ASYRYSGVPS RFSGSGSGTD FTLTISSLQP
EDFATYYCQQ YNNYPFTFGQ GTKLEIKRTV AAPSVFIFPP
SDEQLKSGTA SVVCLLNNFY PREAKVQWKV DNALQSGNSQ
ESVTEQDSKD STYSLSSTLT LSKADYEKHK VYACEVTHQG
LSSPVTKSFN RGEC
```

Polynucleotide Encoding The Amino Acid Sequence Of The hBRCA84D-2 Light Chain (SEQ ID NO: 118):

```
gacatccagc tgacccagtc ccctccttc ctgtctgcct
ccgtgggcga cagagtgacc atcacatgca aggcctccca
gaacgtggac accaacgtgg cctggtatca gcagaagcct
ggcaaggccc ctaaggcgct gatctactcc gcctcctacc
ggtactccgg cgtgccttcc aggttctccg gctccggctc
tggcaccgac ttcaccctga ccatctccag cctgcagcct
gaggacttcg ccacctacta ctgccagcag tacaacaact
acccttttcac cttcggccag ggcaccaagc tggaaatcaa
gcgtacggtg gctgcaccat ctgtcttcat cttcccgcca
tctgatgagc agttgaaatc tggaactgcc tctgttgtgt
gcctgctgaa taacttctat cccagagagg ccaaagtaca
gtggaaggtg gataacgccc tccaatcggg taactcccag
gagagtgtca cagagcagga cagcaaggac agcacctaca
gcctcagcag caccctgacg ctgagcaaag cagactacga
gaaacacaaa gtctacgcct gcgaagtcac ccatcagggc
ctgagctcgc ccgtcacaaa gagcttcaac aggggagagt gttag
```

Amino Acid Sequence Of The hBRCA84D-2 Heavy Chain (SEQ ID NO: 119):

```
EVQLVESGGG LVQPGGSLRL SCAASGFTFS SFGMHWVRQA
PGKGLEWVAY ISSDSSAIYY ADTVKGRFTI SRDNAKNSLY
LQMNSLRDED TAVYYCGRGR ENIYYGSRLD YWGQGTTVTV
SSASTKGPSV FPLAPSSKST SGGTAALGCL VKDYFPEPVT
VSWNSGALTS GVHTFPAVLQ SSGLYSLSSV VTVPSSSLGT
QTYICNVNHK PSNTKVDKRV EPKSCDKTHT CPPCPAPELV
GGPSVFLLPP KPKDTLMISR TPEVTCVVVD VSHEDPEVKF
NWYVDGVEVH NAKTKPPEEQ YNSTLRVVSV LTVLHQDWLN
GKEYKCKVSN KALPAPIEKT ISKAKGQPRE PQVYTLPPSR
EEMTKNQVSL TCLVKGFYPS DIAVEWESNG QPENNYKTTP
LVLDSDGSFF LYSKLTVDKS RWQQGNVFSC SVMHEALHNH
YTQKSLSLSP GK
```

Polynucleotide Encoding The Amino Acid Sequence Of The hBRCA84D-2 Heavy Chain (SEQ ID NO: 120):

```
gaggtgcagc tggtcgagtc tggcggagga ctggtgcagc
ctggcggctc cctgagactg tcttgcgccg cctccggctt
caccttctcc agcttcggca tgcactgggt ccgccaggct
ccaggcaagg gactggaatg ggtggcctac atctcctccg
actcctccgc catctactac gccgacaccg tgaagggcag
gttcaccatc tcccgggaca cgccaagaa ctccctgtac
ctgcagatga ctccctgcg ggacgaggac accgccgtgt
actactgcgg cagaggccgg gagaatatct actacggctc
ccggctggat tattgggggcc agggcaccac cgtgaccgtg
tcctctgcct ccaccaaggg cccatcggtc ttcccctgg
caccctcctc caagagcacc tctgggggca gcggccct
gggctgcctg gtcaaggact acttccccga accggtgacg
gtgtcgtgga actcaggcgc cctgaccagc ggcgtgcaca
ccttcccggc tgtcctacag tcctcaggac tctactccct
cagcagcgtg gtgaccgtgc cctccagcag cttgggcacc
cagacctaca tctgcaacgt gaatcacaag cccagcaaca
ccaaggtgga caagagagtt gagcccaaat cttgtgacaa
aactcacaca tgcccaccgt gcccagcacc tgaactcgtg
gggggaccgt cagtcttcct cttacccccca aaacccaagg
acaccctcat gatctcccgg accccctgagg tcacatgcgt
ggtggtggac gtgagccacg aagaccctga ggtcaagttc
aactggtacg tggacggcgt ggaggtgcat aatgccaaga
caaagccgcc ggaggagcag tacaacagca cgctccgtgt
ggtcagcgtc ctcaccgtcc tgcaccagga ctggctgaat
ggcaaggagt acaagtgcaa ggtctccaac aaagccctcc
cagcccccat cgagaaaacc atctccaaag ccaaagggca
gccccgagaa ccacaggtgt acaccctgcc cccatcccgg
gaggagatga ccaagaacca ggtcagcctg acctgcctgg
tcaaaggctt ctatcccagc gacatcgccg tggagtggga
gagcaatggg cagccggaga acaactacaa gaccacgcct
ctcgtgctgg actccgacgg ctccttcttc ctctacagca
agctcaccgt ggacaagagc aggtggcagc aggggaacgt
```

```
cttctcatgc tccgtgatgc atgaggctct gcacaaccac tacacgcaga agagcctctc cctgtctccg ggtaaa
```

Figure 14:
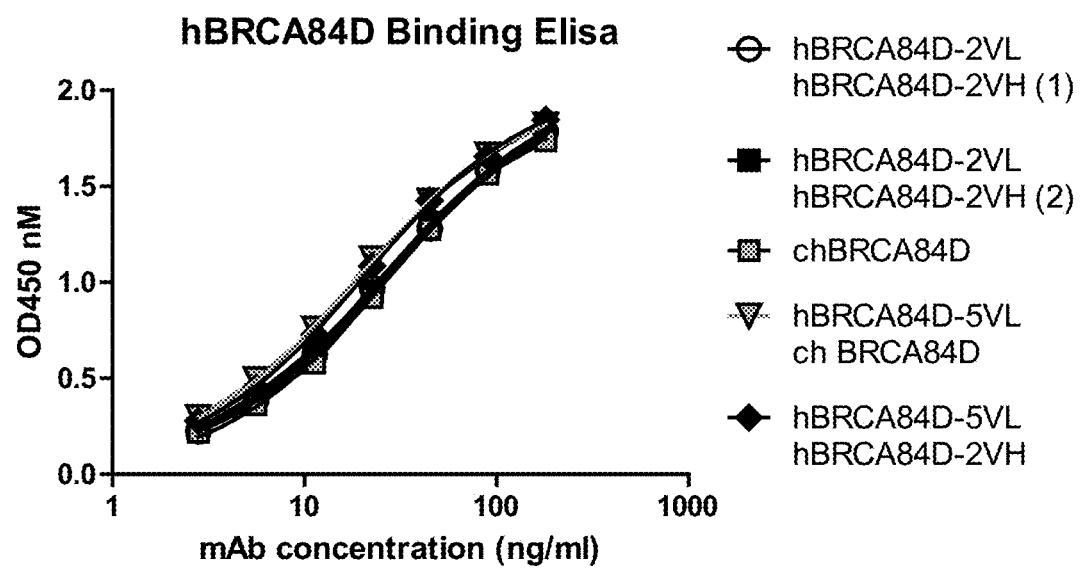
FIG. 14 shows the relative binding affinities of (1) antibodies containing hBRCA84D-2VL and hBRCA84D-2VH (trials 1 and 2), (2) chimeric BRCA84D, (3) antibody containing hBRCA84D-5VL and chimeric BRCA84D-HC and (4) antibody containing hBRCA84D-5VL and hBRCA84D-2VH.

The relative binding affinities of antibodies containing: (1) hBRCA84D-2VL and hBRCA84D-2VH (two trials), (2) chimeric BRCA84D, (3) antibody containing hBRCA84D-5VL and chimeric BRCA84D-HC, and (4) antibody containing hBRCA84D-5VL and hBRCA84D-2VH were compared. The results are shown in FIG. 14.

Example 11

Humanized Anti-B7-H3 Antibodies Inhibit Tumor Growth in Xenografts

In order to demonstrate the ability of humanized anti-B7-H3 antibodies to inhibit tumor growth in vivo, tumor growth of HT-1197 urinary bladder carcinoma cells and of A498 renal carcinoma cells was studied in a murine xenograft. Humanized antibody hBRCA84D-2 (hBRCA84D-2 VL chain/hBRCA84D-2 VL chain) was modified to comprise an Fc region having substitutions L235V, F243L, R292P, Y300L, and P396L.

Figure 15:
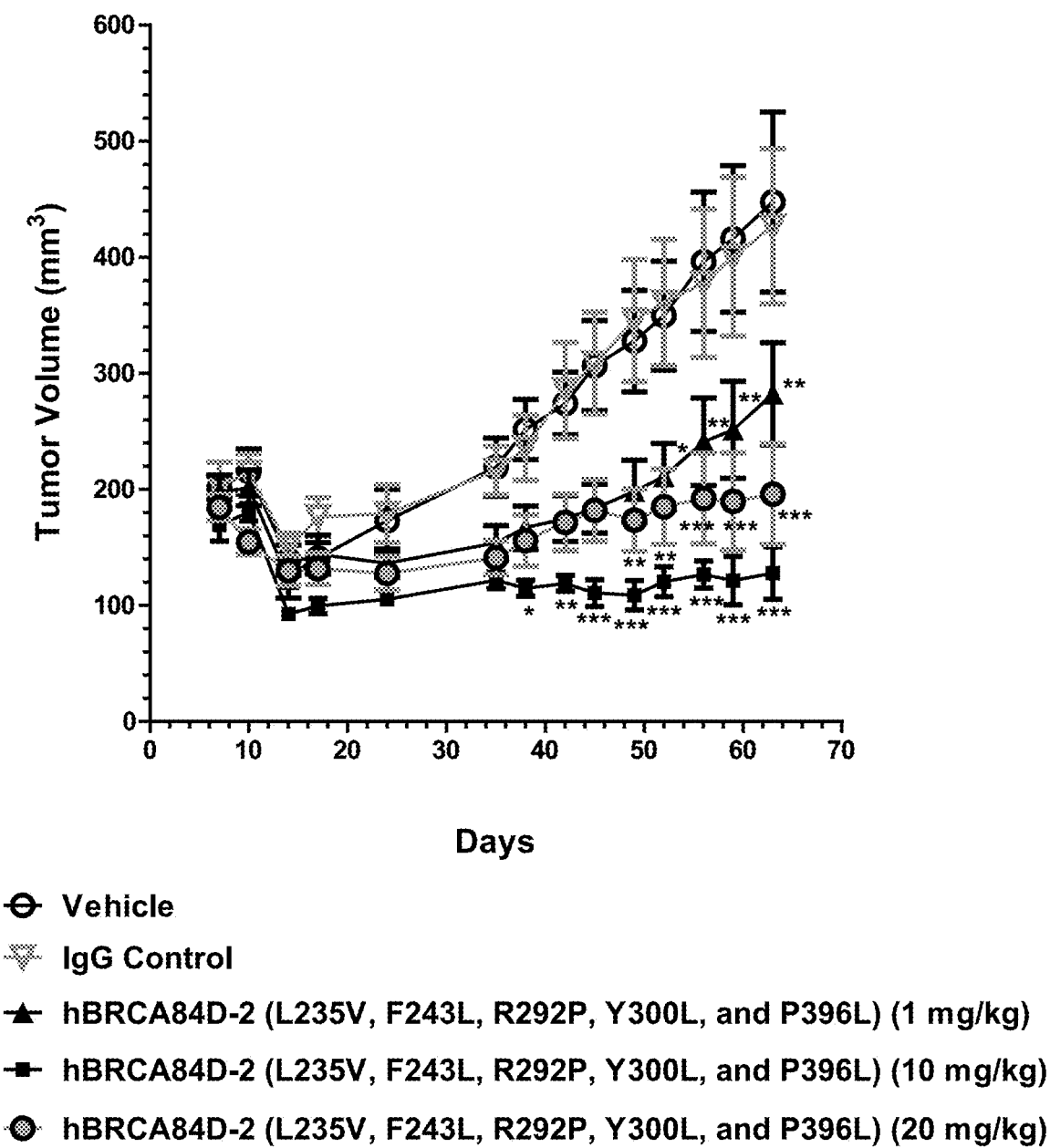
FIG. 15 shows the ability of Fc-modified humanized anti-B7-H3 antibodies to inhibit tumor growth of HT-1197 urinary bladder carcinoma cells in vivo in a murine xenograft model system. The Fc-modified hBRCA84D-2 antibody (comprising Fc modifications L235V, F243L, R292P, Y300L, and P396L) was administered to the mice (at a dose of 1 µg/kg, 10 µg/kg, or 20 µg/kg) 7 days, 14 days, 21 days and 28 days post implantation of the cancer cells.
Figure 16:
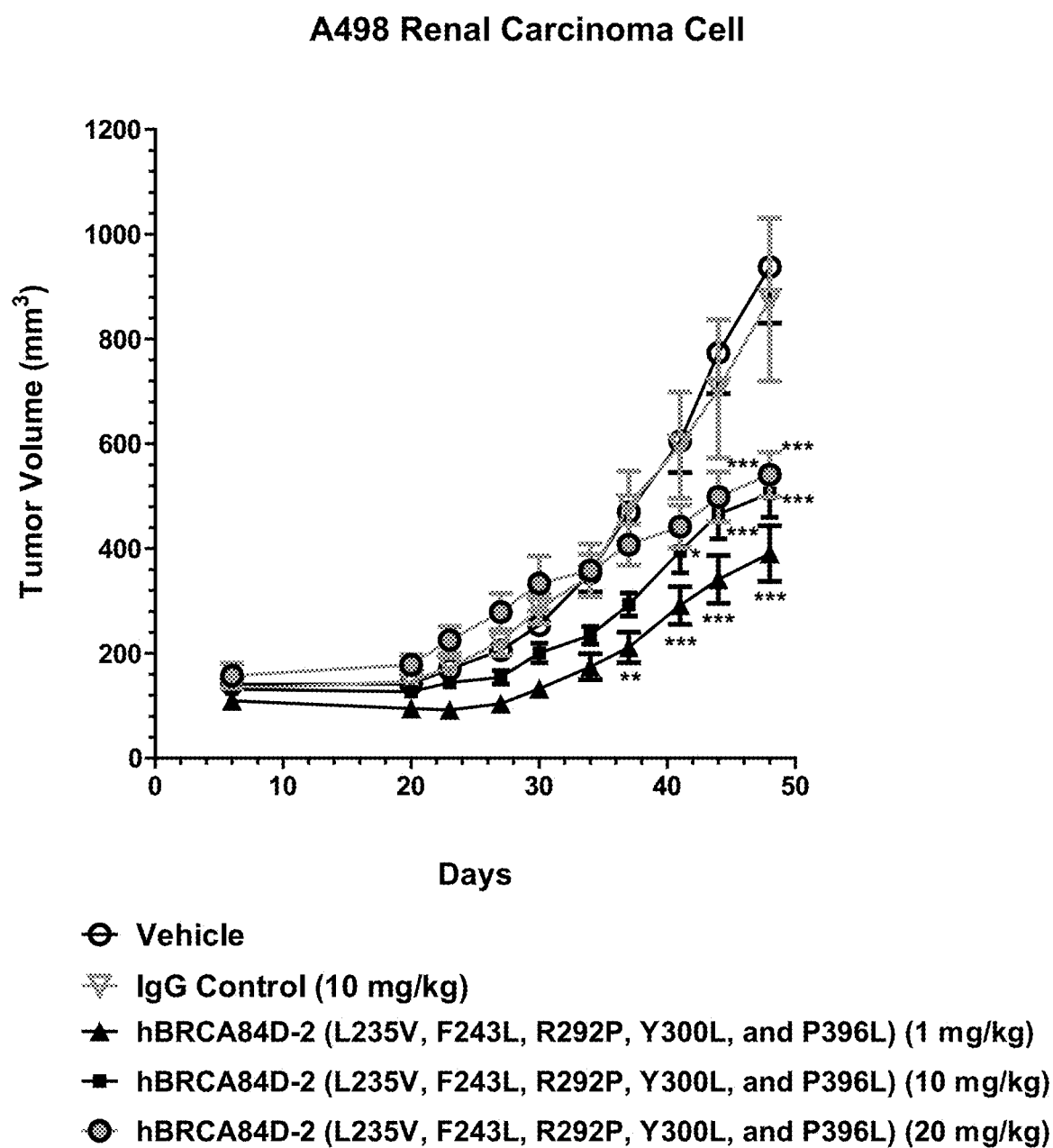
FIG. 16 shows the ability of Fc-modified humanized anti-B7-H3 antibodies to inhibit tumor growth of A498 renal carcinoma cells in vivo in a murine xenograft model system. The Fc-modified hBRCA84D-2 antibody (comprising Fc modifications L235V, F243L, R292P, Y300L, and P396L) was administered to the mice (at a dose of 1 µg/kg, 10 µg/kg, or 20 µg/kg) 7 days, 14 days, 21 days and 28 days post implantation of the cancer cells.
Figure 17A:
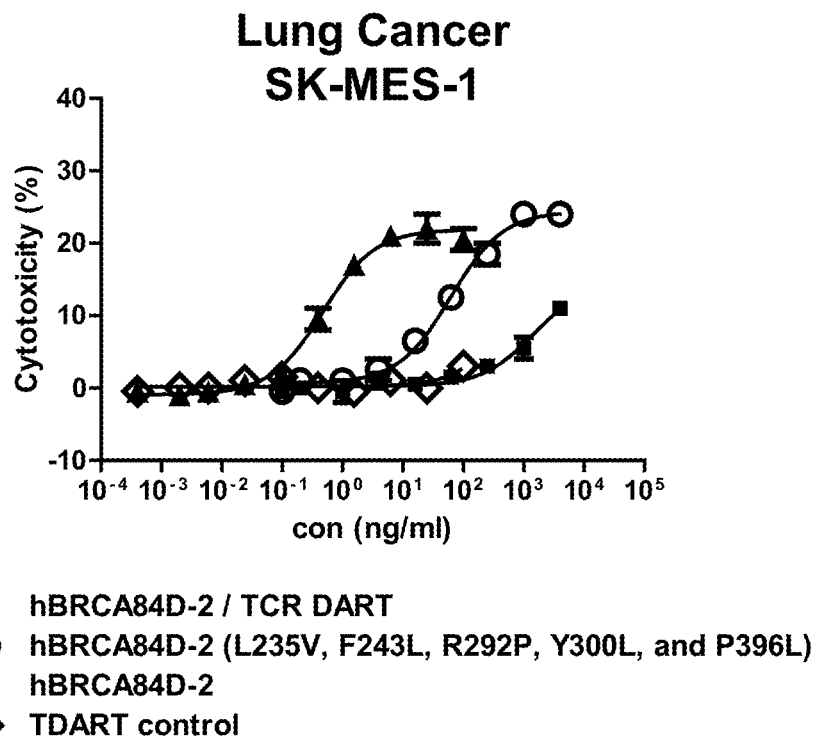
FIGS. 17A-17D demonstrate the ability of the hBRCA84D-2/anti-TCR DART ("T-DART") to mediate redirected killing of SK-MES-1 lung cancer cells, A498 renal carcinoma cells, LNCaP prostate cancer cells, and UACC-62 melanoma cells.
Figure 17B:
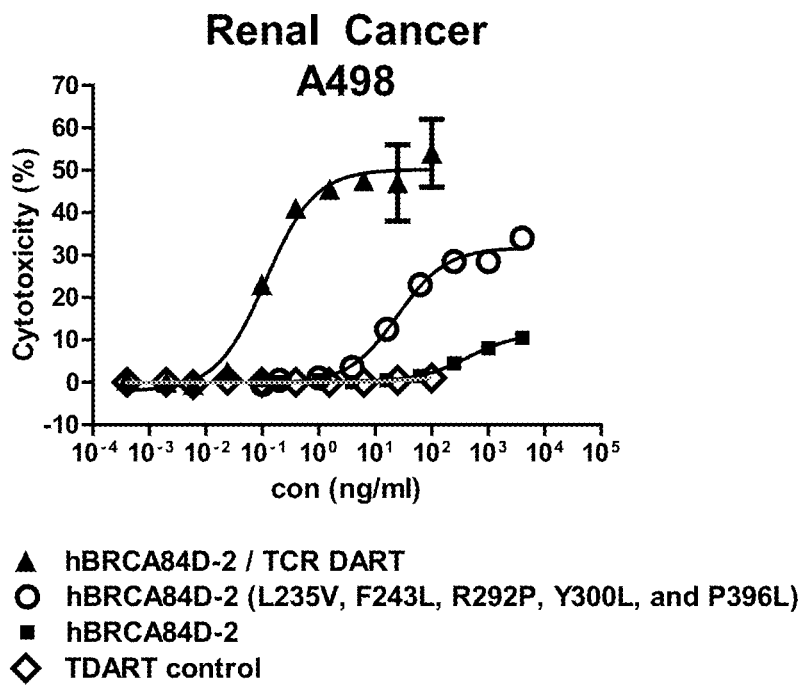
Figure 17C:
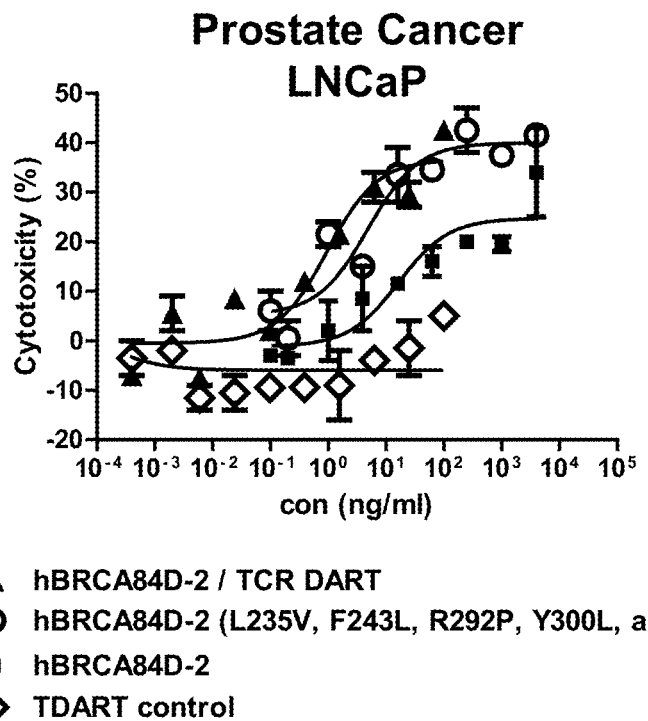
Figure 17D:
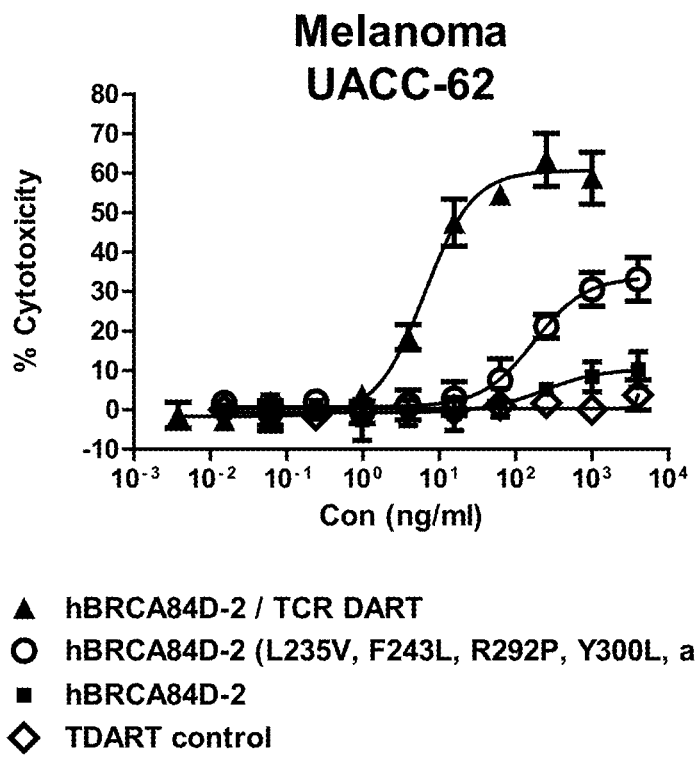

The Fc-modified hBRCA84D-2 antibody was administered to the mice (at a dose of 1 µg/kg, 10 µg/kg, or 20 µg/kg) 7 days, 14 days, 21 days and 28 days post implantation of the cancer cells. The results show that at all doses the administered Fc-modified hBRCA84D-2 antibody was capable of inhibiting tumor growth of HT-1197 urinary bladder carcinoma cells (FIG. 15) and of A498 renal carcinoma cells (FIG. 16).

Example 12

Dual Affinity Retargeting Reagents (DARTs) Specific for B7-H3 and the T-Cell Receptor Mediate Potent Redirected T-Cell Killing Dual affinity retargeting reagents (DARTs) specific for B7-H3 and the T-cell receptor ("TCR") and for the Natural Killer Group 2D (NKG2D) receptor were prepared. Such DARTs have the ability to localize a T-cell (by binding such T-cell to the TCR-binding portion of a TCR-binding DART) or o localize a NK-cell (by binding such NK cell to the NKG2D-binding portion of an NKG2D-binding DART) to the location of a cancer cell (by binding such cancer cell to the B7-H3-binding portion of the DART). The localized T-cell or NK cell can then mediate the killing of the cancer cell in a process termed herein "redirected" killing The dual affinity retargeting reagent (DART) specific for B7-H3 and the T-cell receptor ("TCR") was constructed having the anti-B7-H3 variable domains of hBRCA84D-2 and anti-TCR variable domains TCR VL×hBRCA84D VH-2-E Coil DART Chain (SEQ ID NO: 109):

```
EIVLTQSPAT LSLSPGERAT LSCSATSSVS YMHWYQQKPG

KAPKRWIYDT SKLASGVPSR FSGSGSGTEF TLTISSLQPE

DFATYYCQQW SSNPLTFGQG TKLEIKGGGS GGGGEVQLVE

SGGGLVQPGG SLRLSCAASG FTFSSFGMHW VRQAPGKGLE

WVAYISSDSS AIYYADTVKG RFTISRDNAK NSLYLQMNSL

RDEDTAVYYC GRGRENIYYG SRLDYWGQGT TVTVSSGGCG

GGEVAALEKE VAALEKEVAA LEKEVAALEK
```

Polynucleotide Encoding TCR VL×hBRCA84D VH-2-E Coil DART Chain (SEQ ID NO: 110):

```
gaaattgtgt tgacacagtc tccagccacc ctgtctttgt ctccagggga aagagccacc ctctcctgca gtgccacctc aagtgtaagt tacatgcact ggtatcagca gaaaccaggg aaagcccta agcgctggat ctatgacaca tccaaactgg cttctggggt cccatcaagg ttcagcggca gtggatctgg gacagaattt actctcacaa tcagcagcct gcagcctgaa gattttgcaa cttattactg tcagcagtgg agtagtaacc cgctcacgtt tggccagggg accaagcttg agatcaaagg aggcggatcc ggcggcggag gcgaggtgca gctggtcgag tctggcggag gactggtgca gcctggcggc tccctgagac tgtcttgcgc cgcctccggc ttcaccttct ccagcttcgg catgcactgg gtccgccagg ctccaggcaa gggactggaa tgggtggcct acatctcctc cgactcctcc gccatctact acgccgacac cgtgaagggc aggttcacca tctcccggga caacgccaag aactccctgt acctgcagat gaactccctg cgggacgagg acaccgccgt gtactactgc ggcagaggcc gggagaatat ctactacggc tcccggctgg attattgggg ccagggcacc accgtgaccg tgtcctccgg aggatgtggc ggtggagaag tggccgcact ggagaaagag gttgctgctt tggagaagga ggtcgctgca cttgaaaagg aggtcgcagc cctggagaaa
``` hBRCA84DVL-2×TCR VH-K coil Chain (SEQ ID NO: 111):

```
DIQLTQSPSF LSASVGDRVT ITCKASQNVD TNVAWYQQKP

GKAPKALIYS ASYRYSGVPS RFSGSGSGTD FTLTISSLQP

EDFATYYCQQ YNNYPFTFGQ GTKLEIKGGG SGGGGQVQLV

QSGAEVKKPG ASVKVSCKAS GYKFTSYVMH WVRQAPGQGL

EWIGYINPYN DVTKYNEKFK GRVTITADKS TSTAYLQMNS

LRSEDTAVHY CARGSYYDYD GFVYWGQGTL VTVSSGGCGG

GKVAALKEKV AALKEKVAAL KEKVAALKE
```

Polynucleotide Encoding hBRCA84DVL-2×TCR VH-K coil Chain (SEQ ID NO: 112):

```
gacatccagc tgacccagtc ccctccttc ctgtctgcct ccgtgggcga cagagtgacc atcacatgca aggcctccca gaacgtggac accaacgtgg cctggtatca gcagaagcct
```

```
ggcaaggccc ctaaggcgct gatctactcc gcctcctacc ggtactccgg cgtgccttcc aggttctccg gctccggctc tggcaccgac ttcaccctga ccatctccag cctgcagcct gaggacttcg ccacctacta ctgccagcag tacaacaact acccttcac cttcggccag ggcaccaagc tggaaatcaa gggaggcgga tccggcggcg gaggccaggt tcagctggtg cagtctggag ctgaggtgaa gaagcctggg gcctcagtga aggtctcctg caaggccagc ggttacaagt ttaccagcta cgtgatgcac tgggtgcgac aggcccctgg acaagggctt gagtggatcg gatatattaa tccttacaat gatgttacta agtacaatga aagttcaaa ggcagagtca cgattaccgc ggacaaatcc acgagcacag cctacctgca gatgaacagc ctgagatccg aggacacggc cgtgcactac tgtgcgagag ggagctacta tgattacgac gggtttgttt actggggcca agggactctg gtcactgtga gctccggagg atgtggcggt ggaaaagtgg ccgcactgaa ggagaaagtt gctgctttga aagagaaggt cgccgcactt aaggaaaagg tcgcagccct gaaagag
```

The dual affinity retargeting reagent (DART) specific for B7-H3 and the Natural Killer Group 2D (NKG2D) receptor was constructed having the anti-B7-H3 variable domains of hBRCA84D-2 and anti-TCR variable domains:

NKG2D VL×hBRCA84D VH-2-E Coil DART Chain (SEQ ID NO: 113):

```
QSALTQPASV SGSPGQSITI SCSGSSSNIG NNAVNWYQQL

PGKAPKLLIY YDDLLPSGVS DRFSGSKSGT SAFLAISGLQ

SEDEADYYCA AWDDSLNGPV FGGGTKLTVL GGGSGGGGEV

QLVESGGGLV QPGGSLRLSC AASGFTSSF GMHWVRQAPG

KGLEWVAYIS SDSSAIYYAD TVKGRFTISR DNAKNSLYLQ

MNSLRDEDTA VYYCGRGREN IYYGSRLDYW GQGTTVTVSS

GGCGGGEVAA LEKEVAALEKE VAALEKEVA ALEK
```

Polynucleotide Encoding NKG2D VL×hBRCA84D VH-2-E Coil DART Chain (SEQ ID NO: 114):

```
cagtctgccc tgactcagcc tgcctccgtg tctgggtctc ctggacagtc aatcaccatc tcctgttctg gaagcagctc caacatcgga ataatgctg ttaactggta ccagcagctc ccaggaaagg ctcccaaact cctcatctat tatgatgacc tactgccctc aggggtctct gaccgattct ctggctccaa gtctggcacc tcagcctcc tggcatcag tgggctccag tctgaggatg aggctgatta ttactgtgca gcatgggatg acagcctgaa tggtccagtg ttcggcggag ggaccaagct gaccgtccta ggaggcggat ccggcggcgg aggcgaggtg
```

```
cagctggtcg agtctggcgg aggactggtg cagcctggcg gctccctgag actgtcttgc gccgcctccg gcttcacctt ctccagcttc ggcatgcact gggtccgcca ggctccaggc aagggactgg aatgggtggc ctacatctcc tccgactcct ccgccatcta ctacgccgac accgtgaagg gcaggttcac catctcccgg gacaacgcca agaactccct gtacctgcag atgaactccc tgcgggacga ggacaccgcc gtgtactact gcggcagagg ccgggagaat atctactacg gctcccggct ggattattgg ggccagggca ccaccgtgac cgtgtcctcc ggaggatgtg gcggtggaga agtggccgca ctggagaaag aggttgctgc tttggagaag gaggtcgctg cacttgaaaa ggaggtcgca gccctggaga aa
``` hBRCA84DVL-2×NKG2D VH-K coil Chain (SEQ ID NO: 115):

```
DIQLTQSPSF LSASVGDRVT ITCKASQNVD TNVAWYQQKP

GKAPKALIYS ASYRYSGVPS RFSGSGSGTD FTLTISSLQP

EDFATYYCQQ YNNYPFTFGQ GTKLEIKGGG SGGGGQVQLV

ESGGGLVKPG GSLRLSCAAS GFTFSSYGMH WVRQAPGKGL

EWVAFIRYDG SNKYYADSVK GRFTISRDNS KNTLYLQMNS

LRAEDTAVYY CAKDRGLGDG TYFDYWGQGT TVTVSSGGCG

GGKVAALKEK VAALKEKVAA LKEKVAALKE
```

Polynucleotide Encoding hBRCA84DVL-2×NKG2D VH-K coil Chain (SEQ ID NO: 116):

```
gacatccagc tgacccagtc cccctccttc ctgtctgcct ccgtgggcga cagagtgacc atcacatgca aggcctccca gaacgtggac accaacgtgg cctggtatca gcagaagcct ggcaaggccc ctaaggcgct gatctactcc gcctcctacc ggtactccgg cgtgccttcc aggttctccg gctccggctc tggcaccgac ttcaccctga ccatctccag cctgcagcct gaggacttcg ccacctacta ctgccagcag tacaacaact acccttcac cttcggccag ggcaccaagc tggaaatcaa gggaggcgga tccggcggcg gaggccaggt acagctggtg gagtctgggg gaggcctggt caagcctgga gggtccctga gactctcctg tgcagcgtct ggattcacct tcagtagcta tggcatgcac tgggtccgcc aggctccagg caaggggctg gagtgggtgg catttatacg gtatgatgga agtaataaat actatgcaga ctccgtgaag ggccgattca ccatctccag agacaattcc aagaacacgc tgtatctgca aatgaacagc ctgagagctg aggacacggc tgtgtattac tgtgcgaaag
```

```
                     -continued
atcgaggttt ggggatgga acctactttg actactgggg ccaagggacc acggtcaccg tctcctccgg aggatgtggc ggtggaaaag tggccgcact gaaggagaaa gttgctgctt tgaaagagaa ggtcgccgca cttaaggaaa aggtcgcagc cctgaaagag
```

In order to demonstrate the ability of DARTs to mediate such redirected killing of cancer cells, the above-described hBRCA84D-2/anti-TCR DART ("T-DART"), hBRCA84D-2, hBRCA84D-2 (Fc-modified: L235V, F243L, R292P, Y300L, and P396L), and a TCR-DART control were incubated at various concentrations with target cancer cells (SK-MES-1 lung cancer cells, A498 renal carcinoma cells, LNCaP prostate cancer cells, or UACC-62 melanoma cells) and effector resting PBMC (E:T ratio=30:1) and cytotoxicity was determined (LDH Assay). The results of these investigations are shown in FIGS. 17A-17D and demonstrate the ability of the hBRCA84D-2/anti-TCR DART ("T-DART") to mediate redirected killing of cancer cells.

Example 13

Pharmacokinetic Profile in Tumor-Free Mice

Figure 18A:
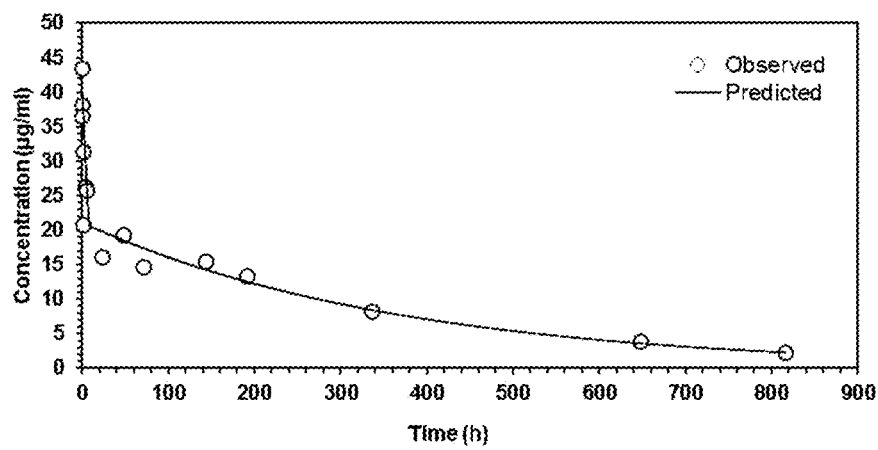
FIGS. 18A-18C show the pharmacokinetic decay of anti-B7-H3 Mab1 in the sera of male tumor-free male mCD16−/−, hCD16A_FOXN1 mice (FIGS. 18A-18B).
Figure 18B:
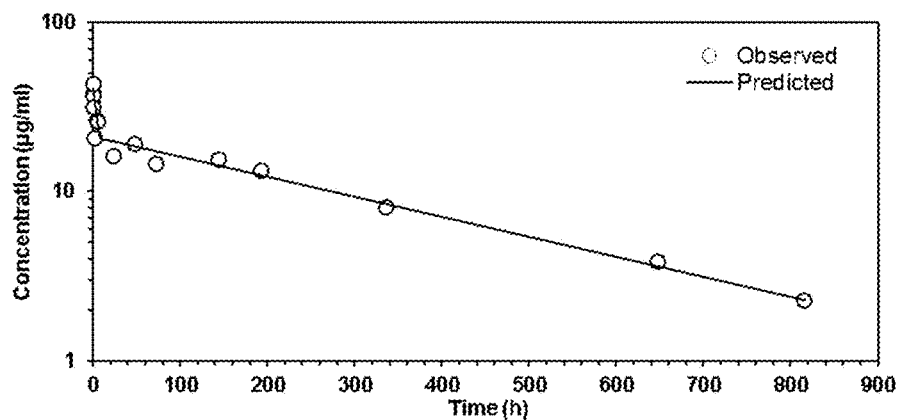
Figure 18C:
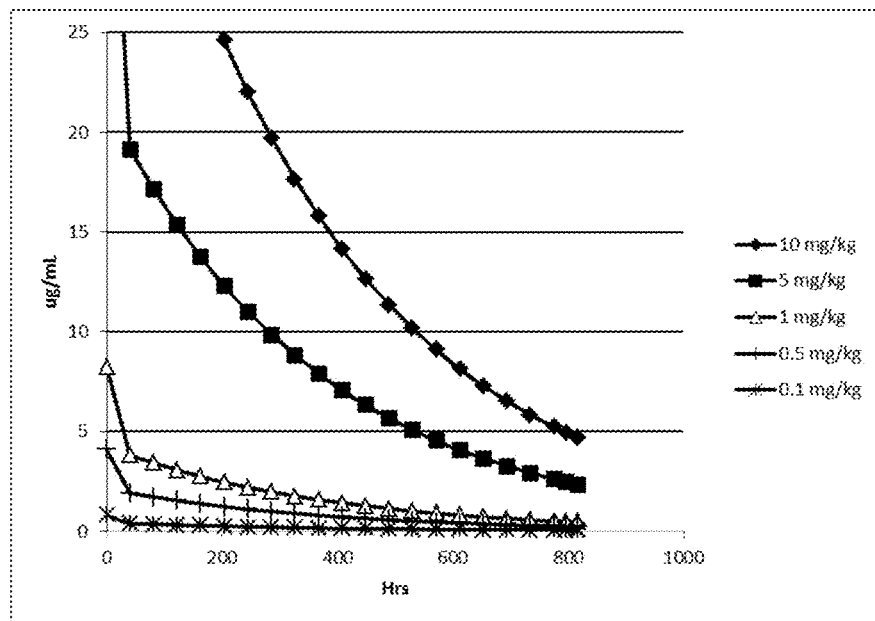

Anti-B7-H3 antibody (Mab1) was injected into male mCD16−/−, hCD16A_FOXN1 mice (5 mg/kg; IV) and serum was assayed (pre-dose and) at 2, 15, 30 min, and 1, 2, 4, 6 hr, and 1, 2, 3, 6, 8, 14, 21, and 28 days after injection. The antibody was found to have a T ½ of 10.54 days and a $C_{max}$ of 43.493 µg/ml. The concentration of antibody over time was found to be biphasic, fitting into a two-component model (FIGS. 18A-18B). The predicted pharmacokinetic profiles generated using a 2-compartment model with parameters from the 5 mg/kg dose are shown in FIG. 18C.

Example 14

Figure 19:
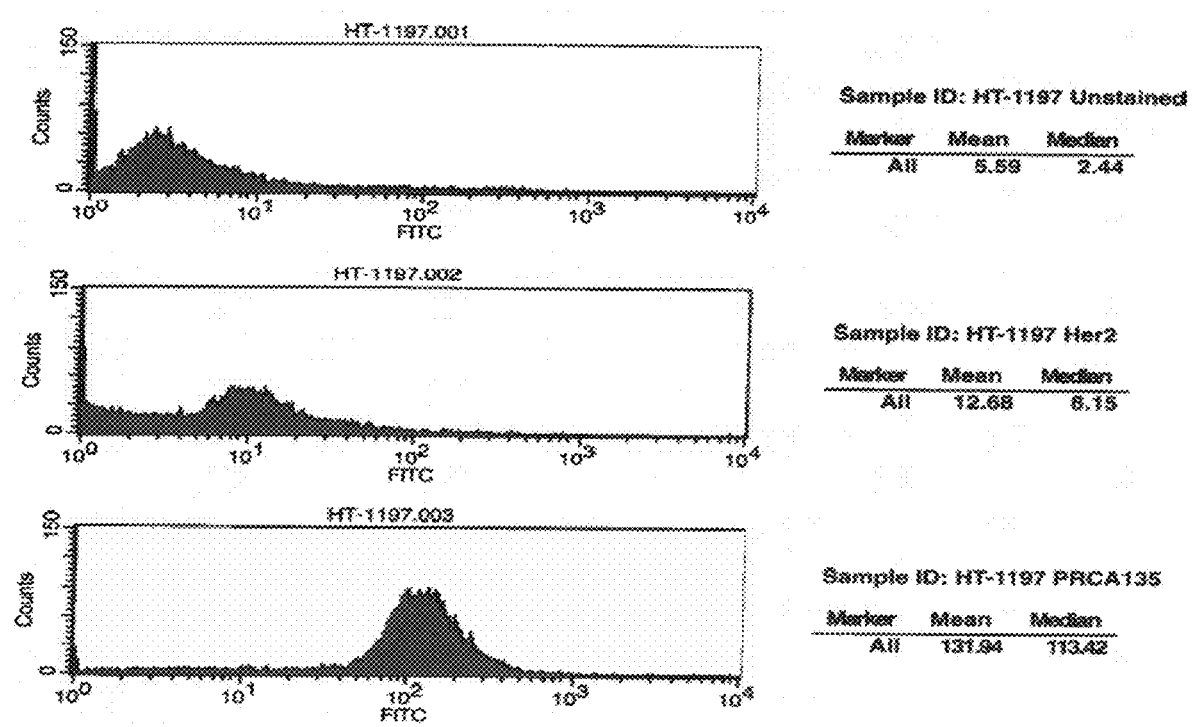
FIG. 19 shows the relative expression of HER2 and PRCA135 by the HT-1197 bladder cancer line.
Figure 20:
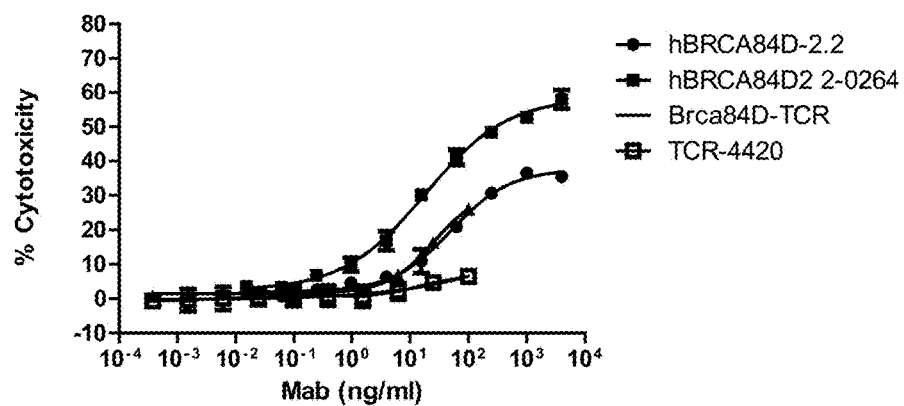
FIG. 20 shows the binding affinity of anti-B7-H3 antibody hBRCA84D variants to HT-1197 cells.

Ability of Anti-B7-H3 Antibody to Bind HT-1197 Urinary Bladder Cancer Cells and Prevent or Inhibit Tumor Development in a Murine Xenograft Model The above-described anti-B7-H3 antibody (Mab1) was assessed for its ability to bind HT-1197, a human B7-H3-expressing urinary bladder carcinoma cell line. As shown in FIG. 19, such cells exhibit greater expression of PRCA135 than HER2, and thus are particularly suitable for assessing the therapeutic potential of the antibodies of the present invention in remediating HT-1197 tumors. In accordance with this conclusion, anti-B7-H3 antibody hBRCA84D variants were found to be capable of binding to HT-1197 cells. FIG. 20 shows the binding affinity of Mab1 antibodies to HT-1197 cells.

Mice (mCD16−/−, hCD16A+_FoxN1) were implanted subcutaneously on their flanks with 8×10⁶ HT-1197 cells. The tumor cells were implanted in 200 µl of Ham's F12 Medium diluted 1:1 with MATRIGEL™. Treatment with Mab1 was initiated within 7 days of implantation via iv Q7Dx5 using doses of 0.1, 0.5, 1, 5, or 10 mg/kg (eight female mice per dose). Centuximab (anti-EGRF antibody) was administered to a control group of mice at doses of 1, 5, or 15 mg/kg (eight female mice per dose). Eight female mice were also injected with vehicle or with 10 mg/kg IgG control. Tumor measurements were made every 3-4 days.

Figure 21A:
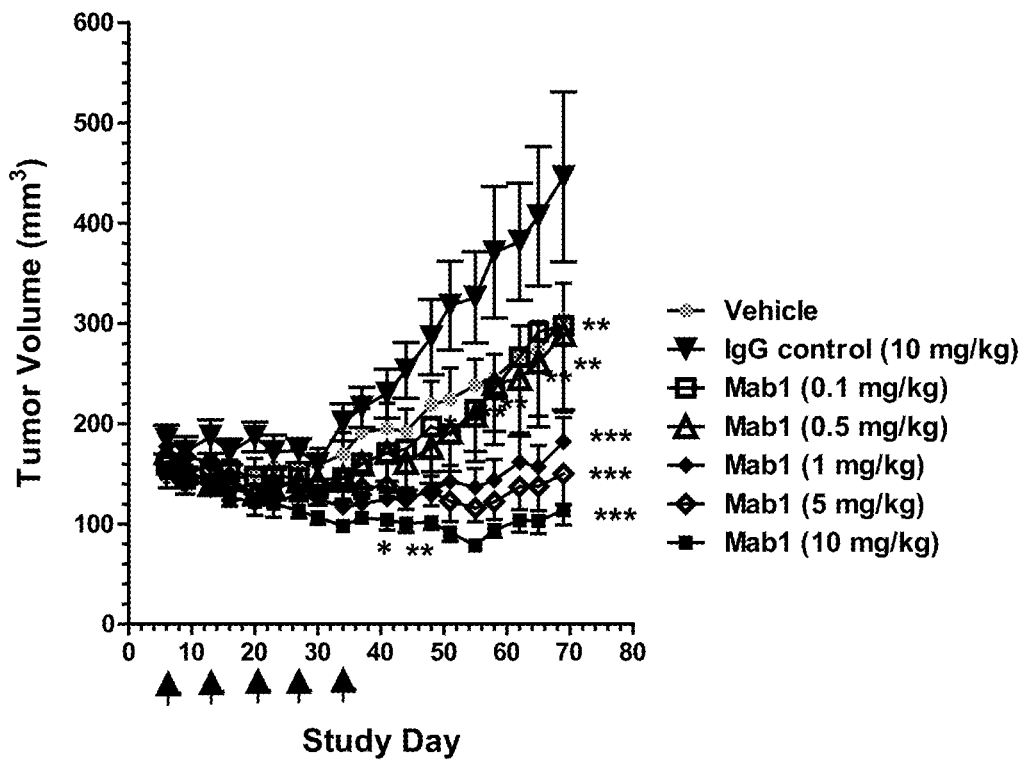
FIGS. 21A-21C show the results of a murine xenograft analysis for HT-1197. Groups of 8 female mice received vehicle or 10 mg/kg IgG control, or centuximab at a dose of 1, 5, or 15 mg/kg or anti-B7-H3 antibody Mab1 at a dose of 0.1, 0.5, 1, 5, or 10 mg/kg (Q7D×5). Tumor measurements were made every 3-4 days.
Figure 21B:
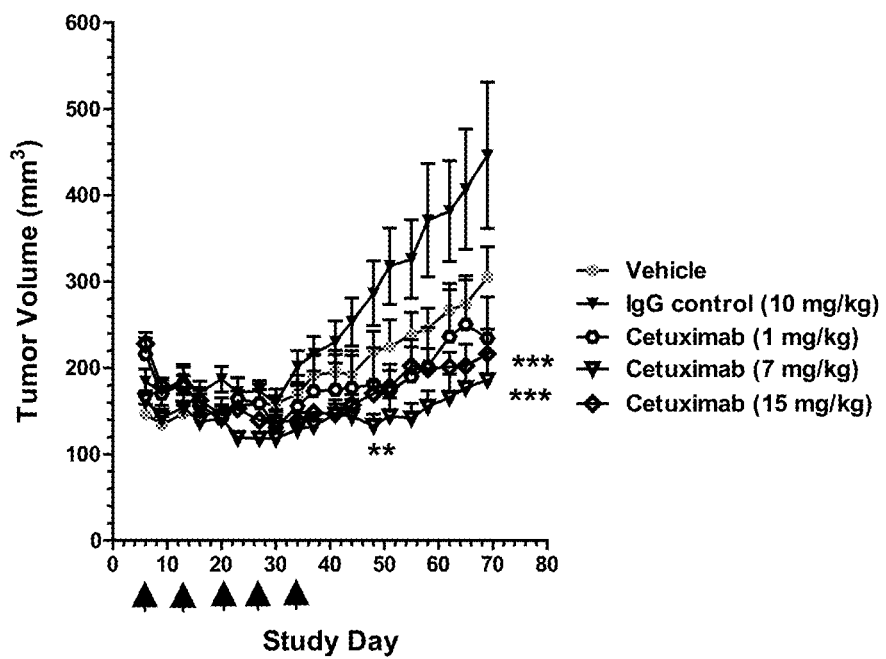
Figure 21C:
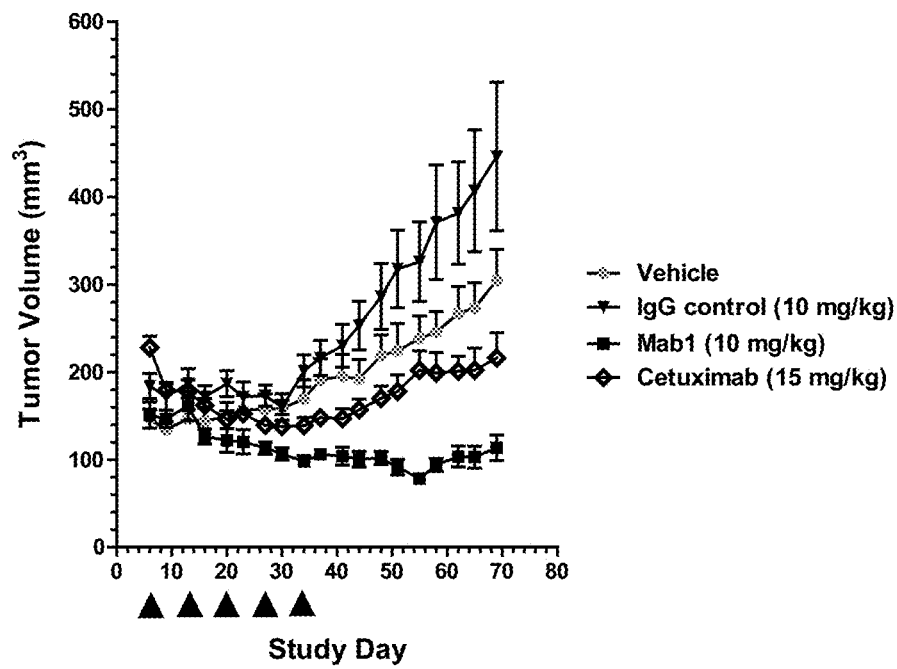

The results of the experiment (FIG. 21A) show that Mab1 was capable of preventing or inhibiting urinary bladder tumor development in the murine xenograft model. FIG. 21B shows the results obtained using centimab. A comparison of FIGS. 21A and 21B demonstrate that the antibodies of the present invention are more effective than centimab in preventing or inhibiting urinary bladder tumor development in the murine xenograft model. FIG. 21C compares the results obtained at the maximum doses tested.

Example 15

Figure 22A:
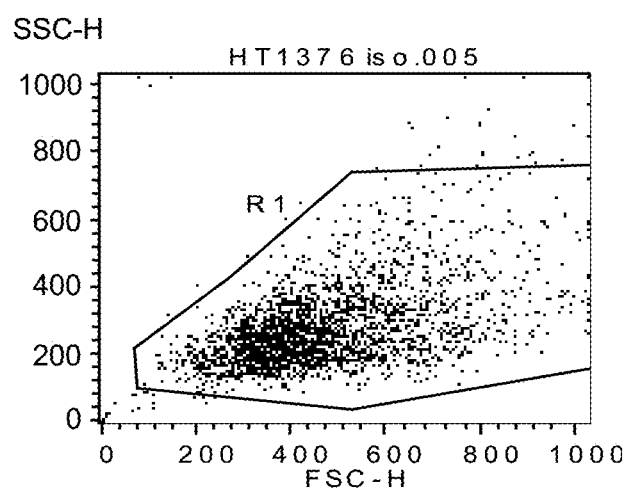
FIGS. 22A-22B show the relative expression of HER2 and PMSA by the HT-1376 bladder cancer line.
Figure 22B:
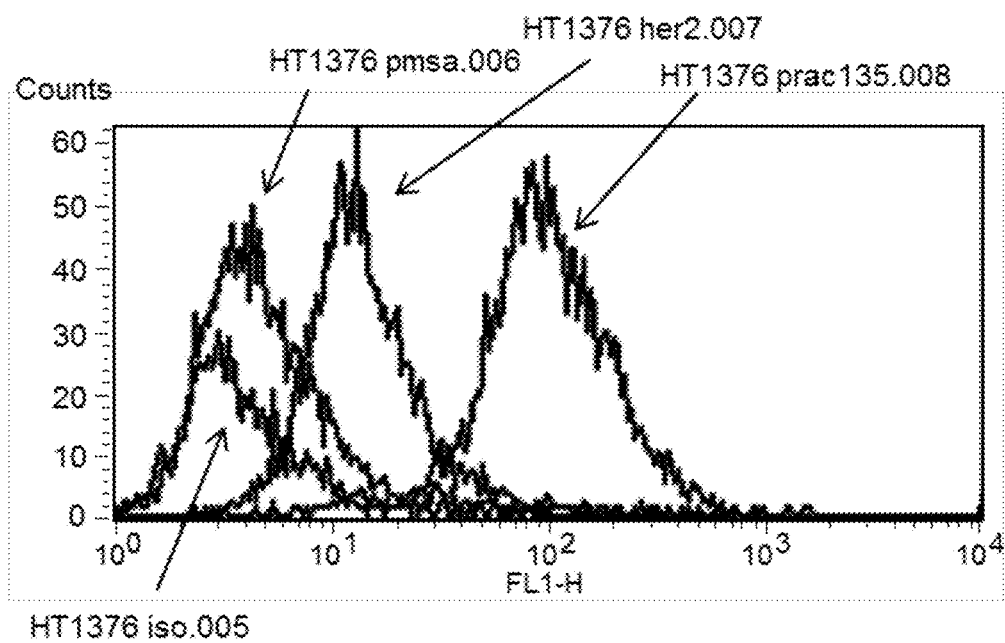

Ability of Anti-B7-H3 Antibody to Bind HT-1376 Urinary Bladder Cancer Cells and Prevent or Inhibit Tumor Development in a Murine Xenograft Model The above-described anti-B7-H3 antibody (Mab1) was assessed for its ability to bind HT-1376, a human B7-H3-expressing urinary bladder carcinoma cell line. As shown in FIGS. 22A-22B, such cells exhibit greater expression of PRCA135 than HER2 or PMSA, and thus are particularly suitable for assessing the therapeutic potential of the antibodies of the present invention in remediating HT-1376 tumors. In accordance with this conclusion, anti-B7-H3 antibody hBRCA84D variants were found to be capable of binding to HT-1376 cells. FIGS. 22A-22B show the binding affinity of Mab1 antibodies to HT-1376 cells.

Figure 23:
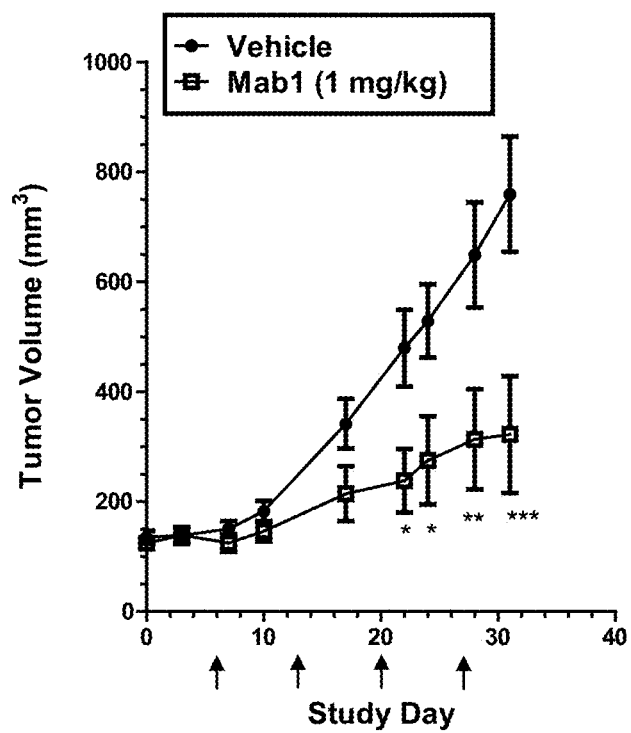
FIG. 23 shows the results of a murine xenograft analysis for HT-1376. Groups of mice received vehicle or 1.0 mg/kg of anti-B7-H3 antibody Mab1 (Q7D×4).

Mice (mCD16−/−, hCD16A+_FoxN1) were implanted subcutaneously on their flanks with 5×10⁶ HT-1376 cells. The tumor cells were implanted in 200 µl of Ham's F12 Medium diluted 1:1 with MATRIGEL™. Treatment with Mab1 was initiated within 7 days of implantation via iv Q7Dx4 at a dose of 1 mg/kg. The results of the experiment (FIG. 23) show that Mab1 was capable of preventing or inhibiting urinary bladder tumor development in the murine xenograft model.

Example 16

Ability of Anti-B7-H3 Antibody to Bind Cancer Cells

Anti-B7-H3 antibody BRCA84D was assessed via FACS analysis for its ability to bind: SW480 and SW620 colorectal cancer cells; AGS gastric cancer cells; M-14 and LOX IMVI melanoma cells; 22rv prostate cancer cells; AsPC-1 and BxPc-3 pancreatic cancer cells; A498 and 786-0 renal cancer cells. The antibody was found to be able to bind to all such cells.

Example 17

Figure 24:
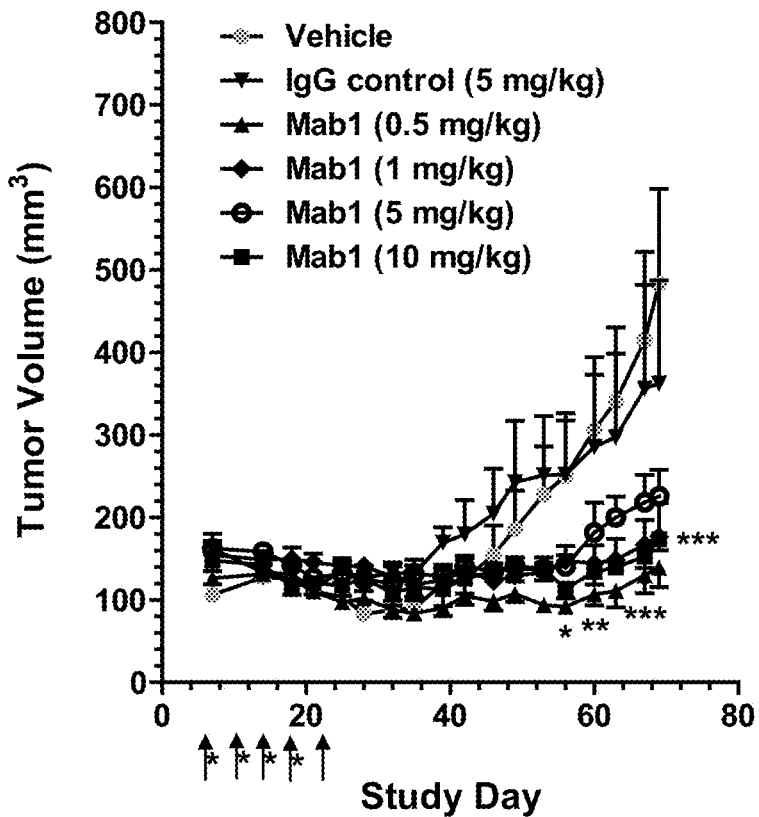
FIG. 24 show the results of a murine xenograft analysis for AGS. Groups of mice received vehicle or 10 mg/kg anti-B7-H3 antibody Mab1 at a dose of 0.5, 1, 5, or 10 mg/kg (Q7D×5).

Ability of Anti-B7-H3 Antibody Prevent or Inhibit Gastric Tumor Development in a Murine Xenograft Model Mice (mCD16−/−, hCD16A+_FoxN1) were implanted subcutaneously on their flanks with 5×10⁶ AGS cells. The tumor cells were implanted in 200 µl of Ham's F12 Medium diluted 1:1 with MATRIGEL™. Treatment with Mab1 was initiated within 7 days of implantation via iv Q7Dx5 using doses of 0.5, 1, 5, or 10 mg/kg. The results of the experiment (FIG. 24) show that Mab1 was capable of preventing or inhibiting gastric tumor development in the murine xenograft model.

Example 18

Figure 25:
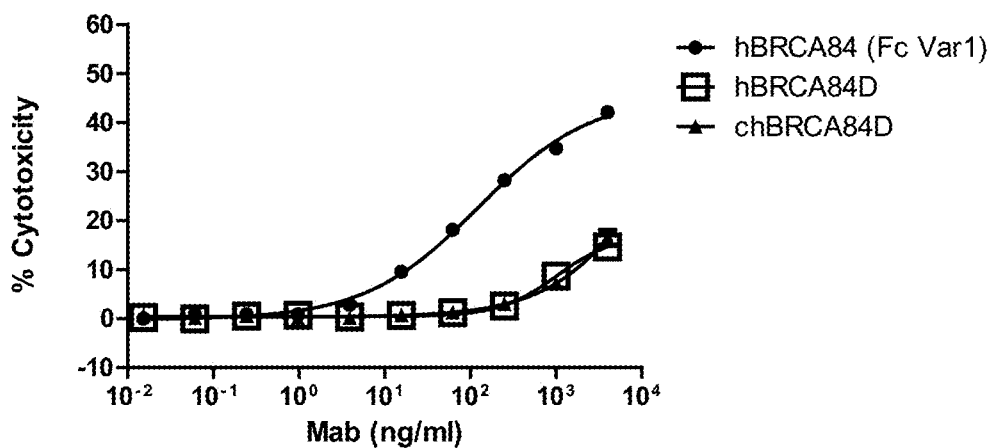
FIG. 25 show the results an in vitro cytotoxicity assay of A549 lung cancer cells upon incubation with hBRCA84D, chBRCA84D and hBRCA84 (Fc Var 1) variant anti-B7-H3 antibodies (E:T Ratio=25:1; Effector=Human PBMC; LDH Assay readout).

Ability of Anti-B7-H3 Antibody to Bind Lung Cancer Cells and Prevent or Inhibit Tumor Development in a Murine Xenograft Model A549 lung cancer cells were incubated in the presence of hBRCA84D, chBRCA84D and hBRCA84 (0264 Fc) variant and the cytotoxic effect of these antibodies was determined. The results of this experiment are shown in FIG. 25, and indicate that all three of the antibodies were cytotoxic to A549 cells.

Figure 26:
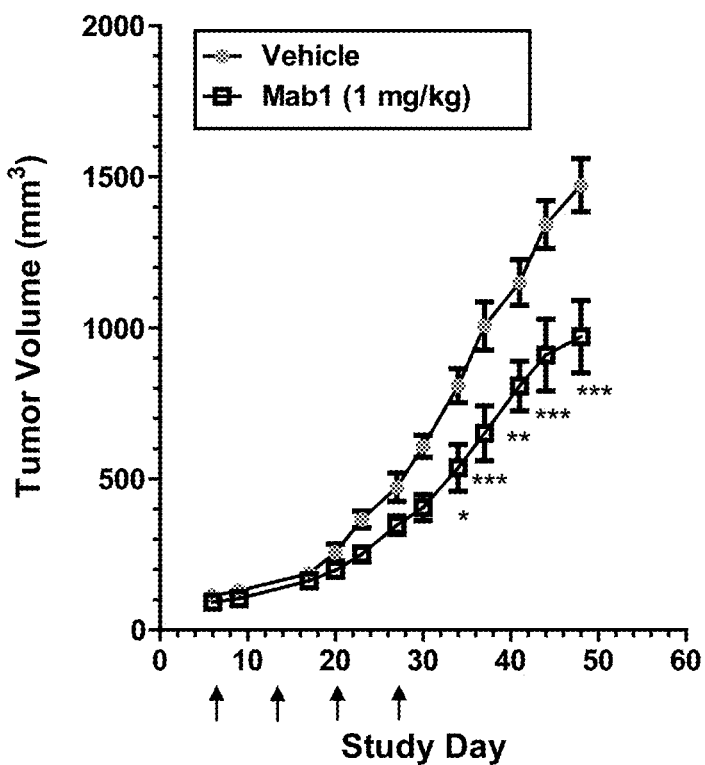
FIG. 26 shows the results of a murine xenograft analysis for A549. Groups of mice received vehicle or 1.0 mg/kg of anti-B7-H3 antibody Mab1 (Q7D×4).

Mice (mCD16−/−, hCD16A+_FoxN1) were implanted subcutaneously on their flanks with $8 \times 10^6$ A549 cells. The tumor cells were implanted in 200 μl of Ham's F12 Medium diluted 1:1 with MATRIGEL™. Treatment with Mab1 was initiated within 7 days of implantation via iv Q7D×4 using a dose of 1 mg/kg. The results of the experiment (FIG. 26) show that Mab1 was capable of preventing or inhibiting of lung cancer tumor development in the murine xenograft model.

Figure 27:
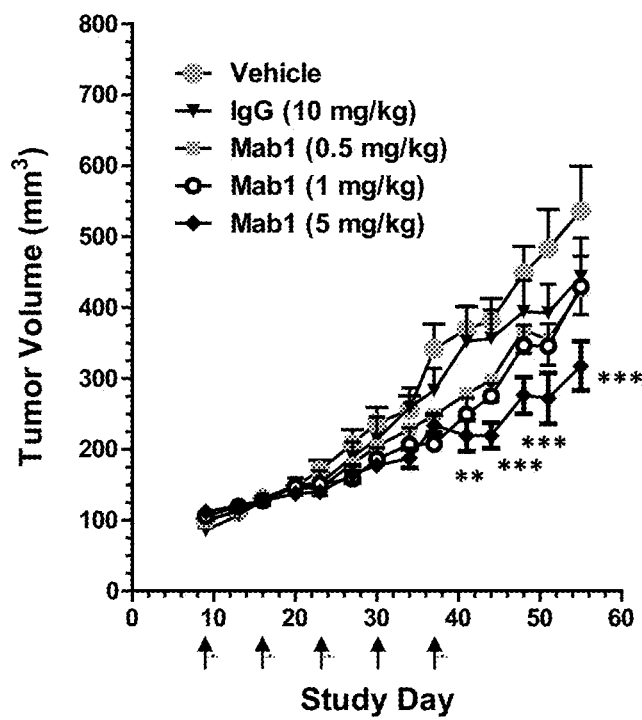
FIG. 27 show the results of a murine xenograft analysis for CaLu3. Groups of mice received vehicle or 0.5, 1, or 5 mg/kg (Q7D×5) anti-B7-H3 antibody Mab1 or IgG control (10 mg/ml).

FACS analysis was conducted on CaLu3 lung cancer cells in order to determine whether such cells bind anti-B7-H3 antibodies. The experiment confirmed that such cells express B7-H3 and bind to the antibodies of the present invention. To determine whether the antibodies of the present invention were effective to prevent or inhibit lung cancer tumor development, mice (mCD16−/−, hCD16A+_FoxN1) were implanted subcutaneously on their flanks with $5 \times 10^6$ CaLu3 cells. The tumor cells were implanted in 200 μl of Ham's F12 Medium diluted 1:1 with MATRIGEL™. Treatment with Mab1 was initiated within 7 days of implantation via iv Q7D×4 using a dose of 0.5, 1, or 5 mg/kg. The results of the experiment (FIG. 27) show that Mab1 was capable of preventing or inhibiting of lung cancer tumor development in the murine xenograft model.

Example 19

Figure 28A:
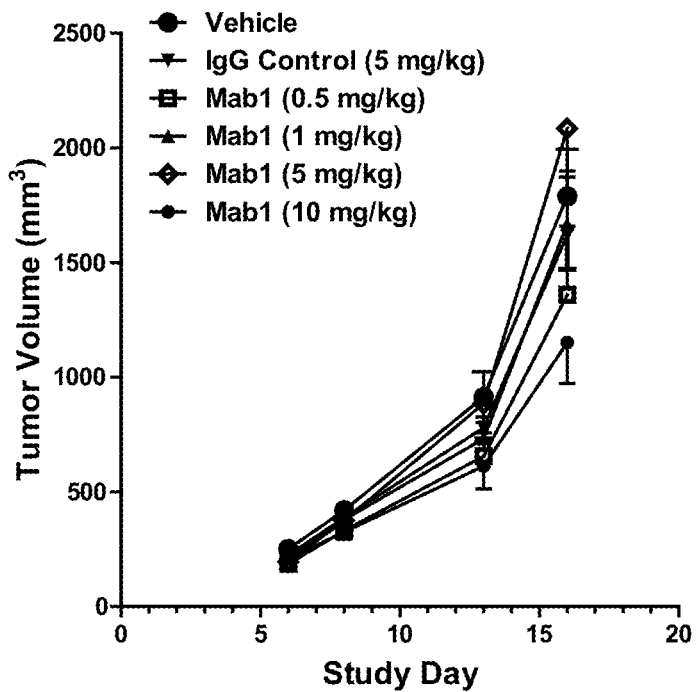
FIGS. 28A-28C show the results of a murine xenograft analysis for LOX-IMVI melanoma cancer cells. Groups of 8 female mice received vehicle or 5 mg/kg IgG control, or Docetaxel at a dose of 5, 10 or 20 mg/kg or anti-B7-H3 antibody Mab1 at a dose of 0.5, 1, 5, or 10 mg/kg.
Figure 28B:
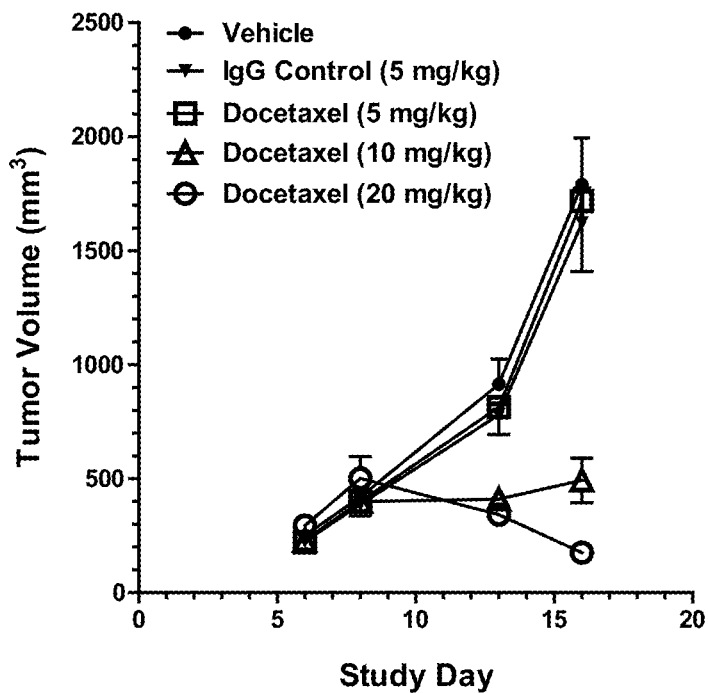
Figure 28C:
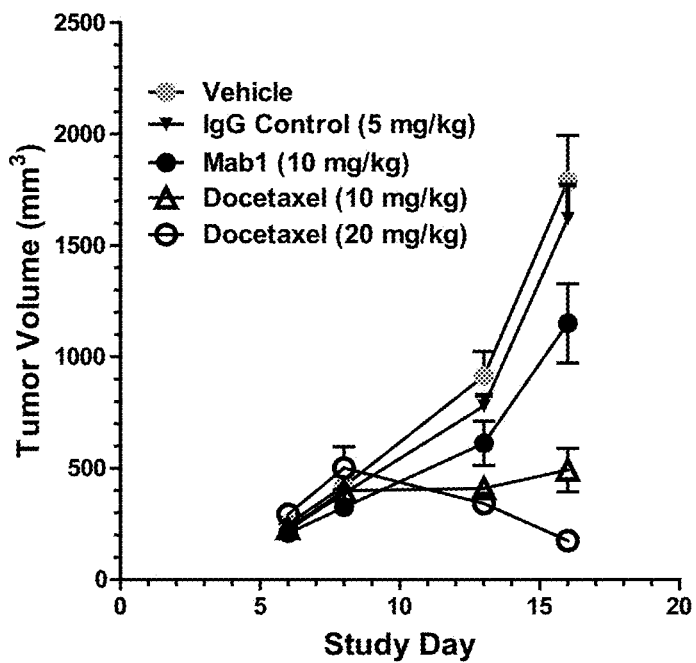

Ability of Anti-B7-H3 Antibody to Prevent or Inhibit LOX Melanoma Tumor Development in a Murine Xenograft Model Mice (eight female mCD16−/−, hCD16A+_FoxN1) were implanted subcutaneously on their flanks with LOX-IMVI melanoma cancer cells and then inoculated iv/Q7D×3 with PBS control, IgG control (5/mg/kg), Mab1 (0.5, 1, 5 or 10 mg/kg), or ip/BIW×2 with Docetaxel (5, 10 or 20 mg/kg). The tumor cells were implanted in 200 μl of Ham's F12 Medium diluted 1:1 with MATRIGEL™. Treatment with Mab1 was initiated within 7 days of implantation. The results of the experiment (FIGS. 28A-28C) show that Mab1 was capable of preventing or inhibiting of melanoma cancer tumor development in the murine xenograft model.

Example 20

Figure 29:
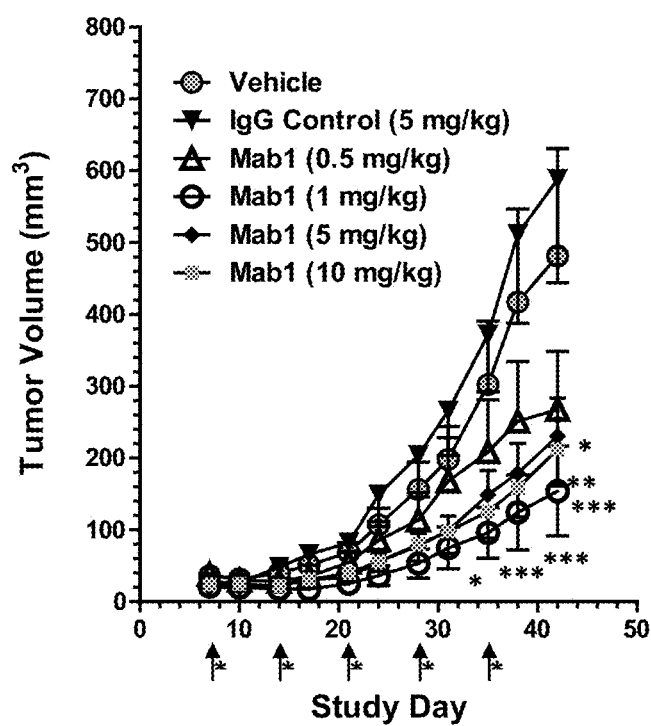
FIG. 29 shows the result of a murine xenograft analysis for UACC-62 melanoma cancer cells. Groups of mice received vehicle or 5 mg/kg IgG control, or anti-B7-H3 antibody Mab1 at a dose of 0.5, 1, 5, or 10 mg/kg.

Ability of Anti-B7-H3 Antibody to Prevent or Inhibit UACC-62 Melanoma Tumor Development in a Murine Xenograft Model Mice (eight female mCD16−/−, hCD16A+_FoxN1) were implanted subcutaneously on their flanks with UACC-62 melanoma cancer cells and then inoculated iv/Q7D×5 with PBS control, IgG control (5/mg/kg) or Mab1 (0.5, 1, 5 or 10 mg/kg). The tumor cells were implanted in 200 μl of Ham's F12 Medium diluted 1:1 with MATRIGEL™. Treatment with Mab1 was initiated within 7 days of implantation. The results of the experiment (FIG. 29) show that Mab1 was capable of preventing or inhibiting of melanoma cancer tumor development in the murine xenograft model.

Example 21

Figure 30A:
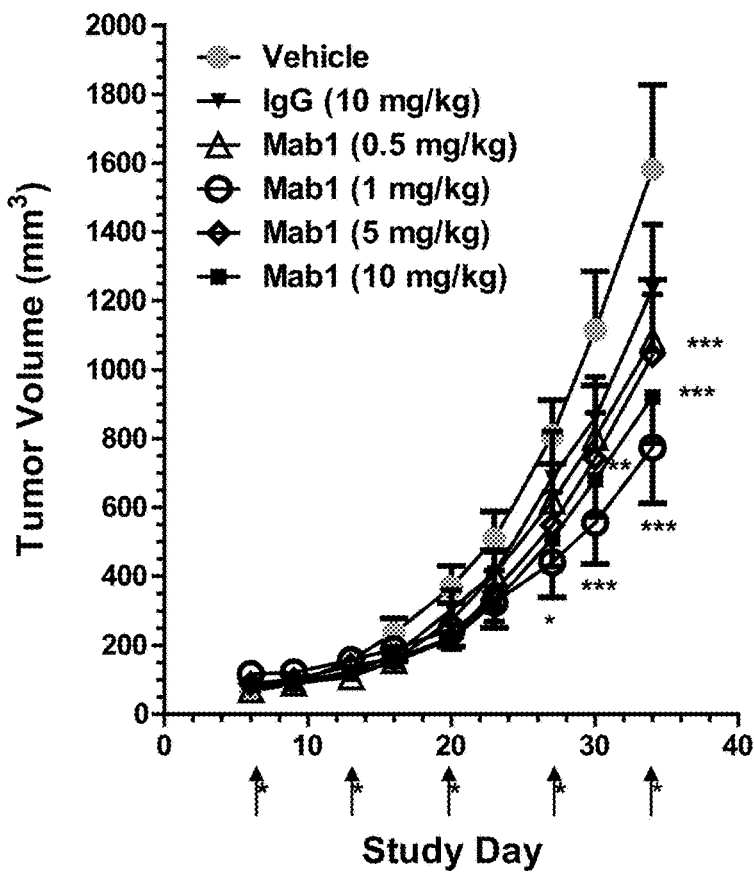
FIGS. 30A-30C show the results of a murine xenograft analysis for 2rv prostate cancer cells. Groups of 8 female mice received vehicle or 10 mg/kg IgG control, or trastuzumab at a dose of 1, 7 or 15 mg/kg or anti-B7-H3 antibody Mab1 at a dose of 0.5, 1, 5, or 10 mg/kg.
Figure 30B:
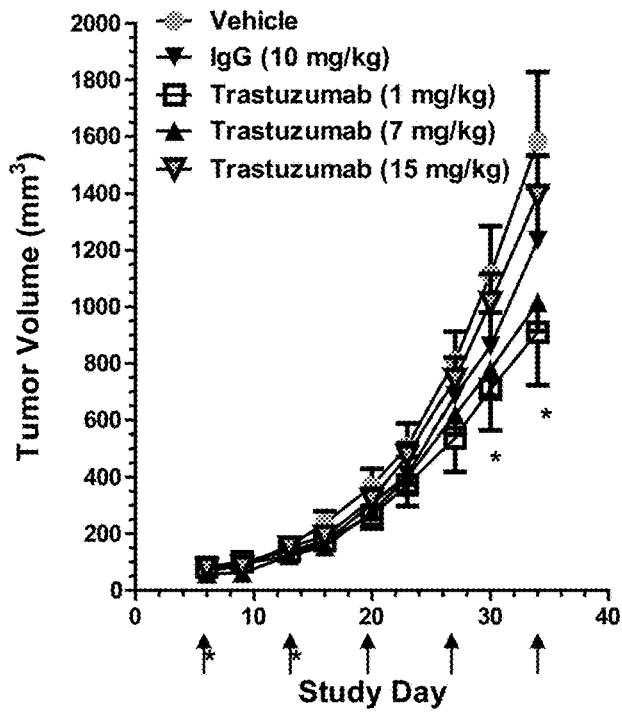
Figure 30C:
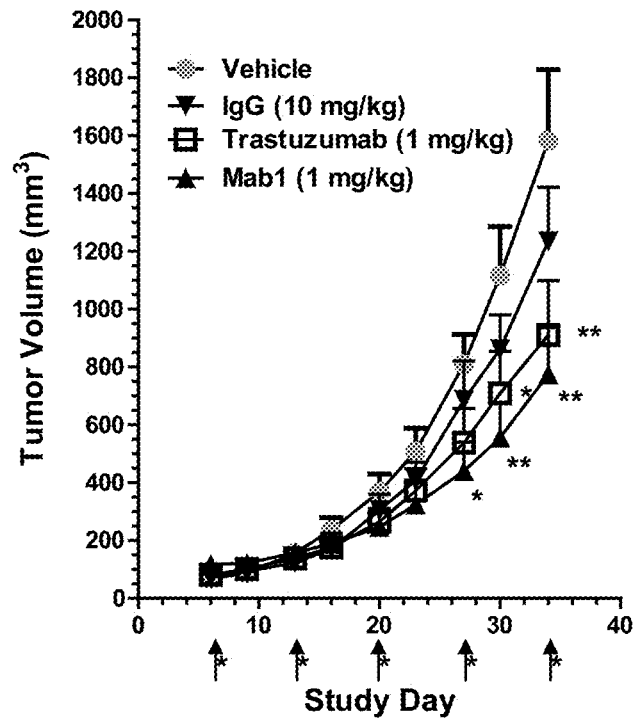

Ability of Anti-B7-H3 Antibody to Prevent or Inhibit 22rv Prostate Tumor Development in a Murine Xenograft Model Mice (mCD16−/−, hCD16A+_FoxN1) were implanted subcutaneously on their flanks with $6 \times 10^6$ 22 rv prostate cancer cells and then inoculated iv/Q7D×4 with PBS control, IgG (10 mg/kg), Mab1 (0.5, 1, 5, or 10 mg/kg; Q7D×5) or trastuzumab (1. 7 or 15 mg/kg). The tumor cells were implanted in 200 μl of Ham's F12 Medium diluted 1:1 with MATRIGEL™. Treatment with Mab1 was initiated within 7 days of implantation. The results of the experiment (FIGS. 30A-30C) show that Mab1 was capable of preventing or inhibiting of prostate cancer tumor development in the murine xenograft model.

Example 22

Figure 31:
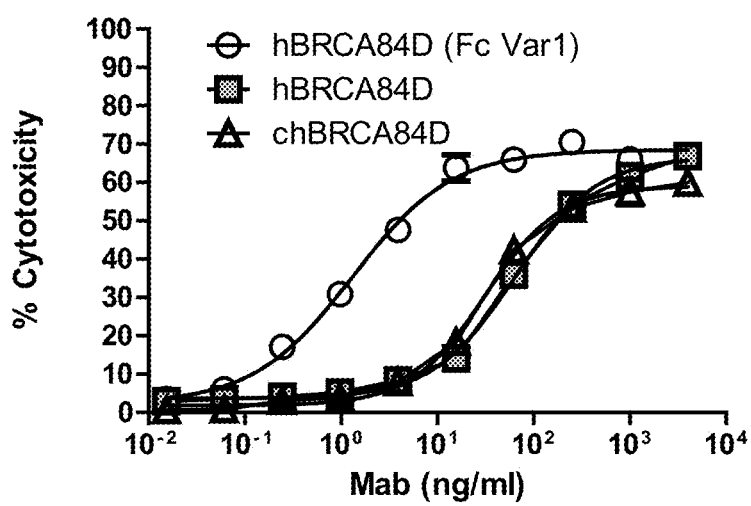
FIG. 31 show the results an in vitro cytotoxicity assay of A498 renal cancer cells upon incubation with hBRCA84D, chBRCA84D and hBRCA84 (Fc Var 1) variant anti-B7-H3 antibodies (E:T Ratio=25:1; Effector=Human PBMC; LDH Assay readout).

Ability of Anti-B7-H3 Antibody to Bind Renal Cancer Cells and Prevent or Inhibit Tumor Development in a Murine Xenograft Model A498 renal cancer cells were incubated in the presence of hBRCA84D, chBRCA84D and hBRCA84 (0264 Fc) variant and the cytotoxic effect of these antibodies was determined. The results of this experiment are shown in FIG. 31, and indicate that all three of the antibodies were cytotoxic to A498 cells.

IHC analysis of the A498 xenograft tumor tissue was conducted using biotinylated BRCA84D antibody (20 μg/ml), BRCA69D (5 μg/ml) and anti-Her2 antibody (20 μg/ml). BRCA84D antibody was found to bind 20-40% of tumor tissue (weakly to moderately: + or ++); BRCA69D was found to bind 80-100% of tumor tissue (moderately to strongly: ++ or +++). BRCA84D antibody was found to weakly bind 40% of UMUC-3 tumor tissue (+); BRCA69D was found to moderately or strongly bind 70% of such tumor tissue (++ or +++); anti-Her2 antibody was found to variably bind 20% of such tumor tissue (+-+++). As controls, anti-Her2 antibody was found to bind SKBR-3 cells (+++) and BRCA84D and BRCA69D were found to be able to bind Hs 700T cells (+++)

Figure 32:
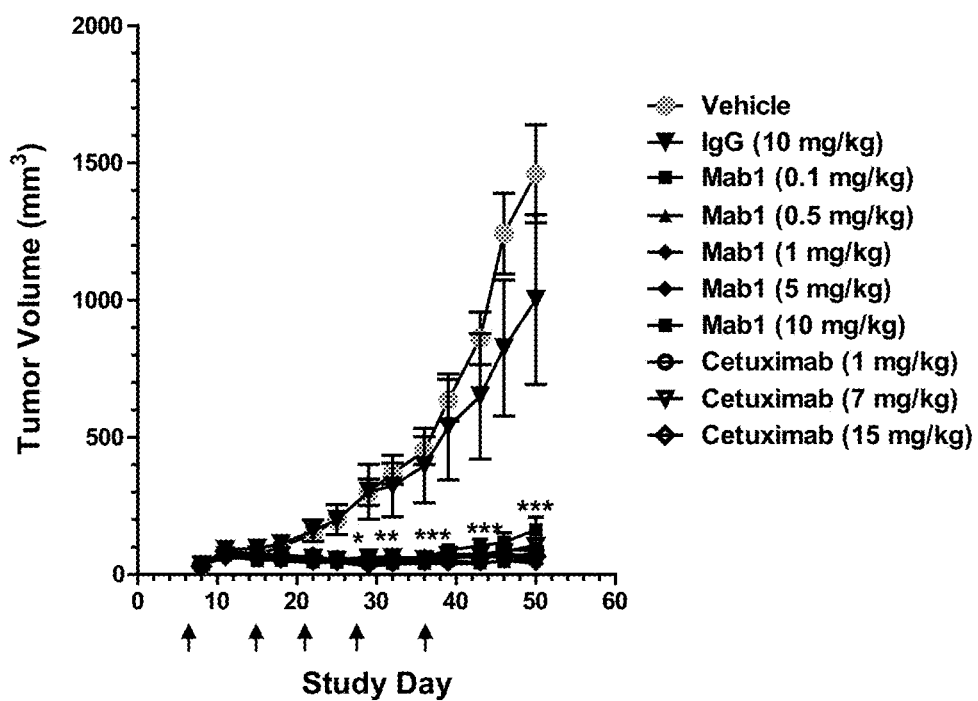
FIG. 32 shows the result of a murine xenograft analysis for A498 renal cancer cells. Groups of mice received vehicle or 10 mg/kg IgG control, or anti-B7-H3 antibody Mab1 at a dose of 0.1, 0.5, 1, 5, or 10 mg/kg. Centuximab (anti-EGRF antibody) was administered to a control group of mice at doses of 1, 7, or 15 mg/kg.

Mice (mCD16−/−, hCD16A+_FoxN1) were implanted subcutaneously on their flanks with $5 \times 10^6$ A498 renal cancer cells. The tumor cells were implanted in 200 μl of Ham's F12 Medium diluted 1:1 with MATRIGEL™. Treatment with Mab1 was initiated within 7 days of implantation via iv Q7D×5 using doses of 0.1, 0.5, 1, 5, or 10 mg/kg. Centuximab (anti-EGRF antibody) was administered to a control group of mice at doses of 1, 7, or 15 mg/kg. Additional control mice were injected with vehicle or with 10 mg/kg IgG control. The results of the experiment (FIG. 32) show that Mab1 was capable of preventing or inhibiting renalcancer tumor development in the murine xenograft model.

Figure 33A:
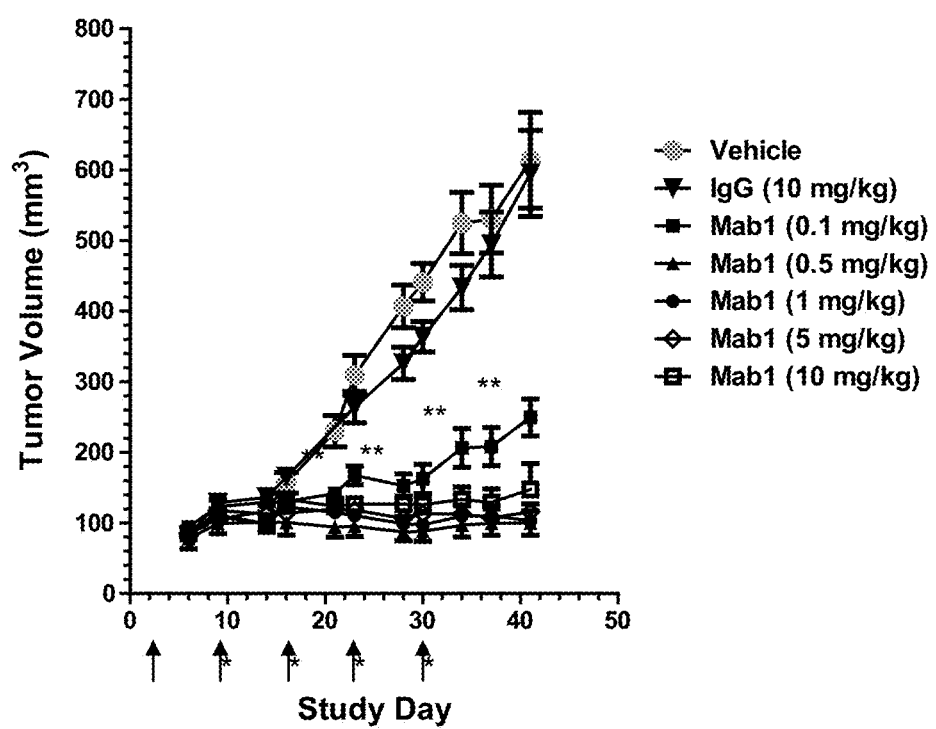
FIGS. 33A-33B show the result of a murine xenograft analysis for 786-0 renal cancer cells compared to centuximab. Groups of mice received vehicle or 10 mg/kg IgG control, or anti-B7-H3 antibody Mab1 at a dose of 0.1, 0.5, 1, 5, or 10 mg/kg. Centuximab (anti-EGRF antibody) was administered to a control group of mice at doses of 1, 7, or 15 mg/kg.
Figure 33B:
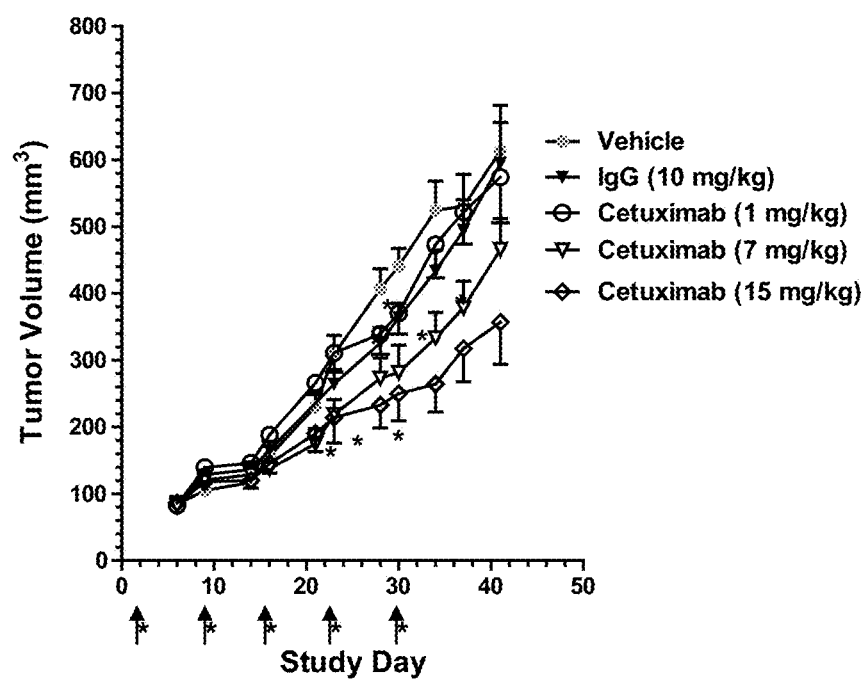

Mice (mCD16−/−, hCD16A+_FoxN1) were alternatively implanted subcutaneously on their flanks with $5 \times 10^6$ 786-0 renal cancer cells. The tumor cells were implanted in 200 μl of Ham's F12 Medium diluted 1:1 with MATRIGEL™. Treatment with Mab1 was initiated within 7 days of implantation via iv Q7D×5 using doses of 0.1, 0.5, 1, 5, or 10 mg/kg. Centuximab (anti-EGRF antibody) was administered to a control group of mice at doses of 1, 7, or 15 mg/kg. Additional control mice were injected with vehicle or with 10 mg/kg IgG control. The results of the experiment (FIGS. 33A-33B) show that Mab1 was capable of preventing or inhibiting renal cancer tumor development in the murine xenograft model.

Figure 34:
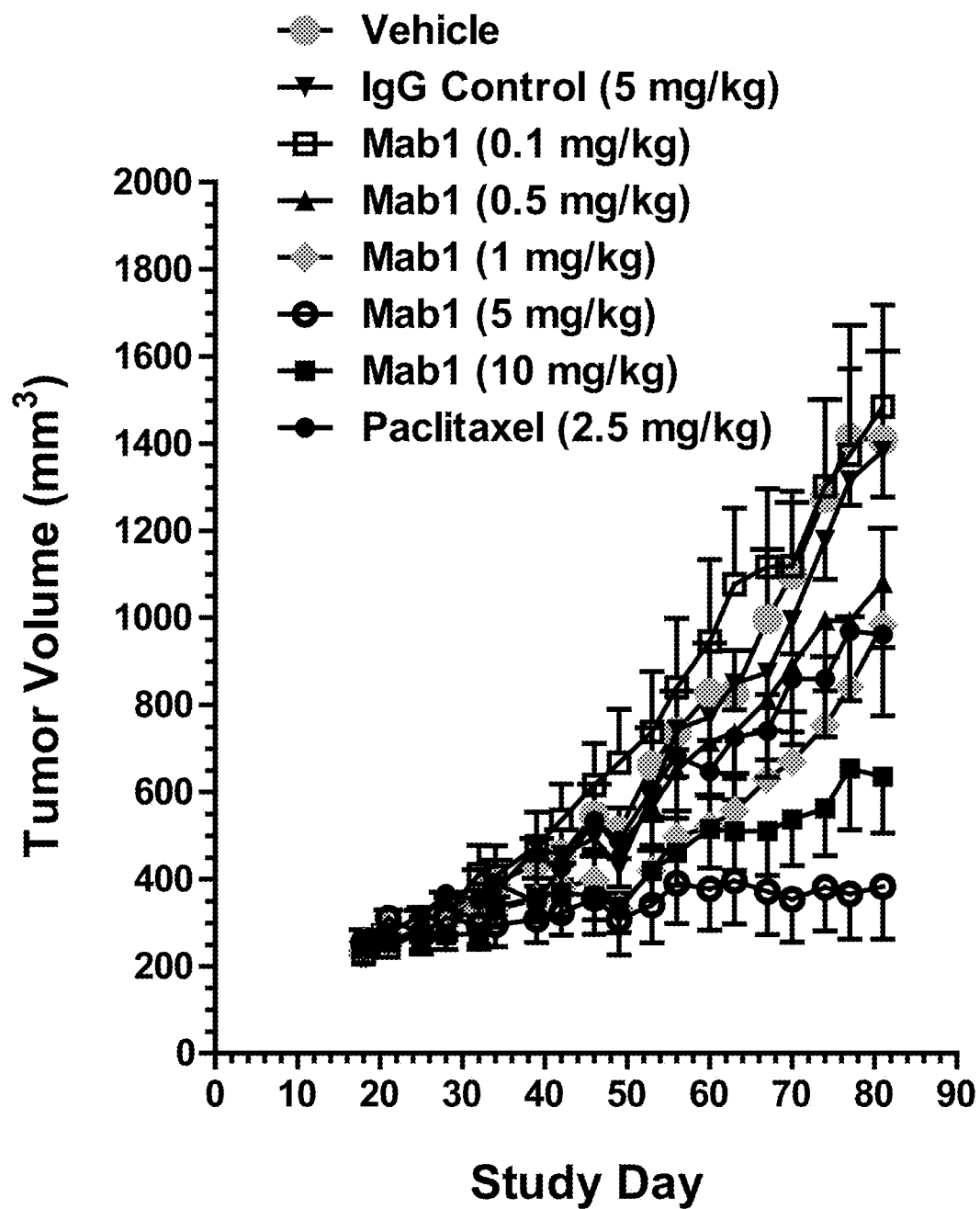
FIG. 34 shows the result of a murine xenograft analysis for 786-0 renal cancer cells compared to paclitaxel. Groups of mice received vehicle or 5 mg/kg IgG control, or anti-B7-H3 antibody Mab1 at a dose of 0.1, 0.5, 1, 5, or 10 mg/kg. Paclitaxel was administered to a control group of eight such mice at a dose of 2.5 mg/kg.

The activity of Mab1 was compared with that of paclitaxel, a mitotic inhibitor used in cancer chemotherapy. Groups of eight female mice (mCD16−/−, hCD16A+_FoxN1) were implanted subcutaneously on their flanks with 786-0 renal cancer cells and then provided with Mab1 via iv Q7D at doses of 0.1, 0.5, 1, 5, or 10 mg/kg. Paclitaxel was administered to a control group of eight such mice at a dose of 2.5 mg/kg on study day 21, 28, and 35. Additional control mice (seven female per group) were injected with vehicle or with 5 mg/kg IgG control. The results of the experiment (FIG. 34) show that Mab1 was capable of preventing or inhibiting renal cancer tumor development in the murine xenograft model.

Example 23

Cynomolgous Monkey Toxicology Study

A cynomolgous monket toxicology study is conducted in order to assess acute toxicology profile after a single dose of Mab1, determine the pharmacokinetic profile for Mab1, establish a time vs. dose relationship for induction of cytokines associated with effector cell activation, and assess the effect of drug treatment on the level of circulating leukocytes (e.g., NK and T-cells).

Such a study may be designed to involve four groups of 6 monkeys (3 males and 3 females) and to extend 7 weeks from initial treatment to final necropsy. Group 1 would comprise a control group that would receive only vehicle for weeks 1 and 2. Four members of Group 1 (two males and two females) would be sacrificed at week 3. The remaining members of Group 1 would receive additional vehicle at week 3 and be sacrificed for necropsy at week 7. Groups 2-4 are experimental groups that would receive vehicle at week 1, and B7-H3 antibody (1, 30, or 100 mg/kg, respectively) at week 2. Four members of each Group (two males and two females) would be sacrificed at week 3. The remaining members of each Group would receive additional vehicle at week 3 and be sacrificed for necropsy at week 7.

All infusions are well tolerated and no mortality or significant changes in body weight, clinical signs or serum chemistry are observed. Dose-dependent reductions in circulating NK cells but not in circulating B- and T-cells are observed.

The study provides verification of cynomolgus monkey as a relevant toxicological species. When contacted with normal human tissue, antibody BRCA84D showed various degrees of staining intensity in liver, pancreas, colon, lung and adrenal cortex. Liver staining was relatively restricted to sinusoid lining cells (fibroblast and kupffer cells). Pancreas staining was observed in collagen fiber mainly and a small percentage of the epithelium (acinar cells and/or intercalated duct cells). Colon staining was relatively restricted in apical membrane of crypt epithelium and fibroblast in mucosa. Lung showed very weak and patchy staining in the epithelium. BRCA84D showed good cross-reactivity in cynomolgus monkey tissues in comparison to the human tissue profile with the exception of the lack of staining in the liver and pancreas, and possible expression of B7-H3 in cynomolgus monkey pituitary cells.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of detecting the presence or absence of a cancer cell in a subject, comprising:
   contacting cells from said subject with a polypeptide comprising the amino acid sequence of SEQ ID NO: 117 and a polypeptide comprising the amino acid sequence of SEQ ID NO: 119; and
   detecting a complex of B7-H3 from said cells and said polypeptides, if any, wherein said cancer cell expresses B7-H3.

2. The method of claim 1, wherein said polypeptides bind to B7-H3 that is endogenously expressed on the surface of said cancer cell.

3. The method of claim 1, wherein said cancer cell is selected from the group consisting of a cancer cell of a bladder cancer, a cervical cancer, a colon cancer, a colorectal cancer, a gastric cancer, a liver cancer, a lung cancer, an ovarian cancer, a pancreatic cancer, a prostate cancer, a kidney cancer, a breast cancer, a head and neck cancer, a skin cancer, a sarcoma, a brain tumor, a brain and spinal cord cancer, an adrenal cancer, a uterine cancer, a neuroblastoma, a small round cell tumor, a peripheral nerve sheath tumor, a bone cancer, a rhabdoid tumor, a lymphoma, a multiple myeloma, a leukemia, a neuroendocrine tumor, and a melanoma.

4. The method of claim 1, wherein said polypeptides are an antibody.

5. The method of claim 4, wherein said antibody is a humanized antibody or a chimeric antibody.

6. The method of claim 4, wherein said antibody is a monoclonal antibody or a bispecific antibody.

7. A diagnostic system for detecting B7-H3 expressed by a cancer cell in a sample, said diagnostic system comprising a polypeptide comprising the amino acid sequence of SEQ ID NO: 117 and a polypeptide comprising the amino acid sequence of SEQ ID NO: 119.

8. The diagnostic system of claim 7, wherein said polypeptides are an antibody.

9. The diagnostic system of claim 8, wherein said antibody is a humanized antibody or a chimeric antibody.

10. The diagnostic system of claim 8, wherein said antibody is a monoclonal antibody or a bispecific antibody.

11. The diagnostic system of claim 7, wherein said sample comprises a bodily fluid selected from the group consisting of blood, saliva, urine, pulmonary fluid, or ascites fluid.

12. The diagnostic system of claim 7, wherein said sample comprises a tissue sample selected from the group consisting of ovary tissue, breast tissue, lung tissue, prostate tissue, colon tissue, cervical tissue, kidney tissue, skin tissue, thyroid tissue, brain tissue, heart tissue, liver tissue, stomach tissue, nerve tissue, blood vessel tissue, bone tissue, upper digestive tract tissue, and pancreas tissue.

13. The diagnostic system of claim 7, further comprising a detectable label conjugated to at least one of said polypeptides.

14. A pharmaceutical composition for diagnosing or monitoring a disease or disorder in a subject, said composition comprising a polypeptide comprising the amino acid sequence of SEQ ID NO: 117 and a polypeptide comprising the amino acid sequence of SEQ ID NO: 119.

15. The pharmaceutical composition of claim 14, wherein said polypeptides are an antibody.

16. The pharmaceutical composition of claim 15, wherein said antibody is a humanized antibody or a chimeric antibody.

17. The pharmaceutical composition of claim 15, wherein said antibody is a monoclonal antibody or a bispecific antibody.

18. The pharmaceutical composition of claim 14, wherein said disease or disorder is an inflammatory or autoimmune disease or disorder.

19. The pharmaceutical composition of claim 14, wherein said disease or disorder is cancer.

20. The pharmaceutical composition of claim 19, wherein said cancer is selected from the group consisting of a bladder cancer, a cervical cancer, a colon cancer, a colorectal cancer, a gastric cancer, a liver cancer, a lung cancer, an ovarian cancer, a pancreatic cancer, a prostate cancer, a kidney cancer, a breast cancer, a head and neck cancer, a skin cancer, a sarcoma, a brain tumor, a brain and spinal cord cancer, an adrenal cancer, a uterine cancer, a neuroblastoma, a small round cell tumor, a peripheral nerve sheath tumor, a bone cancer, a rhabdoid tumor, a lymphoma, a multiple myeloma, a leukemia, a neuroendocrine tumor, and a melanoma.

* * * * *

SEQUENCE LISTING

<160> NUMBER OF SEQ ID NOS: 120

<210> SEQ ID NO 1
<211> LENGTH: 316
<212> TYPE: PRT
<213> ORGANISM: Homo sapiens

<400> SEQUENCE: 1

```
Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
            85                  90                  95
```

```
Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
            115                 120                 125

Phe Gly Ser Ala Ala Val Ser Leu Gln Val Ala Ala Pro Tyr Ser Lys
            130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Val Leu
            195                 200                 205

Arg Val Val Leu Gly Ala Asn Gly Thr Tyr Ser Cys Leu Val Arg Asn
            210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Asn Ala Gly Ala Glu Asp Gln
            275                 280                 285

Asp Gly Glu Gly Glu Gly Ser Lys Thr Ala Leu Gln Pro Leu Lys His
            290                 295                 300

Ser Asp Ser Lys Glu Asp Asp Gly Gln Glu Ile Ala
305                 310                 315

<210> SEQ ID NO 2
<211> LENGTH: 948
<212> TYPE: DNA
<213> ORGANISM: Homo sapiens

<400> SEQUENCE: 2
atgctgcgtc ggcggggcag ccctggcatg ggtgtgcatg tgggtgcagc cctgggagca      60
ctgtggttct gcctcacagg agccctggag gtccaggtcc ctgaagaccc agtggtggca     120
ctggtgggca ccgatgccac cctgtgctgc tccttctccc tgagcctggc cttcagcctg     180
gcacagctca acctcatctg gcagctgaca gataccaaac agctggtgca cagctttgct     240
gagggccagg accagggcag cgcctatgcc aaccgcacgg ccctcttccc ggacctgctg     300
gcacagggca acgcatccct gaggctgcag cgcgtgcgtg tggcggacga gggcagcttc     360
acctgcttcg tgagcatccg ggatttcggc agcgctgccg tcagcctgca ggtggccgct     420
ccctactcga agcccagcat gaccctggag cccaacaagg acctgcggcc aggggacacg     480
gtgaccatca cgtgctccag ctaccggggc taccctgagg ctgaggtgtt ctggcaggat     540
gggcagggtg tgcccctgac tggcaacgtg accacgtcgc agatggccaa cgagcagggc     600
ttgtttgatg tgcacagcgt cctgcgggtg gtgctgggtg cgaatggcac ctacagctgc     660
ctggtgcgca accccgtgct gcagcaggat gcgcacggct ctgtcaccat cacgggcag     720
cctatgacat tcccccagga ggccctgtgg gtgaccgtgg gctgtctgt ctgtctcatt     780
gcactgctgg tggccctggc tttcgtgtgc tggagaaaga tcaaacagag ctgtgaggag     840
```

```
gagaatgcag gagctgagga ccaggatggg gagggagaag gctccaagac agccctgcag    900
cctctgaaac actctgacag caaagaagat gatggacaag aaatagcc               948
```

<210> SEQ ID NO 3
<211> LENGTH: 107
<212> TYPE: PRT
<213> ORGANISM: Artificial Sequence
<220> FEATURE:
<223> OTHER INFORMATION: Amino Acid Sequence of BRCA84D Variable Light
      Chain

<400> SEQUENCE: 3

```
Asp Ile Ala Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Glu Tyr Phe Cys Gln Gln Tyr Asn Asn Tyr Pro Phe
                85                  90                  95

Thr Phe Gly Ser Gly Thr Lys Leu Glu Ile Lys
            100                 105
```

<210> SEQ ID NO 4
<211> LENGTH: 321
<212> TYPE: DNA
<213> ORGANISM: Artificial Sequence
<220> FEATURE:
<223> OTHER INFORMATION: Polynucleotide Sequence Encoding BRCA84D
      Variable Light Chain

<400> SEQUENCE: 4

```
gacattgcga tgacccagtc tcaaaaattc atgtccacat cagtaggaga cagggtcagc    60
gtcacctgca aggccagtca gaatgtggat actaatgtag cctggtatca acagaaacca   120
gggcaatctc ctaaagcact gatttactcg gcatcctacc ggtacagtgg agtccctgat   180
cgcttcacag gcagtggatc tgggacagat ttcactctca ccatcaacaa tgtgcagtct   240
gaagacttgg cagagtattt ctgtcagcaa tataacaact atccattcac gttcggctcg   300
gggacaaagt tggaaataaa a                                             321
```

<210> SEQ ID NO 5
<211> LENGTH: 11
<212> TYPE: PRT
<213> ORGANISM: Artificial Sequence
<220> FEATURE:
<223> OTHER INFORMATION: BRCA84D Variable Light Chain CDR1

<400> SEQUENCE: 5

```
Lys Ala Ser Gln Asn Val Asp Thr Asn Val Ala
1               5                   10
```

<210> SEQ ID NO 6
<211> LENGTH: 33
<212> TYPE: DNA
<213> ORGANISM: Artificial Sequence
<220> FEATURE:
<223> OTHER INFORMATION: Polynucleotide Sequence Encoding BRCA84D Variable Light Chain CDR1

<400> SEQUENCE: 6
aaggccagtc agaatgtgga tactaatgta gcc                                    33

<210> SEQ ID NO 7
<211> LENGTH: 7
<212> TYPE: PRT
<213> ORGANISM: Artificial Sequence
<220> FEATURE:
<223> OTHER INFORMATION: BRCA84D Variable Light Chain CDR2

<400> SEQUENCE: 7

Ser Ala Ser Tyr Arg Tyr Ser
1               5

<210> SEQ ID NO 8
<211> LENGTH: 21
<212> TYPE: DNA
<213> ORGANISM: Artificial Sequence
<220> FEATURE:
<223> OTHER INFORMATION: Polynucleotide Sequence Encoding BRCA84D
      Variable Light Chain CDR2

<400> SEQUENCE: 8
tcggcatcct accggtacag t                                                 21

<210> SEQ ID NO 9
<211> LENGTH: 9
<212> TYPE: PRT
<213> ORGANISM: Artificial Sequence
<220> FEATURE:
<223> OTHER INFORMATION: BRCA84D Variable Light Chain CDR3

<400> SEQUENCE: 9

Gln Gln Tyr Asn Asn Tyr Pro Phe Thr
1               5

<210> SEQ ID NO 10
<211> LENGTH: 27
<212> TYPE: DNA
<213> ORGANISM: Artificial Sequence
<220> FEATURE:
<223> OTHER INFORMATION: Polynucleotide Sequence Encoding BRCA84D
      Variable Light Chain CDR3

<400> SEQUENCE: 10
cagcaatata caactatcc attcacg                                            27

<210> SEQ ID NO 11
<211> LENGTH: 122
<212> TYPE: PRT
<213> ORGANISM: Artificial Sequence
<220> FEATURE:
<223> OTHER INFORMATION: Amino Acid Sequence of BRCA84D Variable Heavy
      Chain

<400> SEQUENCE: 11

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Asp Ser Ser Ala Ile Tyr Tyr Ala Asp Thr Val

```
                50                  55                  60
Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Gly Arg Gly Arg Glu Asn Ile Tyr Tyr Gly Ser Arg Leu Asp Tyr Trp
            100                 105                 110

Gly Gln Gly Thr Thr Leu Thr Val Ser Ser
        115                 120

<210> SEQ ID NO 12
<211> LENGTH: 366
<212> TYPE: DNA
<213> ORGANISM: Artificial Sequence
<220> FEATURE:
<223> OTHER INFORMATION: Polynucleotide Sequence Encoding BRCA84D
      Variable Heavy Chain

<400> SEQUENCE: 12
gatgtgcagc tggtggagtc tgggggaggc ttagtgcagc ctggagggtc ccggaaactc     60
tcctgtgcag cctctggatt cactttcagt agctttggaa tgcactgggt tcgtcaggct    120
ccagagaagg ggctggagtg ggtcgcatac attagtagtg acagtagtgc catctactat    180
gcagacacag tgaagggccg attcaccatc tccagagaca atcccaagaa caccctgttc    240
ctgcaaatga ccagtctaag gtctgaggac acggccatgt attactgtgg aagagggagg    300
gaaaacattt actacggtag taggcttgac tactggggcc aaggcaccac tctcacagtc    360
tcctca                                                              366

<210> SEQ ID NO 13
<211> LENGTH: 4
<212> TYPE: PRT
<213> ORGANISM: Artificial Sequence
<220> FEATURE:
<223> OTHER INFORMATION: BRCA84D Variable Heavy Chain CDR1

<400> SEQUENCE: 13

Phe Gly Met His
1

<210> SEQ ID NO 14
<211> LENGTH: 12
<212> TYPE: DNA
<213> ORGANISM: Artificial Sequence
<220> FEATURE:
<223> OTHER INFORMATION: Polynucleotide Sequence Encoding BRCA84D
      Variable Heavy Chain CDR1

<400> SEQUENCE: 14
tttggaatgc ac                                                        12

<210> SEQ ID NO 15
<211> LENGTH: 16
<212> TYPE: PRT
<213> ORGANISM: Artificial Sequence
<220> FEATURE:
<223> OTHER INFORMATION: BRCA84D Variable Heavy Chain CDR2

<400> SEQUENCE: 15

Tyr Ile Ser Ser Asp Ser Ser Ala Ile Tyr Tyr Ala Asp Thr Val Lys
1               5                   10                  15
```

```
<210> SEQ ID NO 16
<211> LENGTH: 48
<212> TYPE: DNA
<213> ORGANISM: Artificial Sequence
<220> FEATURE:
<223> OTHER INFORMATION: Polynucleotide Sequence Encoding BRCA84D
      Variable Heavy Chain CDR2

<400> SEQUENCE: 16
tacattagta gtgacagtag tgccatctac tatgcagaca cagtgaag                48

<210> SEQ ID NO 17
<211> LENGTH: 13
<212> TYPE: PRT
<213> ORGANISM: Artificial Sequence
<220> FEATURE:
<223> OTHER INFORMATION: BRCA84D Variable Heavy Chain CDR3

<400> SEQUENCE: 17

Gly Arg Glu Asn Ile Tyr Tyr Gly Ser Arg Leu Asp Tyr
1               5                   10

<210> SEQ ID NO 18
<211> LENGTH: 39
<212> TYPE: DNA
<213> ORGANISM: Artificial Sequence
<220> FEATURE:
<223> OTHER INFORMATION: Polynucleotide Sequence Encoding BRCA84D
      Variable Heavy Chain CDR3

<400> SEQUENCE: 18
gggagggaaa acatttacta cggtagtagg cttgactac                          39

<210> SEQ ID NO 19
<211> LENGTH: 107
<212> TYPE: PRT
<213> ORGANISM: Artificial Sequence
<220> FEATURE:
<223> OTHER INFORMATION: Amino Acid Sequence of BRCA69D Variable Light
      Chain

<400> SEQUENCE: 19

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Asp Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys
            100                 105

<210> SEQ ID NO 20
<211> LENGTH: 321
<212> TYPE: DNA
<213> ORGANISM: Artificial Sequence
<220> FEATURE:
<223> OTHER INFORMATION: Polynucleotide Sequence Encoding BRCA69D
      Variable Light Chain
```

<400> SEQUENCE: 20

```
gatatccaga tgacacagac tacatcctcc ctgtctgcct ctctgggaga cagagtcacc      60
atcagttgca gggcaagtca ggacattagt aattatttaa actggtatca gcagaaacca     120
gatggaactg ttaaactcct gatctactac acatcacgat acactcagg  agtcccatca     180 aggttcagtg gcagtgggtc tggaacagat tattctctca ccattgacaa cctggagcaa     240
gaagatattg ccacttactt ttgccaacag ggtaatacgc ttcctccgac gttcggtgga     300
ggcaccaaac tggaaatcaa a                                                321
```

<210> SEQ ID NO 21
<211> LENGTH: 11
<212> TYPE: PRT
<213> ORGANISM: Artificial Sequence
<220> FEATURE:
<223> OTHER INFORMATION: BRCA69D Variable Light Chain CDR1

<400> SEQUENCE: 21

Arg Ala Ser Gln Asp Ile Ser Asn Tyr Leu Asn
1               5                   10

<210> SEQ ID NO 22
<211> LENGTH: 33
<212> TYPE: DNA
<213> ORGANISM: Artificial Sequence
<220> FEATURE:
<223> OTHER INFORMATION: Polynucleotide Sequence Encoding BRCA69D
      Variable Light Chain CDR1

<400> SEQUENCE: 22

```
agggcaagtc aggacattag taattattta aac                                   33
```

<210> SEQ ID NO 23
<211> LENGTH: 7
<212> TYPE: PRT
<213> ORGANISM: Artificial Sequence
<220> FEATURE:
<223> OTHER INFORMATION: BRCA69D Variable Light Chain CDR2

<400> SEQUENCE: 23

Tyr Thr Ser Arg Leu His Ser
1               5

<210> SEQ ID NO 24
<211> LENGTH: 21
<212> TYPE: DNA
<213> ORGANISM: Artificial Sequence
<220> FEATURE:
<223> OTHER INFORMATION: Polynucleotide Sequence Encoding BRCA69D
      Variable Light Chain CDR2

<400> SEQUENCE: 24

```
tacacatcac gattacactc a                                                21
```

<210> SEQ ID NO 25
<211> LENGTH: 9
<212> TYPE: PRT
<213> ORGANISM: Artificial Sequence
<220> FEATURE:
<223> OTHER INFORMATION: BRCA69D Variable Light Chain CDR3

<400> SEQUENCE: 25

Gln Gln Gly Asn Thr Leu Pro Pro Thr
1               5

<210> SEQ ID NO 26
<211> LENGTH: 27
<212> TYPE: DNA
<213> ORGANISM: Artificial Sequence
<220> FEATURE:
<223> OTHER INFORMATION: Polynucleotide Sequence Encoding BRCA69D
      Variable Light Chain CDR3

<400> SEQUENCE: 26
caacagggta atacgcttcc tccgacg                                        27

<210> SEQ ID NO 27
<211> LENGTH: 120
<212> TYPE: PRT
<213> ORGANISM: Artificial Sequence
<220> FEATURE:
<223> OTHER INFORMATION: Amino Acid Sequence of BRCA69D Variable Heavy
      Chain

<400> SEQUENCE: 27

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Arg Gly Ile Pro Arg Leu Trp Tyr Phe Asp Val Trp Gly Ala
            100                 105                 110

Gly Thr Thr Val Thr Val Ser Ser
        115                 120

<210> SEQ ID NO 28
<211> LENGTH: 360
<212> TYPE: DNA
<213> ORGANISM: Artificial Sequence
<220> FEATURE:
<223> OTHER INFORMATION: Polynucleotide Sequence Encoding BRCA69D
      Variable Heavy Chain

<400> SEQUENCE: 28
caggttcagc tccagcagtc tggggctgag ctggcaagac ctggggcttc agtgaagttg    60
tcctgcaagg cttctggcta cacctttact agctactgga tgcagtgggt aaaacagagg   120
cctggacagg gtctggaatg gattgggact atttatcctg gagatggtga ctactaggtac   180 actcagaagt tcaagggcaa ggccacattg actgcagata atcctccag cacagcctac    240 atgcaactca gcagcttggc atctgaggac tctgcggtct attactgtgc aagaagaggg   300
attccacggc tttggtactt cgatgtctgg ggcgcaggga ccacggtcac cgtctcctca   360

<210> SEQ ID NO 29
<211> LENGTH: 5
<212> TYPE: PRT
<213> ORGANISM: Artificial Sequence
<220> FEATURE:
<223> OTHER INFORMATION: BRCA69D Variable Heavy Chain CDR1

-continued

<400> SEQUENCE: 29

Ser Tyr Trp Met Gln
1               5

<210> SEQ ID NO 30
<211> LENGTH: 15
<212> TYPE: DNA
<213> ORGANISM: Artificial Sequence
<220> FEATURE:
<223> OTHER INFORMATION: Polynucleotide Sequence Encoding BRCA69D
      Variable Heavy Chain CDR1

<400> SEQUENCE: 30
agctactgga tgcag                                                          15

<210> SEQ ID NO 31
<211> LENGTH: 17
<212> TYPE: PRT
<213> ORGANISM: Artificial Sequence
<220> FEATURE:
<223> OTHER INFORMATION: BRCA69D Variable Heavy Chain CDR2

<400> SEQUENCE: 31

Thr Ile Tyr Pro Gly Asp Gly Asp Thr Arg Tyr Thr Gln Lys Phe Lys
1               5                   10                  15

Gly

<210> SEQ ID NO 32
<211> LENGTH: 51
<212> TYPE: DNA
<213> ORGANISM: Artificial Sequence
<220> FEATURE:
<223> OTHER INFORMATION: Polynucleotide Sequence Encoding BRCA69D
      Variable Heavy Chain CDR2

<400> SEQUENCE: 32
actatttatc ctggagatgg tgatactagg tacactcaga agttcaaggg c                  51

<210> SEQ ID NO 33
<211> LENGTH: 11
<212> TYPE: PRT
<213> ORGANISM: Artificial Sequence
<220> FEATURE:
<223> OTHER INFORMATION: BRCA69D Variable Heavy Chain CDR3

<400> SEQUENCE: 33

Arg Gly Ile Pro Arg Leu Trp Tyr Phe Asp Val
1               5                   10

<210> SEQ ID NO 34
<211> LENGTH: 33
<212> TYPE: DNA
<213> ORGANISM: Artificial Sequence
<220> FEATURE:
<223> OTHER INFORMATION: Polynucleotide Sequence Encoding BRCA69D
      Variable Heavy Chain CDR3

<400> SEQUENCE: 34
agagggattc cacggctttg gtacttcgat gtc                                      33

<210> SEQ ID NO 35
<211> LENGTH: 108
<212> TYPE: PRT
<213> ORGANISM: Artificial Sequence

```
<220> FEATURE:
<223> OTHER INFORMATION: Amino Acid Sequence of PRCA157 Variable Light
      Chain

<400> SEQUENCE: 35

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Ser Ile Tyr Ser Tyr
                20                  25                  30

Leu Ala Trp Tyr Gln Gln Lys Gln Gly Lys Ser Pro Gln Leu Leu Val
            35                  40                  45

Tyr Asn Thr Lys Thr Leu Pro Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Arg Tyr Tyr Cys Gln His His Tyr Gly Thr Pro Pro
                85                  90                  95

Trp Thr Phe Gly Gly Gly Thr Asn Leu Glu Ile Lys
            100                 105

<210> SEQ ID NO 36
<211> LENGTH: 324
<212> TYPE: DNA
<213> ORGANISM: Artificial Sequence
<220> FEATURE:
<223> OTHER INFORMATION: Polynucleotide Sequence Encoding PRCA157
      Variable Light Chain

<400> SEQUENCE: 36
gacatccaga tgactcagtc tccagcctcc ctatctgtat ctgtgggaga aactgtcacc      60
attacatgtc gagcaagtga gagtatttac agttatttag catggtatca gcagaaacag    120
ggaaaatctc ctcagctcct ggtctataat acaaaaacct accagagggg tgtgccatca    180
aggttcagtg gcagtggatc aggcacacag ttttctctga agatcaacag cctgcagcct    240
gaagattttg ggagatatta ctgtcaacat cattatggta ctcctccgtg gacgttcggt    300
ggaggcacca acctggaaat caaa                                           324

<210> SEQ ID NO 37
<211> LENGTH: 11
<212> TYPE: PRT
<213> ORGANISM: Artificial Sequence
<220> FEATURE:
<223> OTHER INFORMATION: PRCA157 Variable Light Chain CDR1

<400> SEQUENCE: 37

Arg Ala Ser Glu Ser Ile Tyr Ser Tyr Leu Ala
1               5                   10

<210> SEQ ID NO 38
<211> LENGTH: 33
<212> TYPE: DNA
<213> ORGANISM: Artificial Sequence
<220> FEATURE:
<223> OTHER INFORMATION: Polynucleotide Sequence Encoding PRCA157
      Variable Light Chain CDR1

<400> SEQUENCE: 38
cgagcaagtg agagtattta cagttattta gca                                   33

<210> SEQ ID NO 39
<211> LENGTH: 7
```

```
<212> TYPE: PRT
<213> ORGANISM: Artificial Sequence
<220> FEATURE:
<223> OTHER INFORMATION: PRCA157 Variable Light Chain CDR2

<400> SEQUENCE: 39

Asn Thr Lys Thr Leu Pro Glu
1               5

<210> SEQ ID NO 40
<211> LENGTH: 21
<212> TYPE: DNA
<213> ORGANISM: Artificial Sequence
<220> FEATURE:
<223> OTHER INFORMATION: Polynucleotide Sequence Encoding PRCA157
      Variable Light Chain CDR2

<400> SEQUENCE: 40
aatacaaaaa ccttaccaga g                                          21

<210> SEQ ID NO 41
<211> LENGTH: 9
<212> TYPE: PRT
<213> ORGANISM: Artificial Sequence
<220> FEATURE:
<223> OTHER INFORMATION: PRCA157 Variable Light Chain CDR3

<400> SEQUENCE: 41

Gln His His Tyr Gly Thr Pro Pro Trp
1               5

<210> SEQ ID NO 42
<211> LENGTH: 27
<212> TYPE: DNA
<213> ORGANISM: Artificial Sequence
<220> FEATURE:
<223> OTHER INFORMATION: Polynucleotide Sequence Encoding PRCA157
      Variable Light Chain CDR3

<400> SEQUENCE: 42
caacatcatt atggtactcc tccgtgg                                    27

<210> SEQ ID NO 43
<211> LENGTH: 117
<212> TYPE: PRT
<213> ORGANISM: Artificial Sequence
<220> FEATURE:
<223> OTHER INFORMATION: Amino Acid Sequence of PRCA157 Variable Heavy
      Chain

<400> SEQUENCE: 43

Glu Val Gln Gln Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Asn Ser Gly Gly Ser Asn Thr Tyr Tyr Pro Asp Ser Leu
    50                  55                  60

Lys Gly Arg Phe Thr Ile Ser Arg Asp Asn Ala Lys Asn Thr Leu Tyr
65                  70                  75                  80

Leu Gln Met Arg Ser Leu Lys Ser Glu Asp Thr Ala Met Tyr Tyr Cys
                85                  90                  95

Ala Arg His Asp Gly Gly Ala Met Asp Tyr Trp Gly Gln Gly Thr Ser
```

```
                100               105               110
Val Thr Val Ser Ser
        115

<210> SEQ ID NO 44
<211> LENGTH: 351
<212> TYPE: DNA
<213> ORGANISM: Artificial Sequence
<220> FEATURE:
<223> OTHER INFORMATION: Polynucleotide Sequence Encoding PRCA157
      Variable Heavy Chain

<400> SEQUENCE: 44
gaggtgcagc aggtggagtc gggggggagac ttagtgaagc ctggagggtc cctgaaactc      60
tcctgtgcag cctctggatt cactttcagt tcctatggca tgtcttgggt tcgccagact     120
ccagacaaga ggctggagtg ggtcgcaacc attaatagtg gtggaagtaa cacctactat     180
ccagacagtt tgaaggggcg attcaccatc tccagagaca tgccaagaa caccctttac      240 ctgcaaatgc gcagtctgaa gtctgaggac acagccatgt attactgtgc aagacatgac     300
gggggagcta tggactactg gggtcaagga acctcagtca ccgtctcctc a              351

<210> SEQ ID NO 45
<211> LENGTH: 5
<212> TYPE: PRT
<213> ORGANISM: Artificial Sequence
<220> FEATURE:
<223> OTHER INFORMATION: PRCA157 Variable Heavy Chain CDR1

<400> SEQUENCE: 45

Ser Tyr Gly Met Ser
1               5

<210> SEQ ID NO 46
<211> LENGTH: 15
<212> TYPE: DNA
<213> ORGANISM: Artificial Sequence
<220> FEATURE:
<223> OTHER INFORMATION: Polynucleotide Sequence Encoding PRCA157
      Variable Heavy Chain CDR1

<400> SEQUENCE: 46
tcctatggca tgtct                                                       15

<210> SEQ ID NO 47
<211> LENGTH: 19
<212> TYPE: PRT
<213> ORGANISM: Artificial Sequence
<220> FEATURE:
<223> OTHER INFORMATION: PRCA157 Variable Heavy Chain CDR2

<400> SEQUENCE: 47

Val Ala Thr Ile Asn Ser Gly Gly Ser Asn Thr Tyr Tyr Pro Asp Ser
1               5                   10                  15

Leu Lys Gly

<210> SEQ ID NO 48
<211> LENGTH: 57
<212> TYPE: DNA
<213> ORGANISM: Artificial Sequence
<220> FEATURE:
<223> OTHER INFORMATION: Polynucleotide Sequence Encoding PRCA157
      Variable Heavy Chain CDR2
```

<400> SEQUENCE: 48
gtcgcaacca ttaatagtgg tggaagtaac acctactatc cagacagttt gaagggg     57

<210> SEQ ID NO 49
<211> LENGTH: 8
<212> TYPE: PRT
<213> ORGANISM: Artificial Sequence
<220> FEATURE:
<223> OTHER INFORMATION: PRCA157 Variable Heavy Chain CDR3

<400> SEQUENCE: 49

His Asp Gly Gly Ala Met Asp Tyr
1               5

<210> SEQ ID NO 50
<211> LENGTH: 24
<212> TYPE: DNA
<213> ORGANISM: Artificial Sequence
<220> FEATURE:
<223> OTHER INFORMATION: Polynucleotide Sequence Encoding PRCA157
      Variable Heavy Chain CDR3

<400> SEQUENCE: 50
catgacgggg gagctatgga ctac                                          24

<210> SEQ ID NO 51
<211> LENGTH: 218
<212> TYPE: PRT
<213> ORGANISM: Homo sapiens

<400> SEQUENCE: 51

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys

```
<210> SEQ ID NO 52
<211> LENGTH: 8
<212> TYPE: PRT
<213> ORGANISM: Artificial Sequence
<220> FEATURE:
<223> OTHER INFORMATION: Amino Acid Linker Sequence

<400> SEQUENCE: 52

Gly Gly Gly Ser Gly Gly Gly Gly
1               5

<210> SEQ ID NO 53
<211> LENGTH: 24
<212> TYPE: DNA
<213> ORGANISM: Artificial Sequence
<220> FEATURE:
<223> OTHER INFORMATION: Polynucleotide Encoding Amino Acid Linker
      Sequence

<400> SEQUENCE: 53
ggaggcggat ccggaggcgg aggc                                              24

<210> SEQ ID NO 54
<211> LENGTH: 4
<212> TYPE: PRT
<213> ORGANISM: Artificial Sequence
<220> FEATURE:
<223> OTHER INFORMATION: DART C-Terminal Amino acid Sequence

<400> SEQUENCE: 54

Leu Gly Gly Cys
1

<210> SEQ ID NO 55
<211> LENGTH: 13
<212> TYPE: PRT
<213> ORGANISM: Artificial Sequence
<220> FEATURE:
<223> OTHER INFORMATION: Hinge Domain

<400> SEQUENCE: 55

Glu Pro Lys Ser Cys Asp Lys Thr His Thr Cys Pro Pro
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Hinge Domain

<400> SEQUENCE: 56

Glu Ser Lys Tyr Gly Pro Pro Cys Pro Ser
1               5                   10

<210> SEQ ID NO 57
<211> LENGTH: 6
<212> TYPE: PRT
<213> ORGANISM: Artificial Sequence
<220> FEATURE:
<223> OTHER INFORMATION: DART C-Terminal Amino Acid Sequence

<400> SEQUENCE: 57

Val Glu Pro Lys Ser Cys
1               5
```

<210> SEQ ID NO 58
<211> LENGTH: 18
<212> TYPE: DNA
<213> ORGANISM: Artificial Sequence
<220> FEATURE:
<223> OTHER INFORMATION: Polynucleotide Encoding DART C-Terminal
      Sequence

<400> SEQUENCE: 58
gttgagccca aatcttgt                                                  18

<210> SEQ ID NO 59
<211> LENGTH: 10
<212> TYPE: PRT
<213> ORGANISM: Artificial Sequence
<220> FEATURE:
<223> OTHER INFORMATION: DART Cysteine-Containing Sequence

<400> SEQUENCE: 59

Leu Gly Gly Cys Phe Asn Arg Gly Glu Cys
1               5                   10

<210> SEQ ID NO 60
<211> LENGTH: 30
<212> TYPE: DNA
<213> ORGANISM: Artificial Sequence
<220> FEATURE:
<223> OTHER INFORMATION: Polynucleotide Encoding DART C-Terminal
      Cysteine-Containing Sequence

<400> SEQUENCE: 60
ctgggaggct gcttcaacag gggagagtgt                                     30

<210> SEQ ID NO 61
<211> LENGTH: 6
<212> TYPE: PRT
<213> ORGANISM: Artificial Sequence
<220> FEATURE:
<223> OTHER INFORMATION: DART Cysteine Containing Sequence

<400> SEQUENCE: 61

Phe Asn Arg Gly Glu Cys
1               5

<210> SEQ ID NO 62
<211> LENGTH: 18
<212> TYPE: DNA
<213> ORGANISM: Artificial Sequence
<220> FEATURE:
<223> OTHER INFORMATION: Polynucleotide Encoding DART Cysteine-
      Containing Sequence

<400> SEQUENCE: 62
ttcaacaggg gagagtgt                                                  18

<210> SEQ ID NO 63
<211> LENGTH: 28
<212> TYPE: PRT
<213> ORGANISM: Artificial Sequence
<220> FEATURE:
<223> OTHER INFORMATION: DART E-Coil Amino acid Sequence

<400> SEQUENCE: 63

Glu Val Ala Ala Leu Glu Lys Glu Val Ala Ala Leu Glu Lys Glu Val
1               5                   10                  15

```
Ala Ala Leu Glu Lys Glu Val Ala Leu Glu Lys
            20                  25

<210> SEQ ID NO 64
<211> LENGTH: 28
<212> TYPE: PRT
<213> ORGANISM: Artificial Sequence
<220> FEATURE:
<223> OTHER INFORMATION: DART K-Coil Amino Acid Sequence

<400> SEQUENCE: 64

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 65
<211> LENGTH: 5
<212> TYPE: PRT
<213> ORGANISM: Artificial Sequence
<220> FEATURE:
<223> OTHER INFORMATION: Linker

<400> SEQUENCE: 65

Gly Gly Gly Asn Ser
1               5

<210> SEQ ID NO 66
<211> LENGTH: 383
<212> TYPE: PRT
<213> ORGANISM: Homo sapiens

<400> SEQUENCE: 66

Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Arg Tyr Asn Leu
            20                  25                  30

Thr Val Leu Ser Trp Asp Gly Ser Val Gln Ser Gly Phe Leu Thr Glu
        35                  40                  45

Val His Leu Asp Gly Gln Pro Phe Leu Arg Cys Asp Arg Gln Lys Cys
    50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
    130                 135                 140

Leu Glu Thr Lys Glu Trp Thr Met Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
            180                 185                 190

Arg Tyr Leu Lys Ser Gly Val Val Leu Arg Arg Thr Val Pro Pro Met
        195                 200                 205
```

```
Val Asn Val Thr Arg Ser Glu Ala Ser Glu Gly Asn Ile Thr Val Thr
210                 215                 220

Cys Arg Ala Ser Gly Phe Tyr Pro Trp Asn Ile Thr Leu Ser Trp Arg
225                 230                 235                 240

Gln Asp Gly Val Ser Leu Ser His Asp Thr Gln Gln Trp Gly Asp Val
            245                 250                 255

Leu Pro Asp Gly Asn Gly Thr Tyr Gln Thr Trp Val Ala Thr Arg Ile
                260                 265                 270

Cys Gln Gly Glu Glu Gln Arg Phe Thr Cys Tyr Met Glu His Ser Gly
            275                 280                 285

Asn His Ser Thr His Pro Val Pro Ser Gly Lys Val Leu Val Leu Gln
        290                 295                 300

Ser His Trp Gln Thr Phe His Val Ser Ala Val Ala Ala Ala Ala Ile
305                 310                 315                 320

Phe Val Ile Ile Ile Phe Tyr Val Arg Cys Cys Lys Lys Lys Thr Ser
                325                 330                 335

Ala Ala Glu Gly Pro Glu Leu Val Ser Leu Gln Val Leu Asp Gln His
            340                 345                 350

Pro Val Gly Thr Ser Asp His Arg Asp Ala Thr Gln Leu Gly Phe Gln
            355                 360                 365

Pro Leu Met Ser Asp Leu Gly Ser Thr Gly Ser Thr Glu Gly Ala
            370                 375                 380

<210> SEQ ID NO 67
<211> LENGTH: 305
<212> TYPE: PRT
<213> ORGANISM: Homo sapiens

<400> SEQUENCE: 67

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asp Val Leu Gly Ala Lys Thr Trp Asp Thr Glu Thr Glu Asp
50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asp
            100                 105                 110

Gly Glu Leu Phe Leu Ser Gln Asn Leu Glu Thr Gln Glu Ser Thr Val
        115                 120                 125

Pro Gln Ser Ser Arg Ala Gln Thr Leu Ala Met Asn Val Thr Asn Phe
130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Leu Pro Pro Met Val Asn Val Ile
                165                 170                 175

Cys Ser Glu Val Ser Glu Gly Asn Ile Thr Val Thr Cys Arg Ala Ser
            180                 185                 190

Ser Phe Tyr Pro Arg Asn Ile Thr Leu Thr Trp Arg Gln Asp Gly Val
        195                 200                 205
```

Ser Leu Ser His Asn Thr Gln Gln Trp Gly Asp Val Leu Pro Asp Gly
    210                 215                 220

Asn Gly Thr Tyr Gln Thr Trp Val Ala Thr Arg Ile Arg Gln Gly Glu
225                 230                 235                 240

Glu Gln Arg Phe Thr Cys Tyr Met Glu His Ser Gly Asn His Gly Thr
                245                 250                 255

His Pro Val Pro Ser Gly Lys Ala Leu Val Leu Gln Ser Gln Arg Thr
            260                 265                 270

Asp Phe Pro Tyr Val Ser Ala Ala Met Pro Cys Phe Val Ile Ile Ile
        275                 280                 285

Ile Leu Cys Val Pro Cys Cys Lys Lys Lys Thr Ser Ala Ala Glu Gly
    290                 295                 300

Pro
305

<210> SEQ ID NO 68
<211> LENGTH: 107
<212> TYPE: PRT
<213> ORGANISM: Artificial Sequence
<220> FEATURE:
<223> OTHER INFORMATION: Humanized BRCA84D-1 Variable Light Chain

<400> SEQUENCE: 68

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105

<210> SEQ ID NO 69
<211> LENGTH: 321
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Light Chain

<400> SEQUENCE: 69
gacatccagc tgacccagtc ccctccttc ctgtctgcct ccgtgggcga cagagtgacc        60
atcacatgca aggcctccca gaacgtggac accaacgtgg cctggtatca gcagaagcct      120
ggcaaggccc ctaagctgct gatctactcc gcctcctacc ggtactccgg cgtgccttcc      180
aggttctccg gctccggctc tggcaccgac ttcaccctga ccatctccag cctgcagcct      240
gaggacttcg ccacctacta ctgccagcag tacaacaact ccctttcac cttcggccag      300 ggcaccaagc tggaaatcaa g                                                321

<210> SEQ ID NO 70
<211> LENGTH: 11

```
<212> TYPE: PRT
<213> ORGANISM: Artificial Sequence
<220> FEATURE:
<223> OTHER INFORMATION: Humanized BRCA84D-1 Variable Light Chain CDR1

<400> SEQUENCE: 70

Lys Ala Ser Gln Asn Val Asp Thr Asn Val Ala
1               5                   10

<210> SEQ ID NO 71
<211> LENGTH: 33
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Light Chain CDR1

<400> SEQUENCE: 71
aaggccagtc agaatgtgga tactaatgta gcc                              33

<210> SEQ ID NO 72
<211> LENGTH: 7
<212> TYPE: PRT
<213> ORGANISM: Artificial Sequence
<220> FEATURE:
<223> OTHER INFORMATION: Humanized BRCA84D-1 Variable Light Chain CDR2

<400> SEQUENCE: 72

Ser Ala Ser Tyr Arg Tyr Ser
1               5

<210> SEQ ID NO 73
<211> LENGTH: 21
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Light Chain CDR2

<400> SEQUENCE: 73
tcggcatcct accggtacag t                                           21

<210> SEQ ID NO 74
<211> LENGTH: 9
<212> TYPE: PRT
<213> ORGANISM: Artificial Sequence
<220> FEATURE:
<223> OTHER INFORMATION: Humanized BRCA84D-1 Variable Light Chain CDR3

<400> SEQUENCE: 74

Gln Gln Tyr Asn Asn Tyr Pro Phe Thr
1               5

<210> SEQ ID NO 75
<211> LENGTH: 27
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Light Chain CDR3

<400> SEQUENCE: 75
cagcaatata caactatcc attcacg                                      27

<210> SEQ ID NO 76
<211> LENGTH: 534
<212> TYPE: PRT
```

<213> ORGANISM: Homo sapiens

<400> SEQUENCE: 76

```
Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
        355                 360                 365

Pro Asn Lys Asp Leu Arg Pro Gly Asp Thr Val Thr Ile Thr Cys Ser
370                 375                 380

Ser Tyr Arg Gly Tyr Pro Glu Ala Glu Val Phe Trp Gln Asp Gly Gln
385                 390                 395                 400
```

Gly Val Pro Leu Thr Gly Asn Val Thr Thr Ser Gln Met Ala Asn Glu
                    405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
        435                 440                 445

Ala His Gly Ser Val Thr Ile Thr Gly Gln Pro Met Thr Phe Pro Pro
    450                 455                 460

Glu Ala Leu Trp Val Thr Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
        515                 520                 525

Asp Gly Gln Glu Ile Ala
    530

<210> SEQ ID NO 77
<211> LENGTH: 1602
<212> TYPE: DNA
<213> ORGANISM: Homo sapiens

<400> SEQUENCE: 77

```
atgctgcgtc ggcggggcag ccctggcatg ggtgtgcatg tgggtgcagc cctgggagca      60
ctgtggttct gcctcacagg agccctggag gtccaggtcc ctgaagaccc agtggtggca     120
ctggtgggca ccgatgccac cctgtgctgc tccttctccc ctgagcctgg cttcagcctg     180
gcacagctca acctcatctg cagctgacag ataccaaaca gctggtgca  cagctttgct     240
gagggccagg accagggcag cgcctatgcc aaccgcacgg ccctcttccc ggacctgctg     300
gcacagggca acgcatccct gaggctgcag cgcgtgcgtg tggcggacga gggcagcttc     360
acctgcttcg tgagcatccg ggatttcggc agcgctgccg tcagcctgca ggtggccgct     420
ccctactcga agcccagcat gaccctggag cccaacaagg acctgcggcc aggggacacg     480
gtgaccatca cgtgctccag ctaccagggc taccctgagg ctgaggtgtt ctggcaggat     540
gggcagggtg tgcccctgac tggcaacgtg accacgtcgc agatggccaa cgagcagggc     600
ttgtttgatg tgcacagcat cctgcgggtg gtgctgggtg caaatggcac ctacagctgc     660
ctggtgcgca cccccgtgct gcagcaggat gcgcacagct ctgtcaccat cacaccccag     720
agaagcccca caggagccgt ggaggtccag gtccctgagg acccggtggt ggccctagtg     780
ggcaccgatg ccaccctgcg ctgctccttc tcccccgagc ctggcttcag cctggcacag     840
ctcaacctca tctggcagct gacagacacc aaacagctgg tgcacagttt caccgaaggc     900
cgggaccagg gcagcgccta tgccaaccgc acggccctct cccggacct  gctggcacaa     960
ggcaatgcat ccctgaggct gcagcgcgtg cgtgtggcgg acgagggcag cttcacctgc    1020
ttcgtgagca tccgggattt cggcagcgct gccgtcagcc tgcaggtggc cgctccctac    1080
tcgaagccca gcatgaccct ggagcccaac aaggacctgc ggccagggga cacggtgacc    1140
atcacgtgct ccagctaccg gggctaccct gaggctgagg tgttctggca ggatgggcag    1200
ggtgtgcccc tgactggcaa cgtgaccacg tcgcagatgg ccaacgagca gggcttgttt    1260
gatgtgcaca gcgtcctgcg ggtggtgctg ggtgcgaatg gcacctacag ctgcctggtg    1320
```

```
cgcaacccog tgctgcagca ggatgcgcac ggctctgtca ccatcacagg gcagcctatg   1380
acattccccc cagaggccct gtgggtgacc gtggggctgt ctgtctgtct cattgcactg   1440
ctggtggccc tggctttcgt gtgctggaga aagatcaaac agagctgtga ggaggagaat   1500
gcaggagctg aggaccagga tggggaggga gaaggctcca agacagccct gcagcctctg   1560
aaacactctg acagcaaaga agatgatgga caagaaatag cc                    1602
```

<210> SEQ ID NO 78

<400> SEQUENCE: 78

000

<210> SEQ ID NO 79

<400> SEQUENCE: 79

000

<210> SEQ ID NO 80
<211> LENGTH: 122
<212> TYPE: PRT
<213> ORGANISM: Artificial Sequence
<220> FEATURE:
<223> OTHER INFORMATION: Amino Acid Sequence of Humanized BRCA84D-1
      Variable Heavy Chain

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Gly Arg Glu Asn Ile Tyr Tyr Gly Ser Arg Leu Asp Tyr Trp
            100                 105                 110

Gly Gln Gly Thr Thr Val Thr Val Ser Ser
        115                 120

<210> SEQ ID NO 81
<211> LENGTH: 366
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Heavy Chain

<400> SEQUENCE: 81

```
gaggtgcagc tggtcgagtc tggcggagga ctggtgcagc ctggcggctc cctgagactg     60
tcttgcgccg cctccggctt caccttctcc agcttcggca tgcactgggt ccgccaggct    120
ccaggcaagg gactggaatg ggtggcctac atctcctccg actcctccgc catctactac    180
gccgacaccg tgaagggcag gttcaccatc tcccgggaca cgccaagaa ctccctgtac    240 ctgcagatga actccctgcg ggacgaggac accgccgtgt actactgcgc cagaggccgg    300
```

```
gagaatatct actacggctc ccggctggat tattggggcc agggcaccac cgtgaccgtg      360
tcctct                                                                 366
```

<210> SEQ ID NO 82
<211> LENGTH: 4
<212> TYPE: PRT
<213> ORGANISM: Artificial Sequence
<220> FEATURE:
<223> OTHER INFORMATION: Humanized BRCA84D-1 Variable Heavy Chain CDR1

<400> SEQUENCE: 82

Phe Gly Met His
1

<210> SEQ ID NO 83
<211> LENGTH: 12
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Heavy Chain CDR1

<400> SEQUENCE: 83

```
tttggaatgc ac                                                          12
```

<210> SEQ ID NO 84
<211> LENGTH: 16
<212> TYPE: PRT
<213> ORGANISM: Artificial Sequence
<220> FEATURE:
<223> OTHER INFORMATION: Humanized BRCA84D Variable Heavy Chain CDR2

<400> SEQUENCE: 84

Tyr Ile Ser Ser Asp Ser Ser Ala Ile Tyr Tyr Ala Asp Thr Val Lys
1               5                   10                  15

<210> SEQ ID NO 85
<211> LENGTH: 48
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Heavy Chain CDR2

<400> SEQUENCE: 85

```
tacattagta gtgacagtag tgccatctac tatgcagaca cagtgaag                   48
```

<210> SEQ ID NO 86
<211> LENGTH: 13
<212> TYPE: PRT
<213> ORGANISM: Artificial Sequence
<220> FEATURE:
<223> OTHER INFORMATION: Humanized BRCA84D-1 Variable Heavy Chain CDR3

<400> SEQUENCE: 86

Gly Arg Glu Asn Ile Tyr Tyr Gly Ser Arg Leu Asp Tyr
1               5                   10

<210> SEQ ID NO 87
<211> LENGTH: 39
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Heavy Chain CDR3

<400> SEQUENCE: 87
gggagggaaa acatttacta cggtagtagg cttgactac                39

<210> SEQ ID NO 88

<400> SEQUENCE: 88

000

<210> SEQ ID NO 89
<211> LENGTH: 107
<212> TYPE: PRT
<213> ORGANISM: Artificial Sequence
<220> FEATURE:
<223> OTHER INFORMATION: hBRCA84D-2VL

<400> SEQUENCE: 89

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105

<210> SEQ ID NO 90
<211> LENGTH: 321
<212> TYPE: DNA
<213> ORGANISM: Artificial Sequence
<220> FEATURE:
<223> OTHER INFORMATION: Polynucleotide Encoding hBRCA84D-2VL

<400> SEQUENCE: 90
gacatccagc tgacccagtc cccctccttc ctgtctgcct ccgtgggcga cagagtgacc       60
atcacatgca aggcctccca gaacgtggac accaacgtgg cctggtatca gcagaagcct      120
ggcaaggccc ctaaggcgct gatctactcc gcctcctacc ggtactccgg cgtgccttcc      180
aggttctccg gctccggctc tggcaccgac ttcaccctga ccatctccag cctgcagcct      240
gaggacttcg ccacctacta ctgccagcag tacaacaact accctttcac cttcggccag      300
ggcaccaagc tggaaatcaa g                                                321

<210> SEQ ID NO 91
<211> LENGTH: 107
<212> TYPE: PRT
<213> ORGANISM: Artificial Sequence
<220> FEATURE:
<223> OTHER INFORMATION: hBRCA84D-3VL

<400> SEQUENCE: 91

Asp Ile Gln Leu Thr Gln Ser Pro Ser Phe Leu Ser Ala Ser Val Gly
1               5                   10                  15

Asp Arg Val Ser Val Thr Cys Lys Ala Ser Gln Asn Val Asp Thr Asn
            20                  25                  30

```
Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105
```

<210> SEQ ID NO 92
<211> LENGTH: 321
<212> TYPE: DNA
<213> ORGANISM: Artificial Sequence
<220> FEATURE:
<223> OTHER INFORMATION: Polynucleotide Encoding hBRCA84D-3VL

<400> SEQUENCE: 92

```
gacatccagc tgacccagtc cccctccttc ctgtctgcct ccgtgggcga cagagtgtcc    60
gtcacatgca aggcctccca gaacgtggac accaacgtgg cctggtatca gcagaagcct   120
ggcaaggccc ctaagctgct gatctactcc gcctcctacc ggtactccgg cgtgccttcc   180
aggttctccg gctccggctc tggcaccgac ttcaccctga ccatctccag cctgcagcct   240
gaggacttcg ccacctacta ctgccagcag tacaacaact acccttcac cttcggccag   300 ggcaccaagc tggaaatcaa g                                             321
```

<210> SEQ ID NO 93
<211> LENGTH: 107
<212> TYPE: PRT
<213> ORGANISM: Artificial Sequence
<220> FEATURE:
<223> OTHER INFORMATION: hBRCA84D-4VL

<400> SEQUENCE: 93

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
                20                  25                  30

Val Ala Trp Tyr Gln Gln Lys Pro Gly Gln Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105
```

<210> SEQ ID NO 94
<211> LENGTH: 321
<212> TYPE: DNA
<213> ORGANISM: Artificial Sequence
<220> FEATURE:
<223> OTHER INFORMATION: Polynucleotide Encoding hBRCA84D-4VL

<400> SEQUENCE: 94

```
gacatccagc tgacccagtc ccctccttc ctgtctgcct ccgtgggcga cagagtgacc      60
atcacatgca aggcctccca gaacgtggac accaacgtgg cctggtatca gcagaagcct    120
ggccaggccc ctaagctgct gatctactcc gcctcctacc ggtactccgg cgtgccttcc    180
aggttctccg gctccggctc tggcaccgac ttcaccctga ccatctccag cctgcagcct    240
gaggacttcg ccacctacta ctgccagcag tacaacaact acccttcac cttcggccag     300 ggcaccaagc tggaaatcaa g                                              321
```

<210> SEQ ID NO 95
<211> LENGTH: 107
<212> TYPE: PRT
<213> ORGANISM: Artificial Sequence
<220> FEATURE:
<223> OTHER INFORMATION: hBRCA84D-5VL

<400> SEQUENCE: 95

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Gln Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105
```

<210> SEQ ID NO 96
<211> LENGTH: 321
<212> TYPE: DNA
<213> ORGANISM: Artificial Sequence
<220> FEATURE:
<223> OTHER INFORMATION: Polynucleotide Encoding hBRCA84D-5VL

<400> SEQUENCE: 96

```
gacatccagc tgacccagtc ccctccttc ctgtctgcct ccgtgggcga cagagtgacc      60
atcacatgca aggcctccca gaacgtggac accaacgtgg cctggtatca gcagaagcct    120
ggccaggccc ctaaggcgct gatctactcc gcctcctacc ggtactccgg cgtgccttcc    180
aggttctccg gctccggctc tggcaccgac ttcaccctga ccatctccag cctgcagcct    240
gaggacttcg ccacctacta ctgccagcag tacaacaact acccttcac cttcggccag     300 ggcaccaagc tggaaatcaa g                                              321
```

<210> SEQ ID NO 97
<211> LENGTH: 107
<212> TYPE: PRT
<213> ORGANISM: Artificial Sequence
<220> FEATURE:
<223> OTHER INFORMATION: hBRCA84D-6VL

<400> SEQUENCE: 97

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
```

```
                20                  25                  30
Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Glu Tyr Tyr Cys Gln Gln Tyr Asn Asn Tyr Pro Phe
                85                  90                  95

Thr Phe Gly Gln Gly Thr Lys Leu Glu Ile Lys
            100                 105
```

<210> SEQ ID NO 98
<211> LENGTH: 321
<212> TYPE: DNA
<213> ORGANISM: Artificial Sequence
<220> FEATURE:
<223> OTHER INFORMATION: Polynucleotide Encoding hBRCA84D-6VL

<400> SEQUENCE: 98

```
gacatccagc tgacccagtc cccctccttc ctgtctgcct ccgtgggcga cagagtgacc      60
atcacatgca aggcctccca gaacgtggac accaacgtgg cctggtatca gcagaagcct     120
ggcaaggccc ctaagctgct gatctactcc gcctcctacc ggtactccgg cgtgccttcc     180
aggttctccg gctccggctc tggcaccgac ttcaccctga ccatctccag cctgcagcct     240
gaggacttcg ccgagtacta ctgccagcag tacaacaact acccttttac cttcggccag     300
ggcaccaagc tggaaatcaa g                                               321
```

<210> SEQ ID NO 99
<211> LENGTH: 122
<212> TYPE: PRT
<213> ORGANISM: Artificial Sequence
<220> FEATURE:
<223> OTHER INFORMATION: hBRCA84D-2VH

<400> SEQUENCE: 99

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser
        115                 120
```

<210> SEQ ID NO 100
<211> LENGTH: 366
<212> TYPE: DNA
<213> ORGANISM: Artificial Sequence
<220> FEATURE:

<223> OTHER INFORMATION: Polynucleotide Encoding hBRCA84D-2VH

<400> SEQUENCE: 100

```
gaggtgcagc tggtcgagtc tggcggagga ctggtgcagc tggcggctc cctgagactg      60
tcttgcgccg cctccggctt caccttctcc agcttcggca tgcactgggt ccgccaggct    120
ccaggcaagg gactggaatg ggtggcctac atctcctccg actcctccgc catctactac    180
gccgacaccg tgaagggcag gttcaccatc tcccgggaca cgccaagaa ctccctgtac     240
ctgcagatga actccctgcg ggacgaggac accgccgtgt actactgcgg cagaggccgg    300
gagaatatct actacggctc ccggctggat tattggggcc agggcaccac cgtgaccgtg    360
tcctct                                                               366
```

<210> SEQ ID NO 101
<211> LENGTH: 122
<212> TYPE: PRT
<213> ORGANISM: Artificial Sequence
<220> FEATURE:
<223> OTHER INFORMATION: hBRCA84D-3VH

<400> SEQUENCE: 101

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Met Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser
        115                 120
```

<210> SEQ ID NO 102
<211> LENGTH: 366
<212> TYPE: DNA
<213> ORGANISM: Artificial Sequence
<220> FEATURE:
<223> OTHER INFORMATION: Polynucleotide Encoding hBRCA84D-3VH

<400> SEQUENCE: 102

```
gaggtgcagc tggtcgagtc tggcggagga ctggtgcagc tggcggctc cctgagactg      60
tcttgcgccg cctccggctt caccttctcc agcttcggca tgcactgggt ccgccaggct    120
ccaggcaagg gactggaatg ggtggcctac atctcctccg actcctccgc catctactac    180
gccgacaccg tgaagggcag gttcaccatc tcccgggaca cgccaagaa ctccctgtac     240
ctgcagatga actccctgcg ggacgaggac accgccatgt actactgcgg cagaggccgg    300
gagaatatct actacggctc ccggctggat tattggggcc agggcaccac cgtgaccgtg    360
tcctct                                                               366
```

<210> SEQ ID NO 103
<211> LENGTH: 122

<212> TYPE: PRT
<213> ORGANISM: Artificial Sequence
<220> FEATURE:
<223> OTHER INFORMATION: hBRCA84D-4VH

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ser Glu Asp Thr Ala Val Tyr Tyr Cys
                85                  90                  95

Ala Arg Gly Arg Glu Asn Ile Tyr Tyr Gly Ser Arg Leu Asp Tyr Trp
            100                 105                 110

Gly Gln Gly Thr Thr Val Thr Val Ser Ser
        115                 120

<210> SEQ ID NO 104
<211> LENGTH: 366
<212> TYPE: DNA
<213> ORGANISM: Artificial Sequence
<220> FEATURE:
<223> OTHER INFORMATION: Polynucleotide Encoding hBRCA84D-4VH

<400> SEQUENCE: 104
gaggtgcagc tggtcgagtc tggcggagga ctggtgcagc ctggcggctc cctgagactg      60
tcttgcgccg cctccggctt caccttctcc agcttcggca tgcactgggt ccgccaggct     120
ccaggcaagg gactggaatg ggtggcctac atctcctccg actcctccgc catctactac     180
gccgacaccg tgaagggcag gttcaccatc tcccgggaca cgccaagaa ctccctgtac      240 ctgcagatga actccctgcg gagcgaggac accgccgtgt actactgcgc cagaggccgg     300
gagaatatct actacggctc ccggctggat tattggggcc agggcaccac cgtgaccgtg     360
tcctct                                                                366

<210> SEQ ID NO 105
<211> LENGTH: 214
<212> TYPE: PRT
<213> ORGANISM: Artificial Sequence
<220> FEATURE:
<223> OTHER INFORMATION: chBRCA84D Light Chain

<400> SEQUENCE: 105

Asp Ile Ala Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Glu Tyr Phe Cys Gln Gln Tyr Asn Asn Tyr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 106
<211> LENGTH: 645
<212> TYPE: DNA
<213> ORGANISM: Artificial Sequence
<220> FEATURE:
<223> OTHER INFORMATION: Polynucleotide Encoding chBRCA84D Light Chain

<400> SEQUENCE: 106
gacattgcga tgacccagtc tcaaaaattc atgtccacat cagtaggaga cagggtcagc    60
gtcacctgca aggccagtca gaatgtggat actaatgtag cctggtatca acagaaacca   120
gggcaatctc ctaaagcact gatttactcg gcatcctacc ggtacagtgg agtccctgat   180
cgcttcacag gcagtggatc tgggacagat ttcactctca ccatcaacaa tgtgcagtct   240
gaagacttgg cagagtattt ctgtcagcaa tataacaact atccattcac gttcggctcg   300
gggacaaagt tggaaataaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag              645

<210> SEQ ID NO 107
<211> LENGTH: 452
<212> TYPE: PRT
<213> ORGANISM: Artificial Sequence
<220> FEATURE:
<223> OTHER INFORMATION: chBRCA84D Heavy Chain

<400> SEQUENCE: 107

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

```
Ala Tyr Ile Ser Ser Asp Ser Ser Ala Ile Tyr Tyr Ala Asp Thr Val
 50                  55                  60

Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Gly Arg Gly Arg Glu Asn Ile Tyr Tyr Gly Ser Arg Leu Asp Tyr Trp
            100                 105                 110

Gly Gln Gly Thr Thr Leu Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
450
```

<210> SEQ ID NO 108
<211> LENGTH: 1359
<212> TYPE: DNA
<213> ORGANISM: Artificial Sequence
<220> FEATURE:
<223> OTHER INFORMATION: Polynucleotide Encoding chBRCA84D Heavy Chain

<400> SEQUENCE: 108

```
gatgtgcagc tggtggagtc tgggggaggc ttagtgcagc ctggagggtc ccggaaactc      60
tcctgtgcag cctctggatt cactttcagt agctttggaa tgcactgggt tcgtcaggct     120
ccagagaagg ggctggagtg ggtcgcatac attagtagtg acagtagtgc catctactat     180
gcagacacag tgaagggccg attcaccatc tccagagaca tcccaagaa cacctgttc      240
ctgcaaatga ccagtctaag gtctgaggac acggccatgt attactgtgg aagagggagg     300
gaaaacattt actacggtag taggcttgac tactggggcc aaggcaccac tctcacagtc     360
tcctcagcct ccaccaaggg cccatcggtc ttccccctgg caccctcctc aagagcacc      420
tctggggca gcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagagagtt     660
gagcccaaat cttgtgacaa aactcacaca tgcccaccgt gcccagcacc tgaactcctg     720
gggggaccgt cagtcttcct cttcccccca aaacccaagg acaccctcat gatctcccgg     780
accccctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgtgt ggtcagcgtc ctcaccgtcc tgcaccagga ctggctgaat     960
ggcaaggagt acaagtgcaa ggtctccaac aaagccctcc cagccccat cgagaaaacc     1020
atctccaaag ccaaagggca gccccgagaa ccacaggtgt acaccctgcc cccatcccgg     1080
gatgagctga ccaagaacca ggtcagcctg acctgcctgg tcaaaggctt ctatcccagc     1140
gacatcgccg tggagtggga gagcaatggg cagccggaga caactacaa gaccacgcct     1200
cccgtgctgg actccgacgg ctccttcttc ctctacagca agctcaccgt ggacaagagc     1260
aggtggcagc aggggaacgt cttctcatgc tccgtgatgc atgaggctct gcacaaccac     1320
tacacgcaga agagcctctc cctgtctccg ggtaaatga                           1359
```

<210> SEQ ID NO 109
<211> LENGTH: 270
<212> TYPE: PRT
<213> ORGANISM: Artificial Sequence
<220> FEATURE:
<223> OTHER INFORMATION: TCR VL x hBRCA84D VH-2-E Coil DART Chain

<400> SEQUENCE: 109

```
Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80
```

Asp Phe Ala Thr Tyr Tyr Cys Gln Gln Trp Ser Ser Asn Pro Leu Thr
                85                  90                  95

Phe Gly Gln Gly Thr Lys Leu Glu Ile Lys Gly Gly Ser Gly Gly
            100                 105                 110

Gly Gly Glu Val Gln Leu Val Glu Ser Gly Gly Leu Val Gln Pro
        115                 120                 125

Gly Gly Ser Leu Arg Leu Ser Cys Ala Ala Ser Gly Phe Thr Phe Ser
    130                 135                 140

Ser Phe Gly Met His Trp Val Arg Gln Ala Pro Gly Lys Gly Leu Glu
145                 150                 155                 160

Trp Val Ala Tyr Ile Ser Ser Asp Ser Ser Ala Ile Tyr Tyr Ala Asp
                165                 170                 175

Thr Val Lys Gly Arg Phe Thr Ile Ser Arg Asp Asn Ala Lys Asn Ser
            180                 185                 190

Leu Tyr Leu Gln Met Asn Ser Leu Arg Asp Glu Asp Thr Ala Val Tyr
        195                 200                 205

Tyr Cys Gly Arg Gly Arg Glu Asn Ile Tyr Tyr Gly Ser Arg Leu Asp
    210                 215                 220

Tyr Trp Gly Gln Gly Thr Thr Val Thr Val Ser Ser Gly Gly Cys Gly
225                 230                 235                 240

Gly Gly Glu Val Ala Ala Leu Glu Lys Glu Val Ala Ala Leu Glu Lys
                245                 250                 255

Glu Val Ala Ala Leu Glu Lys Glu Val Ala Ala Leu Glu Lys
            260                 265                 270

<210> SEQ ID NO 110
<211> LENGTH: 810
<212> TYPE: DNA
<213> ORGANISM: Artificial Sequence
<220> FEATURE:
<223> OTHER INFORMATION: Polynucleotide Encoding TCR VL x hBRCA84D VH-2-
      E Coil DART Chain

<400> SEQUENCE: 110
gaaattgtgt tgacacagtc tccagccacc ctgtctttgt ctccagggga aagagccacc        60
ctctcctgca gtgccacctc aagtgtaagt tacatgcact ggtatcagca gaaaccaggg       120
aaagccccta gcgctggat ctatgacaca tccaaactgg cttctggggt cccatcaagg        180
ttcagcggca gtggatctgg gacagaattt actctcacaa tcagcagcct gcagcctgaa       240
gattttgcaa cttattactg tcagcagtgg agtagtaacc cgctcacgtt tggccagggg       300
accaagcttg agatcaaagg aggcggatcc ggcggcggag gcgaggtgca gctggtcgag       360
tctggcggag gactggtgca gcctggcggc tccctgagac tgtcttgcgc cgcctccggc       420
ttcaccttct ccagcttcgg catgcactgg gtccgccagg ctccaggcaa gggactggaa       480
tgggtggcct acatctcctc cgactcctcc gccatctact acgccgacac cgtgaagggc       540
aggttcacca tctcccggga caacgccaag aactccctgt acctgcagat gaactccctg       600
cgggacgagg acaccgccgt gtactactgc ggcagaggcc gggagaatat ctactacggc       660
tcccggctgg attattgggg ccagggcacc accgtgaccg tgtcctccgg aggatgtggc       720
ggtggagaag tggccgcact ggagaaagag gttgctgctt tggagaagga ggtcgctgca       780
cttgaaaagg aggtcgcagc cctggagaaa                                       810

<210> SEQ ID NO 111
<211> LENGTH: 269

<212> TYPE: PRT
<213> ORGANISM: Artificial Sequence
<220> FEATURE:
<223> OTHER INFORMATION: hBRCA84DVL-2 x TCR VH - K coil Chain

<400> SEQUENCE: 111

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Lys Phe
130                 135                 140

Thr Ser Tyr Val Met His Trp Val Arg Gln Ala Pro Gly Gln Gly Leu
145                 150                 155                 160

Glu Trp Ile Gly Tyr Ile Asn Pro Tyr Asn Asp Val Thr Lys Tyr Asn
                165                 170                 175

Glu Lys Phe Lys Gly Arg Val Thr Ile Thr Ala Asp Lys Ser Thr Ser
            180                 185                 190

Thr Ala Tyr Leu Gln Met Asn Ser Leu Arg Ser Glu Asp Thr Ala Val
        195                 200                 205

His Tyr Cys Ala Arg Gly Ser Tyr Tyr Asp Tyr Asp Gly Phe Val Tyr
    210                 215                 220

Trp Gly Gln Gly Thr Leu Val Thr Val Ser Ser Gly Cys Gly Gly
225                 230                 235                 240

Gly Lys Val Ala Ala Leu Lys Glu Lys Val Ala Ala Leu Lys Glu Lys
                245                 250                 255

Val Ala Ala Leu Lys Glu Lys Val Ala Ala Leu Lys Glu
            260                 265

<210> SEQ ID NO 112
<211> LENGTH: 807
<212> TYPE: DNA
<213> ORGANISM: Artificial Sequence
<220> FEATURE:
<223> OTHER INFORMATION: Polynucleotide Encoding hBRCA84DVL-2 x TCR VH -
      K coil Chain

<400> SEQUENCE: 112
gacatccagc tgacccagtc ccctccttc ctgtctgcct ccgtgggcga cagagtgacc      60
atcacatgca aggcctccca gaacgtggac accaacgtgg cctggtatca gcagaagcct    120
ggcaaggccc ctaaggcgct gatctactcc gcctcctacc ggtactccgg cgtgccttcc    180
aggttctccg gctccggctc tggcaccgac ttcaccctga ccatctccag cctgcagcct    240
gaggacttcg ccacctacta ctgccagcag tacaacaact acccctttac cttcggccag    300

```
ggcaccaagc tggaaatcaa gggaggcgga tccggcggcg aggccaggt tcagctggtg      360 cagtctggag ctgaggtgaa gaagcctggg gcctcagtga aggtctcctg caaggccagc      420
ggttacaagt ttaccagcta cgtgatgcac tgggtgcgac aggcccctgg acaagggctt      480
gagtggatcg gatatattaa tcctacaat gatgttacta agtacaatga aagttcaaa        540 ggcagagtca cgattaccgc ggacaaatcc acgagcacag cctacctgca gatgaacagc      600
ctgagatccg aggacacggc cgtgcactac tgtgcgagag ggagctacta tgattacgac      660
gggtttgttt actggggcca agggactctg gtcactgtga gctccggagg atgtggcggt      720
ggaaaagtgg ccgcactgaa ggagaaagtt gctgctttga agagaaggt cgccgcactt      780 aaggaaaagg tcgcagccct gaaagag                                         807
```

<210> SEQ ID NO 113
<211> LENGTH: 274
<212> TYPE: PRT
<213> ORGANISM: Artificial Sequence
<220> FEATURE:
<223> OTHER INFORMATION: NKG2D VL x hBRCA84D VH-2-E Coil DART Chain

<400> SEQUENCE: 113

```
Gln Ser Ala Leu Thr Gln Pro Ala Ser Val Ser Gly Ser Pro Gly Gln
1               5                   10                  15

Ser Ile Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Ser Phe Gly Met His Trp Val Arg Gln Ala Pro Gly
145                 150                 155                 160

Lys Gly Leu Glu Trp Val Ala Tyr Ile Ser Ser Asp Ser Ser Ala Ile
                165                 170                 175

Tyr Tyr Ala Asp Thr Val Lys Gly Arg Phe Thr Ile Ser Arg Asp Asn
            180                 185                 190

Ala Lys Asn Ser Leu Tyr Leu Gln Met Asn Ser Leu Arg Asp Glu Asp
        195                 200                 205

Thr Ala Val Tyr Tyr Cys Gly Arg Gly Arg Glu Asn Ile Tyr Tyr Gly
    210                 215                 220

Ser Arg Leu Asp Tyr Trp Gly Gln Gly Thr Thr Val Thr Val Ser Ser
225                 230                 235                 240

Gly Gly Cys Gly Gly Gly Glu Val Ala Ala Leu Glu Lys Glu Val Ala
                245                 250                 255

Ala Leu Glu Lys Glu Val Ala Ala Leu Glu Lys Glu Val Ala Ala Leu
            260                 265                 270
```

Glu Lys

<210> SEQ ID NO 114
<211> LENGTH: 822
<212> TYPE: DNA
<213> ORGANISM: Artificial Sequence
<220> FEATURE:
<223> OTHER INFORMATION: Polynucleotide Encoding NKG2D VL x hBRCA84D VH-
      2-E Coil DART Chain

<400> SEQUENCE: 114

```
cagtctgccc tgactcagcc tgcctccgtg tctgggtctc ctggacagtc aatcaccatc      60
tcctgttctg gaagcagctc aacatcgga ataatgctg ttaactggta ccagcagctc      120
ccaggaaagg ctcccaaact cctcatctat tatgatgacc tactgccctc agggggtctct    180
gaccgattct ctggctccaa gtctggcacc tcagccttcc tggccatcag tgggctccag    240
tctgaggatg aggctgatta ttactgtgca gcatgggatg acagcctgaa tggtccagtg    300
ttcggcggag ggaccaagct gaccgtccta ggaggcggat ccggcggcgg aggcgaggtg    360
cagctggtcg agtctggcgg aggactggtg cagcctggcg gctccctgag actgtcttgc    420
gccgcctccg gcttcaccttt ctccagcttc ggcatgcact gggtccgcca ggctccaggc    480
aagggactgg aatgggtggc ctacatctcc tccgactcct ccgccatcta ctacgccgac    540
accgtgaagg gcaggttcac catctcccgg gacaacgcca agaactccct gtacctgcag    600
atgaactccc tgcgggacga ggacaccgcc gtgtactact gcggcagagg ccggagaat    660
atctactacg ctcccggct ggattattgg ggccagggca ccaccgtgac cgtgtcctcc    720
ggaggatgtg gcggtggaga agtggccgca ctggagaaag aggttgctgc tttggagaag    780
gaggtcgctg cacttgaaaa ggaggtcgca gccctggaga aa                        822
```

<210> SEQ ID NO 115
<211> LENGTH: 270
<212> TYPE: PRT
<213> ORGANISM: Artificial Sequence
<220> FEATURE:
<223> OTHER INFORMATION: hBRCA84DVL-2 x NKG2D VH - K coil Chain

<400> SEQUENCE: 115

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Glu Ser Gly Gly Gly Leu Val Lys
        115                 120                 125

Pro Gly Gly Ser Leu Arg Leu Ser Cys Ala Ala Ser Gly Phe Thr Phe
    130                 135                 140

Ser Ser Tyr Gly Met His Trp Val Arg Gln Ala Pro Gly Lys Gly Leu
```

```
145                 150                 155                 160
Glu Trp Val Ala Phe Ile Arg Tyr Asp Gly Ser Asn Lys Tyr Tyr Ala
                165                 170                 175
Asp Ser Val Lys Gly Arg Phe Thr Ile Ser Arg Asp Asn Ser Lys Asn
                180                 185                 190
Thr Leu Tyr Leu Gln Met Asn Ser Leu Arg Ala Glu Asp Thr Ala Val
                195                 200                 205
Tyr Tyr Cys Ala Lys Asp Arg Gly Leu Gly Asp Gly Thr Tyr Phe Asp
                210                 215                 220
Tyr Trp Gly Gln Gly Thr Thr Val Thr Val Ser Ser Gly Gly Cys Gly
225                 230                 235                 240
Gly Gly Lys Val Ala Ala Leu Lys Glu Lys Val Ala Ala Leu Lys Glu
                245                 250                 255
Lys Val Ala Ala Leu Lys Glu Lys Val Ala Ala Leu Lys Glu
                260                 265                 270

<210> SEQ ID NO 116
<211> LENGTH: 810
<212> TYPE: DNA
<213> ORGANISM: Artificial Sequence
<220> FEATURE:
<223> OTHER INFORMATION: Polynucleotide Encoding hBRCA84DVL-2 x NKG2D
      VH - K coil Chain

<400> SEQUENCE: 116
gacatccagc tgacccagtc cccctccttc ctgtctgcct ccgtgggcga cagagtgacc     60
atcacatgca aggcctccca gaacgtggac accaacgtgg cctggtatca gcagaagcct    120
ggcaaggccc ctaaggcgct gatctactcc gcctcctacc ggtactccgg cgtgccttcc    180
aggttctccg gctccggctc tggcaccgac ttcaccctga ccatctccag cctgcagcct    240
gaggacttcg ccacctacta ctgccagcag tacaacaact accctttcac cttcggccag    300
ggcaccaagc tggaaatcaa gggaggcgga tccggcggcg aggccaggt acagctggtg    360
gagtctgggg gaggcctggt caagcctgga gggtccctga ctctcctg tgcagcgtct    420
ggattcacct tcagtagcta tggcatgcac tgggtccgcc aggctccagg caaggggctg    480
gagtgggtgg catttatacg gtatgatgga agtaataaat actatgcaga ctccgtgaag    540
ggccgattca ccatctccag agacaattcc aagaacacgc tgtatctgca aatgaacagc    600
ctgagagctg aggacacggc tgtgtattac tgtgcgaaag atcgaggttt ggggatgga    660
acctactttg actactgggg ccaagggacc acggtcaccg tctcctccgg aggatgtggc    720
ggtggaaaag tggccgcact gaaggagaaa gttgctgctt tgaaagagaa ggtcgccgca    780
cttaaggaaa aggtcgcagc cctgaaagag                                    810

<210> SEQ ID NO 117
<211> LENGTH: 214
<212> TYPE: PRT
<213> ORGANISM: Artificial Sequence
<220> FEATURE:
<223> OTHER INFORMATION: Amino Acid Sequence Of The hBRCA84D-2 Light
      Chain

<400> SEQUENCE: 117

Asp Ile Gln Leu Thr Gln Ser Pro Ser Phe Leu Ser Ala Ser Val Gly
1               5                   10                  15
Asp Arg Val Thr Ile Thr Cys Lys Ala Ser Gln Asn Val Asp Thr Asn
                20                  25                  30
```

```
Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Phe
                 85                  90                  95

Thr Phe Gly Gln Gly Thr Lys Leu Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 118
<211> LENGTH: 645
<212> TYPE: DNA
<213> ORGANISM: Artificial Sequence
<220> FEATURE:
<223> OTHER INFORMATION: Polynucleotide Encoding The Amino Acid Sequence
      Of The hBRCA84D-2 Light Chain

<400> SEQUENCE: 118

```
gacatccagc tgacccagtc ccctccttc ctgtctgcct ccgtgggcga cagagtgacc      60
atcacatgca aggcctccca gaacgtggac accaacgtgg cctggtatca gcagaagcct    120
ggcaaggccc ctaaggcgct gatctactcc gcctcctacc ggtactccgg cgtgccttcc    180
aggttctccg gctccggctc tggcaccgac ttcaccctga ccatctccag cctgcagcct    240
gaggacttcg ccacctacta ctgccagcag tacaacaact accctttcac cttcggccag    300
ggcaccaagc tggaaatcaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645
```

<210> SEQ ID NO 119
<211> LENGTH: 452
<212> TYPE: PRT
<213> ORGANISM: Artificial Sequence
<220> FEATURE:
<223> OTHER INFORMATION: Amino Acid Sequence Of The hBRCA84D-2 Heavy
      Chain

<400> SEQUENCE: 119

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Val
225                 230                 235                 240

Gly Gly Pro Ser Val Phe Leu Leu Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Leu Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Leu Val Leu Asp Ser Asp Gly Ser Phe Phe Leu Tyr Ser Lys Leu Thr
```

```
                        405                 410                 415
Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
    450

<210> SEQ ID NO 120
<211> LENGTH: 1356
<212> TYPE: PRT
<213> ORGANISM: Artificial Sequence
<220> FEATURE:
<223> OTHER INFORMATION: Polynucleotide Encoding The Amino Acid Sequence
      Of The hBRCA84D-2 Heavy Chain

<400> SEQUENCE: 120

Gly Ala Gly Gly Thr Gly Cys Ala Gly Cys Thr Gly Thr Cys Thr Gly
1               5                   10                  15

Ala Gly Thr Cys Thr Gly Gly Cys Gly Gly Ala Gly Gly Ala Cys Thr
                20                  25                  30

Gly Gly Thr Gly Cys Ala Gly Cys Cys Thr Gly Gly Cys Gly Gly Cys
            35                  40                  45

Thr Cys Cys Cys Thr Gly Ala Gly Ala Cys Thr Gly Thr Cys Thr Thr
    50                  55                  60

Gly Cys Gly Cys Cys Gly Cys Cys Thr Cys Cys Gly Gly Cys Thr Thr
65                  70                  75                  80

Cys Ala Cys Cys Thr Thr Cys Thr Cys Cys Ala Gly Cys Thr Thr Cys
                85                  90                  95

Gly Gly Cys Ala Thr Gly Cys Ala Cys Thr Gly Gly Gly Thr Cys Cys
            100                 105                 110

Gly Cys Cys Ala Gly Gly Cys Thr Cys Cys Ala Gly Gly Cys Ala Ala
        115                 120                 125

Gly Gly Gly Ala Cys Thr Gly Gly Ala Ala Thr Gly Gly Gly Thr Gly
    130                 135                 140

Gly Cys Cys Thr Ala Cys Ala Thr Cys Thr Cys Cys Thr Cys Cys Gly
145                 150                 155                 160

Ala Cys Thr Cys Cys Thr Cys Cys Gly Cys Cys Ala Thr Cys Thr Ala
                165                 170                 175

Cys Thr Ala Cys Gly Cys Cys Gly Ala Cys Ala Cys Cys Gly Thr Gly
            180                 185                 190

Ala Ala Gly Gly Gly Cys Ala Gly Gly Thr Thr Cys Ala Cys Cys Ala
        195                 200                 205

Thr Cys Thr Cys Cys Gly Gly Gly Ala Cys Ala Ala Cys Gly Cys Cys
    210                 215                 220

Cys Ala Ala Gly Ala Ala Cys Thr Cys Cys Thr Gly Thr Ala Cys Cys
225                 230                 235                 240

Cys Thr Gly Cys Ala Gly Ala Thr Gly Ala Ala Cys Thr Cys Cys Cys
                245                 250                 255

Thr Gly Cys Gly Gly Gly Ala Cys Gly Ala Gly Gly Ala Cys Ala Cys
            260                 265                 270

Cys Gly Cys Cys Gly Thr Gly Thr Ala Cys Thr Ala Cys Thr Gly Cys
        275                 280                 285

Gly Gly Cys Ala Gly Ala Gly Gly Cys Cys Gly Gly Gly Ala Gly Ala
    290                 295                 300
```

-continued

```
Ala Thr Ala Thr Cys Thr Ala Cys Thr Ala Cys Gly Gly Cys Thr Cys
305                 310                 315                 320

Cys Cys Gly Gly Cys Thr Gly Ala Thr Thr Ala Thr Thr Gly Gly
                325                 330                 335

Gly Gly Cys Cys Ala Gly Gly Cys Ala Cys Ala Cys Cys Gly
                340                 345                 350

Thr Gly Ala Cys Cys Gly Thr Gly Thr Cys Cys Thr Cys Thr Gly Cys
        355                 360                 365

Cys Thr Cys Cys Ala Cys Cys Ala Ala Gly Gly Cys Cys Cys Ala
    370                 375                 380

Thr Cys Gly Gly Thr Cys Thr Thr Cys Cys Cys Cys Thr Gly Gly
385                 390                 395                 400

Cys Ala Cys Cys Cys Thr Cys Cys Thr Cys Cys Ala Ala Gly Ala Gly
                405                 410                 415

Cys Ala Cys Cys Thr Cys Thr Gly Gly Gly Gly Cys Ala Cys Ala
                420                 425                 430

Gly Cys Gly Gly Cys Cys Cys Thr Gly Gly Gly Cys Thr Gly Cys Cys
        435                 440                 445

Thr Gly Gly Thr Cys Ala Ala Gly Gly Ala Cys Thr Ala Cys Thr Thr
    450                 455                 460

Cys Cys Cys Cys Gly Ala Ala Cys Cys Gly Gly Thr Gly Ala Cys Gly
465                 470                 475                 480

Gly Thr Gly Thr Cys Gly Thr Gly Gly Ala Ala Cys Thr Cys Ala Gly
                485                 490                 495

Gly Cys Gly Cys Cys Cys Thr Gly Ala Cys Cys Ala Gly Cys Gly Gly
                500                 505                 510

Cys Gly Thr Gly Cys Ala Cys Ala Cys Cys Thr Thr Cys Cys Cys Gly
        515                 520                 525

Gly Cys Thr Gly Thr Cys Cys Thr Ala Cys Ala Gly Thr Cys Cys Thr
    530                 535                 540

Cys Ala Gly Gly Ala Cys Thr Cys Thr Ala Cys Thr Cys Cys Cys Thr
545                 550                 555                 560

Cys Ala Gly Cys Ala Gly Cys Gly Thr Gly Gly Thr Gly Ala Cys Cys
                565                 570                 575

Gly Thr Gly Cys Cys Cys Thr Cys Cys Ala Gly Cys Ala Gly Cys Thr
            580                 585                 590

Thr Gly Gly Gly Cys Ala Cys Cys Ala Gly Ala Cys Cys Thr Ala
    595                 600                 605

Cys Ala Thr Cys Thr Gly Cys Ala Ala Cys Gly Thr Gly Ala Ala Thr
    610                 615                 620

Cys Ala Cys Ala Ala Gly Cys Cys Cys Ala Gly Cys Ala Ala Cys Ala
625                 630                 635                 640

Cys Cys Ala Ala Gly Gly Thr Gly Gly Ala Cys Ala Ala Gly Ala Gly
                645                 650                 655

Ala Gly Thr Thr Gly Ala Gly Cys Cys Cys Ala Ala Ala Thr Cys Thr
            660                 665                 670

Thr Gly Thr Gly Ala Cys Ala Ala Ala Cys Thr Cys Ala Cys Ala
        675                 680                 685

Cys Ala Thr Gly Cys Cys Cys Ala Cys Cys Gly Thr Gly Cys Cys Cys
    690                 695                 700

Ala Gly Cys Ala Cys Cys Thr Gly Ala Ala Cys Thr Cys Gly Thr Gly
705                 710                 715                 720

Gly Gly Gly Gly Gly Ala Cys Cys Gly Thr Cys Ala Gly Thr Cys Thr
```

-continued

```
                725                 730                 735
Thr Cys Cys Thr Cys Thr Thr Ala Cys Cys Cys Cys Ala Ala Ala
                740                 745                 750
Ala Cys Cys Cys Ala Ala Gly Gly Ala Cys Ala Cys Cys Thr Cys
                755                 760                 765
Ala Thr Gly Ala Thr Cys Thr Cys Cys Gly Gly Ala Cys Cys Cys
                770                 775                 780
Cys Thr Gly Ala Gly Gly Thr Cys Ala Cys Ala Thr Gly Cys Gly Thr
785                 790                 795                 800
Gly Gly Thr Gly Gly Thr Gly Ala Cys Gly Thr Gly Ala Gly Cys
                805                 810                 815
Cys Ala Cys Gly Ala Ala Gly Ala Cys Cys Cys Thr Gly Ala Gly Gly
                820                 825                 830
Thr Cys Ala Ala Gly Thr Thr Cys Ala Ala Cys Thr Gly Gly Thr Ala
                835                 840                 845
Cys Gly Thr Gly Gly Ala Cys Gly Gly Cys Gly Thr Gly Gly Ala Gly
                850                 855                 860
Gly Thr Gly Cys Ala Thr Ala Ala Thr Gly Cys Cys Ala Ala Gly Ala
865                 870                 875                 880
Cys Ala Ala Ala Gly Cys Cys Gly Cys Gly Gly Ala Gly Gly Ala
                885                 890                 895
Gly Cys Ala Gly Thr Ala Cys Ala Ala Cys Ala Gly Cys Ala Cys Gly
                900                 905                 910
Cys Thr Cys Cys Gly Thr Gly Thr Gly Gly Thr Cys Ala Gly Cys Gly
                915                 920                 925
Thr Cys Cys Thr Cys Ala Cys Cys Gly Thr Cys Cys Thr Gly Cys Ala
                930                 935                 940
Cys Cys Ala Gly Gly Ala Cys Thr Gly Gly Cys Thr Gly Ala Ala Thr
945                 950                 955                 960
Gly Gly Cys Ala Ala Gly Gly Ala Gly Thr Ala Cys Ala Ala Gly Thr
                965                 970                 975
Gly Cys Ala Ala Gly Gly Thr Cys Thr Cys Cys Ala Ala Cys Ala Ala
                980                 985                 990
Ala Gly Cys Cys Cys Thr Cys Cys  Cys Ala Gly Cys Cys  Cys Cys Cys
                995                 1000                1005
Ala Thr Cys Gly Ala Gly Ala  Ala Ala Cys Cys  Ala Thr Cys
                1010                1015                1020
Thr Cys Cys Ala Ala Ala Gly  Cys Cys Ala Ala Ala  Gly Gly Gly
                1025                1030                1035
Cys Ala Gly Cys Cys Cys Cys  Gly Ala Gly Ala Ala  Cys Cys Ala
                1040                1045                1050
Cys Ala Gly Gly Thr Gly Thr  Ala Cys Ala Cys Cys  Cys Thr Gly
                1055                1060                1065
Cys Cys Cys Cys Cys Ala Thr  Cys Cys Cys Gly Gly  Gly Ala Gly
                1070                1075                1080
Gly Ala Gly Ala Thr Gly Ala  Cys Cys Ala Ala Gly  Ala Ala Cys
                1085                1090                1095
Cys Ala Gly Gly Thr Cys Ala  Gly Cys Cys Thr Gly  Ala Cys Cys
                1100                1105                1110
Thr Gly Cys Cys Thr Gly Gly  Thr Cys Ala Ala Ala  Gly Gly Cys
                1115                1120                1125
Thr Thr Cys Thr Ala Thr Cys  Cys Cys Ala Gly Cys  Gly Ala Cys
                1130                1135                1140
```

```
Ala Thr Cys Gly Cys Cys Gly Thr Gly Gly Ala Gly Thr Gly Gly
    1145            1150              1155

Gly Ala Gly Ala Gly Cys Ala Ala Thr Gly Gly Gly Cys Ala Gly
    1160            1165              1170

Cys Cys Gly Gly Ala Gly Ala Ala Cys Ala Ala Cys Thr Ala Cys
    1175            1180              1185

Ala Ala Gly Ala Cys Ala Cys Gly Cys Cys Thr Cys Thr Cys
    1190            1195              1200

Gly Thr Gly Cys Thr Gly Gly Ala Cys Thr Cys Cys Gly Ala Cys
    1205            1210              1215

Gly Gly Cys Thr Cys Cys Thr Thr Cys Thr Thr Cys Cys Thr Cys
    1220            1225              1230

Thr Ala Cys Ala Gly Cys Ala Ala Gly Cys Thr Cys Ala Cys Cys
    1235            1240              1245

Gly Thr Gly Gly Ala Cys Ala Ala Gly Ala Gly Cys Ala Gly Gly
    1250            1255              1260

Thr Gly Gly Cys Ala Gly Cys Ala Gly Gly Gly Ala Ala Cys
    1265            1270              1275

Gly Thr Cys Thr Thr Cys Thr Cys Ala Thr Gly Cys Thr Cys Cys
    1280            1285              1290

Gly Thr Gly Ala Thr Gly Cys Ala Thr Gly Ala Gly Gly Cys Thr
    1295            1300              1305

Cys Thr Gly Cys Ala Cys Ala Ala Cys Cys Ala Cys Thr Ala Cys
    1310            1315              1320

Ala Cys Gly Cys Ala Gly Ala Ala Gly Ala Gly Cys Cys Thr Cys
    1325            1330              1335

Thr Cys Cys Cys Thr Gly Thr Cys Thr Cys Cys Gly Gly Gly Thr
    1340            1345              1350

Ala Ala Ala
    1355
```